US008084200B2

(12) United States Patent
Ashkenazi et al.

(10) Patent No.: US 8,084,200 B2
(45) Date of Patent: Dec. 27, 2011

(54) COMPOSITIONS AND METHODS FOR THE DIAGNOSIS AND TREATMENT OF TUMOR

(75) Inventors: Avi J. Ashkenazi, San Mateo, CA (US); Gretchen Frantz, San Francisco, CA (US); Audrey Goddard, San Francisco, CA (US); Lino Gonzalez, Hollister, CA (US); Austin L. Gurney, Belmont, CA (US); Paul Polakis, Burlingame, CA (US); Andrew Polson, San Francisco, CA (US); William I. Wood, Hillsborough, CA (US); Thomas D. Wu, San Francisco, CA (US); Zemin Zhang, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/402,434

(22) Filed: Mar. 11, 2009

(65) Prior Publication Data
US 2009/0186363 A1   Jul. 23, 2009

Related U.S. Application Data

(63) Continuation of application No. 11/486,298, filed on Jul. 13, 2006, now abandoned, which is a continuation of application No. 10/712,892, filed on Nov. 12, 2003, now abandoned.

(60) Provisional application No. 60/437,344, filed on Dec. 31, 2002, provisional application No. 60/431,250, filed on Dec. 6, 2002, provisional application No. 60/426,847, filed on Nov. 15, 2002.

(51) Int. Cl.
*C12Q 1/68* (2006.01)
(52) U.S. Cl. .......................................................... 435/6
(58) Field of Classification Search .................. None
See application file for complete search history.

(56) References Cited

U.S. PATENT DOCUMENTS

| | | | |
|---|---|---|---|
| 4,816,567 A | 3/1989 | Cabilly et al. | |
| 5,227,158 A | 7/1993 | Jardieu | |
| 5,521,073 A | 5/1996 | Davis et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,571,894 A | 11/1996 | Wels et al. | |
| 5,587,458 A | 12/1996 | King et al. | |
| 5,625,126 A | 4/1997 | Lonberg et al. | |
| 5,633,425 A | 5/1997 | Lonberg et al. | |
| 5,641,756 A | 6/1997 | Robinson | |
| 5,641,870 A | 6/1997 | Rinderknecht | |
| 5,650,490 A | 7/1997 | Davis et al. | |
| 5,661,016 A | 8/1997 | Lonberg et al. | |
| 5,750,373 A | 5/1998 | Garrard et al. | |
| 5,814,464 A | 9/1998 | Davis et al. | |
| 6,150,117 A * | 11/2000 | Zetter et al. ............ | 435/7.1 |
| 6,348,350 B1 | 2/2002 | Goddard et al. | |
| 6,372,491 B1 | 4/2002 | Goddard et al. | |
| 6,455,496 B1 | 9/2002 | Goddard et al. | |
| 6,475,753 B1 | 11/2002 | Ruben et al. | |
| 6,582,959 B2 | 6/2003 | Kim et al. | |
| 6,627,741 B2 | 9/2003 | Ruben et al. | |
| 6,673,545 B2 | 1/2004 | Faris et al. | |
| 6,680,175 B2 | 1/2004 | Blaschuk et al. | |
| 6,703,020 B1 | 3/2004 | Thorpe et al. | |
| 6,756,219 B1 | 6/2004 | Ishizaki et al. | |
| 6,884,879 B1 | 4/2005 | Baca et al. | |
| 7,368,254 B2 | 5/2008 | Jorgensen et al. | |
| 7,371,384 B2 | 5/2008 | Gerber | |
| 2002/0119463 A1 | 8/2002 | Faris et al. | |
| 2003/0055006 A1 | 3/2003 | Siemeister et al. | |
| 2003/0065151 A1 | 4/2003 | Ruben et al. | |
| 2003/0190317 A1 | 10/2003 | Baca et al. | |
| 2003/0199058 A1 | 10/2003 | Baker et al. | |
| 2003/0203409 A1 | 10/2003 | Kim | |
| 2003/0206899 A1 | 11/2003 | Ferrara et al. | |
| 2003/0207348 A1 | 11/2003 | Shimkets et al. | |
| 2003/0207350 A1 | 11/2003 | Baker et al. | |
| 2003/0207351 A1 | 11/2003 | Baker et al. | |
| 2003/0207352 A1 | 11/2003 | Baker et al. | |
| 2003/0207353 A1 | 11/2003 | Baker et al. | |
| 2003/0207356 A1 | 11/2003 | Baker et al. | |
| 2003/0207357 A1 | 11/2003 | Baker et al. | |
| 2003/0207359 A1 | 11/2003 | Baker et al. | |
| 2003/0207360 A1 | 11/2003 | Baker et al. | |
| 2003/0207371 A1 | 11/2003 | Baker et al. | |
| 2003/0207374 A1 | 11/2003 | Baker et al. | |
| 2003/0207375 A1 | 11/2003 | Baker et al. | |
| 2003/0207376 A1 | 11/2003 | Baker et al. | |
| 2003/0207389 A1 | 11/2003 | Baker et al. | |
| 2003/0207422 A1 | 11/2003 | Baker et al. | |
| 2003/0207423 A1 | 11/2003 | Baker et al. | |
| 2003/0207424 A1 | 11/2003 | Baker et al. | |
| 2003/0207425 A1 | 11/2003 | Baker et al. | |
| 2003/0207426 A1 | 11/2003 | Baker et al. | |
| 2003/0207427 A1 | 11/2003 | Baker et al. | |
| 2003/0208055 A1 | 11/2003 | Baker et al. | |
| 2003/0215451 A1 | 11/2003 | Ferrara et al. | |
| 2003/0219885 A1 | 11/2003 | Baker et al. | |
| 2004/0133357 A1 | 7/2004 | Pingyu et al. | |
| 2004/0249141 A1 | 12/2004 | Goddard et al. | |

(Continued)

FOREIGN PATENT DOCUMENTS

CN  1315451  10/2001

(Continued)

OTHER PUBLICATIONS

"Supplementary European Search Report mailed Dec. 28, 2010 in European Application No. 03783432.2".

(Continued)

*Primary Examiner* — Sean E Aeder
(74) *Attorney, Agent, or Firm* — Grant Kalinowski; Jeffery P. Bernhardt; Arnold & Porter LLP

(57) ABSTRACT

The present invention is directed to compositions of matter useful for the diagnosis and treatment of tumor in mammals and to methods of using those compositions of matter for the same.

3 Claims, 47 Drawing Sheets

U.S. PATENT DOCUMENTS

| | | | |
|---|---|---|---|
| 2005/0112126 A1 | 5/2005 | Baca et al. | |
| 2005/0123925 A1 | 6/2005 | Ashkenazi et al. | |
| 2005/0233361 A1 | 10/2005 | Clerc et al. | |
| 2005/0239706 A1 | 10/2005 | Backhed et al. | |
| 2006/0093607 A1 | 5/2006 | Gerber et al. | |
| 2006/0222645 A1 | 10/2006 | Lee et al. | |
| 2007/0026002 A1 | 2/2007 | Gerber et al. | |

FOREIGN PATENT DOCUMENTS

| | | |
|---|---|---|
| CN | 1343725 | 4/2002 |
| EP | 0 666 868 B1 | 4/2002 |
| EP | 1 403 367 A1 | 3/2004 |
| JP | 2000-308488 | 11/2000 |
| WO | WO 93/11161 | 6/1993 |
| WO | WO 93/16185 | 8/1993 |
| WO | WO 94/10202 | 5/1994 |
| WO | WO 96/30046 | 10/1996 |
| WO | WO 98/45331 | 10/1998 |
| WO | WO 98/45332 | 10/1998 |
| WO | WO99/15653 | 4/1999 |
| WO | WO99/15654 | 4/1999 |
| WO | WO 99/32515 | 7/1999 |
| WO | WO 99/45135 | 9/1999 |
| WO | WO 99/66041 | 12/1999 |
| WO | WO 99/67382 | 12/1999 |
| WO | WO 00/52165 | 9/2000 |
| WO | WO00/53753 | 9/2000 |
| WO | WO 00/61629 | 10/2000 |
| WO | WO 00/63380 | 10/2000 |
| WO | WO 01/02429 A2 | 1/2001 |
| WO | WO 01/05825 A2 | 1/2001 |
| WO | WO 01/05971 A2 | 1/2001 |
| WO | WO01/40466 | 6/2001 |
| WO | WO 01/40466 * | 6/2001 |
| WO | 01/53455 | 7/2001 |
| WO | 01/53486 | 7/2001 |
| WO | WO 01/54477 A2 | 8/2001 |
| WO | WO 01/57188 A2 | 8/2001 |
| WO | WO 01/77151 A2 | 10/2001 |
| WO | WO 02/77013 | 10/2002 |
| WO | WO 02/101039 A1 | 12/2002 |
| WO | WO 03/000865 A2 | 1/2003 |
| WO | WO 03/010205 A1 | 2/2003 |
| WO | WO 03/025138 A2 | 3/2003 |
| WO | WO 03/040329 A2 | 5/2003 |
| WO | WO 03/040330 A2 | 5/2003 |
| WO | WO 03/048185 A2 | 6/2003 |
| WO | WO 03/060071 A2 | 7/2003 |
| WO | WO 03/103581 A2 | 12/2003 |
| WO | WO2004/045516 | 6/2004 |
| WO | WO 2005/012359 A2 | 2/2005 |
| WO | WO 2005/044853 A2 | 5/2005 |
| WO | WO 2006/014678 A2 | 2/2006 |
| WO | WO 2006/014729 A2 | 2/2006 |
| WO | WO 2006/014729 A3 | 2/2006 |

OTHER PUBLICATIONS

Costello, at al., "Dissection of the Inflammatory Bowel Disease Transciptome Using Genome-Wide cDNA microarrays" *PLOS Medicine* 2 (8) : 771-787 (Aug. 2005).

Gieseg, et al., "Expression profiling of human renal carcinomas with functional taxonomic analysis" *BMC Bioinformatics* 3 (26) : 1-13 (Sep. 2002).

Morimoto, "Gene expression profiling of human colon xenograft tumors following treatment with SU11248, a multitargeted tyrosine kinase inhibitor" *Oncogene* 23:1618-1626 (2004).

Munro, et al., "E-Cadherin and OB-Cadherin mRNA Levels in Normal Human Colon and Colon Carcinoma" *Experimental and Molecular Pathology* 62:118-122 (1995).

Oremek, et al., "The Pyruvate Kinase Isoenzyme Tumor M2 (Tu M2-PK) as a Tumor Marker for Renal Carcinoma" *Anticancer Research* 19 (4A) :2599-2601 (Jul. 1999).

UniProtKB/Swiss-Prot entry P55287, 2011.

Vila, at al., "Increased Glyceraldehyde-3 Phosphate Dehydrogenase Expression in Renal Cell Carcinoma Identified by RNA-Based, Arbitrarily Primed Polymerase Chain Reaction" *Cancer* 89 (1) :152-164 (Jan. 1, 2000).

Mandard et al., "The direct peroxisome proliferator-activated receptor target fasting-induced adipose factor (FIAF/PGAR/ANGPTL4) is present in blood plasma as a truncated protein that is increased by fenofibrate treatment" J Biol Chem. 279(33):34411-34420, (2004).

Mandard et al., "The fasting-induced adipose factor/angiopoietin-like protein 4 is physically associated with lipoproteins and governs plasma lipid levels and adiposity" J Biol Chem. 281(2):934-944, (2006).

Marshall et al., "The role of alpha v-integrins in tumour progression and metastasis" Semin Cancer Biol. 7(3):129-138, (1996).

Melnyk et al., "Vascular endothelial growth factor promotes tumor dissemination by a mechanism distinct from its effect on primary tumor growth" Cancer Research 56(4):921-924, (1996).

Mesiano et al., "Role of Vascular Endothelial Growth Factor in Ovarian Cancer: Inhibition of Ascites Formation by Immunoneutralization" American Journal of Pathology vol. 153, No. 4 pp. 1249-1256 (1998), XP002373802, ISSN: 0002-9440.

Millauer, "Dominant-negative inhibition of Flk-1 suppresses the growth of many tumor types in vivo" Cancer Research 56(7):1615-1620, (1996).

Millauer, "Glioblastoma growth inhibited in vivo by a dominant-negative Flk-1 mutant" Nature 67(6463): 576-579, (1994).

Minn et al., "Genes that mediate breast cancer metastasis to lung" Nature 436(7050):518-524, (2005).

Mitani et al., "Delivering therapeutic genes-matching approach and application" TIBTECH 11(5):162-166 (1993).

Morgan and Anderson, "Human gene therapy" Annu Rev Biochem 62:191-217 (1993).

Mujumdar et al., "Mechanism of constrictive vascular remodeling by homocysteine: role of PPAR" Am. J Physiol. Cell Physiol. 282:C1009-C1015, (2002).

Mulligan, "The basic science of gene therapy" Science 260(5110):926-932, (1993).

Nejjari, et al., "Expression, Regulation, and function of aV integrins in hepatocellular carcinoma: an in vivo and in vitro study", Hapatology, vol. 36, No. 2, pp. 418-426, (2002).

Office Action mailed Dec. 15, 2008—U.S. Appl. No. 11/540,430.

Office Action mailed Jan. 8, 2008—U.S. Appl. No. 11/540,884.

Office Action mailed Jul. 14, 2008 U.S. Appl. No. 11/540,884.

Office Action mailed Jun. 5, 2009—U.S. Appl. No. 11/540,430.

Office Action mailed May 22, 2009—U.S. Appl. No. 11/540,884.

Popkov et al., "Human/mouse cross-reactive anti-VEGF receptor 2 recombinant antibodies selected from an immune b9 allotype rabbit antibody library" J Immunol Methods 288(1-2):149-164, (2004).

Presta et al., "Humanization of an Antibody Directed Against IgE" J. Immunol. 151(5):2623-263, (1993).

Presta et al., "Humanization of an Anti-Vascular Endothelial Growth Factor Monoclonal Antibody for the Therapy of Solid Tumors and Other Disorders" Cancer Research 57(20):4593-4599, (1997).

Procopio et al., "Angiopoietin-1 and -2 coiled coil domains mediate distinct homo-oligomerization patterns, but fibrinogen-like domains mediate ligand activity" J Biol Chem. 274(42):30196-30201, (1999).

Ramsay, T.G. et al., "Hormonal regulation of postnatal chicken preadipocyte differentiation in vitro" Comparative Biochemistry and Physiology Part B(136):245-253, (2003).

Robinson and Stringer, "The splice variants of vascular endothelial growth factor (VEGF) and their receptors" J Cell Sci. 114(5):853-865, (2001).

Robinson, "Gene therapy—proceeding from laboratory to clinic" TIBTECH 11(5):155 (May 1993).

Rupnick et al., "Adipose tissue mass can be regulated through the vasculature" Proc Natl Acad Sci U S A 99(16):10730-10735, (2002).

Sato, "Molecular diagnosis of tumor angiogenesis and anti-angiogenic cancer therapy" Int J Clin Oncol. 8(4):200-206, (2003).

Schier et al., "Identification of functional and structural amino-acid residues by parsimonious mutagenesis" Gene 169(2):147-155, (1996).

Schmuth et al., "Peroxisome proliferator-activated receptor (PPAR)-beta/delta stimulates differentiation and lipid accumulation in keratinocytes" Journal of Investigative Dermatology 122:971-983, (2004).

Shimizugawa et al., "ANGPTL3 Decreases Very Low Density Lipoprotein Triglyceride Clearance by Inhibition of Lipoprotein Lipase" The Journal of Biological Chemistry 277(37):33742-33748, (2002).

Shweiki et al., "Induction of vascular endothelial growth factor expression by hypoxia and by glucose deficiency in multicell spheroids: implications for tumor angiogenesis" Proc Natl Acad Sci U S A. 92(3):768-772, (1995).

Siemeister at al., "The pivotal role of VEGF in tumor angiogenesis: molecular facts and therapeutic opportunities" Cancer Metastasis Rev. 17(2):241-248, (1998).

Siemeister et al., "Two independent mechanisms essential for tumor angiogenesis: inhibition of human melanoma xenograft growth by interfering with either the vascular endothelial growth factor receptor pathway or the Tie-2 pathway" Cancer Research 59(13):3185-3191 (Jul. 1, 1999).

Sierra-Honigmann et al., "Biological action of leptin as an angiogenic factor" Science 81(5393): 1683-1686, (1998).

Sims et al., "A Humanized CD18 Antibody Can Block Function Without Cell Destruction" The Journal of Immunology 151(4):2296-2308, (1993).

Smith et al., "Interaction of integrins alpha v beta 3 and glycoprotein IIb-IIIa with Differential peptide recognition accounts for distinct binding sites" J Biol Chem. 265(21):12267-12271, (1990).

Strausberg et al. (MGC Program Team), "Generation and initial analysis of more than 15,000 full-lengh human and mouse cDNA sequences" Proc. Natl. Acad. Sci. USA 99(26):16899-16903, (2002).

Streit and Detmar, "Angiogenesis, lymphangiogenesis, and melanoma metastasis" Oncogene 2(20) :3172-3179 (2003).

Stupack et al., "Get a ligand, get a life: integrins, signaling and cell survival" J Cell Sci. 115(Pt 19):3729-2738, (2002).

Suri et al., "Requisite role of angiopoietin-1, a ligand for the TIE2 receptor, during embryonic angiogenesis" Cell 87(7):1171-1180, (1996).

Tolstoshev, "Gene Therapy, concepts, current trials and future directions" Annual review of pharmacology and toxicology 32:573-596, (1993).

Tomayko & Reynolds, "Determination of subcutaneous in athymic (nude) mice" Cancer Chemother tumor size 24(3):148-154, (1989).

Tonini et al., "Molecular basis of angiogenesis and cancer" Oncogene 22(42):6549-6556, (2003).

Valenzuela et al., "Angiopoietins 3 and 4: diverging gene counterparts in mice and humans" Proc Natl Acad Sci U S A. 96(5):1904-1909, (1999).

Ward et al., "The angiopoietins and Tie2/Tek: adding to the complexity of cardiovascular development" Semin Cell Dev Biol. 13(1):19-27, (2002).

Warren et al., "Regulation by vascular endothelial growth factor of human colon cancer tumorigenesis in a mouse model of experimental liver metastasis" J. Clin. Invest. 95(4):1789-1797, (1995).

Wedge et al., "ZD4190: an orally active inhibitor of vascular endothelial growth factor signaling with broad-spectrum antitumor efficacy" Cancer Research 60(4):970-975, (2000).

Wei-Ching et al., "Cross Species Vascular Endothelial Growth Factor (VEGF)-Blocking Antibodies Completely Inhibit the Growth of Human Tumor Xenografts and Measure the Contribution of Stromal VEGF" Journal of Biological Chemistry vol. 281, No. 2, pp. 951-960 (2006) XP002373804 ISSN: 0021-9258.

Wiesner et al., "Food restriction regulates adipose-specific cytokines in pituitary gland but not in hypothalamus" J Endocrinol. 180(3):R1-R6, (2004).

Wood et al., "PTK787/ZK 222584, a novel and potent inhibitor of vascular endothelial growth factor receptor tyrosine kinases, impairs vascular endothelial growth factor-induced responses and tumor growth after oral administration" Cancer Research 60(8):2178-2189 (2000).

Wu and Wu, "Delivery systems for gene therapy" Biotherapy 3(1):87-95, (1991).

Fan, et al., "In vitro evaluation of combination chemotherapy against human tumor cells Review)", Oncology Reports, 5: 1035-1042, (1998).

Hurwitz, et al., "Bevaizumab plus Irinotecan, Fluorouracil, and Leucovorin for metastatic colorectal cancer", The New England Journal of Medicine, 350: 2335-2342, (2004).

Kennett, et al., "Antibodies to target integrins expressed on tumor vasculature", Current opinion in oncologic, Endocrine & Metabolic Investigational Drugs, 2(4): 376-380, (2000).

Kerbel, et al., "Tumor angiogenesis: past, present and the near future", Carcinogenesis; vol. 21, No. 3, pp. 505-515, (2000).

Kim, et al., "Distinct response of experimental neuroblastoma to combination antiangiogenic strategies", J. Pediatr. Surg., 37: 518-522, (2002).

Schiffeiers, et al., "Cancer siRNA therapy by tumor selective delivery with ligand-targeted sterically stabilized nanoparticle", Nucleic Acids Research, vol. 32, No. 19, e149, pp. 1-10, (2004).

Verheul, et al., "Combination oral antiangiogenic therapy with thalidomide and sulindac inhibits tumour growth in rabbits", British Journal of Cancer, 79(1): 114-118, (1999).

Xu et al., "Angiopoietin-like protein 4 decreases blood glucose and improves glucose tolerance but induces hyperlipidcmia and hepatic steatosis in mice" Proc Natl Acad Sci U S A. 102(17):6086-6091, (2005).

Yang, et al., "Suppression of the Raf/MEK/ERK signaling cascade and inhibition of angiogenesis by the carboxyl terminus of angiopoietin-like protein 4", Arteriosclerosis, Thrombosis and vascular biology, 28: 835, (2008).

Yang, Jun et al., "Galactosylated alginate as a scaffold for hepatocytes entrapment" Biomaterials 23:471-479, (2002).

Yoon et al., "Peroxisome proliferator-activated receptor gamma target gene encoding a novel angiopoietin-related protein associated with adipose differentiation" Mol Cell Biol. 20(14):5343-5349, (2000).

Yoshida et al., "Angiopoietin-like protein 4 is a potent hyperlipidemia-inducing factor in mice and inhibitor of lipoprotein lipase" J Lipid Res. 43(11):1770-1772, (2002).

Yu et al., "Inhibition of cardiac lipoprotein utilization by transgenic overexpression of Angptl4 in the heart" Natl Acad Sci U S A. 102(5):1767-1772, (2005).

Zamecnik et al., "Inhibition of Replication and Expression of Human T-Cell Lymphotropic Virus Type III in Cultured Cells by Exogenous Synthetic Oligonucleotides Complementary to Viral RNA" Proc. Natl. Acad. Scil 83:4143-4146, (1986).

Zhu H. et al., "Expression and function of hepatocellular carcinoma-related gene pp1158 (NCBI Abstract)" (Oncogene & Related Genes National Laboratory Shanghai Cancer Institute, Shanghai, China), (2002).

Adamis et al., "Inhibition of Vascular Endothelial Growth Factor Prevents Retinal Ischemia-Associated Iris Neovascularization in a Nonhuman Primate" Arch. Ophthalmology 114(1):66-71, (1996).

Akiyama et al., "Conditional disruption of the peroxisome proliferator-activated receptor gamma gene in mice results in lowered expression of ABCA1, ABCG1, and apoE in macrophages and reduced cholesterol efflux" Molecular .& Cellular Biology 22(8):2607-2619, (Apr. 2002).

Anderson, W.F., "Human Gene Therapy" Science 256(5058):808-813, (1992).

Asano et al., "Inhibition of tumor growth and metastasis by an immunoneutralizing monoclonal antibody to human vascular endothelial growth factor/vascular permeability factor121" Cancer Research 55(22):5296-5301, (1995).

Borgstrom et al., "Complete inhibition of angiogenesis and growth of microtumors by anti-vascular endothelial growth factor neutralizing antibody: novel concepts of angiostatic therapy from intravital videomicroscopy" Cancer Research 56(17):4032-4039, (1996).

Byzova et al., "A mechanism for modulation of cellular responses to VEGF: activation of the integrins" Mol Cell 6(4):851-860, (2000).

Camenisch et al., "ANGPTL3 stimulates endothelial cell adhesion and migration via integrin alpha vbeta and induces blood vessel formation in vivo" J Biol Chem. 277(19):17281-17290, (2002).

Carmeliet and Jain, "Angiogenesis in cancer and other diseases" Nature 407(6801):249-257, (2000).

Carmeliet, "Mechanisms of angiogenesis and arteriogenesis" Nature Medicine 6(3):389-395, (2000).

Davis et al., "Isolation of angiopoietin-1, a ligand for the TIE2 receptor, by secretion-trap expression.cloning" Cell 87(7):1161-1169, (1996).

Drugstore.com (http://www.drugstore.com/qxn50242006001_33181_sespider/avastin/avastin.htm).Retrieved on Apr. 24, 2009.

Eliceiri and Cheresh, "Adhesion events in angiogenesis" Curr Opin Cell Biol. 13(5):563-568, (2001).

Eliceiri and Cheresh, "The role of alphav integrins during angiogenesis" Mol Med. 4(12):741-750, (1998).

Eliceiri, et al., "The roles of av integrins during angiogenesis: insights into potential mechanisms of action and clinical development", The journal of Clinical Investigation, vol. 103, No. 9, pp. 1227-1230, (1999).

Ferrara and Alitalo, "Clinical applications of angiogenic growth factors and their inhibitors" Nat Med. 5(12):1359-1364, (1999).

Ferrara and Davis-Smyth, "The Biology of Vascular Endothelial Growth Factor" Endocrine Reviews 18(1):4-25, (1997).

Ferrara and Kerbel, "Angiogenesis as a therapeutic target" Nature 438(7070):967-974, (2005).

Ferrara et al., "Discovery and Development of Bevacizumab, an Anti-VEGF Antibody for Treating Cancer" Nature Reviews-Drug Discovery. 3:391-400, (2004).

Ferrara et al., "The biology of VEGF and its. receptors" Nat Med. 9(6):669-676, (2003).

Ferrara, N., "Molecular and biological properties of vascular endothelial growth factor" J Mol Med. 77527-77543, (1999).

Folkman and D'Amore, "Blood vessel formation: what is its molecular basis?" Cell 87(7):1153-1155, (1996).

Fong et al., "SU5416 is a potent and selective inhibitor of the vascular endothelial growth factor receptor (FLK-1/KDR) that inhibits tyrosine kinase catalysis, tumor vascularization, and growth of multiple tumor types" Cancer Research 59(1):99-106, (1999).

Friedlander et al., "Definition of two angiogenic pathways by distinct alpha v integrins" Science 270(5241):1500-1502, (1995).

Friedmann, "Gene therapy—a new kind of medicine" TIBTECH 11(5):156-159, (1993).

Fukumura et al., "Paracrine regulation of angiogenesis and adipocyte differentiation during in vivo adipogenesis" Circ Res. (e88-e97) 93(9):1-10, (2003).

Galaup et al. Angiopoietin-like 4 prevents metastasis through inhibition of vascular permeability and tumor cell motility and invasiveness. PNAS vol. 103, No. 49 18721-18726 Dec. 5, 2006.

Ge et al., "Differential regulation and properties of angiopoietin-like proteins 3 and 4" J Lipid Res. 46(7):1484-1490, (2005).

Ge et al., "OligomerizatiFEstate-dependent hyperlipidemic effect of angiopoietin-like protein 4" J Lipid Res. 45(11):2071-2079, (2004).

Ge et al., "Oligomerization and regulated proteolytic processing of angiopoietin-like protein 4" J Biol. Chem. 279(3):2038-2045, (2004).

Ge Hongfei, et al., "Oligomerization and regulated proteolytic processing of angiopoietin like protein 4" Diabetes, (2430-PO) 53(Suppl. 2):A576, (2004).

Gerber et al., "Complete inhibition of rhabdomyosarcoma xenograft growth and neovascularization requires blockade of both tumor and host vascular endothelial growth factor" Cancer Research 60(22):6253-6258, (2000).

Goldman et al., "Paracrine expression of a native soluble vascular endothelial growth factor receptor inhibits tumor growth, metastasis, and mortality rate" Proc Natl Acad Sci U S A. 95(15):8795-800, (1998).

Goldspiel et al., "Human gene therapy" Clin Pharm. 12(7):488-505, (1993).

Gong, Dawei et al., "New progress in adipocytokine research" Current Opinion in Endocrinology and Diabetes 10(2):115-121, (2003).

Hermann et al., "Angiopoietin-like-4 is a potential angiogenic mediator in arthritis" Clin Immunol 115(1):93-101, (2005).

Hesser et al., "Down syndrome critical region protein 1 (DSCR1), a novel VEGF target gene that regulates expression of inflammatory markers on activated endothelial cells" Blood 104(1):149-158 (2004).

Holash et al., "New model of tumor angiogenesis: dynamic balance between vessel regression and growth mediated by angiopoietins and VEGF" Oncogene 18(38):5356-5362, (1999).

Hood and Cheresh, "Role of integrins in cell invasion and migration" Nat Rev Cancer 2(2):91-100, (2002).

Houck et al., "The Vascular Endothelial Growth Factor Family: Identification of a Fourth Molecular Species and Characterization of Alternative Splicing of RNA" Mol. Endocrinol. 5(12):1806-181, (1991).

Hynes and Bader, "Targeted mutations in integrins and their ligands: their implications for vascular biology" Thromb Haemost. 78(1):83-87, (1997).

Hynes et al., "Integrins in vascular development" Braz J Med Biol Res. 32(5):501-510, (1999).

Inukai et al., "ANGPTL3 is increased in both insulin-deficient and -resistant diabetic states" Biochemical and Biophysical Research Communications 317:1075-1079, (2004).

Ito et al. Inhibition of Angiogenesis and Vascular Leakiness by Angiopoietin-Related Protein 4. Cancer Research 63, 6651-6657, Oct. 15, 2003.

Jain RK. Normalizing tumor vasculature with anti-angiogenic therapy: A new paradigm for combination therapy. Nature Medicine vol. 7, No. 9, Sep. 2001.

Kersten et al., "Characterization of the fasting-induced adipose factor FIAF, a novel peroxisome proliferator-activated receptor target gene" J Biol Chem. 275(37):28488-28493, (2000).

Kim et al., "Hepatic expression, synthesis and secretion of a novel fibrinogen/angiopoietin-related protein that prevents endothelial-cell apoptosis" Biochemical Journal 346(Pt 3):603-610, (2000).

Kim et al., "Inhibition of Vascular Endothelial Growth Factor-Induced Angiogenesis Suppresses Tumour Growth in vivo" Nature 362:841-844, (1993).

Kimura, Metsutoshi et al., "Stimulation of DNA synthesis and proliferation by prostaglandins in primary cultures of adult rat hepatocytes" European Journal of Pharmacology 404(3):259-271, (2000).

Klagsbrun and D'Amore, "Regulators of angiogenesis" Ann. Rev. Physiol. 53:217-239, (1991).

Koishi et al., "Angptl3 regulates Lipid metabolism in mice" Nat Genet. 30(2):151-157, (2002).

Koster et al., "Transgenic angiopoietin-like (angptl)4 overexpression and targeted disruption of angptl4 and angptl3: regulation of triglyceride metabolism" Endocrinology 146(11):4943-4950, (2005).

Landegren, "Measurement of cell Numbers by means of the endogenous enzyme hexosaminidase. Applications to detection of lymphokines and cell surface antigens" J Tinmunol Methods 67(21:379-388, (1984).

Le'Jan et al., "Angiopoietin-like 4 is a proangiogenic factor produced during ischemia and in conventional renal cell carcinoma" Am J Pathol. 162(5):1521-1528, (2003).

Leung et al., "Vascular Endothelial Growth Factor is a Secreted Angiogcnic Mitogcn" Science 246:1306-1309, (1989.

Lin et al., "Antiangiogenic gene therapy targeting the endothelium-specific receptor tyrosine kinase Tie2" Proc Natl Acad Sci U S A. 95(15):8829-8834, (1998).

Maisonpierre et al., "Angiopoietin-2, a Natural Antagonist for Tie2 that Disrupts in vivo Angiogenesis" Science 277:55-60, (1997).

Zhu, et al., "[Cloning of a novel gene, ANGPTL4 and the functional study of angiogenesis]", Zhonghua Yi Xue Za Zhi. Jan. 25, 2002;82(2):94-9, (Abstract).

Desai et al., Lipid-lowering effects of anti-angiopoietin-like 4 antibody recapitulate the lipid phenotype found in angiopoietin-like 4 knockout mice, Proc. Natl. Acad. Sci. USA, 104(28):11766-11771, Jul. 10, 2007.

Accession No. NM_020581.1, GI No. 10181163 (Accession was first seen at NCBI on Sep. 18, 2000).

Accession No. NM_139314.1, GI No. 21536397 (Accession was first seen at NCBI on Jun. 21, 2002).

Accession No. Q9BY76, GI No. 25008123 (Accession was first seen at NCBI on Nov. 15, 2002).

Accession No. Q9Z1P8, GI No. 25008127 (Accession was first seen at NCBI on Nov. 15, 2002).

Ajioka et al., "Expression of Vascular Endothelial Growth Factor Promotes Colonization, Vascularization, and Growth of Transplanted Hepatic Tissues in the Mouse" Hepatology 29:396-402, (1999).

Assy et al., "Effect of vascular e.othelial growth factor on hepatic regenerative activity following partial hepatectomy in rats" Journal of Hepatology 30:911-915, (1999).
Baruch et al., "Basic fibroblast growth factor is hepatotropic for rat liver in regeneration" J. Hepatol. 23:328-332, (1995).
Bouloumie et al., "leptin, the product of Ob gene, promotes angiogenesis" Circ Res. 83(10):1059-1066 (1998).
Campfield et al., "Recombinant mouse ob protein: evidence for a peripheral signal linking adiposity and central neural networks" Science 269:546-549, (1995).
Chehab et al., "Correction of the sterility defect in homozygous obese female mice by treatment with the human recombinant leptin" Nat Genet. 12(3):318-320, (1996).
Chen et al., "Evidence that the diabetes gene encodes the leptin receptor: identification of a mutation in the leptin receptor gene in db/db mice" Cell 84:491-495,(1996).
Cioffi et al., "Novel B219/08 receptor isoforms: possible role of leptin in hematopoiesis and reproduction" Nature Medicine 2(5):585-589, (1996).
Clement et al., "A mutation in the human leptin receptor gene causes obesity and pituitary dysfunction" Nature 392(6674):398-401, (1998).
Collins, "Generation and initial analysis of more than 15,000 full-length human and mouse cDNA sequences", PNAS, vol. 99, No. 26, pp. 16899-16903, (2002).
Drakes et al., "In Vivo Administration of flt3 Ligand Markedly Stimulates Generation of Dendritic Cell Progenitors from Mouse Liver" J. Immunol. 159:4268-4278 (1997).
Folkman and Klagsbrun, "Angiogenic factors" Science 235:442-447, (1987).
Fujiwara et al., "Stimulation of Liver Growth by Exogenous Human Hepatocyte Growth Factor in Normal an PArtially Hepatectomized Rats" Hepatol. 18:1443-1449, (1993).
Gainsford et al., "Leptin can induce proliferation, differentiation, and functional activation of hemopoietic cells" Proc. Natl. Acad. Sci. USA 93:14564-14568, (1996).
Gbaguidi et al., "Peroxisome proliferator-activatcd receptor (PPAR) agonists decrease lipoprotein lipase secretion and glycated LDL uptake by human macrophages" FEBS Letters 512(1-3):85-90, (2002).
Gerber et al., "VEGF is required for growth and survival in neonatal mice" Development 126:1149-1159 (1999).
Gregoire et al., "Understanding adipocyte differentiation" Physiol Rev. 78(3):783-809, (1998).
Halaas et al., "Weight-reducing effects of the plasma protein encoded by the obese gene", Science 269:543-546, (1995).
Ito et al., "Heparin-Binding EGF-like Growth Factor is a Potent Mitogen for Rat Hepatocytes" Biochem. & Biophys. Res. Comm. 198:25-31, (1994).
Kamohara et al., "Acute stimulation of glucose metabolism in mice by leptin treatment" Nature 389(6649):374-377, (1997).
Kim et al., "ADD1/SREBP1 Promotes Adipocyte Differentiation and Gene Expression Linked to Fatty Acid Metabolism" Genes & Development 10:1096-1107, (1996).
Kolonin et al., "Reversal of obesity by targeted ablation of adipose tissue" Nat Med. 10(6):625-632, (2004).
Kubota et al., "Ligand for peroxisome proliferator-activated receptor y (troglitazone) has antitumor effect against human prostate cancer both in vivo and potent in vivo" Cancer 58(15):3344-3352.
La Cava and Matarese, "The weight of leptin in immunity" Nat Rev Immunol. 4(5):371-379, (2004).
Landegren, "Measurement of cell numbers by means of the endogenous enzyme hexosaminidase Applications to detection of lymphokines and cell surface antigens" J Immunol Methods 67(2):379-.388, (1984).

Lee, G. et al., "Abnormal splicing of the leptin receptor in diabetic mice" Nature 379:632-635, (1996).
Loffreda et al., "Leptin regulates proinflammatory immune responses" FASEB J. 12(1):57-65, (1998).
Lord et al., "Leptin modulates the T-cell immune response and reverses starvation-induced immunosuppression" Nature 394(6696):897-901, (1998).
Michalopoulos and DeFrances, "Liver Regeneration" Science 276:60-65, (1997).
Millipore, online catalogue, "Anti-integrin αVβb, clone PIF6", 2008, accessed Dec. 8, 2008.
Mochida et al., "Increased Expressions of Vascular Endothelial Growth Factor and Its Receptors, flt-1 and KDR/flk-1, in Regenerating Rat Liver" Biochem. & Biophys. Res. Comm. 226:176-179, (1996).
Nakamura et al., "Partial purification and characterization of hepatocyte growth factor from serum of hepatectomized rats" Biochem. & Biophys. Res. Comm. 122(3):1450-1459, (1984).
Omori et al., "Partial Cloning of,Rat CD34 cDNA and Expression During Stem Cell-Dependent Liver Regeneration in the Adult Rat" Hepatology 26:720-727, (1997).
Pelleymounter et al., "Effects of the obese gene product on body weight regulation in ob/ob mice" Science 269:540-543, (1995).
Pinkerton, et al., "Angiopoietin-like 4 exacerbates collagen-induced arthritis abd increases the phosphorylation of Akt in mouse endothelial cells", FASEB J., 18(4-5): Abstract, 778, (2004).
Ren et al., "PPARgamma knockdown by engineered transcription factors: exogenous PARgamma2 but not PPARgammal reactivates adipogenesis". Genes Dev. 16(1):27-32, (2002).
Rodgers et al., "Histologic Alterations in Dermal Repair after Thermal Injury Effects of Topical Angiotensin II" J. Burn Care Rehabil. 18:381-388, (1997).
Rosen and Spiegelman, "Molecular regulation of adipogenesis" Annu Rev Cell Dev Biol. 16:145-171, (2000).
Rosen et al., "C/EBPalpha induces adipogenesis through PPARgamma: a unified pathway" Genes Dev. 16(1):22 (2002).
Rosen et al., "PPAR gamma is required for the differentiation of adipose tissue in vivo and in vitro" Mol Cell. 4(4):611-617, (1999).
Sears et al., "Differentiation-dependent expression of the brown adipocyte uncoupling protein gene: regulation by peroxisome proliferator-activated receptor gamma" Mol Cell Biol.16(7):3410-3419, (1996).
Stroebel et al., "A leptin missense mutation associated with hypogonadism and morbid obesity" Nat Genet. 18:213-215, (1998).
Suzuma et al., "Vascular Endothelial Growth Factor Induces Expression of Connective Tissue Growth Factor via KDR, Fltl, and Phosphatidylinositol 3-Kinase-Akt-dependent Pathways in Retinal Vascular Cells" Journal of Biological Chemistry 275:40725-40731, (2000).
Tartaglia et al., "Identification and expression cloning of a leptin receptor, ob-r" Cell 83:1263-1271, (1995).
Wu et al., "Transcriptional activation of adipogenesis" Curr Opin Cell Biol. 11(6):689-694, (1999).
Yamane et al., "A new communnication system between hepatocyte and sinusoidal endothelial cells in liver through vascular endothelial growth factor and Flt tyrosine kinase receptor family (Flt-1 and KDR/Flk-1)" *Oncogene* 9:2683-2690, (1994).
Yoshimura et al., "Expression of peroxisome proliferator-activated receptors (PPARs) in human urinary bladder carcinoma and growth inhibition by its agonists" Int J Cancer 104(5):597-602, (2003).
Zhang et al., "Crystal structure of the obese protein leptin-E100" Nature 387(6629):206-209, (1997).
Zhang et al., "Positional cloning of the mouse obese gene and its human homologue" Nature 372:425-431, (1994).

\* cited by examiner

FIGURE 1

```
CGGCAGCCCTGACGTGATGAGCTCAACCAGCAGAGACATTCCATCCCAAGAGAGGTCTGCGTGACGCGTCCGGGAGG
CCACCCTCAGCAAGACCACCGTACAGTTGGTGGAAGGGGTGACAGCTGCATTCTCCTGTGCCTACCACGTAACCAAA
AATGAAGGAGAACTACTGTTTACAAGCCGCCCTGGTGTGCCTGGGCATGCTGTGCCACAGCCATGCCTTTGCCCCAG
AGCGGCGGGGGCACCTGCGGCCCTCCTTCCATGGGCACCATGAGAAGGGCAAGGAGGGGCAGGTGCTACAGCGCTCC
AAGCGTGGCTGGGTCTGGAACCAGTTCTTCGTGATAGAGGAGTACACCGGGCCTGACCCCGTGCTTGTGGGCAGGCT
TCATTCAGATATTGACTCTGGTGATGGGAACATTAAATACATTCTCTCAGGGGAAGGAGCTGGAACCATTTTTGTGA
TTGATGACAAATCAGGGAACATTCATGCCACCAAGACGTTGGATCGAGAAGAGAGAGCCCAGTACACGTTGATGGCT
CAGGCGGTGGACAGGGACACCAATCGGCCACTGGAGCCACCGTCGGAATTCATTGTCAAGGTCCAGGACATTAATGA
CAACCCTCCGGAGTTCCTGCACGAGACCTATCATGCCAACGTGCCTGAGAGGTCCAATGTGGGAACGTCAGTAATCC
AGGTGACAGCTTCAGATGCAGATGACCCCACTTATGGAAATAGCGCCAAGTTAGTGTACAGTATCCTCGAAGGACAA
CCCTATTTTTCGGTGGAAGCACAGACAGGTATCATCAGAACAGCCCTACCCAACATGGACAGGGAGGCCAAGGAGGA
GTACCACGTGGTGATCCAGGCCAAGGACATGGGTGGACATATGGGCGGACTCTCAGGGACAACCAAAGTGACGATCA
CACTGACCGATGTCAATGACAACCCACCAAAGTTTCCGCAGAGGCTATACCAGATGTCTGTGTCAGAAGCAGCCGTC
CCTGGGGAGGAAGTAGGAAGAGTGAAAGCTAAAGATCCAGACATTGGAGAAAATGGCTTAGTCACATACAATATTGT
TGATGGAGATGGTATGGAATCGTTTGAAATCACAACGGACTATGAAACACAGGAGGGGGTGATAAAGCTGAAAAAGC
CTGTAGATTTTGAAACCGAAAGAGCCTATAGCTTGAAGGTAGAGGCAGCCAACGTGCACATCGACCCGAAGTTTATC
AGCAATGGCCCTTTCAAGGACACTGTGACCGTCAAGATCTCAGTAGAAGATGCTGATGAGCCCCCTATGTTCTTGGC
CCCAAGTTACATCCACGAAGTCCAAGAAAATGCAGCTGCTGGCACCGTGGTTGGGAGAGTGCATGCCAAAGACCCTG
ATGCTGCCAACAGCCCGATAAGGTATTCCATCGATCGTCACACTGACCTCGACAGATTTTTCACTATTAATCCAGAG
GATGGTTTTATTAAAACTACAAAACCTCTGGATAGAGAGGAAACAGCCTGGCTCAACATCACTGTCTTTGCAGCAGA
AATCCACAATCGGCATCAGGAAGCCCAAGTCCCAGTGGCCATTAGGGTCCTTGATGTCAACGATAATGCTCCCAAGT
TTGCTGCCCCTTATGAAGGTTTCATCTGTGAGAGTGATCAGACCAAGCCACTTTCCAACCAGCCAATTGTTACAATT
AGTGCAGATGACAAGGATGACACGGCCAATGGACCAAGATTTATCTTCAGCCTACCCCCTGAAATCATTCACAATCC
AAATTTCACAGTCAGAGACAACCGAGATAACACAGCAGGCGTGTACGCCCGGCGTGGAGGGTTCAGTCGGCAGAAGC
AGGACTTGTACCTTCTGCCCATAGTGATCAGCGATGGCGGCATCCCGCCCATGAGTAGCACCAACACCCTCACCATC
AAAGTCTGCGGGTGCGACGTGAACGGGGCACTGCTCTCCTGCAACGCAGAGGCCTACATTCTGAACGCCGGCCTGAG
CACAGGCGCCCTGATCGCCATCCTCGCCTGCATCGTCATTCTCCTGGTCATTGTAGTATTGTTTGTGACCCTGAGAA
GGCAAAAGAAAGAACCACTCATTGTCTTTGAGGAAGAAGATGTCCGTGAGAACATCATTACTTATGATGATGAAGGG
GGTGGGGAAGAAGACACAGAAGCCTTTGATATTGCCACCCTCCAGAATCCTGATGGTATCAATGGATTTATCCCCCG
CAAAGACATCAAACCTGAGTATCAGTACATGCCTAGACCTGGGCTCCGGCCAGCGCCCAACAGCGTGGATGTCGATG
ACTTCATCAACACGAGAATACAGGAGGCAGACAATGACCCCACGGCTCCTCCTTATGACTCCATTCAAATCTACGGT
TATGAAGGCAGGGGCTCAGTGGCCGGGTCCCTGAGCTCCCTAGAGTCGGCCACCACAGATTCAGACTTGGACTATGA
TTATCTACAGAACTGGGGACCTCGTTTTAAGAAACTAGCAGATTTGTATGGTTCCAAAGACACTTTTGATGACGATT
CTTAACAATAACGATACAAATTTGGCCTTAAGAACTGTGTCTGGCGTTCTCAAGAATCTAGAAGATGTGTAACAGGT
ATTTTTT
```

FIGURE 2

AACTCAAACTCCTCTCTCTGGGAAAACGCGGTGCTTGCTCCTCCCGGAGTGGCCTTGGCAGGGTGTTGGAGCCCTCG
GTCTGCCCCGTCCGGTCTCTGGGGCCAAGGCTGGGTTTCCCTATGTATGGCAAGAGCTCTACTCGTGCGGTGCTTC
TTCTCCTTGGCATACAGCTCACAGCTCTTTGGCCTATAGCAGCTGTGGAAATTTATACCTCCCGGGTGCTGGAGGCT
GTTAATGGGACAGATGCTCGGTTAAAATGCACTTTCTCCAGCTTTGCCCCTGTGGGTGATGCTCTAACAGTGACCTG
GAATTTTCGTCCTCTAGACGGGGACCTGAGCAGTTTGTATTCTACTACCACATAGATCCCTTCCAACCCATGAGTG
GGCGGTTTAAGGACCGGGTGTCTTGGGATGGGAATCCTGAGCGGTACGATGCCTCCATCCTTCTCTGGAAACTGCAG
TTCGACGACAATGGGACATACACCTGCCAGGTGAAGAACCCACCTGATGTTGATGGGGTGATAGGGGAGATCCGGCT
CAGCGTCGTGCACACTGTACGCTTCTCTGAGATCCACTTCCTGGCTCTGGCCATTGGCTCTGCCTGTGCACTGATGA
TCATAATAGTAATTGTAGTGGTCCTCTTCCAGCATTACCGGAAAAAGCGATGGGCCGAAAGAGCTCATAAAGTGGTG
GAGATAAAATCAAAAGAAGAGGAAAGGCTCAACCAAGAGAAAAAGGTCTCTGTTTATTTAGAAGACACAGACTAACA
ATTTTAGATGGAAGCTGAGATGATTTCCAAGAACAAGAACCCTAGTATTTCTTGAAGTTAATGGAAACTTTTCTTTG
GCTTTTCCAGTTGTGACCCGTTTTCCAACCAGTTCTGCAGCATATTAGATTCTAGACAAGCAACACCCCTCTGGAGC
CAGCACAGTGCTCCTCCATATCACCAGTCATACACAGCCTCATTATTAAGGTCTTATTTAATTTCAGAGTGTAAATT
TTTTCAAGTGCTCATTAGGTTTTATAAACAAGAAGCTACATTTTTGCCCTTAAGACACTACTTACAGTGTTATGACT
TGTATACACATATATTGGTATCAAAGGGGATAAAAGCCAATTTGTCTGTTACATTTCCTTTCACGTATTTCTTTTAG
CAGCACTTCTGCTACTAAAGTTAATGTGTTTACTCTCTTTCCTTCCCACATTCTCAATTAAAAGGTGAGCTAAGCCT
CCTCGGTGTTTCTGATTAACAGTAAATCCTAAATTCAAACTGTTAAATGACATTTTTATTTTTATGTCTCTCCTTAA
CTATGAGACACATCTTGTTTTACTGAATTTCTTTCAATATTCCAGGTGATAGATTTTTGTCG

FIGURE 3

```
GGCACGAGGCGATTCAGGGGAGGGAGCAACTGGAGCCTCAGGCCCTCCAGAGTAGTCTGCCTGACCACCCTGGAGCC
CACAGAAGCCCAGGACGTCTCCCGCGAGGCCTCCCCGTGTGTGGCTGAGGATGGCTGAGCAGCAGGGCCGGGAGCTT
GAGGCTGAGTGCCCCGTCTGCTGGAACCCCTTCAACAACACGTTCCATACCCCCAAAATGCTGGATTGCTGCCACTC
CTTCTGCGTGGAATGTCTGGCCCACCTCAGCCTTGTGACTCCAGCCCGGCGCCGCCTGCTGTGCCCACTCTGTCGCC
AGCCCACAGTGCTGGCCTCAGGGCAGCCTGTCACTGACTTGCCCACGGACACTGCCATGCTCACCCTGCTCCGCCTG
GAGCCCCACCATGTCATCCTGGAAGGCCATCAGCTGTGCCTCAAGGACCAGCCCAAGAGCCGCTACTTCCTGCGCCA
GCCTCGAGTCTACACGCTGGACCTTGGCCCCCAGCCTGGGGGCCAGACTGGGCCGCCCCAGACACGGCCTCTGCCA
CCGTGTCTACGCCCATCCTCATCCCCAGCCACCACTCTTTGAGGGAGTGTTTCCGCAACCCTCAGTTCCGCATCTTT
GCCTACCTGATGGCCGTCATCCTCAGTGTCACTCTGTTGCTCATATTCTCCATCTTTTGGACCAAGCAGTTCCTTTG
GGGTGTGGGGTGAGTGCTGTTCCCAGACAAGAAACCAAACCTTTTTCGGTTGCTGCTGGGTATGGTGACTACGGAGC
CTCATTTGGTATTGTCTTCCTTTGTAGTGTTGTTTATTTTACAATCCAGGGATTGTTCAGGCCATGTGTTTGCTTCT
GGGAACAATTTAAAAAAAAAACAAAAAAACGAAAAGCTTGAAGGACTGGGAGATGTGGAGCGACCTCCGGGTGTGAG
TGTGGCGTCATGGAAGGGCAGAGAAGCGGTTCTGACCACAGAGCTCCACAGCAAGTTGTGCCAAAGGGCTGCACAGT
GGTATCCAGGAACCTGACTAGCCCAAATAGCAAGTTGCATTTCTCACTGGAGCTGCTTCAAAATCAGTGCATATTTT
TTTGAGTTGCTCTTTTACTATGGGTTGCTAAAAAAAAAAAAAAAAAAATTGGGAAGTGAGCTTCAATTCTGTGGGTA
AATGTGTGTTTGTTTCTCTTTGAATGTCTTGCCACTGGTTGCAGTAAAAGTGTTCTGTATTCATTAAAAAAAAAAAA
AAAAAAAAAAAAAAAAAAAAAAAAAAAAAAAAAAAAAAA
```

FIGURE 4

GAAGCGCGCTCCCGGGGAGGTGTTGCAGCCATGGCTACGGCAGCCGGCGCGACCTACTTTCAGCGAGGCAGTCTGTT
CTGGTTCACAGTCATCACCCTCAGCTTTGGCTACTACACATGGGTTGTCTTCTGGCCTCAGAGTATCCCTTATCAGA
ACCTTGGGCCCCTGGGCCCCTTCACTCAGTACTTGGTGGACCACCATCACACCCTCCTTTGCAATGGGTATTGGCTT
GCCTGGCTGATTCATGTGGGAGAGTCCTTGTATGCCATAGCATTGTGCAAGCATAAAGGCATCACAAGTGGTCGGGC
TCAGCTACTCTGGTTCCTACAGACTTTCTTCTTTGGGATAGCGTCTCTCACCATCTTGATTGCTTACAAACGGAAGC
GCCAAAAACAAACTTGAAGTTGTCTGAAAGCTTGCTCTACACTTTTACATTCATCCTCACCCTTTTTTTGTGGGGT
AGAGGAGGTGCAGTAATTTACTCAGTGATCTTTCTACTTTCTAGAAACTGTCCTTCAAAGCTCTTTAAGACCCCCTC
GTTAGTCAGTTTCTTCTCTTATATGCTCTGGTTGAGCTTGAATAGACCAGTTGTTACTTAAGAAAGAAACAGAGAAA
GATTTTAGCTTTTCAATCCTATTTGGCAGAGGACTTCAGCTACCTTCTTACAGTCTTTGGCTGTGTTGGTACCCTCG
TGTGCTCTGAGCTAAGCCACATACTAAACTGACTTTTTGGTTTGTATACCCTTGCTCCCGCCTTCTGATGAAAACAC
CTTACCCTCACAACCACCATCTTTCCTCTCCTTTCCAAAGCTCTTTCCACCTTGCTGCACTAAGATAAAGTGACACT
TCCACTATATGTCAATTCCACACACATTTATTAGGTACCTGTGAGGTAGGATCCTATCCTCTCAAACTTCCATTTCT
CATGCTACAGAGAAAGATAAGGAAGATGAGCAAGTGCCTGGAATGGGGCAGGCTGAGCAGTCACACAGGCATAGAGG
CACGCTGAGAACCTGGAGGGGAGACTGCAGAGTGCCTTCCCTGATGCTGCAGCCGGAAGTGATCCTTCCCTCCACCT
GGCCCCTGGGACACTGTGCTCTGCAGTGTGCAGGGCCTGATGGCACTGCTAGATTGCTCCTTCAGCTCAGGGCCACA
GCTTAAACAGCTTTACCTTTCCCCTCAGCACCTGTCCCACTATCTTGCACACAGGTGCTCTAACCATGTTTATTGAA
CAAAGGAGGGAAACTGATTTCACTTTCACTTGTTCATTATCATTCCAATTTTTATGTGAAAATGGCACAACCCATTT
GGGGTACCCTCACCCCAAAATAAAAGCCCAAGTCTACCTTTGACTGGTACCACCTTTTTTGTGGTTTCGTTGGTGAG
AAACCTTTATCTTTTTCATACCTTTCTATTCTCAATCACTTCTCCAAAAGTGTGTCTTTCCAGCTCTGATTTATTCA
AAACACAAGCATTTCTGTTTAGAGATTCTAGCCCATGGGTTATCTGGCTAGTTATTACCTCTCCTGTTCACTTAGTT
ATACTTTATTATTGCTCACAGGCTGGGGAGGCAGAATGACTCTGTCACCACTAGGAGCCATTAGGGCTTCTTCCCTG
GAGGACTGCCTGCTTGCTTTCTGGGGACACTAGCCCTCATTTCCCTTCTGTGGTACAGTGGGGCAAATTATTTGTAT
TAAGCAAACATTTATGGGAAACAACCCGCTCCCGAAAACGGAGCCCCCAAGTAAAGCACAACCCTGAAAGATTATGA
ACTATGAATTGTCTCTAGTAGAGATAAATTTCTGCAAACATATCTCAGTCTTCCCTCTGTTTCTCTGGTGATTAAGA
AGTTCCTTTTTGGTAAGGAAAAGGATTTTTAACCATAGAGTTAGGCATCATGGAAATTCAAACCAGATTTCTTAATA
CCTGGTCTTCCTCAAAGAGAAATAATAACAGTAATAGTGGTGCTGGGAACAATATGGCAGATTATTGAATGAAATTG
ATTAACTTGAATAAAATGCTGTGAATTTTC

FIGURE 5

GGCACGAGGCCGCAGCGGACTGCCCTTTCCCAAGATGGCGTCGAAGATAGGTTCGAGACGGTGGATGTTGCAGCTGA
TCATGCAGTTGGGTTCGGTGCTGCTCACACGCTGCCCCTTTTGGGGCTGCTTCAGCCAGCTCATGCTGTACGCTGAG
AGGGCTGAGGCACGCCGGAAGCCCGACATCCCAGTGCCTTACCTGTATTTCGACATGGGGGCAGCCGTGCTGTGCGC
TAGTTTCATGTCCTTTGGCGTGAAGCGGCGCTGGTTCGCGCTGGGGCCGCACTCCAATTGGCCATTAGCACCTACG
CCGCCTACATCGGGGGCTACGTCCACTACGGGGACTGGCTGAAGGTCCGTATGTACTCGCGCACAGTTGCCATCATC
GGCGGCTTTCTTGTGTTGGCCAGCGGTGCTGGGGAGCTGTACCGCCGGAAACCTCGCAGCCGCTCCCTGCAGTCCAC
CGGCCAGGTGTTCCTGGGTATCTACCTCATCTGTGTGGCCTACTCACTGCAGCACAGCAAGGAGGACCGGCTGGCGT
ATCTGAACCATCTCCCAGGAGGGGAGCTGATGATCCAGCTGTTCTTCGTGCTGTATGGCATCCTGGCCCTGGCCTTT
CTGTCAGGCTACTACGTGACCCTCGCTGCCCAGATCCTGGCTGTACTGCTGCCCCCTGTCATGCTGCTCATTGATGG
CAATGTTGCTTACTGGCACAACACGCGGCGTGTTGAGTTCTGGAACCAGATGAAGCTCCTTGGAGAGAGTGTGGGCA
TCTTCGGAACTGCTGTCATCCTGGCCACTGATGGCTGAGTTTTATGGCAAGAGGCTGAGATGGGCACAGGGAGCCAC
TGAGGGTCACCCTGCCTTCCTCCTTGCTGGCCCAGCTGCTGTTTATTTATGCTTTTTGGTCTGTTTGTTTGATCTTT
TGCTTTTTTAAAATTGTTTTTTGCAGTTAAGAGGCAGCTCATTTGTCCAAATTTCTGGGCTCAGCGCTTGGGAGGGC
AGGAGCCCTGGCACTAATGCTGTACAGGTTTTTTTCCTGTTAGGAGAGCTGAGGCCAGCTGCCCACTGAGTCTCCTG
TCCCTGAGAAGGGAGTATGGCAGGGCTGGATGCGGCTACTGAGAGTGGGAGAGTGGGAGACAGAGGAAGGAAGATG
GAGATTGGAAGTGAGCAAATGTGAAAAATTCCTCTTTGAACCTGGCAGATGCAGCTAGGCTCTGCAGTGCTGTTTGG
AGACTGTGAGAGGGAGTGTGTGTGTTGACACATGTGGATCAGGCCCAGGAAGGGCACAGGGGCTGAGCACTACAGAA
GTCACATGGGTTCTCAGGGTATGCCAGGGGCAGAAACAGTACCGGCTCTCTGTCACTCACCTTGAGAGTAGAGCAGA
CCCTGTTCTGCTCTGGGCTGTGAAGGGGTGGAGCAGGCAGTGGCCAGCTTTGCCCTTCCTGCTGTCTCTGTTTCTAG
CTCCATGGTTGGCCTGGTGGGGGTGGAGTTCCCTCCCAAACACCAGACCACACAGTCCTCCAAAAATAAACATTTTA
TATAGACAAAAAAAAAAAAAAAAAAAAAAAAA

FIGURE 6

```
GGCCGCGGCTCGCCTTTGGCCCTTCTTATCAGGATGAAAACGCTTCTGTTTGGTGTCTGGGCCCTGCTGGCCTTGAT
CCTTTGCCCAGGGGTCCCGGAAGAGTTGTTTGAGGTTTCTATTTGGCCAAGTCAGGCCCTGGTGGAGTTTGGACAGT
CCCTAGTGTGCAACTGCAGCACTACTTGCCCAGACCCAGGACCCAGTGGAATTGAGACCTTCTTAAAGAAAACTCAG
GTGGACAAAGGGCCTCAGTGGAAAGAGTTTCTTCTGGAGGATGTCACAGAGAATTCCATCCTGCAGTGCTTCTTCTC
TTGTGCAGGGATTCAAAAGGACACAAGCCTTGGCATCACTGTGTATCAGCCACCAGAGCAAGTGATCCTGGAGCTGC
AGCCTGCCTGGGTGGCCGTGGACGAAGCCTTCACAGTGAAGTGTCATGTACCCAGTGTAGCACCCTTGGAGAGTCTC
ACCCTTGCCCTTCTCCAGGGTAACCAAGAACTGCATAGAAAGAACTTTACGAGCTTGGCTGTGGCCTCCCAAAGAGC
TGAAGTCATCATCAGTGTCAGAGCCCAAAAGGAGAATGACAGATGCAATTCTTCCTGCCATGCAGAACTGGACTTGA
GTTTGCAAGGTGGGAGGCTCTTTCAAGGCAGCTCACCCATCAGAATAGTCCGGATCTTTGAATTCTCTCAGAGTCCC
CACATCTGGGTCTCTTCCCTTTTGGAGGCTGGGATGGCGGAGACTGTGAGCTGCGAGGTGGCTAGGGTGTTTCCAGC
CAAAGAAGTTATGTTCCACATGTTCCTGGAAGACCAAGAGCTGAGCTCCTCCCTTTCCTGGGAGGGGGACACAGCAT
GGGCCAATGCTACCATTCGGACCATGGAGGCTGGTGATCAGGAACTGTCTTGCTTTGCATCTCTGGGTGCAATGGAA
CAGAAGACAAGAAAGCTAGTGCATAGCTACAGCTTCCCTCCACCAATCCTGGAGCTAAAAGAATCATACCCATTGGC
AGGGACCGACATTAATGTGACCTGCTCAGGGCATGTATTAACATCACCCAGCCCTACTCTTCGGCTTCAGGGAGCCC
CAGACCTCCCTGCTGGGGAGCCTGCCTGGCTTCTACTTACTGCCAGGGAGGAAGATGATGGCXGAAATTTCTCCTGC
GAGGCCTCTTTGGTGGTGCAGGGTCAGCGGTTGATGAAAACCACTGTGATCCAGCTCCATATCCTAAAGCCACAGTT
AGAGGAATCCAGTTGCCCTGGCAAACAGACCTGGCTGGAAGGGATGGAACACACGCTCGCCTGCGTCCCAAAGGGAA
ACCCAGCTCCAGCCTTGGTGTGTACCTGGAATGGGGTGGTCTTTGACCTTGAAGTGCCACAGAAGGCAACCTAGAAC
CACACTGGAACCTACCGCTACACAGCCACTAACCAGCTGGGCTCTGTCAGCAAAGACATTGCTGT
```

FIGURE 7

CCACGCGTCCGTTCTGAGGTGCATTCTTTTTTTGATGAGAGGCATCTCTAGGTACCATCCCTGACCTGGTCCTCATG
CTGCCGAGGCTGTTGCTGTTGATCTGTGCTCCACTCTGTGAACCTGCCGAGCTGTTTTTGATAGCCAGCCCCTCCCA
TCCCACAGAGGGGAGCCCAGTGACCCTGACGTGTAAGATGCCCTTTCTACAGAGTTCAGATGCCCAGTTCCAGTTCT
GCTTTTTCAGAGACACCCGGGCCTTGGGCCCAGGCTGGAGCAGCTCCCCCAAGCTCCAGATCGCTGCCATGTGGAAA
GAAGACACAGGGTCATACTGGTGCGAGGCACAGACAATGGCGTCCAAAGTCTTGAGGAGCAGGAGATCCCAGATAAA
TGTGCACATCCCGGTGTCTCGCCCAATCCTCATGCTCAGGGCTCCCAGGGCCCAGGCTGCAGTGGAGGATGTGCTGG
AGCTTCACTGTGAGGCCCTGAGAGGCTCTCCTCCAATCCTGTACTGGTTTTATCACGAGGATATCACCCTGGGGAGC
AGGTCGGCCCCCTCTGGAGGAGGAGCCTCCTTCAACCTTTCCCTGACTGAAGAACATTCTGGAAACTACTCCTGTGA
GGCCAACAATGGCCTGGGGGCCCAGCGCAGTGAGGCGGTGACACTCAACTTCACAGTGCCTACTGGGCCAGAAGCA
ATCATCTTACCTCAGGAGTCATTGAGGGGCTGCTCAGCACCCTTGGTCCAGCCACCGTGGCCTTATTATTTTGCTAC
GGCCTCAAAAGAAAAATAGGAAGACGTTCAGCCAGGGATCCACTCAGGAGCCTTCCAGCCTTACCCCAAGAGTTCAC
CTACCTCAACTCACCTACCCCAGGGCAGCTACAGCCTATATATGAAAATGTGAATGTTGTAAGTGGGGATGAGGTTT
ATTCACTGGCGTACTATAACCAGCCGGAGCAGGAATCAGTAGCAGCAGAAACCCTGGGGACACATATGGAGGACAAG
GTTTCCTTAGACATCTATTCCAGGCTGAGGAAAGCAAACATTACAGATGTGGACTATGAAGATGCTATGTAAGGTTA
TGGAAGATTCTGCTCTTTGAAAACCATCCATGACCCCAAGCCTCAGGCCTGATATGTTCTTCAGAGATCCTGGGCA
TTAGCTTTCCAGTATACCTCTTCTGGATGCCATTCTCCATGGCACTATTCCTTCATCTACTGTGAAGTGAAGTTGGC
GCAGCCCTGAAGAAACTACCTAGGAGAACTAATAGACACAGGAGTGACAGGGACTTTGTTATCAGAACCAGATTCCT
GCCGGCTCCTTTGAAAACAGGTCATATTGTGCTCTTCTGTTTACAAGAGGAAACAAGATGGAATAAAAGAAATTGGG
ATCTTGGGTTGGAGGGACAGTGAAGCTTAGAGCACATGAACTCAAGGTTAGTGACTCTGCAGGACTTCACAGAGAGA
GCTGTGCCCATCATTCAGTCCAAGTGCTTTCTCTGCCCAGACAGCACAGAACTCCAGCCCCGCTACTTACATGGATC
ATCGAGTTTCCACCTAAAATATGATTCTATTTATTTTGAGTCACTGTTACCAAATTAGAACTAAAACAAAGTTACAT
AAAAAGTTATTGTGACTCCACTTAATTTTAGTGACGTATTTTTGTATATATAGGCCAACCTATACCACATCCAAAAT
TATGTATCTATTACAGCCCCTAGAAGCTTTATAAATACAGTGTGTCTTCTTTTATTCACAAAATTTTTGAAATCGTG
GTAATATGGTTTGAAACCTGTATCTTAATTATTTTTTTTTAAATTGAGACAGGGTCTCACTCTGTCACTCAATCTG
GAATGCAGTGGCACAATCTTGCCTCACTGCAACGCCTGCCTCTCAGGCTCAAGCAAACCTCTCACCTCAGCCTGCTG
AGTAGCTGGGACTACAGGCACATGCCACCAAACTTGGCCATTTTTTGTCTTACGTAGAGACAAGATTTCACCGTTTT
GCCCAGGCTGGTCTCAAACTCCTGGGCTCAAGCAATGTATTGAATTTTAAAATAACCAGGCACTCACTCTTATGAAT
TAATAAACATTTGGAGGTATATAAAGTAAAAAGTTAAAGTCTTTCCTGTAAGTTAACACAAATGTTAACTATTGTTA
AAAACTTTACAGGTAGCTCTCTAGATATTTTTCTATTTTTGTATGTATACTTATGCATACATGTAAGTATATAAACA
TTTAGAAGTGTACCTATCTAACAAACTATTATGAAATACTTTCAAATCTGTAAATAGATCTATTATACTATTTTAAA
AGTCTCTATAGTAGTGTGTTATATAGATAAATCATAACTTTTTCTTTTTTATTGTAGTAAATATGCACAACATAA
AATTGATCATTTTAACCATTTTTAAGTGTACAATTCAGTGGCATTAAGTACTATCATAATATATTTTAATCCTTCTC
ATCACTGGTGGACATTAAGGAGACTCTCAAAAAATTCATATTATAAAAACAAAGTTCAAACAAATGTCTTTGTACTA
GCATATTATGGCACTCCTGCTGGATTATCTGAAGGATAAATTTGTAAATCTAGTATTGCTAGATTATGCATATTAAA
TATTCTTGTTAAATAGTCAAAAAAAAAAAAAAAA

FIGURE 8

```
CTCAATCAGCTTTATGCAGAGAAGAAGCTTACTGAGCTCACTGCTGGTGCTGGTGTAGGCAAGTGCTGCTTTGGCAA
TCTGGGCTGACCTGGCTTGTCTCCTCAGAACTCCTTCTCCAACCCTGGAGCAGGCTTCCATGCTGCTGTGGGCGTCC
TTGCTGGCCTTTGCTCCAGTCTGTGGACAATCTGCAGCTGCACACAAACCTGTGATTTCCGTCCATCCTCCATGGAC
CACATTCTTCAAAGGAGAGAGAGTGACTCTGACTTGCAATGGATTTCAGTTCTATGCAACAGAGAAAACAACATGGT
ATCATCGGCACTACTGGGGAGAAAAGTTGACCCTGACCCCAGGAAACACCCTCGAGGTTCGGGAATCTGGACTGTAC
AGATGCCAGGCCCGGGGCTCCCCACGAAGTAACCCTGTGCGCTTGCTCTTTTCTTCAGACTCCTTAATCCTGCAGGC
ACCATATTCTGTGTTTGAAGGTGACACATTGGTTCTGAGATGCCACAGAAGAAGGAAAGAGAAATTGACTGCTGTGA
AATATACTTGGAATGGAAACATTCTTTCCATTTCTAATAAAAGCTGGGATCTTCTTATCCCACAAGCAAGTTCAAAT
AACAATGGCAATTATCGATGCATTGGATATGGAGATGAGAATGATGTATTTAGATCAAATTTCAAAATAATTAAAAT
TCAAGAACTATTTCCACATCCAGAGCTGAAAGCTACAGACTCTCAGCCTACAGAGGGGAATTCTGTAAACCTGAGCT
GTGAAACACAGCTTCCTCCAGAGCGGTCAGACACCCCACTTCACTTCAACTTCTTCAGAGATGGCGAGGTCATCCTG
TCAGACTGGAGCACGTACCCGGAACTCCAGCTCCCAACCGTCTGGAGAGAAAACTCAGGATCCTATTGGTGTGGTGC
TGAAACAGTGAGGGGTAACATCCACAAGCACAGTCCCTCGCTACAGATCCATGTGCAGCGGATCCCTGTGTCTGGGG
TGCTCCTGGAGACCCAGCCCTCAGGGGGCCAGGCTGTTGAAGGGGAGATGCTGGTCCTTGTCTGCTCCGTGGCTGAA
GGCACAGGGGATACCACATTCTCCTGGCACCGAGAGGACATGCAGGAGAGTCTGGGGAGGAAAACTCAGCGTTCCCT
GAGAGCAGAGCTGGAGCTCCCTGCCATCAGACAGAGCCATGCAGGGGATACTACTGTACAGCAGACAACAGCTACG
GCCCTGTCCAGAGCATGGTGCTGAATGTCACTGTGAGAGAGACCCCAGGCAACAGAGATGGCCTTGTCGCCGCGGGA
GCCACTGGAGGGCTGCTCAGTGCTCTTCTCCTGGCTGTGGCCCTGCTGTTTCACTGCTGGCGTCGGAGGAAGTCAGG
AGTTGGTTTCTTGGGAGACGAAACCAGGCTCCCTCCCGTCCAGGCCCAGGAGAGTCCTCCCATTCCATCTGCCCTG
CCCAGGTGGAGCTTCAGTCGTTGTATGTTGATGTACACCCCAAAAAGGGAGATTTGGTATACTCTGAGATCCAGACT
ACTCAGCTGGGAGAAGAAGAGGAAGCTAATACCTCCAGGACACTTCTAGAGGATAAGGATGTCTCAGTTGTCTACTC
TGAGGTAAAGACACAACACCCAGATAACTCAGCTGGAAAGATCAGCTCTAAGGATGAAGAAAGTTAAGAGAATGAAA
AGTTACGGGAACGTCCTACTCATGTGATTTCTCCCTTGTCCAAAGTCCCAGGCCCAGTGCAGTCCTTGCGGCACCTG
GAATGATCAACTCATTCCAGCTTTCTAATTCTTCTCATGCATATGCATTCACTCCCAGGAATACTCATTCGTCTACT
CTGATGTTGGGATGGAATGGCCTCTGAAAGACTTCACTAAAATGACCAGGATCCACAGTTAAGAGAAGACCCTGTAG
TATTTGCTGTGGGCCTGACCTAATGCATTCCCTAGGGTCTGCTTTAGAGAAGGGGGATAAAGAGAGAGAAGGACTGT
TATGAAAAACAGAAGCACAAATTTTGGTGAATTGGGATTTGCAGAGATGAAAAAGACTGGGTGACCTGGATCTCTGC
TTAATACATCTACAACCATTGTCTCACTGGAGACTCACTTGCATCAGTTTGTTTAACTGTGAGTGGCTGCACAGGCA
CTGTGCAAACAATGAAAAGCCCCTTCACTTCTGCCTGCACAGCTTACACTGTCAGGATTCAGTTGCAGATTAAAGAA
CCCATCTCGGAATGGTTTACAGAGAGAGGAATTTAAAAGAGGACATCAGAAGAGCTGGAGATGCAAGCTCTAGGCTGC
GCTTCCAAAAGCAAATGATAATTATGTTAATGTCATTAGTGACAAAGATTTGCAACATTAGAGAAAAGAGACACAAA
TATAAAATTAAAAACTTAAGTACCAACTCTCCAAAACTAAATTTGAACTTAAAATATTAGTATAAACTCATAATAAA
CTCTGCCTTTAAAAAAAGATAAATATTTCCTACGTCTGTTCACTGAAATAATTACCAACCCCTTAGCAATAAGCACT
CCTTGCAGAGAGGTTTTATTCTCTAAATACCATTCCCTTCTCAAAGGAAATAAGGTTGCTTTTCTTGTAGGAACTGT
GTCTTTGAGTTACTAATTAGTTTATATGAGAATAATTCTTGCAATAAATGAAGAAGGAATAAAAGAAATAGGAAGCC
ACAAATTTGTATGGATATTTCATGATACACCTACTGGTTAAATAATTGACAAAAACCAGCAGCCAAATATTAGAGGT
CTCCTGATGGAAGTGTACAATACCACCTACAAATTATCCATGCCCAAGTGTTAAAACTGAATCCATTCAAGTCTTT
CTAACTGAATACTTGTTTTATAGAAAATGCATGGAGAAAAGGAATTTGTTTAAATAACATTATGGGATTGCAACCAG
CAAAACATAAACTGAGAAAAAGTTCTATAGGGCAAATCACCTGGCTTCTATAACAAATAAATGGGAAAAAATGAAA
TAAAAGAAGAGAGGGAGGAAGAAAGGGAGAGAGAAGAAAAGAAAAATGAAGAAAAGTAATTAGAATATTTTCAACA
TAAAGAAAAGACGAATATTTAAGGTGACAGATATCCCAACTACGCTGATTTGATCTTTACAAATTATATGAGTGTAT
GAATTTGTCACATGTATCACCCCCAAAAAAAGAGAAAAAGAAAAATAGAAGACATATAAATTAAATGAGACGAGACA
TGTCGACCAAAAGGAATGTGTGGGTCTTGTTTGGATCCTGACTCAAATTAAGAAAAAATAAAACTACCTACGAAATA
CTAAGAAAATTTGTATACTAATATTAAGAAATTGTTGTGTGTTTTGGATATAAGTGATAGTTTATTGTAGTGATGT
TTTTATAAAAGCAAAAGGATATTCACTTTCAGCGCTTATACTGAAGTATTAGATTAAAGCTTATTAACGTA
```

FIGURE 9

GCCGAGCTGAGCGGATCCTCACATGACTGTGATCCGATTCTTTCCAGCGGCTTCTGCAACCAAGCGGGTCTTACCCC
CGGTCCTCCGCGTCTCCAGTCCTCGCACCTGGAACCCCAACGTCCCCGAGAGTCCCCGAATCCCCGCTCCCAGGCTA
CCTAAGAGGATGAGCGGTGCTCCGACGGCCGGGGCAGCCCTGATGCTCTGCGCCGCCACCGCCGTGCTACTGAGCGC
TCAGGGCGGACCCGTGCAGTCCAAGTCGCCGCGCTTTGCGTCCTGGGACGAGATGAATGTCCTGGCGCACGGACTCC
TGCAGCTCGGCCAGGGGCTGCGCGAACACGCGGAGCGCACCCGCAGTCAGCTGAGCGCGCTGGAGCGGCGCCTGAGC
GCGTGCGGGTCCGCCTGTCAGGGAACCGAGGGGTCCACCGACCTCCCGTTAGCCCCTGAGAGCCGGGTGGACCCTGA
GGTCCTTCACAGCCTGCAGACACAACTCAAGGCTCAGAACAGCAGGATCCAGCAACTCTTCCACAAGGTGGCCCAGC
AGCAGCGGCACCTGGAGAAGCAGCACCTGCGAATTCAGCATCTGCAAAGCCAGTTTGGCCTCCTGGACCACAAGCAC
CTAGACCATGAGGTGGCCAAGCCTGCCCGAAGAAAGAGGCTGCCCGAGATGGCCCAGCCAGTTGACCCGGCTCACAA
TGTCAGCCGCCTGCACCGGCTGCCCAGGGATTGCCAGGAGCTGTTCCAGGTTGGGGAGAGGCAGAGTGGACTATTTG
AAATCCAGCCTCAGGGGTCTCCGCCATTTTTGGTGAACTGCAAGATGACCTCAGATGGAGGCTGGACAGTAATTCAG
AGGCGCCACGATGGCTCAGTGGACTTCAACCGGCCCTGGGAAGCCTACAAGGCGGGGTTTGGGGATCCCCACGGCGA
GTTCTGGCTGGGTCTGGAGAAGGTGCATAGCATCACGGGGGACCGCAACAGCCGCCTGGCCGTGCAGCTGCGGGACT
GGGATGGCAACGCCGAGTTGCTGCAGTTCTCCGTGCACCTGGGTGGCGAGGACACGGCCTATAGCCTGCAGCTCACT
GCACCCGTGGCCGGCCAGCTGGGCGCCACCACCGTCCCACCCAGCGGCCTCTCCGTACCCTTCTCCACTTGGGACCA
GGATCACGACCTCCGCAGGGACAAGAACTGCGCCAAGAGCCTCTCTGGAGGCTGGTGGTTTGGCACCTGCAGCCATT
CCAACCTCAACGGCCAGTACTTCCGCTCCATCCCACAGCAGCGGCAGAAGCTTAAGAAGGGAATCTTCTGGAAGACC
TGGCGGGGCCGCTACTACCCGCTGCAGGCCACCACCATGTTGATCCAGCCCATGGCAGCAGAGGCAGCCTCCTAGCG
TCCTGGCTGGGCCTGGTCCCAGGCCCACGAAAGACGGTGACTCTTGGCTCTGCCCGAGGATGTGGCCGTTCCCTGCC
TGGGCAGGGGCTCCAAGGAGGGGCCATCTGGAAACTTGTGGACAGAGAAGAAGACCACGACTGGAGAAGCCCCCTTT
CTGAGTGCAGGGGGGCTGCATGCGTTGCCTCCTGAGATCGAGGCTGCAGGATATGCTCAGACTCTAGAGGCGTGGAC
CAAGGGGCATGGAGCTTCACTCCTTGCTGGCCAGGGAGTTGGGGACTCAGAGGGACCACTTGGGGCCAGCCAGACTG
GCCTCAATGGCGGACTCAGTCACATTGACTGACGGGGACCAGGGCTTGTGTGGGTCGAGAGCGCCCTCATGGTGCTG
GTGCTGTTGTGTGTAGGTCCCCTGGGGACACAAGCAGGCGCCAATGGTATCTGGGCGGAGCTCACAGAGTTCTTGGA
ATAAAAGCAACCTCAGAACAC

FIGURE 10

GATGTGCTCCTTGGAGCTGGTGTGCAGTGTCCTGACTGTAAGATCAAGTCCAAACCTGTTTTGGAATTGAGGAAACT
TCTCTTTTGATCTCAGCCCTTGGTGGTCCAGGTCTTCATGCTGCTGTGGGTGATATTACTGGTCCTGGCTCCTGTCA
GTGGACAGTTTGCAAGGACACCCAGGCCCATTATTTTCCTCCAGCCTCCATGGACCACAGTCTTCCAAGGAGAGAGA
GTGACCCTCACTTGCAAGGGATTTCGCTTCTACTCACCACAGAAAACAAAATGGTACCATCGGTACCTTGGGAAAGA
ATACTAAGAGAAACCCCAGACAATATCCTTGAGGTTCAGGAATCTGGAGAGTACAGATGCCAGGCCCAGGGCTCCC
CTCTCAGTAGCCCTGTGCACTTGGATTTTTCTTCAGAGATGGGATTTCCTCATGCTGCCCAGGCTAATGTTGAACTC
CTGGGCTCAAGTGATCTGCTCACCTAGGCCTCTCAAAGCGCTGGGATTACAGCTTCGCTGATCCTGCAAGCTCCACT
TTCTGTGTTTGAAGGAGACTCTGTGGTTCTGAGGTGCCGGGCAAAGGCGGAAGTAACACTGAATAATACTATTTACA
AGAATGATAATGTCCTGGCATTCCTTAATAAAAGAACTGACTTCCAAAAAAAAAAAAAAAAAAAAAAAA

FIGURE 11A

CGCCCGCGCGCTGCAGCCCCATCTCCTAGCGGCAGCCCAGGCGCGGAGGGAGCGAGTCCGCCCCGAGGTAGGTCCAG
GACGGGCGCACAGCAGCAGCCGAGGCTGGCCGGGAGAGGGAGGAAGAGGATGGCAGGGCCACGCCCCAGCCCATGGG
CCAGGCTGCTCCTGGCAGCCTTGATCAGCGTCAGCCTCTCTGGGACCTTGGCAAACCGCTGCAAGAAGCCCCAGTG
AAGAGCTGCACGGAGTGTGTCCGTGTGGATAAGGACTGCGCCTACTGCACAGACGAGATGTTCAGGGACCGGCGCTG
CAACACCCAGGCGGAGCTGCTGGCCGCGGGCTGCCAGCGGGAGAGCATCGTGGTCATGGAGAGCAGCTTCCAAATCA
CAGAGGAGACCCAGATTGACACCACCCTGCGGCGCAGCCAGATGTCCCCCAAGGCCTGCGGGTCCGTCTGCGGCCC
GGTGAGGAGCGGCATTTTGAGCTGGAGGTGTTTGAGCCACTGGAGAGCCCCGTGGACCTGTACATCCTCATGGACTT
CTCCAACTCCATGTCCGATGATCTGGACAACCTCAAGAAGATGGGGCAGAACCTGGCTCGGGTCCTGAGCCAGCTCA
CCAGCGACTACACTATTGGATTTGGCAAGTTTGTGGACAAAGTCAGCGTCCCGCAGACGGACATGAGGCCTGAGAAG
CTGAAGGAGCCCTGGCCCAACAGTGACCCCCCCTTCTCCTTCAAGAACGTCATCAGCCTGACAGAAGATGTGGATGA
GTTCCGGAATAAACTGCAGGGAGAGCGGATCTCAGGCAACCTGGATGCTCCTGAGGGCGGCTTCGATGCCATCCTGC
AGACAGCTGTGTGCACGAGGGACATTGGCTGGCGCCCGGACAGCACCCACCTGCTGGTCTTCTCCACCGAGTCAGCC
TTCCACTATGAGGCTGATGGCGCCAACGTGCTGGCTGGCATCATGAGCCGCAACGATGAACGGTGCCACCTGGACAC
CACGGGCACCTACACCCAGTACAGGACACAGGACTACCCGTCGGTGCCCACCCTGGTGCGCCTGCTCGCCAAGCACA
ACATCATCCCCATCTTTGCTGTCACCAACTACTCCTATAGCTACTACGAGAAGCTTCACACCTATTTCCCTGTCTCC
TCACTGGGGGTGCTGCAGGAGGACTCGTCCAACATCGTGGAGCTGCTGGAGGAGGCCTTCAATCGGATCCGCTCCAA
CCTGGACATCCGGGCCCTAGACAGCCCCGAGGCCTTCGGACAGAGGTCACCTCCAAGATGTTCCAGAAGACGAGGA
CTGGGTCCTTTCACATCCGGCGGGGGAAGTGGGTATATACCAGGTGCAGCTGCGGGCCCTTGAGCACGTGGATGGG
ACGCACGTGTGCCAGCTGCCGGAGGACCAGAAGGGCAACATCCATCTGAAACCTTCCTTCTCCGACGGCCTCAAGAT
GGACGCGGGCATCATCTGTGATGTGTGCACCTGCGAGCTGCAAAAAGAGGTGCGGTCAGCTCGCTGCAGCTTCAACG
GAGACTTCGTGTGCGGACAGTGTGTGTGCAGCGAGGGCTGGAGTGGCCAGACCTGCAACTGCTCCACCGGCTCTCTG
AGTGACATTCAGCCCTGCCTGCGGGAGGGCGAGGACAAGCCGTGCTCCGGCCGTGGGGAGTGCCAGTGCGGGCACTG
TGTGTGCTACGGCGAAGGCCGCTACGAGGGTCAGTTCTGCGAGTATGACAACTTCCAGTGTCCCCGCACTTCCGGGT
TCCTCTGCAATGACCGAGGACGCTGCTCCATGGGCCAGTGTGTGTGTGAGCCTGGTTGGACAGGCCCAAGCTGTGAC
TGTCCCCTCAGCAATGCCACCTGCATCGACAGCAATGGGGGCATCTGTAATGGACGTGGCCACTGTGAGTGTGGCCG
CTGCCACTGCCACCAGCAGTCGCTCTACACGGACACCATCTGCGAGATCAACTACTCGGCGATCCACCCGGGCCTCT
GCGAGGACCTACGCTCCTGCGTGCAGTGCCAGGCGTGGGGCACCGGCGAGAAGAAGGGGCGCACGTGTGAGGAATGC
AACTTCAAGGTCAAGATGGTGGACGAGCTTAAGAGAGCCGAGGAGGTGGTGGTGCGCGCTGCTCCTTCCGGGACGAGGA
TGACGACTGCACCTACAGCTACACCATGGAAGGTGACGGCGCCCTGGGCCCAACAGCACTGTCCTGGTGCACAAGA
AGAAGGACTGCCCTCCGGGCTCCTTCTGGTGGCTCATCCCCCTGCCTCCTCCTCCTGCCGCTCCTGGCCCTGCTA
CTGCTGCTATGCTGGAAGTACTGTGCCTGCTGCAAGGCCTGCCTGGCACTTCTCCCGTGCTGCAACCGAGGTCACAT
GGTGGGCTTTAAGGAAGACCACTACATGCTGCGGGAGAACCTGATGGCCTCTGACCACTTGGACACGCCCATGCTGC
GCAGCGGGAACCTCAAGGGCCGTGACGTGGTCCGCTGGAAGGTCACCAACAACATGCAGCGGCCTGGCTTTGCCACT
CATGCCGCCAGCATCAACCCCACAGAGCTGGTGCCCTACGGGCTGTCCTTGCGCCTGGCCCGCCTTTGCACCGAGAA
CCTGCTGAAGCCTGACACTCGGGAGTGCGCCCAGCTGCGCCAGGAGGTGGAGGAGAACCTGAACGAGGTCTACAGGC
AGATCTCCGGTGTACACAAGCTCCAGCAGACCAAGTTCCGGCAGCAGCCCAATGCCGGGAAAAAGCAAGACCACACC
ATTGTGGACACAGTGCTGATGGCGCCCCGCTCGGCCAAGCCGGCCCTGCTGAAGCTTACAGAGAAGCAGGTGGAACA
GAGGGCCTTCCACGACCTCAAGGTGGCCCCCGGCTACTACACCCTCACTGCAGACCAGGACGCCCGGGGCATGGTGG
AGTTCCAGGAGGGCGTGGAGCTGGTGGACGTACGGGTGCCCCTCTTTATCCGGCCTGAGGATGACGACGAGAAGCAG
CTGCTGGTGGAGGCCATCGACGTGCCCGCAGGCACTGCCACCCTCGGCCGCCGCCTGGTAAACATCCATCATCAA
GGAGCAAGCCAGAGACGTGGTGTCCTTTGAGCAGCCTGAGTTCTCGGTCAGCCGCGGGGACCAGGTGGCCCGCATCC
CTGTCATCCGGCGTGTCCTGGACGGCGGGAAGTCCCAGGTCTCCTACCGCACACAGGATGGCACCGCGCAGGGCAAC
CGGGACTACATCCCCGTGGAGGGTGAGCTGCTGTTCCAGCCTGGGGAGGCCTGGAAAGAGCTGCAGGTGAAGCTCCT
GGAGCTGCAAGAAGTTGACTCCCTCCTGCGGGGCCGCAGGTCCGCCGTTTCCACGTCCAGCTCAGCAACCCTAAGT
TTGGGGCCCACCTGGGCCAGCCCCACTCCACCACCATCATCATCAGGGACCCAGATGAACTGGACCGGAGCTTCACG
AGTCAGATGTTGTCATCACAGCCACCCCCTCACGGCGACCTGGGCGCCCCGCAGAACCCCAATGCTAAGGCCGCTGG
GTCCAGGAAGATCCATTTCAACTGGCTGCCCCCTTCTGGCAAGCCAATGGGGTACAGGGTAAAGTACTGGATTCAGG
GTGACTCCGAATCCGAAGCCCACCTGCTCGACAGCAAGGTGCCCTCAGTGGAGCTCACCAACCTGTACCCGTATTGC
GACTATGAGATGAAGGTGTGCGCCTACGGGCTCAGGGCGAGGGACCCTACAGCTCCCTGGTGTCCTGCCGCACCCA
CCAGGAAGTGCCCAGCGAGCCAGGGCGTCTGGCCTTCAATGTCGTCTCCTCCACGGTGACCCAGCTGAGCTGGGCTG
AGCCGGCTGAGACCAACGGTGAGATCACAGCCTACGAGGTCTGCTATGGCCTGGTCAACGATGACAACCGACCTATT
GGGCCCATGAAGAAAGTGCTGGTTGACAACCCTAAGAACCGGATGCTGCTTATTGAGAACCTTCGGGAG

FIGURE 11B

```
TCCCAGCCCTACCGCTACACGGTGAAGGCGCGCAACGGGGCCGGCTGGGGGCCTGAGCGGGAGGCCATCATCAACCT
GGCCACCCAGCCCAAGAGGCCCATGTCCATCCCCATCATCCCTGACATCCCTATCGTGGACGCCCAGAGCGGGGAGG
ACTACGACAGCTTCCTTATGTACAGCGATGACGTTCTACGCTCTCCATCGGGCAGCCAGAGGCCCAGCGTCTCCGAT
GACACTGAGCACCTGGTGAATGGCCGGATGGACTTTGCCTTCCCGGGCAGCACCAACTCCCTGCACAGGATGACCAC
GACCAGTGCTGCTGCCTATGGCACCCACCTGAGCCCACACGTGCCCCACCGCGTGCTAAGCACATCCTCCACCCTCA
CACGGGACTACAACTCACTGACCCGCTCAGAACACTCACACTCGACCACACTGCCGAGGGACTACTCCACCCTCACC
TCCGTCTCCTCCCACGACTCTCGCCTGACTGCTGGTGTGCCCGACACGCCCACCCGCCTGGTGTTCTCTGCCCTGGG
GCCCACATCTCTCAGAGTGAGCTGGCAGGAGCCGCGGTGCGAGCGGCCGCTGCAGGGCTACAGTGTGGAGTACCAGC
TGCTGAACGGCGGTGAGCTGCATCGGCTCAACATCCCCAACCCTGCCCAGACCTCGGTGGTGGTGGAAGACCTCCTG
CCCAACCACTCCTACGTGTTCCGCGTGCGGGCCCAGAGCCAGGAAGGCTGGGCCGAGAGCGTGAGGGTGTCATCAC
CATTGAATCCCAGGTGCACCCGCAGAGCCCACTGTGTCCCCTGCCAGGCTCCGCCTTCACTTTGAGCACTCCCAGTG
CCCCAGGCCCGCTGGTGTTCACTGCCCTGAGCCCAGACTCGCTGCAGCTGAGCTGGGAGCGGCCACGGAGGCCCAAT
GGGGATATCGTCGGCTACCTGGTGACCTGTGAGATGGCCCAAGGAGGAGGGCCAGCCACCGCATTCCGGGTGGATGG
AGACAGCCCCGAGAGCCGGCTGACCGTGCCGGGCCTCAGCGAGAACGTGCCCTACAAGTTCAAGGTGCAGGCCAGGA
CCACTGAGGGCTTCGGGCCAGAGCGCGAGGGCATCATCACCATAGAGTCCCAGGATGGAGGACCCTTCCCGCAGCTG
GGCAGCCGTGCCGGGCTCTTCCAGCACCCGCTGCAAAGCGAGTACAGCAGCATCACCACCACCCACACCAGCGCCAC
CGAGCCCTTCCTAGTGGATGGGCCGACCCTGGGGGCCCAGCACCTGGAGGCAGGCGGCTCCCTCACCCGGCATGTGA
CCCAGGAGTTTGTGAGCCGGACACTGACCACCAGCGGAACCCTTAGCACCCACATGGACCAACAGTTCTTCCAAACT
TGACCGCACCCTGCCCCACCCCCGCCATGTCCCACTAGGCGTCCTCCCGACTCCTCTCCCGGAGCCTCCTCAGCTAC
TCCATCCTTGCACCCCTGGGGGCCCAGCCCACCCGCATGCACAGAGCAGGGGCTAGGTGTCTCCTGGGAGGCATGAA
GGGGGCAAGGTCCGTCCTCTGTGGGCCCAAACCTATTTGTAACAAAGAGCTGGGAGCAGCACAAGGACCCAGCCTT
TGTTCTGCACTTAATAAATGGTTTTGCTACTG
```

FIGURE 12A

```
GCCTTCAACTACCATCCCACCACCTGCTGAGGAGAAAAATTCTTCAAGACTCAGAGCACACAGCCAGCACCAGAGGC
CCCATGACCCTGGACAGACCAGGGGAGGGGGCCACCATGCTGAAGACATTCACTGTTTTGCTCTTTTGCATTCGGAT
GAGTCTGGGTATGACATCGATAGTGATGGACCCTCAACCGGAGTTGTGGATAGAGTCCAACTACCCCCAGGCCCCTT
GGGAGAACATCACGCTTTGGTGCCGAAGCCCCTCTCGGATATCAAGCAAGTTCCTGCTGCTGAAGGATAAGACACAA
ATGACCTGGATCCGCCCTTCCCACAAGACCTTCCAAGTTTCATTCCTTATAGGTGCCCTTACTGAGTCCAATGCAGG
TCTTTACCGGTGCTGCTACTGGAAGGAGACAGGCTGGTCAAAGCCCAGTAAAGTTCTAGAGTTGGAGGCACCAGGCC
AACTGCCCAAGCCCATCTTCTGGATTCAGGCTGAGACCCCCGCTCTTCCTGGGTGTAATGTTAACATCCTCTGCCAT
GGCTGGCTGCAGGATTTGGTATTCATGCTGTTTAAAGAGGGATATGCAGAGCCTGTGGATTACCAAGTCCCAACTGG
GACAATGGCCATATTCTCCATTGACAACCTGACACCTGAGGATGAAGGGGTTTACATCTGCCGCACTCATATCCAGA
TGCTCCCCACCCTGTGGTCAGAGCCCAGCAACCCCTGAAGCTGGTTGTAGCAGGACTCTACCCCAAACCAACTTTG
ACAGCCCATCCTGGGCCCATCATGGCACCTGGAGAAAGCCTGAATCTCAGGTGCCAAGGGCCAATCTATGGAATGAC
CTTTGCTCTAATGAGGGTTGAAGACTTGGAGAAGTCCTTTTACCACAAGAAGCAATAAAAAATGAGGCAAATTTCT
TCTTCCAGTCTTTGAAGATCCAAGATACTGGACATTACCTCTGTTTTTACTATGACGCATCATATAGAGGTTCACTC
CTTAGTGATGTCCTGAAAATCTGGGTAACTGACACTTTCCCCAAGACCTGGCTACTTGCTCGGCCAGTGCTGTGGT
CCAAATGGGTCAGAATGTGAGCCTACGGTGTCGAGGACCAGTGGATGGAGTGGGTCTTGCACTCTATAAGAAAGGAG
AAGACAAACCACTTCAATTTTTGGATGCCACCAGCATCGATGACAACACATCATTCTTCCTCAACAATGTAACCTAC
AGTGATACTGGCATCTATAGCTGCCACTATCTTCTCACCTGGAAGACCTCCATTAGGATGCCATCACACAACACTGT
GGAGCTTATGGTTGTAGATAAGCCCCCAAACCCTCCCTGTCAGCTTGGCCAAGCACTGTGTTCAAGCTAGGAAAGG
CCATCACCCTTCAGTGCCGAGTATCTCATCCAGTACTGGAATTTTCTCTGGAATGGGAAGAAAGAGAAACATTCCAA
AGATTCTCAGTAAACGGAGACTTCATCATCAGTAATGTTGACGGGAAAGGCACAGGGACCTACAGTTGCAGCTATCG
CGTAGAGACACATCCTAACATGTGGTCACATCGCAGTGAGCCCCTGAAGCTGATGGGGCCAGCAGGCTATCTCACCT
GGAATTACGTTCTGAATGAAGCTATCAGGTTGTCTCTAATCATGCAGCTTGTTGCCTTGCTGTTGGTAGTGCTGTGG
ATAAGGTGGAAGTGTCGGAGACTCAGAATCAGAGAAGCCTGGTTGCTGGGAACAGCTCAAGGGGTCACCATGCTCTT
CATAGTCACGGCCCTTCTCTGCTGTGGACTGTGCAATGGGGTATTGATAGAAGAGACTGAAATAGTCATGCCAACCC
CTAAGCCTGAGCTGTGGGCAGAGACCAACTTTCCTCTGGCCCCGTGGAAGAACTTAACCCTCTGGTGCAGAAGCCCT
TCTGGCTCAACTAAGGAGTTTGTGTTGCTGAAGGATGGGACCGGGTGGATCGCCACTCGCCCGGCCTCAGAGCAGGT
CCGGGCTGCCTTCCCCCTTGGCGCCCTGACCCAGAGCCACACCGGGAGCTACCACTGCCATTCATGGGAGGAGATGG
CTGTATCGGAGCCCAGTGAGGCACTTGAGCTGGTGGGACAGACATCCTCCCCAAACCTGTCATTTCTGCTTCCCCC
ACAATCCGGGGCCAGGAACTACAACTCCGGTGCAAAGGATGGCTGGCAGGCATGGGGTTTGCTCTGTATAAGGAGGG
AGAGCAAGAACCTGTCCAGCAACTTGGTGCTGTTGAAGAGAAGCCTTCTTTACAATCCAGAGAATGGAGGATAAAG
ACGAAGGCAATTACAGCTGCCGCACTCACACTGAAAAACTCCCCTTCAAGTGGTCTGAGCCCAGTGAGCCGCTGGAG
CTTGTCATAAAAGAAATGTACCCTAAGCCCTTCTTCAAGACATGGGCCAGCCCTGTGGTCACCCCTGGTGCCCGAGT
GACTTTCAATTGCTCCACCCCCCACCAGCATATGAGCTTTATTCTTTACAAAGATGGAAGTGAAATAGCATCCAGTG
ACAGGTCCTGGGCAAGTCCGGGGCCAGTGCAGCTCACTTTCTAATCATTTCGGTGGGCATTGGTGATGGAGGGAAT
TACAGCTGCCGATATTATGACTTTTCTATCTGGTCTGAGCCCAGCGACCCTGTGGAGCTCGTGGTGACAGAATTCTA
CCCCAAACCCACTCTCCTGGCACAGCCAGGTCCTGTGGTGTTTCCTGGGAAGAGTGTGATCCTGCGCTGCCAAGGGA
CTTTCCAGGGCATGAGGTTCGCCCTCTTGCAGGAGGGAGCCCATGTTCCCTTACAGTTTCGGAGTGTCTCAGGGAAC
TCAGCTGACTTCCTTCTCCACACTGTTGGAGCAGAGGACTCTGGGAACTATAGCTGTATCTACTATGAGACAACCAT
GTCAAACAGGGGGTCATATCTCAGTATGCCCCTTATGATCTGGGTGACTGACACATTCCCTAAGCCATGGTTGTTTG
CTGAGCCCAGTTCTGTGGTTCCCATGGGGCAGAATGTTACTCTCGGTGCCGAGGGCCGGTCCATGGAGTAGGATAC
ATTCTGCACAAAGAAGGAGAAGCCACTTCAATGCAGCTCTGGGGATCCACCAGTAATGACGGGGCATTCCCCATCAC
CAATATATCTGGTACTAGCATGGGGCGTTACAGCTGCTGCTACCACCCTGACTGGACCAGTTCTATCAAGATACAAC
CTAGCAACACCCTGGAACTCCTAGTCACAGGCTTACTCCCCAAACCCAGCCTATTAGCCCAGCCTGGTCCCATGGTG
GCCCCTGGCGAAAATATGACTCTTCAGTGTCAAGGGGAACTGCCAGACTCAACATTTGTGCTGTTGAAGGAGGGGGC
TCAGGAGCCTTTAGAGCAACAGAGGCCAAGTGGGTACAGGGCTGACTTCTGGATGCCAGCAGTGAGAGGTGAAGACT
CTGGGATCTATAGCTGTGTTTATTATTTGGACTCTACTCCCTTTGCAGCTTCAAATCACAGTGACTCCCTGGAGATC
TGGGTGACTGATAAGCCCCCTAAACCCTCTCTGTCAGCCTGGCCCAGCACCATGTTCAAGTTAGGGAAGGACATCAC
CCTTCAGTGCCGAGGACCCCTGCCAGGTGTTGAATTTGTTCTAGAACATGATGGAGAAGAAGCACCTCAGCAGTTTT
CAGAGGATGGAGACTTTGTCATCAACAACGTAGAAGGAAAGGCATTGGAAACTACAGCTGCAGCTACCGCTCCAG
GCCTACCCTGATATCTGGTCAGAGCCTAGTGATCCCCTGGAGCTGGTGGGGGCAGCAGGGCCTGTTGCTCAGGAGTG
CACTGTAGGGAACATTGTCCGAAGTAGCCTAATCGTGGTGGTTGTTGTAGCCTTGGGGGTAGTGCTAGCCATAGAGT
GGAAGAAGTGGCCTCGACTGCGAACCAGAGGCTCAGAGACAGACGGAAGAGACCAGACCATTGCCCTTG
```

FIGURE 12B

AAGAGTGTAACCAAGAAGGAGAACCAGGCACCCCTGCCAATTCTCCTTCATCAACCTCTCAGAGAATCTCTGTGGAA
CTGCCCGTTCCAATATAATAATCTCCTCCTTTACAAGAGCTTTCCTCTCCTCTCTCTTGCTCTCAGAGACCTATAAA
TCCAACCAGTTACCCTGCAAGTCAGCCCCATCTGCTGTTCCTTGGTCTCTAATCACCTGAGCTGGGTAAAGGGGATT
CTGGGAGTTGAGAGCTCTGCCAGGGTGAGATGTTTCCTGAAGAGAGGTTCCCCACCCCTGTAACTCCTCACTGTACT
GATTTACTGGCGCATGAAATTCTATTAAAAATGCATTCTTCTGAATAAAAAGAGTATTCACTATTTAACTTCAATTT

FIGURE 13A

```
CGGGAGCGGCGGGAGCGGTGGCGGCGGCAGAGGCGGCGGCTCCAGCTTCGGCTCCGGCTCGGGCTCGGGCTCCGGCT
CCGGCTCCGGCTCCGGCTCCAGCTCGGGTGGCGGTGGCGGGAGCGGGACCAGGTGGAGGCGGCGGCGGCAGAGGAGT
GGGAGCAGCGGCCCTAGCGGCTTGCGGGGGGACATGCGGACCGACGGCCCCTGGATAGGCGGAAGGAGTGGAGGCCC
TGGTGCCCGGCCCTTGGTGCTGAGTATCCAGCAAGAGTGACCGGGGTGAAGAAGCAAAGACTCGGTTGATTGTCCTG
GGCTGTGGCTGGCTGTGGAGCTAGAGCCCTGGATGGCCCCTGAGCCAGCCCCAGGGAGGACGATGGTGCCCCTTGTG
CCTGCACTGGTGATGCTTGGTTTGGTGGCAGGCGCCCATGGTGACAGCAAACCTGTCTTCATTAAAGTCCCTGAGGA
CCAGACTGGGCTGTCAGGAGGGGTAGCCTCCTTCGTGTGCCAAGCTACAGGAGAACCCAAGCCGCGCATCACATGGA
TGAAGAAGGGGAAGAAAGTCAGCTCCCAGCGCTTCGAGGTCATTGAGTTTGATGATGGGGCAGGGTCAGTGCTTCGG
ATCCAGCCATTGCGGGTGCAGCGAGATGAAGCCATCTATGAGTGTACAGCTACTAACAGCCTGGGTGAGATCAACAC
TAGTGCCAAGCTCTCAGTGCTCGAAGAGGAACAGCTGCCCCTGGGTTCCCTTCCATCGACATGGGGCCTCAGCTGA
AGGTGGTGGAGAAGGCACGCACAGCCACCATGCTATGTGCCGCAGGCGGAAATCCAGACCCTGAGATTTCTTGGTTC
AAGGACTTCCTTCCTGTAGACCCTGCCACGAGCAACGGCCGCATCAAGCAGCTGCGTTCAGGTGCCTTGCAGATAGA
GAGCAGTGAGGAATCCGACCAAGGCAAGTACGAGTGTGTGGCGACCAACTCGGCAGGCACACGTTACTCAGCCCCTG
CGAACCTGTATGTGCGAGTGCGCCGCGTGGCTCCTCGTTTCTCCATCCCTCCCAGCAGCCAGGAGGTGATGCCAGGC
GGCAGCGTGAACCTGACATGCGTGGCAGTGGGTGCACCCATGCCCTACGTGAAGTGGATGATGGGGCCGAGGAGCT
CACCAAGGAGGATGAGATGCCAGTTGGCCGCAACGTCCTGGAGCTCAGCAATGTCGTACGCTCTGCCAACTACACCT
GTGTGGCCATCTCCTCGCTGGGCATGATCGAGGCCACAGCCCAGGTCACAGTGAAAGCTCTTCCAAAGCCTCCGATT
GATCTTGTGGTGACAGAGACAACTGCCACCAGTGTCACCCTCACCTGGGACTCTGGGAACTCGGAGCCTGTAACCTA
CTATGGCATCCAGTACCGCGCAGCGGGCACGGAGGGCCCCTTTCAGGAGGTGGATGGTGTGGCCACCACCCGCTACA
GCATTGGCGGCCTCAGCCCTTTCTCGGAATATGCCTTCCGCGTGCTGGCGGTGAACAGCATCGGGCGAGGGCCGCCC
AGCGAGGCAGTGCGGGCACGCACGGGAGAACAGGCGCCCTCCAGCCCACCGCGCCGCGTGCAGGCACGCATGCTGAG
CGCCAGCACCATGCTGGTGCAGTGGGAGCCTCCCGAGGAGCCCAACGGCCTGGTGCGGGGATACCGCGTCTACTATA
CTCCGGACTCCCGCCGCGCCCCCGAACGCCTGGCACAAGCACAACACCGACGCGGGGCTCCTCACGACCGTGGGCAGC
CTGCTGCCTGGCATCACCTACAGCCTGCGCGTGCTTGCCTTCACCGCCGTGGGCGATGGCCCTCCCAGCCCACCAT
CCAGGTCAAGACGCAGCAGGGAGTGCCTGCCCAGCCCGCGGACTTCCAGGCCGAGGTGGAGTCGGACACCAGGATCC
AGCTCTCGTGGCTGCTGCCCCCTCAGGAGCGGATCATCATGTATGAACTGGTGTACTGGGCGGCAGAGGACGAAGAC
CAACAGCACAAGGTCACCTTCGACCCAACCTCCTCCTACACACTAGAGGACCTGAAGCCTGACACACTCTACCGCTT
CCAGCTGGCTGCACGCTCGGATATGGGGGTGGGCGTCTTCACCCCCACCATTGAGGCCCGCACAGCCCAGTCCACCC
CCTCCGCCCCTCCCCAGAAGGTGATGTGTGTGAGCATGGGCTCCACCACGGTCCGGGTAAGTTGGGTCCCGCCGCCT
GCCGACAGCCGCAACGGCGTTATCACCCAGTACTCCGTGGCCCACGAGGCGGTGGACGGCGAGGACCGCGGGCGGCA
TGTGGTGGATGGCATCAGCCGTGAGCACTCCAGCTGGGACCTGGTGGGCCTGGAGAAGTGGACGGAGTACCGGGTGT
GGGTGCGGGCACACACAGACGTGGGCCCCGGCCCCGAGAGCGGCGGTGCTGGTGCGCACCGATGAGGACGTGCCCC
AGCGGGCCTCCGGGAAGGTGGAGGTGGAGCCACTGAACTCCACTGCTGTGCATGTCTACTGGAAGCTGCCTGTCCC
CAGCAAGCAGCATGGCCAGATCCGCGGCTACCAGGTCACCTACGTGCGGCTGGAGAATGGCGAGCCCCGTGGACTCC
CCATCATCCAAGACGTCATGCTAGCCGAGGCCCAGTGGCGGCCAGAGGAGTCCGAGGACTATGAAACCACTATCAGC
GGCCTGACCCCGGAGACCACCTACTCCGTTACTGTTGCTGCCTATACCACCAAGGGGGATGGTGCCCGCAGCAAGCC
CAAAATTGTCACTACAACAGGTGCAGTCCCAGGCCGGCCCACCATGATGATCAGCACCACGGCCATGAACACTGCGC
TGCTCCAGTGGCACCCACCCAAGGAACTGCCTGGCGAGCTGCTGGGCTACCGGCTGCAGTACTGCCGGGCCGACGAG
GCGCGGCCCAACACCATAGATTTCGGCAAGGATGACCAGCACTTCACAGTCACCGGCCTGCACAAGGGGACCACCTA
CATCTTCCGGCTTGCTGCCAAGAACCGGGCTGGCTTGGGTGAGGAGTTCGAGAAGGAGATCAGGACCCCCGAGGACC
TGCCCAGCGGCTTCCCCCAAAACCTGCATGTGACAGGACTGACCACGTCTACCACAGAACTGGCCTGGGACCCGCCA
GTGCTGGCGGAGAGGAACGGGCATCATCAGCTACACCTGGTGTTCCGAGACATCAACAGCCAACAGGAGCTGCA
GAACATCACGACAGACACCCGCTTTACCCTTACTGGCCTCAAGCCAGACACCACTTACGACATCAAGGTCCGCGCAT
GGACCAGCAAAGGCTCTGGCCCACTCAGCCCCAGCATCCAGTCCCGGACCATGCCGGTGGAGCAAGTGTTTGCCAAG
AACTTCCGGGTGGCGGCTGCAATGAAGACGTCTGTGCTGCTCAGCTGGGAGGTTCCCGACTCCTATAAGTCAGCTGT
GCCCTTTAAGATTCTGTACAATGGGCAGAGTGTGGAGGTGGACGGGCACTCGATGCGGAAGCTGATCGCAGACCTGC
AGCCCAACACAGAGTACTCGTTTGTGCTGATGAACCGTGGCAGCAGCGCAGGGGCCTGCAGCACCTGGTGTCCATC
CGCACAGCCCCCGACCTCCTGCCTCACAAGCCGCTGCCTGCCTCTGCCTACATAGAGGACGGCCGCTTCGATCTCTC
CATGCCCCATGTGCAAGACCCCTCGCTTGTCAGGTGGTTCTACATTGTTGTGGTACCCATTGACCGTGTGGGCGGGA
GCATGCTGACGCCAAGGTGGAGCACACCCGAGGAACTGGAGCTGGACGAGCTTCTAGAAGCCATCGAGCAAGGCGGA
GAGGAGCAGCGGCGGCGGCGGCGGCAGGCAGAACGTCTGAAGCCATATGTGGCTGCTCAACTGGATGTGCTCCCGGA
GACCTTTACCTTGGGGGACAAGAAGAACTACCGGGGCTTCTACAACCGGCCCCTGTCTCCGGACTTGAGCT
```

FIGURE 13B

```
ACCAGTGCTTTGTGCTTGCCTCCTTGAAGGAACCCATGGACCAGAAGCGCTATGCCTCCAGCCCCTACTCGGATGAG
ATCGTGGTCCAGGTGACACCAGCCCAGCAGCAGGAGGAGCCGGAGATGCTGTGGGTGACGGGTCCCGTGCTGGCAGT
CATCCTCATCATCCTCATTGTCATCGCCATCCTCTTGTTCAAAAGGAAAAGGACCCACTCTCCGTCCTCTAAGGATG
AGCAGTCGATCGGACTGAAGGACTCCTTGCTGGCCCACTCCTCTGACCCTGTGGAGATGCGGAGGCTCAACTACCAG
ACCCCAGGTATGCGAGACCACCCACCCATCCCCATCACCGACCTGGCGGACAACATCGAGCGCCTCAAAGCCAACGA
TGGCCTCAAGTTCTCCCAGGAGTATGAGTCCATCGACCCTGGACAGCAGTTCACGTGGGAGAATTCAAACCTGGAGG
TGAACAAGCCCAAGAACCGCTATGCGAATGTCATCGCCTACGACCACTCTCGAGTCATCCTTACCTCTATCGATGGC
GTCCCCGGGAGTGACTACATCAATGCCAACTACATCGATGGCTACCGCAAGCAGAATGCCTACATCGCCACGCAGGG
CCCCCTGCCCGAGACCATGGGCGATTTCTGGAGAATGGTGTGGGAACAGCGCACGGCCACTGTGGTCATGATGACAC
GGCTGGAGGAGAAGTCCCGGGTAAAATGTGATCAGTACTGGCCAGCCCGTGGCACCGAGACCTGTGGCCTTATTCAG
GTGACCCTGTTGGACACAGTGGAGCTGGCCACATACACTGTGCGCACCTTCGCACTCCACAAGAGTGGCTCCAGTGA
GAAGCGTGAGCTGCGTCAGTTTCAGTTCATGGCCTGGCCAGACCATGGAGTTCCTGAGTACCCAACTCCCATCCTGG
CCTTCCTACGACGGGTCAAGGCCTGCAACCCCCTAGACGCAGGGCCCATGGTGGTGCACTGCAGCGCGGGCGTGGGC
CGCACCGGCTGCTTCATCGTGATTGATGCCATGTTGGAGCGGATGAAGCACGAGAAGACGGTGGACATCTATGGCCA
CGTGACCTGCATGCGATCACAGAGGAACTACATGGTGCAGACGGAGGACCAGTACGTGTTCATCCATGAGGCGCTGC
TGGAGGCTGCCACGTGCGGCCACACAGAGGTGCCTGCCCGCAACCTGTATGCCCACATCCAGAAGCTGGGCCAAGTG
CCTCCAGGGGAGAGTGTGACCGCCATGGAGCTCGAGTTCAAGTTGCTGGCCAGCTCCAAGGCCCACACGTCCCGCTT
CATCAGCGCCAACCTGCCCTGCAACAAGTTCAAGAACCGGCTGGTGAACATCATGCCCCTACGAATTGACCCGTGTGT
GTCTGCAGCCCATCCGTGGTGTGGAGGGCTCTGACTACATCAATGCCAGCTTCCTGGATGGTTATAGACAGCAGAAG
GCCTACATAGCTACACAGGGGCCTCTGGCAGAGAGCACCGAGGACTTCTGGCGCATGCTATGGGAGCACAATTCCAC
CATCATCGTCATGCTGACCAAGCTTCGGGAGATGGGCAGGGAGAAATGCCACCAGTACTGGCCAGCAGAGCGCTCTG
CTCGCTACCAGTACTTTGTTGTTGACCCGATGGCTGAGTACAACATGCCCCAGTATATCCTGCGTGAGTTCAAGGTC
ACGGATGCCCGGGATGGGCAGTCAAGGACAATCCGGCAGTTCCAGTTCACAGACTGGCCAGAGCAGGGCGTGCCCAA
GACAGGCGAGGGATTCATTGACTTCATCGGGCAGGTGCATAAGACCAAGGAGCAGTTTGGACAGGATGGGCCTATCA
CGGTGCACTGCAGTGCTGGCGTGGGCCGCACCGGGGTGTTCATCACTCTGAGCATCGTCCTGGAGCGCATGCGCTAT
GAGGGCGTGGTCGACATGTTTCAGACCGTGAAGACCCTGCGTACACAGCGTCCTGCCATGGTGCAGACAGAGGACCA
GTATCAGCTGTGCTACCGTGCGGCCCTGGAGTACCTCGGCAGCTTTGACCACTATGCAACGTAACTACCGCTCCCCT
CTCCTCCGCCACCCCGCCGTGGGGCTCCGGAGGGGACCCAGCTCCTCTGAGCCATACCGACCATCGTCCAGCCCTC
CTACGCAGATGCTGTCACTGGCAGAGCACAGCCCACGGGGATCACAGCGTTTCAGGAACGTTGCCACACCAATCAGA
GAGCCTAGAACATCCCTGGGCAAGTGGATGGCCCAGCAGGCAGGCACTGTGGCCCTTCTGTCCACCAGACCCACCTG
GAGCCCGCTTCAAGCTCTCTGTTGCGCTCCCGCATTTCTCATGCTTCTTCTCATGGGGTGGGGTTGGGGCAAAGCCT
CCTTTTTAATACATTAAGTGGGGTAGACTGAGGGATTTTAGCCTCTTCCCTCTGATTTTTCCTTTCGCGAATCCGTA
TCTGCAGAATGGGCCACTGTAGGGGTTGGGGTTTATTTTGTTTTGTTTTTTTTTTTTTTGTATGACTTCTGCTGA
AGGACAGAACATTGCCTTCCTCGTGCAGAGCTGGGGCTGCCAGCCTGAGCGGAGGCTCGGCCGTGGGCCGGGAGGCA
GTGCTGATCCGGCTGCTCCTCCAGCCCTTCAGACGAGATCCTGTTTCAGCTAAATGCAGGGAAACTCAATGTTTTTT
TAAGTTTTGTTTTCCCTTTAAAGCCTTTTTTTAGGCCACATTGACAGTGGTGGGCGGGGAGAAGATAGGGAACACTC
ATCCCTGGTCGTCTATCCCAGTGTGTGTTTAACATTCACAGCCCAGAACCACAGATGTGTCTGGGAGAGCCTGGCAA
GGCATTCCTCATCACCATCGTGTTTGCAAAGGTTAAAACAAAACAAAAAACCACAAAAATAAAAAACAAAAAAAAC
AAAAAACCCAAAAAAAAAAAAAAAAAGAGTCAGCCCTTGGCTTCTGCTTCAAACCCTCAAGAGGGGAAGCAACTCCG
TGTGCCTGGGGTTCCCGAGGGAGCTGCTGGCTGACCTGGGCCCACAGAGCCTGGCTTTGGTCCCCAGCATTGCAGTA
TGGTGTGGTGTTTGTAGGCTGTGGGGTCTGGCTGTGTGGCCAAGGTGAATAGCACAGGTTAGGGTGTGTGCCACACC
CCATGCACCTCAGGGCCAAGCGGGGCGTGGCTGGCCTTTCAGGTCCAGGCCAGTGGGCCTGGTAGCACATGTCTGT
CCTCAGAGCAGGGGCCAGATGATTTTCCTCCCTGGTTTGCAGCTGTTTTCAAAGCCCCCGATAATCGCTCTTTTCCA
CTCCAAGATGCCCTCATAAACCAATGTGGCAAGACTACTGGACTTCTATCAATGGTACTCTAATCAGTCCTTATTAT
CCCAGCTTGCTGAGGGGCAGGGAGAGCGCCTCTTCCTCTGGGCAGCGCTATCTAGATAGGTAAGTGGGGCGGGGAA
GGGTGCATAGCTGTTTTAGCTGAGGGACGTGGTGCCGACGTCCCCAAACCTAGCTAGGCTAAGTCAAGATCAACATT
CCAGGGTTGGTAATGTTGGATGATGAAACATTCATTTTTACCTTGTGGATGCTAGTGCTGTAGAGTTCACTGTTGTA
CACAGTCTGTTTTCTATTTGTTAAGAAAAACTACAGCATCATTGCATAATTCTTGATGGTAATAAATTTGAATAATC
AGATTTCT
```

FIGURE 14

```
GGAGAGGTGCGGGCCGAATCCGAGCCGAGCGAGAGGAATCCGGCAGTAGAGAGCGGACTCCAGCCGGCGGACCCTGC
AGCCCTCGCCTGGGACAGCGGCGCGCTGGGCAGGCGCCCAAGAGAGCATCGAGCAGCGGAACCCGCGAAGCCGGCCC
GCAGCCGCGACCCGCGCAGCCTGCCGCTCTCCCGCCGCCGGTCCGGGCAGCATGAGGCGCGCGGCGCTCTGGCTCTG
GCTGTGCGCGCTGGCGCTGAGCCTGCAGCTGGCCCTGCCGCAAATTGTGGCTACTAATTTGCCCCCTGAAGATCAAG
ATGGCTCTGGGGATGACTCTGACAACTTCTCCGGCTCAGGTGCAGGTGCTTTGCAAGATATCACCTTGTCACAGCAG
ACCCCCTCCACTTGGAAGGACACGCAGCTCCTGACGGCTATTCCCACGTCTCCAGAACCCACCGGCCTGGAGGCTAC
AGCTGCCTCCACCTCCACCCTGCCGGCTGGAGAGGGGCCCAAGGAGGGAGAGGCTGTAGTCCTGCCAGAAGTGGAGC
CTGGCCTCACCGCCCGGGAGCAGGAGGCCACCCCCCGACCCAGGGAGACCACACAGCTCCCGACCACTCATCAGGCC
TCAACGACCACAGCCACCACGGCCCAGGAGCCCGCCACCTCCCACCCCCACAGGGACATGCAGCCTGGCCACCATGA
GACCTCAACCCCTGCAGGACCCAGCCAAGCTGACCTTCACACTCCCCACACAGAGGATGGAGGTCCTTCTGCCACCG
AGAGGGCTGCTGAGGATGGAGCCTCCAGTCAGCTCCCAGCAGCAGAGGGCTCTGGGGAGCAGGACTTCACCTTTGAA
ACCTCGGGGGAGAATACGGCTGTAGTGGCCGTGGAGCCTGACCGCCGGAACCAGTCCCCAGTGGATCAGGGGGCCAC
GGGGGCCTCACAGGGCCTCCTGGACAGGAAAGAGGTGCTGGGAGGGGTCATTGCCGGAGGCCTCGTGGGGCTCATCT
TTGCTGTGTGCCTGGTGGGTTTCATGCTGTACCGCATGAAGAAGAAGGACGAAGGCAGCTACTCCTTGGAGGAGCCG
AAACAAGCCAACGGCGGGGCCTACCAGAAGCCCACCAAACAGGAGGAATTCTATGCCTGACGCGGGAGCCATGCGCC
CCCTCCGCCCTGCCACTCACTAGGCCCCCACTTGCCTCTTCCTTGAAGAACTGCAGGCCCTGGCCTCCCCTGCCACC
AGGCCACCTCCCCAGCATTCCAGCCCCTCTGGTCGCTCCTGCCCACGGAGTCGTGGGTGTGCTGGGAGCTCCACTCT
GCTTCTCTGACTTCTGCCTGGAGACTTAGGGCACCAGGGGTTTCTCGCATAGGACCTTTCCACCACAGCCAGCACCT
GGCATCGCACCATTCTGACTCGGTTTCTCCAAACTGAAGCAGCCTCTCCCCAGGTCCAGCTCTGGAGGGGAGGGGGA
TCCGACTGCTTTGGACCTAAATGGCCTCATGTGGCTGGAAGATCTGCGGGTGGGGCTTGGGGCTCACACACCTGTAG
CACTTACTGGTAGGACCAAGCATCTTGGGGGGGTGGCCGCTGAGTGGCAGGGACAGGAGTCACTTTGTTTCGTGGGG
AGGTCTAATCTAGATATCGACTTGTTTTGCACATGTTTCCTCTAGTTCTTTGTTCATAGCCCAGTAGACCTTGTTA
CTTCTGAGGTAAGTTAAGTAAGTTGATTCGGTATCCCCCATCTTGCTTCCCTAATCTATGGTCGGGAGACAGCATC
AGGGTTAAGAAGACTTTTTTTTTTTTTTTAAACTAGGAGAACCAAATCTGGAAGCCAAAATGTAGGCTTAGTTTG
TGTGTTGTCTCTTGAGTTTGTCGCTCATGTGTGCAACAGGGTATGGACTATCTGTCTGGTGGCCCCGTTTCTGGTGG
TCTGTTGGCAGGCTGGCCAGTCCAGGCTGCCGTGGGGCCGCCGCCTCTTTCAAGCAGTCGTGCCTGTGTCCATGCGC
TCAGGGCCATGCTGAGGCCTGGGCCGCTGCCACGTTGGAGAAGCCCGTGTGAGAAGTGAATGCTGGGACTCAGCCTT
CAGACAGAGAGGACTGTAGGGAGGGCGGCAGGGGCCTGGAGATCCTCCTGCAGACCACXCCCGTCCTGCCTGTGCGC
CGTCTCCAGGGGCTGCTTCCTCCTGGAAATTGACGAGGGGTGTCTTGGGCAGAGCTGGCTCTGAGCGCCTCCATCCA
AGGCCAGGTTCTCCGTTAGCTCCTGTGGCCCCACCCTGGGCCCTGGGCTGGAATCAGGAATATTTTCCAAAGAGTGA
TAGTCTTTTGCTTTTGGCAAAACTCTACTTAATCCAATGGGTTTTTCCCTGTACAGTAGATTTTCCAAATGTAATAA
ACTTTAATATAAAGT
```

FIGURE 15

GCTCCGGCCAGCCGCGGTCCAGAGCGCGCGAGGTTCGGGGAGCTCCGCCAGGCTGCTGGTACCTGCGTCCGCCCGGC
GAGCAGGACAGGCTGCTTTGGTTTGTGACCTCCAGGCAGGACGGCCATCCTCTCCAGAATGAAGATCTTCTTGCCAG
TGCTGCTGGCTGCCCTTCTGGGTGTGGAGCGAGCCAGCTCGCTGATGTGCTTCTCCTGCTTGAACCAGAAGAGCAAT
CTGTACTGCCTGAAGCCGACCATCTGCTCCGACCAGGACAACTACTGCGTGACTGTGTCTGCTAGTGCCGGCATTGG
GAATCTCGTGACATTTGGCCACAGCCTGAGCAAGACCTGTTCCCCGGCCTGCCCCATCCCAGAAGGCGTCAATGTTG
GTGTGGCTTCCATGGGCATCAGCTGCTGCCAGAGCTTTCTGTGCAATTTCAGTGCGGCCGATGGCGGGCTGCGGGCA
AGCGTCACCCTGCTGGGTGCCGGGCTGCTGCTGAGCCTGCTGCCGGCCCTGCTGCGGTTTGGCCCCTGACCGCCCAG
ACCCTGTCCCCGATCCCCCAGCTCAGGAAGGAAAGCCCAGCCCTTTCTGGATCCCACAGTGTATGGGAGCCCCTGA
CTCCTCACGTGCCTGATCTGTGCCCTTGGTCCCAGGTCAGGCCCACCCCCTGCACCTCCACCTGCCCCAGCCCCTGC
CTCTGCCCAAGTGGGCCAGCTGCCCTCACTTCTGGGGTGGATGATGTGACCTTCCTTGGGGACTGCGGAAGGGACG
AGGGTTCCCTGGAGTCTTACGGTCCAACATCAGACCAAGTCCCATGGACATGCTGACAGGGTCCCCAGGGAGACCGT
GTCAGTAGGGATGTGTGCCTGGCTGTGTACGTGGGTGTGCAGTGCACGTGAGAGCACGTGGCGGCTTCTGGGGCCA
TGTTTGGGGAGGGAGGTGTGCCAGCAGCCTGGAGAGCCTCAGTCCCTGTAGCCCCCTGCCCTGGCACAGCTGCATGC
ACTTCAAGGGCAGCCTTTGGGGGTTGGGGTTTCTGCCACTTCCGGGTCTAGGCCCTGCCCAAATCCAGCCAGTCCTG
CCCCAGCCCACCCCCACATTGGAGCCCTCCTGCTGCTTTGGTGCCTCAAATAAATACAGATGTCCCC

FIGURE 16

CAGCAGGTCACAGCCCCTCGAGGCGACAGCGGCCCCGCCGCACCAGAGCAGTGGTACAGGCATGGATGGGAAGAAAT
GCAGCGTATGGATGTTCCTACCTCTTGTATTTACTTTGTTTACTTCAGCTGGATTGTGGATAGTATACTTCATAGCT
GTGGAAGATGACAAAATTTTACCATTAAATTCAGCTGAAAGGAAACCTGGTGTGAAGCATGCACCATATATAAGCAT
TGCAGGTGATGATCCTCCTGCAAGCTGTGTGTTTAGTCAAGTTATGAACATGGCAGCCTTCCTAGCCCTTGTGGTAG
CTGTTCTGCGCTTCATACAACTGAAACCGAAGGTTTTAAACCCGTGGCTGAATATTAGTGGATTGGTGGCTCTGTGT
CTGGCTTCCTTCGGAATGACCTTACTTGGTAATTTTCAGCTCACAAATGATGAAGAAATCCATAACGTCGGAACTTC
CTTGACCTTTGGATTTGGCACATTGACCTGCTGGATCCAGGCTGCGCTGACACTCAAGGTCAACATCAAGAATGAAG
GACGGAGAGTTGGAATTCCACGGGTTATTCTGTCGGCATCTATCACTCTCTGTGTGGTCCTCTACTTCATCCTCATG
GCCCAAAGCATCCACATGTATGCAGCCAGGGTCCAGTGGGGCCTGGTCATGTGCTTCCTGTCTTATTTTGGCACCTT
TGCCGTGGAGTTCCGGCATTACCGCTATGAGATTGTTTGCTCTGAGTACCAGGAGAATTTCCTAAGCTTCTCAGAAA
GCCTGTCAGAAGCTTCTGAATATCAGACTGACCAGGTGTAAACCATCAGTTTTTCCTTGCTGGTGAGGTGGGTGTGA
CAGTGGGGGAGGGGCCAGTAGGACACACTCACAGGACTTGACATAGAACCTCATTTCACACACACACACACACACAC
ATTCATGGCCACATTTGCCAAATGAGCTTTTCAGGGCGAGTTATTTCTTTAATGAAAAAGCACAAGCCCTTATGTGT
CGAAATACACGCTGTTACACTGAAAATATATGCACGACAGAGCAAGAAGCTTGTGCATGATCACTTCTTATCCGTCC
CCTTCCCAGCACTCCCTCCTCTTCCCATTCTCTCCACATGTCTCAAGCACCCTACCGAGTAGGGCAGGCCAAATGTT
CCTTGGGAGTAATGCCAACTCCCGACGTTGCCTTCAGGTCCAAAGGGCTTGGAACCAGCTCGTGAGGAAGTTCTGAA
TCTGGCACTAATATTCTTGAGTGGATAATAGTGTATCATAGAATAGGACGGAAATTGTATTGAGATGTGACCCTGTG
TCGCCTGTGGAAAGGCATAGTGAGAAGAACTTTCCCACGAAAGCCCCCTTCATCGTTGTTCAGTGGTCGGCTGTGTG
GATCCCAGGAGAGACATATGCCACAGACTGTGAGAGCAAAGCCCGCCGCTGTGATCTGGACTTGATGCACTGTGACT
GAGAATGATTTCCAAATGTGAATATGTGTAGGGACGTGGTCTATCAGGCCTGGAACAAGATGGGGGCAGTGAAGGTA
TGGTTTAGTGTTTGCTTTCATAGTATGCCATGTACAATGTTTTATATTTCATAGTTTCTTTTAAGTAACTACCATGA
GTCTCTCTAAGCCTCATGGACAAAGATGTAGACCAAATGCAAGAGCTGAGCTTGCTTTGGGTTCAACCATGATCAAA
GAAAAACTGAGGTCACCTGCAGGCTTACGTGGGAAGCTAAGACAATATC

FIGURE 17

CTGCCTCCACTGCTCTGTGCTGGGATCATGGAACTTGCACTGCTGTGTGGGCTGGTGGTGATGGCTGGTGTGATTCC
AATCCAGGGCGGGATCCTGAACCTGAACAAGATGGTCAAGCAAGTGACTGGGAAAATGCCCATCCTCTCCTACTGGC
CCTACGGCTGTCACTGCGGACTAGGTGGCAGAGGCCAACCCAAAGATGCCACGGACTGGTGCTGCCAGACCCATGAC
TGCTGCTATGACCACCTGAAGACCCAGGGGTGCGGCATCTACAAGGACTATTACAGATACAACTTTTCCCAGGGGAA
CATCCACTGCTCTGACAAGGGAAGCTGGTGTGAGCAGCAGCTGTGTGCCTGTGACAAGGAGGTGGCCTTCTGCCTGA
AGCGCAACCTGGACACCTACCAGAAGCGACTGCGTTTCTACTGGCGGCCCCACTGCCGGGGCAGACCCCTGGGTGC
TAGAAGCCCACACCCTCTACCCTGTTCCTCAGCATGGAGCTCTGGCATCCCCACCTCAGTATCTAACCTGAACCAGC
CTGGCTTTTCAAACACTCCGGGGGGAGGTAGTCCCAGCCTCCCCCGGAACCCTCTACCAATGCCTTCTGACCTTCTG
AAGCTTTCCGAATCCTCCCAGTTGAGGCAGTAGCTGTGTCCTCTGAGGGTGGATGGGAATCTTGGGAGAAGCCCAAG
CAAGGGAGCCCTCAGAGGTGGTGTTTGGACCAAAGCATCGGGGTGGGGAGGGGTCTGCCGCTGTCCCCCACCTGCT
GGCCCCCTTGTCCTTCCTCACCCCCTCCAATATAGTCTCGGAGCTACAACTGCAGCAGCCACTATAAAGGGCAATAT
TGATCTTTCTGTCCATGTGGCTCTATCTTTTAAAACCTCAAGGCCCTCCACTGTCCTAAGATAAAGCCTCTCATAGG
CACTGGGGACCCTGCACAGTCTGGCCATGTGACCCTCTCCCCAGGCAAGCTCTGAAGTCCCTGCAGGTGGAGGCCAT
GCCTGTCTTAAACTCAGTTGCATCCCTGGTGCCCAAAGCAACACCAGAACCAAGAAGGAGCTCCATAAATCCTTCTT
GGGTGAAGCCTAGACAAAGCCGCCAGGTCTTGTGGCTCCAGGCACCAGAGCCTTGAGTACTTTCTCCTGCCTCCAGG
CATTGGCTCAGGGTGAATTACAAGGGGCTACTGAATGGCTATTACTTTCATCACGACTGATCCCCACCTCCTCAGGG
TCAAAGGGCTACTTTCTGGAAGTCTCCCCAGGCTGACTCCTTCTCCCTGACTGCAAGGGCTCACTCCCTCCTCCAAG
CTCCCACAATGCTTCATGGCTCTGCCGCTTACCTAGCTTGGCCTAGAGTGGCAAATGGAACTTCTCTGATCTCCCCC
AACTAGACTGGAGCCCCGAAGGATGGAGACCATGTCTGTGCCATCTCTGTTTCCCCTGTTTTCCCACATACTAGGT
GCTCAATTCATGCCTGTGAATGGCGTGAGCCCATAATGGATACACAGAGGTTGCAGCAGATGGTGTGGGTACCTCAC
CCAGATATCTTCCAGGCCCAAGGCCCCTCTCCCTGAGTGAGGCCAGGTGTTGGCAGCCAACTGCTCCAATCTGCCTC
CTTCCCCTAAATACTGCCCTGGTCTAGTGGGAGCTGCCTTCCCCCTGCCCCACCTCTCCCACCAAGAGGCCACCTGT
CACTCATGGCCAGGAGAGTGACACCATGGAGGGTACAATTGCCAGCTCCCCCGTGTCTGTGCAGCATTGTCTGGGTT
GAATGACACTCTCAAATTGTTCCTGGGATCGGGCTGAGGCCAGGCCTCTCCTGGAACCACCTCTCTGCTTGGTCTGA
CCCCTTGGCCTATCCAGTTTTCCTGGTTCCCTCACAGGTTTCTCCAGAAAGTACTCCCTCAGTAAAGCATTTGCACA
AGAAAAAAAAAAAA

FIGURE 18A

```
GGCTGAAAGAGCCTGAGCTGTGCCTCTCCATTCCACTGCTGTGGCAGGGTCAGAAATCTTGGATAGAGAAAACCTTT
TGCAAACGGGAATGTATCTTTGTAATTCCTAGCACGAAAGACTCTAACAGGTGTTGCTGTGGCCAGTTCACCAACCA
GCATATCCCCCCTCTGCCAAGTGCAACACCCAGCAAAAATGAAGAGGAAAGCAAACAGGTGGAGACTCAGCCTGAGA
AATGGTCTGTTGCCAAGCACACCCAGAGCTACCCAACAGATTCCTATGGAGTTCTTGAATTCCAGGGTGGCGGATAT
TCCAATAAAGCCATGTATATCCGTGTATCCTATGACACCAAGCCAGACTCACTGCTCCATCTCATGGTGAAAGATTG
GCAGCTGGAACTCCCCAAGCTCTTAATATCTGTGCATGGAGGCCTCCAGAACTTTGAGATGCAGCCCAAGCTGAAAC
AAGTCTTTGGGAAAGGCCTGATCAAGGCTGCTATGACCACCGGGGCCTGGATCTTCACCGGGGGTGTCAGCAGGT
GTTATCAGCCACGTAGGGGATGCCTTGAAAGACCACTCCTCCAAGTCCAGAGGCCGGGTTTGTGCTATAGGAATTGC
TCCATGGGGCATCGTGGAGAATAAGGAAGACCTGGTTGGAAAGGATGTAACAAGAGTGTACCAGACCATGTCCAACC
CTCTAAGTAAGCTCTCTGTGCTCAACAACTCCCACACCCACTTCATCCTGGCTGACAATGGCACCCTGGGCAAGTAT
GGCGCCGAGGTGAAGCTGCGAAGGCTGCTGGAAAAGCACATCTCCCTCCAGAAGATCAACACAAGACTGGGGCAGGG
CGTGCCCCTCGTGGGTCTCGTGGTGGAGGGGGGCCCTAACGTGGTGTCCATCGTCTTGGAATACCTGCAAGAAGAGC
CTCCCATCCCTGTGGTGATTTGTGATGGCAGCGGACGTGCCTCGGACATCCTGTCCTTTGCGCACAAGTACTGTGAA
GAAGGCGGAATAATAAATGAGTCCCTCAGGGAGCAGCTTCTAGTTACCATTCAGAAAACATTTAATTATAATAAGGC
ACAATCACATCAGCTGTTTGCAATTATAATGGAGTGCATGAAGAAGAAAGAACTCGTCACTGTGTTCAGAATGGGTT
CTGAGGGCCAGCAGGACATCGAGATGGCAATTTTAACTGCCCTGCTGAAAGGAACAAACGTATCTGCTCCAGATCAG
CTGAGCTTGGCACTGGCTTGGAACCGCGTGGACATAGCACGAAGCCAGATCTTTGTCTTTGGGCCCCACTGGACGCC
CCTGGGAAGCCTGGCACCCCCGACGGACAGCAAAGCCACGGAGAAGGAGAAGAAGCCACCCATGGCCACCACCAAGG
GAGGAAGAGGAAAAGGGAAAGGCAAGAAGAAAGGGAAAGTGAAAGAGGAAGTGGAGGAAGAAACTGACCCCCGGAAG
ATAGAGCTGCTGAACTGGGTGAATGCTTTGGAGCAAGCGATGCTAGATGCTTTAGTCTTAGATCGTGTCGACTTTGT
GAAGCTCCTGATTGAAAACGGAGTGAACATGCAACACTTTCTGACCATTCCGAGGCTGGAGGAGCTCTATAACACAA
GACTGGGTCCACCAAACACACTTCATCTGCTGGTGAGGGATGTGAAAAAGAGCAACCTTCCGCCTGATTACCACATC
AGCCTCATAGACATCGGGCTCGTGCTGGAGTACCTCATGGGAGGAGCCTACCGCTGCAACTACACTCGGAAAAACTT
TCGGACCCTTTACAACAACTTGTTTGGACCAAAGAGGCCTAAAGCTCTTAAACTTCTGGGAATGGAAGATGATGAGC
CTCCAGCTAAAGGGAAGAAAAAAAAAAAAAAGAAAAAGGAGGAAGAGATCGACATTGATGTGGACGACCCTGCCGTG
AGTCGGTTCCAGTATCCCTTCCACGAGCTGATGGTGTGGGCAGTGCTGATGAAACGCCAGAAAATGGCAGTGTTCCT
CTGGCAGCGAGGGGAAGAGAGCATGGCCAAGGCCCTGGTGGCCTGCAAGCTCTACAAGGCCATGGCCCACGAGTCCT
CCGAGAGTGATCTGGTGGATGACATCTCCCAGGACTTGGATAACAATTCCAAAGACTTCGGCCAGCTTGCTTTGGAG
TTATTAGACCAGTCCTATAAGCATGACGAGCAGATCGCTATGAAACTCCTGACCTACGAGCTGAAAAACTGGAGCAA
CTCGACCTGCCTCAAACTGGCCGTGGCAGCCAAACACCGGGACTTCATTGCTCACACCTGCAGCCAGATGCTGCTGA
CCGATATGTGGATGGGAAGACTGCGGATGCGGAAGAACCCCGGCCTGAAGGTTATCATGGGGATTCTTCTACCCCCC
ACCATCTTGTTTTTGGAATTTCGCACATATGATGATTTCTCGTATCAAACATCCAAGGAAAACGAGGATGGCAAAGA
AAAAGAAGAGGAAAATACGGATGCAAATGCAGATGCTGGCTCAAGAAAGGGGATGAGGAGAACGAGCATAAAAAAC
AGAGAAGTATTCCCATCGGAACAAAGATCTGTGAATTCTATAACGCGCCCATTGTCAAGTTCTGGTTTTACACAATA
TCATACTTGGGCTACCTGCTGCTGTTTAACTACGTCATCCTGGTGCGGATGGATGGCTGGCCGTCCCTCCAGGAGTG
GATCGTCATCTCCTACATCGTGAGCCTGGCGTTAGAGAAGATACGAGAGATTCCTCATGTCAGAACCAGGCAAACTCA
GCCAGAAAATCAAAGTTTGGCTTCAGGAGTACTGGAACATCACAGATCTCGTGCCATTTCCACATTCATGATTGGA
GCAATTCTTCGCCTACAGAACCAGCCCTACATGGGCTATGGCCGGGTGATCTACTGTGTGGATATCATCTTCTGGTA
CATCCGTGTCCTGGACATCTTTGGTGTCAACAAGTATCTGGGGCCATACGTGATGATGATTGGAAAGATGATGATCG
ACATGCTGTACTTTGTGGTCATCATGCTGGTCGTGCTCATGAGTTTCGGAGTAGCCCGTCAAGCCATTCTGCATCCA
GAGGAGAAGCCCTCTTGGAAACTGGCCCGAAACATCTTCTACATGCCCTACTGGATGATCTATGGAGAGGTGTTTGC
AGACCAGATAGACCTCTACGCCATGGAAATTAATCCTCCTTGTGGTGAGAACCTATATGATGAGGAGGGCAAGCGGC
TTCCTCCCTGTATCCCCGGCGCCTGGCTCACTCCAGCACTCATGGCGTGCTATCTACTGGTCGCCAACATCCTGCTG
GTGAACCTGCTGATTGCTGTGTTCAACAATACTTTCTTTGAAGTAAAATCAATATCCAACCAGGTGTGGAAGTTCCA
GCGATATCAGCTGATTATGACATTTCATGACAGGCCAGTCCTGCCCCCACCGATGATCATTTTAAGCCACATCTACA
TCATCATTATGCGTCTCAGCGGCCGCTGCAGGAAAAAGAGAGAAGGGGACCAAGAGGAACGGGATCGTGGATTGAAG
CTCTTCCTTAGCGACGAGGAGCTAAAGAGGCTGCATGAGTTCGAGGAGCAGTGCGTGCAGGAGCACTTCCGGGAGAA
GGAGGATGAGCAGCAGTCGTCCAGCGACGAGCGCATCCGGGTCACTTCTGAAAGAGTTGAAAATATGTCAATGAGGT
TGGAAGAAATCAATGAAAGAGAAACTTTTATGAAAACTTCCCTGCAGACTGTTGACCTTCGACTTGCTCAGCTAGAA
GAATTATCTAACAGAATGGTGAATGCTCTTGAAAATCTTGCGGGAATCGACAGGTCTGACCTGATCCAGGCACGGTC
CCGGGCTTCTTCTGAATGTGAGGCAACGTATCTTCTCCGGCAAAGCAGCATCAATAGCGCTGATGGCTACAGCTTGT
ATCGATATCATTTTAACGGAGAAGAGTTATTATTTGAGGATACATCTCTCTCCACGTCACCAGGGACAG
```

FIGURE 18B

```
GAGTCAGGAAAAAAACCTGTTCCTTCCGTATAAAGGAAGAGAAGGACGTGAAAACGCACCTAGTCCCAGAATGTCAG
AACAGTCTTCACCTTTCACTGGGCACAAGCACATCAGCAACCCCAGATGGCAGTCACCTTGCAGTAGATGACTTAAA
GAACGCTGAAGAGTCAAAATTAGGTCCAGATATTGGGATTTCAAAGGAAGATGATGAAAGACAGACAGACTCTAAAA
AAGAAGAAACTATTTCCCCAAGTTTAAATAAAACAGATGTGATACATGGACAGGACAAATCAGATGTTCAAAACACT
CAGCTAACAGTGGAAACGACAAATATAGAAGGCACTATTTCCTATCCCCTGGAAGAAACCAAAATTACACGCTATTT
CCCCGATGAAACGATCAATGCTTGTAAAACAATGAAGTCCAGAAGCTTCGTCTATTCCCGGGGAAGAAAGCTGGTCG
GTGGGGTTAACCAGGATGTAGAGTACAGTTCAATCACGGACCAGCAATTGACGACGGAATGGCAATGCCAAGTTCAA
AAGATCACGCGCTCTCATAGCACAGATATTCCTTACATTGTGTCGGAAGCTGCAGTGCAAGCTGAGCAAAAAGAGCA
GTTTGCAGATATGCAAGATGAACACCATGTCGCTGAAGCAATTCCTCGAATCCCTCGCTTGTCCCTAACCATTACTG
ACAGAAATGGATGGAAAACTTACTGTCTGTGAAGCCAGATCAAACTTTGGGATTCCCATCTCTCAGGTCAAAAAGT
TTACATGGACATCCTAGGAATGTGAAATCCATTCAGGGAAAGTTAGACAGATCTGGACATGCCAGTAGTGTAAGCAG
CTTAGTAATTGTGTCTGGAATGACAGCAGAAGAAAAAAAGGTTAAGAAAGAGAAAGCTTCCACAGAAACTGAATGCT
AGTCTGTTTTGTTTCTTTAATTTTTTTTTTTAACAGTCAGAAACCCACTAATGGGTGTCATCTTGGCCCATCCTAAA
CACATMTCCAATTTCCTAAAAACATTTTCCCTTAAAAAATTTTGGAAATTCAGACTTGATTTACAATTTAATGCACT
AAAAGTAGTATTTTGTTAGXATATGTTAGTAGGCTTAGTTTTTTCAGTTGCAGTAGTATCAAATGAAAGTGATGATA
CTGTAACGAAGATAAATTGGCTAATCAGTATACAAGATTATACAATCTCTTTATTACTGAGGGCCACCAAATAGCCT
AGGAAGTGCCCTCGAGCACTGAAGTCACCATTAGGTCACTCAAGAAGTAAGCAACTAGCTGGGCACAGTGGCTCATG
CCTGTAATCCTAGCACTTTGGGAGGCCAAGGCAGAAAGATAGCTTGAGTCCAGGAGTTTGAGACCAGCCTGGGCAAC
ATAGTGATACCCCATCTCTTAAAAAAAAAAAAAAAAAAA
```

FIGURE 19

CTGAATCTTCGTTTCTCTCCCAGGGACCCTCCATTTTCCATATCCAGGAAAATGTGATGCGCCACAGGTATCAGCGT
CTGGATCGCCACTTCACGTTTTAGCCACAAGTGACTCAGTGGAAGATCCAGAGTCAACAGAGGCTCGTCAGGAAGAT
GTCTACAGAAAAGGTAGACCAAAAGGAGGAAGCTGGGGAAAAAGAGGTGTGCGGAGACCAGATCAAAGGACCGGACA
AAGAGGAGGAACCACCAGCTGCTGCATCCCATGGCCAGGGGTGGCGTCCAGGTGGCAGAGCAGCTAGGAACGCAAGG
CCTGAACCTGGGGCCAGACACCCTGCTCTCCCGGCCATGGTCAACGACCCTCCAGTACCTGCCTTACTGTGGGCCCA
GGAGGTGGGCCAAGTCTTGGCAGGCCGTGCCCGCAGGCTGCTGCTGCAGTTTGGGGTGCTCTTCTGCACCATCCTCC
TTTTGCTCTGGGTGTCTGTCTTCCTCTATGGCTCCTTCTACTATTCCTATATGCCGACAGTCAGCCACCTCAGCCCT
GTGCATTTCTACTACAGGACCGACTGTGATTCCTCCACCACCTCACTCTGCTCCTTCCCTGTTGCCAATGTCTCGCT
GACTAAGGGTGGACGTGATCGGGTGCTGATGTATGGACAGCCGTATCGTGTTACCTTAGAGCTTGAGCTGCCAGAGT
CCCCTGTGAATCAAGATTTGGGCATGTTCTTGGTCACCATTTCCTGCTACACCAGAGGTGGCCGAATCATCTCCACT
TCTTCGCGTTCGGTGATGCTGCATTACCGCTCAGACCTGCTCCAGATGCTGGACACACTGGTCTTCTCTAGCCTCCT
GCTATTTGGCTTTGCAGAGCAGAAGCAGCTGCTGGAGGTGGAACTCTACGCAGACTATAGAGAGAACTCGTACGTGC
CGACCACTGGAGCGATCATTGAGATCCACAGCAAGCGCATCCAGCTGTATGGAGCCTACCTCCGCATCCACGCGCAC
TTCACTGGGCTCAGATACCTGCTATACAACTTCCCGATGACCTGCGCCTTCATAGGTGTTGCCAGCAACTTCACCTT
CCTCAGCGTCATCGTGCTCTTCAGCTACATGCAGTGGGTGTGGGGGGGCATCTGGCCCCGACACCGCTTCTCTTTGC
AGGTTAACATCCGAAAAGAGACAATTCCCGGAAGGAAGTCCAACGAAGGATCTCTGCTCATCAGCCAGGGCCTGAA
GGCCAGGAGGAGTCAACTCCGCAATCAGATGTTACAGAGGATGGTGAGAGCCCTGAAGATCCCTCAGGGACAGAGGG
TCAGCTGTCCGAGGAGGAGAAACCAGATCAGCAGCCCCTGAGCGGAGAAGAGGAGCTAGAGCCTGAGGCCAGTGATG
GTTCAGGCTCCTGGGAAGATGCAGCTTTGCTGACGGAGGCCAACCTGCCTGCTCCTGCTCCTGCTTCTGCTTCTGCC
CCTGTCCTAGAGACTCTGGGCAGCTCTGAACCTGCTGGGGGTGCTCTCCGACAGCGCCCCACCTGCTCTAGTTCCTG
AAGAAAAGGGGCAGACTCCTCACATTCCAGCACTTTCCCACCTGACTCCTCTCCCCTCGTTTTCCTTCAATAAACT
ATTTTGTGTCAGCTTCAAAAAAAAAAAAAAAAAAAAAAAAAAAAA

FIGURE 20A

```
AACCGGCTGCGGGGATGGGGCCACCGCTCCCGCTGCTGCTGCTGCTACTGCTGCTGCTGCCGCCACGCGTCCTGCCT
GCCGCCCCTTCGTCCGTCCCCGCGGCCGGCAGCTCCCGGGGCGTCTGGGCTGCCTGCTCGAGGAGGGCCTCTGCGG
AGCGTCCGAGGCCTGTGTGAACGATGGAGTGTTTGGAAGGTGCCAGAAGGTTCCGGCAATGGACTTTTACCGCTACG
AGGTGTCGCCCGTGGCCCTGCAGCGCCTGCGCGTGGCGTTGCAGAAGCTTTCCGGCACAGGTTTCACGTGGCAGGAT
GACTATACTCAGTATGTGATGGACCAGGAACTTGCAGACCTCCCGAAAACCTACCTGAGGCGTCCTGAAGCATCCAG
CCCAGCCAGGCCCTCAAAACACAGCGTTGGCAGCGAGAGGAGGTACAGTCGGGAGGGCGGTGCTGCCCTGGCCAACG
CCCTCCGACGCCACCTGCCCTTCCTGGAGGCCCTGTCCCAGGCCCCAGCCTCAGACGTGCTCGCCAGGACCCATACG
GCGCAGGACAGACCCCCGCTGAGGGTGATGACCGCTTCTCCGAGAGCATCCTGACCTATGTGGCCCACACGTCTGC
GCTGACGTACCCTCCCGGGCCCCGGACCCAGCTCCGGGAGGACCTCCTGCCGCGGACCCTCGGCCAGCTCAGCCAG
ATGAGCTCAGCCCTAAGGTGGACAGTGGTGTGGACAGACACCATCTGATGGCGGCCCTCAGTGCCTATGCTGCCCAG
AGGCCCCCAGCTCCCCCGGGGAGGGCAGCCTGGAGCCACAGTACCTTCTGCGTGCACCCTCAAGAATGCCCAGGCC
TTTGCTGGCACCAGCCGCCCCCAGAAGTGGCCTTCACCTCTGGGAGATTCCGAAGACCCCTCCAGCACAGGCGATG
GAGCACGGATTCATACCCTCCTGAAGGACCTGCAGAGGCAGCCGGCTGAGGTGAGGGGCCTGAGTGGCCTGGAGCTG
GACGGCATGGCTGAGCTGATGGCTGGCCTGATGCAAGGCGTGGACCATGGAGTAGCTCGAGGCAGCCCTGGGAGAGC
GGCCCTGGGAGAGTCTGGAGAACAGGCGGATGGCCCCAAGGCCACCCTCCGTGGAGACAGCTTTCCAGATGACGGAG
TGCAGGACGACGATGATAGACTTTACCAAGAGGTCCACCGTCTGAGTGCCACACTCGGGGGCCTCCTGCAGGACCAC
GGGTCTCGACTCTTACCTGGAGCCCTCCCCTTTGCAAGGCCCCTCGACATGGAGAGGAAGAAGTCCGAGCACCCTGA
GTCTTCCCTGTCTTCAGAAGAGGAGACTGCCGGAGTGGAGAACGTCAAGAGCCAGACGTATTCCAAAGATCTGCTGG
GGCAGCAGCCGCATTCGGAGCCCGGGGCCGCTGCGTTTGGGGAGCTCCAAAACCAGATGCCTGGGCCTCGAAGGAG
GAGCAGAGCCTTCCAGCGGGTGCTCAGGAGGCCCTCAGCGACGGCCTGCAATTGGAGGTGCCAGCCTTCCGAGGAAGA
GGCGCGGGCTACATCGTGACAGACAGAGACCCCCTGCGCCCCGAGGAAGGAAGGCGGCTGGTGGAGGACGTCGCCC
GCCTCCTGCAGGTGCCCAGCAGTGCGTTCGCTGACGTGGAGGTTCTCGGACCAGCAGTGACCTTCAAAGTGAGCGCC
AATGTCCAAAACGTGACCACTGAGGATGTGGAGAAGGCCACAGTTGACAACAAAGACAAACTGGAGGAAACCTCTGG
ACTGAAAATTCTTCAAACCGGAGTCGGGTCGAAAAGCAAACTCAAGTTCCTGCCTCCTCAGGCGGAGCAAGAAGACT
CCACCAAGTTCATCGCGCTCACCCTGGTCTCCCTCGCCTGCATCCTGGGCGTCCTCCTGGCCTCTGGCCTCATCTAC
TGCCTCCGCCATAGCTCTCAGCACAGGCTGAAGGAGAAGCTCTCGGGACTAGGGGGCGACCCAGGTGCAGATGCCAC
TGCCGCCTACCAGGAGCTGTGCCGCCAGCGTATGGCCACGCGGCCACCAGACCGACCTGAGGGCCCGCACACGTCAC
GCATCAGCAGCGTCTCATCCCAGTTCAGCGACGGGCCGATCCCCAGCCCCTCCGCACGCAGCAGCGCCTCATCCTGG
TCCGAGGAGCCTGTGCAGTCCAACATGGACATCTCCACCGGCCACATGATCCTGTCCTACATGGAGGACCACCTGAA
GAACAAGAACCGGCTGGAGAAGGAGTGGGAAGCGCTGTGCGCCTACCAGGCGGAGCCCAACAGCTCGTTCGTGGCCC
AGAGGGAGGAGAACTGTGCCCAAGAACCGCTCCCTGGCTGTGCTGACCTATGACCACTCCCGGGTCCTGCTGAAGGCG
GAGAACAGCCACAGCCACTCAGACTACATCAACGCTAGCCCCATCATGGATCACGACCCGAGGAACCCCGCGTACAT
CGCCACCCAGGGACCGCTGCCCGCCACCGTGGCTGACTTTTGGCAGATGGTGTGGGAGAGCGGCTGCGTGGTGATCG
TCATGCTGACACCCCTCGCGGAGAACGGCGTCCGGCAGTGCTACCACTACTGGCCGGATGAAGGCTCCAATCTCTAC
CACATCTATGAGGTGAACCTGGTCTCCGAGCACATCTGGTGTGAGGACTTCCTGGTGAGGAGCTTCTATCTGAAGAA
CCTGCAGACCAACGAGACGCGCACCGTGACGCAGTTCCACTTCCTGAGTTGGTATGACGAGGAGTCCCTTCCTCCT
CAAGGTCCCTCCTGGACTTCCGCAGAAAAGTAAACAAATGCTACAGGGGCCGTTCTTGTCCGATAATTGTTCATTGC
AGTGACGGTGCAGGCCGGAGCGGCACCTACGTCCTGATCGACATGGTTCTCAACAAGATGGCCAAAGGTGCTAAAGA
GATTGATATCGCAGCGACCCTGGAGCACTTGAGGGACCAGAGACCCGGCATGGTCCAGACGAAGGAGCAGTTTGAGT
TCGCGCTGACAGCCGTGGCTGAGGAGGTGAACGCCATCCTCAAGGCCCTTCCCCAGTGAGCGGCAGCGTCAGGGCC
TCAGGGGAGCCCCCACCCACGGATGTTGTCAGGAATCATGATCTGACTTTAATTGTGTGTCTTCTTCTATTATAACTGC
ATAGTAATAGGGCCCTTAGCTCTCCCGTAGTCAGCGCAGTTTAGCAGTTAAAAGTGTATTTTTGTTTAATCAAACAA
TAATAAAGAGAGATTTGTGGAAAAATCCAGTTACGGGTGGAGGGGAATCGGTTCATCAATTTTCACTTGCTTAAAAA
AAATACTTTTTCTTAAAGCACCCGTTCACCTTCTTGGTTGAAGTTGTGTTAACAATGCAGTAGCCAGCACGTTCGAG
GCGGTTTCCAGGAAGAGTGTGCTTGTCATCTGCCACTTTCGGGAGGGTGGATCCACTGTGCAGGAGTGGCCGGGGAA
GCTGGCAGCACTCAGTGAGGCCGCCCGGCACACAAGGCACGTTTGGCATTTCTCTTTGAGAGAGTTTATCATTGGGA
GAAGCCGCGGGACAGAACTGAACGTCCTGCAGCTTCGGGGCAAGTGAGACAATCACAGCTCCTCGCTGCGTCTCCA
TCAACACTGCGCCGGGTACCATGGACGGCCCCGTCAGCCACACCGGTCAGCCCAAGCAGAGTGATTCAGGGGCTCCC
CGGGGGCAGACACCTGTGCACCCCATGAGTAGTGCCCACTTGAGGCTGGCACTCCCCTGACCTCACCTTTGCAAAGT
TACAGATGCACCCCAACATTGAGATGTGTTTTTAATGTTAAAATATTGATTTCTACGTTATGAAAACAGATGCCCCC
GTGAATGCTTACCTGTGAGATAACCACAACCAGGAAGAACAAATCTGGGCATTGAGCAAGCTATGAGGGTCCCCGGG
AGCACACGAACCCTGCCAGGCCCCGCTGGCTCCTCCAGGCACGTCCCGGACCTGTGGGGCCCCAGAGA
```

FIGURE 20B

```
GGGGACATTTCCCTCCTGGGAGAGAAGGAGATCAGGGCAACTCGGAGAGGGCTGCGAGCATTTCCCTCCCGGGAGAG
GAAATCAGGGCGACCTGCACGCACTGCGTAGAGCCTGGAAGGGAAGTGAGAAACCAGCCGACCGGCCCTGCCCCTCT
TCCCGGGATCACTTAATGAACCACGTGTTTTGACATCATGTTAACCTAAGCACGTACAGATGATTCCGGATTTGACA
AAATAACATTTGAGTATCCGATTCGCCATCACCCCTACCCCCGAAATAGGACAACTCACTTCATTGACCAGGATGAT
CACATGGAAGGCGGCGCAGAGGCAGCTGTGTGGGCTGCAGATTTCCTGTGTGGGGTTCAGCGTATAAAACGCACCTC
CATCCCGCCCTTCCCACAGCATTCCTCCATCTTAGATAGATGGTACTCTCCAAAGGCCCTACCAGAGGGAACACGGC
CTACTGAGCGGACAGAATGATGCCAAAATATTGCTTATGTCTCTACATGGTATTGTAATGAATATCTGCTTTAATAT
AGCTATCATTTCTTTTCCAAAATTACTTCTCTTTATCTGGAATTTAATTAATCGAAATGAATTTATCTGAATATAGG
AAGCATATGCCTACTTGTAATTTCTAACTACTTATGTTTGAAGAGAAACCTCCGGTGTGAGATATACAAATATATTT
AATTGTGTCATATTAAACTTCCCGGAATTC
```

FIGURE 21

GCATCTGGTTTGTCAGATCCGAGAGGCTCTGAAACTGCGGAGCGGCCACCGGACGCCTTCTGGAGCAGGTAGCAGCA
TGCAGCCGCCTCCAAGTCTGTGCGGACGCGCCCTGGTTGCGCTGGTTCTTGCCTGCGGCCTGTCGCGGATCTGGGGA
GAGGAGAGAGGCTTCCCGCCTGACAGGGCCACTCCGCTTTTGCAAACCGCAGAGATAATGACGCCACCCACTAAGAC
CTTATGGCCCAAGGGTTCCAACGCCAGTCTGGCGCGGTCGTTGGCACCTGCGGAGGTGCCTAAAGGAGACAGGACGG
CAGGATCTCCGCCACGCACCATCTCCCCTCCCCCGTGCCAAGGACCCATCGAGATCAAGGAGACTTTCAAATACATC
AACACGGTTGTGTCCTGCCTTGTGTTCGTGCTGGGGATCATCGGGAACTCCACACTTCTGAGAATTATCTACAAGAA
CAAGTGCATGCGAAACGGTCCCAATATCTTGATCGCCAGCTTGGCTCTGGGAGACCTGCTGCACATCGTCATTGACA
TCCCTATCAATGTCTACAAGCTGCTGGCAGAGGACTGGCCATTTGGAGCTGAGATGTGTAAGCTGGTGCCTTTCATA
CAGAAAGCCTCCGTGGGAATCACTGTGCTGAGTCTATGTGCTCTGAGTATTGACAGATATCGAGCTGTTGCTTCTTG
GAGTAGAATTAAAGGAATTGGGGTTCCAAAATGGACAGCAGTAGAAATTGTTTTGATTTGGGTGGTCTCTGTGGTTC
TGGCTGTCCCTGAAGCCATAGGTTTTGATATAATTACGATGGACTACAAAGGAAGTTATCTGCGAATCTGCTTGCTT
CATCCCGTTCAGAAGACAGCTTTCATGCAGTTTTACAAGACAGCAAAAGATTGGTGGCTGTTCAGTTTCTATTTCTG
CTTGCCATTGGCCATCACTGCATTTTTTTATACACTAATGACCTGTGAAATGTTGAGAAAGAAAAGTGGCATGCAGA
TTGCTTTAAATGATCACCTAAAGCAGAGACGGGAAGTGGCCAAAACCGTCTTTTGCCTGGTCCTTGTCTTTGCCCTC
TGCTGGCTTCCCCTTCACCTCAGCAGGATTCTGAAGCTCACTCTTTATAATCAGAATGATCCCAATAGATGTGAACT
TTTGAGCTTTCTGTTGGTATTGGACTATATTGGTATCAACATGGCTTCACTGAATTCCTGCATTAACCCAATTGCTC
TGTATTTGGTGAGCAAAAGATTCAAAAACTGCTTTAAGTCATGCTTATGCTGCTGGTGCCAGTCATTTGAAGAAAAA
CAGTCCTTGGAGGAAAAGCAGTCGTGCTTAAAGTTCAAAGCTAATGATCACGGATATGACAACTTCCGTTCCAGTAA
TAAATACAGCTCATCTTGAAAGAAAAAAAAAAAAAAAAAAAAAAAAAAAAAAAAAAAAAAAAAAA

FIGURE 22

MKENYCLQAALVCLGMLCHSHAFAPERRGHLRPSFHGHHEKGKEGQVLQRSKRGWVWNQFFVIEEYTGPDPVLVGRL
HSDIDSGDGNIKYILSGEGAGTIFVIDDKSGNIHATKTLDREERAQYTLMAQAVDRDTNRPLEPPSEFIVKVQDIND
NPPEFLHETYHANVPERSNVGTSVIQVTASDADDPTYGNSAKLVYSILEGQPYFSVEAQTGIIRTALPNMDREAKEE
YHVVIQAKDMGGHMGGLSGTTKVTITLTDVNDNPPKFPQRLYQMSVSEAAVPGEEVGRVKAKDPDIGENGLVTYNIV
DGDGMESFEITTDYETQEGVIKLKKPVDFETERAYSLKVEAANVHIDPKFISNGPFKDTVTVKISVEDADEPPMFLA
PSYIHEVQENAAAGTVVGRVHAKDPDAANSPIRYSIDRHTDLDRFFTINPEDGFIKTTKPLDREETAWLNITVFAAE
IHNRHQEAQVPVAIRVLDVNDNAPKFAAPYEGFICESDQTKPLSNQPIVTISADDKDDTANGPRFIFSLPPEIIHNP
NFTVRDNRDNTAGVYARRGGFSRQKQDLYLLPIVISDGGIPPMSSTNTLTIKVCGCDVNGALLSCNAEAYILNAGLS
TGALIAILACIVILLVIVVLFVTLRRQKKEPLIVFEEEDVRENIITYDDEGGGEEDTEAFDIATLQNPDGINGFIPR
KDIKPEYQYMPRPGLRPAPNSVDVDDFINTRIQEADNDPTAPPYDSIQIYGYEGRGSVAGSLSSLESATTDSDLDYD
YLQNWGPRFKKLADLYGSKDTFDDDS

Signal sequence.
amino acids 1-22

Transmembrane domain.
amino acids 617-637

N-glycosylation sites.
amino acids 455-458, 540-543

Glycosaminoglycan attachment sites.
amino acids 83-86, 93-96

N-myristoylation sites.
amino acids 108-113, 215-220, 242-247, 246-251, 247-252, 399-404, 594-599, 599-604, 614-619, 618-623, 749-754, 753-758, 787-792

Cadherins extracellular repeated domain signatures.
amino acids 147-157, 256-266, 476-486

Cadherin cytoplasmic region.
amino acids 641-789

Cadherin domains.
amino acids 59-150, 164-259, 273-375, 388-479, 492-593

FIGURE 23

MYGKSSTRAVLLLLGIQLTALWPIAAVEIYTSRVLEAVNGTDARLKCTFSSFAPVGDALTVTWNFRPLDGGPEQFVF
YYHIDPFQPMSGRFKDRVSWDGNPERYDASILLWKLQFDDNGTYTCQVKNPPDVDGVIGEIRLSVVHTVRFSEIHFL
ALAIGSACALMIIIVIVVVLFQHYRKKRWAERAHKVVEIKSKEEERLNQEKKVSVYLEDTD

Signal sequence.
amino acids 1-21

N-glycosylation sites.
amino acids 39-42, 118-121 cAMP- and cGMP-dependent protein kinase phosphorylation site.
amino acids 205-208

N-myristoylation sites.
amino acids 15-20, 119-124, 159-164

Immunoglobulin domain.
amino acids 40-125

FIGURE 24

MAEQQGRELEAECPVCWNPFNNTFHTPKMLDCCHSFCVECLAHLSLVTPARRRLLCPLCRQPTVLASGQPVTDLPTD
TAMLTLLRLEPHHVILEGHQLCLKDQPKSRYFLRQPRVYTLDLGPQPGGQTGPPPDTASATVSTPILIPSHHSLREC
FRNPQFRIFAYLMAVILSVTLLLIFSIFWTKQFLWGVG

Transmembrane domain.
amino acids 162-182

N-glycosylation site.
amino acids 21-24

N-myristoylation site.
amino acids 68-73

Zinc finger, C3HC4 type, signature.
amino acids 32-41

FIGURE 25

MATAAGATYFQRGSLFWFTVITLSFGYYTWVVFWPQSIPYQNLGPLGPFTQYLVDHHHTLLCNGYWLAWLIHVGESL
YAIALCKHKGITSGRAQLLWFLQTFFFGIASLTILIAYKRKRQKQT

Transmembrane domain.
amino acids 57-77, 92-112

N-myristoylation site.
amino acids 87-92

Leucine zipper pattern.
amino acids 46-67

FIGURE 26

MASKIGSRRWMLQLIMQLGSVLLTRCPFWGCFSQLMLYAERAEARRKPDIPVPYLYFDMGAAVLCASFMSFGVKRRW
FALGAALQLAISTYAAYIGGYVHYGDWLKVRMYSRTVAIIGGFLVLASGAGELYRRKPRSRSLQSTGQVFLGIYLIC
VAYSLQHSKEDRLAYLNHLPGGELMIQLFFVLYGILALAFLSGYYVTLAAQILAVLLPPVMLLIDGNVAYWHNTRRV
EFWNQMKLLGESVGIFGTAVILATDG

Transmembrane domains.
amino acids 6-26, 51-71, 106-126, 138-158, 174-194, 201-221, 237-256

Glycosaminoglycan attachment site.
amino acids 125-128

N-myristoylation site.
amino acids 245-250

FIGURE 27

```
GRGSPLALLIRMKTLLFGVWALLALILCPGVPEELFEVSIWPSQALVEFGQSLVCNCSTTCPDPGPSGIETFLKKTQ
VDKGPQWKEFLLEDVTENSILQCFFSCAGIQKDTSLGITVYQPPEQVILELQPAWVAVDEAFTVKCHVPSVAPLESL
TLALLQGNQELHRKNFTSLAVASQRAEVIISVRAQKENDRCNSSCHAELDLSLQGGRLFQGSSPIRIVRIFEFSQSP
HIWVSSLLEAGMAETVSCEVARVFPAKEVMFHMFLEDQELSSSLSWEGDTAWANATIRTMEAGDQELSCFASLGAME
QKTRKLVHSYSFPPPILELKESYPLAGTDINVTCSGHVLTSPSPTLRLQGAPDLPAGEPAWLLLTAREEDDGXNFSC
EASLVVQGQRLMKTTVIQLHILKPQLEESSCPGKQTWLEGMEHTLACVPKGNPAPALVCTWNGVVFDLEVPQKAT
```

Signal sequence.
amino acids 1-30

N-glycosylation sites.
amino acids 56-59, 169-172, 196-199, 285-288, 339-342, 382-385

N-myristoylation sites.
amino acids 3-8, 242-247, 335-340, 380-385, 425-430

Intercellular adhesion molecule (ICAM) homology.
amino acids 17-123

FIGURE 28

MLPRLLLLICAPLCEPAELFLIASPSHPTEGSPVTLTCKMPFLQSSDAQFQFCFFRDTRALGPGWSSSPKLQIAAMW
KEDTGSYWCEAQTMASKVLRSRRSQINVHIPVSRPILMLRAPRAQAAVEDVLELHCEALRGSPPILYWFYHEDITLG
SRSAPSGGGASFNLSLTEEHSGNYSCEANNGLGAQRSEAVTLNFTVPTGARSNHLTSGVIEGLLSTLGPATVALLFC
YGLKRKIGRRSARDPLRSLPALPQEFTYLNSPTPGQLQPIYENVNVVSGDEVYSLAYYNQPEQESVAAETLGTHMED
KVSLDIYSRLRKANITDVDYEDAM

Signal sequence.
amino acids 1-16

Transmembrane domain.
amino acids 211-231

N-glycosylation sites.
amino acids 167-170, 177-180, 197-200, 322-325

Glycosaminoglycan attachment site.
amino acids 160-163

N-myristoylation sites.
amino acids 31-36, 82-87, 161-166, 163-168, 176-181, 187-192, 203-208, 212-217, 216-221

Amidation site.
amino acids 238-241

Immunoglobulin domains.
amino acids 31-88, 126-182

FIGURE 29

MLLWASLLAFAPVCGQSAAAHKPVISVHPPWTTFFKGERVTLTCNGFQFYATEKTTWYHRHYWGEKLTLTPGNTLEV
RESGLYRCQARGSPRSNPVRLLFSSDSLILQAPYSVFEGDTLVLRCHRRRKEKLTAVKYTWNGNILSISNKSWDLLI
PQASSNNNGNYRCIGYGDENDVFRSNFKIIKIQELFPHPELKATDSQPTEGNSVNLSCETQLPPERSDTPLHFNFFR
DGEVILSDWSTYPELQLPTVWRENSGSYWCGAETVRGNIHKHSPSLQIHVQRIPVSGVLLETQPSGGQAVEGEMLVL
VCSVAEGTGDTTFSWHREDMQESLGRKTQRSLRAELELPAIRQSHAGGYYCTADNSYGPVQSMVLNVTVRETPGNRD
GLVAAGATGGLLSALLLAVALLFHCWRRRKSGVGFLGDETRLPPAPGPGESSHSICPAQVELQSLYVDVHPKKGDLV
YSEIQTTQLGEEEEANTSRTLLEDKDVSVVYSEVKTQHPDNSAGKISSKDEES

Signal sequence.
amino acids 1-15

Transmembrane domain.
amino acids 387-407

N-glycosylation sites.
amino acids 147-150, 209-212, 374-377, 478-481

Glycosaminoglycan attachment site.
amino acids 416-419 cAMP- and cGMP-dependent protein kinase phosphorylation site.
amino acids 413-416

Tyrosine kinase phosphorylation site.
amino acids 457-463

N-myristoylation sites.
amino acids 15-20, 81-86, 89-94, 140-145, 163-168, 205-210, 257-262, 315-320, 355-360, 382-387, 386-391, 391-396, 394-399, 395-400

Amidation site.
amino acids 332-335

Immunoglobulin domains.
amino acids 37-87, 116-169, 205-263, 303-361

FIGURE 30

MTVIRFFPAASATKRVLPPVLRVSSPRTWNPNVPESPRIPAPRLPKRMSGAPTAGAALMLCAATAVLLSAQGGPVQS
KSPRFASWDEMNVLAHGLLQLGQGLREHAERTRSQLSALERRLSACGSACQGTEGSTDLPLAPESRVDPEVLHSLQT
QLKAQNSRIQQLFHKVAQQQRHLEKQHLRIQHLQSQFGLLDHKHLDHEVAKPARRKRLPEMAQPVDPAHNVSRLHRL
PRDCQELFQVGERQSGLFEIQPQGSPPFLVNCKMTSDGGWTVIQRRHDGSVDFNRPWEAYKAGFGDPHGEFWLGLEK
VHSITGDRNSRLAVQLRDWDGNAELLQFSVHLGGEDTAYSLQLTAPVAGQLGATTVPPSGLSVPFSTWDQDHDLRRD
KNCAKSLSGGWWFGTCSHSNLNGQYFRSIPQQRQKLKKGIFWKTWRGRYYPLQATTMLIQPMAAEAAS

Transmembrane domain.
amino acids 49-69

N-glycosylation site.
amino acids 224-227 cAMP- and cGMP-dependent protein kinase phosphorylation sites.
amino acids 46-49, 118-121

N-myristoylation sites.
amino acids 50-55, 129-134, 341-346, 357-362

Fibrinogen beta and gamma chains C-terminal domain signature.
amino acids 396-408

Fibrinogen beta and gamma chains.
amino acids 231-447

FIGURE 31

MLLWVILLVLAPVSGQFARTPRPIIFLQPPWTTVFQGERVTLTCKGFRFYSPQKTKWYHRYLGKEILRETPDNILEV
QESGEYRCQAQGSPLSSPVHLDFSSEMGFPHAAQANVELLGSSDLLT

Signal sequence.
amino acids 1-15

N-myristoylation site.
amino acids 89-94

FIGURE 32

```
MAGPRPSPWARLLLAALISVSLSGTLANRCKKAPVKSCTECVRVDKDCAYCTDEMFRDRRCNTQAELLAAGCQRESI
VVMESSFQITEETQIDTTLRRSQMSPQGLRVRLRPGEERHFELEVFEPLESPVDLYILMDFSNSMSDDLDNLKKMGQ
NLARVLSQLTSDYTIGFGKFVDKVSVPQTDMRPEKLKEPWPNSDPPFSFKNVISLTEDVDEFRNKLQGERISGNLDA
PEGGFDAILQTAVCTRDIGWRPDSTHLLVFSTESAFHYEADGANVLAGIMSRNDERCHLDTTGTYTQYRTQDYPSVP
TLVRLLAKHNIIPIFAVTNYSYSYYEKLHTYFPVSSLGVLQEDSSNIVELLEEAFNRIRSNLDIRALDSPRGLRTEV
TSKMFQKTRTGSFHIRRGEVGIYQVQLRALEHVDGTHVCQLPEDQKGNIHLKPSFSDGLKMDAGIICDVCTCELQKE
VRSARCSFNGDFVCGQCVCSEGWSGQTCNCSTGSLSDIQPCLREGEDKPCSGRGECQCGHCVCYGEGRYEGQFCEYD
NFQCPRTSGFLCNDRGRCSMGQCVCEPGWTGPSCDCPLSNATCIDSNGGICNGRGHCECGRCHCHQQSLYTDTICEI
NYSAIHPGLCEDLRSCVQCQAWGTGEKKGRTCEECNFKVKMVDELKRAEEVVVRCSFRDEDDDCTYSYTMEGDGAPG
PNSTVLVHKKKDCPPGSFWWLIPLLLLLLLPLLALLLLLCWKYCACCKACLALLPCCNRGHMVGFKEDHYMLRENLMA
SDHLDTPMLRSGNLKGRDVVRWKVTNNMQRPGFATHAASINPTELVPYGLSLRLARLCTENLLKPDTRECAQLRQEV
EENLNEVYRQISGVHKLQQTKFRQQPNAGKKQDHTIVDTVLMAPRSAKPALLKLTEKQVEQRAFHDLKVAPGYYTLT
ADQDARGMVEFQEGVELVDVRVPLFIRPEDDDEKQLLVEAIDVPAGTATLGRRLVNITIIKEQARDVVSFEQPEFSV
SRGDQVARIPVIRRVLDGGKSQVSYRTQDGTAQGNRDYIPVEGELLFQPGEAWKELQVKLLELQEVDSLLRGRQVRR
FHVQLSNPKFGAHLGQPHSTTIIIRDPDELDRSFTSQMLSSQPPPHGDLGAPQNPNAKAAGSRKIHFNWLPPSGKPM
GYRVKYWIQGDSESEAHLLDSKVPSVELTNLYPYCDYEMKVCAYGAQGEGPYSSLVSCRTHQEVPSEPGRLAFNVVS
STVTQLSWAEPAETNGEITAYEVCYGLVNDDNRPIGPMKKVLVDNPKNRMLLIENLRESQPYRYTVKARNGAGWGPE
REAIINLATQPKRPMSIPIIPDIPIVDAQSGEDYDSFLMYSDDVLRSPSGSQRPSVSDDTEHLVNGRMDFAFPGSTN
SLHRMTTTSAAAYGTHLSPHVPHRVLSTSSTLTRDYNSLTRSEHSHSTTLPRDYSTLTSVSSHDSRLTAGVPDTPTR
LVFSALGPTSLRVSWQEPRCERPLQGYSVEYQLLNGGELHRLNIPNPAQTSVVVEDLLPNHSYVFRVRAQSQEGWGR
EREGVITIESQVHPQSPLCPLPGSAFTLSTPSAPGPLVFTALSPDSLQLSWERPRRPNGDIVGYLVTCEMAQGGGPA
TAFRVDGDSPESRLTVPGLSENVPYKFKVQARTTEGFGPEREGIITIESQDGGPFPQLGSRAGLFQHPLQSEYSSIT
TTHTSATEPFLVDGPTLGAQHLEAGGSLTRHVTQEFVSRTLTTSGTLSTHMDQQFFQT
```

Signal sequence.
amino acids 1-23
Transmembrane domain.
amino acids 711-731
N-glycosylation sites.
amino acids 327-330, 491-494, 579-582, 617-620, 695-698, 980-983, 1523-1526
Glycosaminoglycan attachment site.
amino acids 513-516
Tyrosine kinase phosphorylation sites.
amino acids 43-50, 401-408, 674-682, 1596-1604
N-myristoylation sites.
amino acids 24-29, 153-158, 234-239, 420-425, 477-482, 487-492, 560-565, 587-592, 588-593, 782-787, 1031-1036, 1089-1094, 1093-1098, 1383-1388, 1563-1568, 1613-1618, 1614-1619, 1635-1640, 1676-1681, 1719-1724, 1739-1744
Amidation sites.
amino acids 875-878, 974-977
Cell attachment sequence.
amino acids 1003-1006
EGF-like domain cysteine pattern signatures.
amino acids 479-490, 562-573
Integrins beta chain cysteine-rich domain signature.
amino acids 512-525, 590-603
Integrin, beta chain homology.
amino acids 37-455
Calx-beta domain.
amino acids 979-1084
Fibronectin type III domain.
amino acids 1127-1208, 1220-1310, 1458-1542, 1571-1658

FIGURE 33

MTLDRPGEGATMLKTFTVLLFCIRMSLGMTSIVMDPQPELWIESNYPQAPWENITLWCRSPSRISSKFLLLKDKTQM
TWIRPSHKTFQVSFLIGALTESNAGLYRCCYWKETGWSKPSKVLELEAPGQLPKPIFWIQAETPALPGCNVNILCHG
WLQDLVFMLFKEGYAEPVDYQVPTGTMAIFSIDNLTPEDEGVYICRTHIQMLPTLWSEPSNPLKLVVAGLYPKPTLT
AHPGPIMAPGESLNLRCQGPIYGMTFALMRVEDLEKSFYHKKTIKNEANFFFQSLKIQDTGHYLCFYYDASYRGSLL
SDVLKIWVTDTFPKTWLLARPSAVVQMGQNVSLRCRGPVDGVGLALYKKGEDKPLQFLDATSIDDNTSFFLNNVTYS
DTGIYSCHYLLTWKTSIRMPSHNTVELMVVDKPPKPSLSAWPSTVFKLGKAITLQCRVSHPVLEFSLEWEERETFQR
FSVNGDFIISNVDGKGTGTYSCSYRVETHPNMWSHRSEPLKLMGPAGYLTWNYVLNEAIRLSLIMQLVALLLVVLWI
RWKCRRLRIREAWLLGTAQGVTMLFIVTALLCCGLCNGVLIEETEIVMPTPKPELWAETNFPLAPWKNLTLWCRSPS
GSTKEFVLLKDGTGWIATRPASEQVRAAFPLGALTQSHTGSYHCHSWEEMAVSEPSEALELVGTDILPKPVISASPT
IRGQELQLRCKGWLAGMGFALYKEGEQEPVQQLGAVGREAFFTIQRMEDKDEGNYSCRTHTEKLPFKWSEPSEPLEL
VIKEMYPKPFFKTWASPVVTPGARVTFNCSTPHQHMSFILYKDGSEIASSDRSWASPGASAAHFLIISVGIGDGGNY
SCRYYDFSIWSEPSDPVELVVTEFYPKPTLLAQPGPVVFPGKSVILRCQGTFQGMRFALLQEGAHVPLQFRSVSGNS
ADFLLHTVGAEDSGNYSCIYYETTMSNRGSYLSMPLMIWVTDTFPKPWLFAEPSSVVPMGQNVTLWCRGPVHGVGYI
LHKEGEATSMQLWGSTSNDGAFPITNISGTSMGRYSCCYHPDWTSSIKIQPSNTLELLVTGLLPKPSLLAQPGPMVA
PGENMTLQCQGELPDSTFVLLKEGAQEPLEQQRPSGYRADFWMPAVRGEDSGIYSCVYYLDSTPFAASNHSDSLEIW
VTDKPPKPSLSAWPSTMFKLGKDITLQCRGPLPGVEFVLEHDGEEAPQQFSEDGDFVINNVEGKGIGNYSCSYRLQA
YPDIWSEPSDPLELVGAAGPVAQECTVGNIVRSSLIVVVVVALGVVLAIEWKKWPRLRTRGSETDGRDQTIALEECN
QEGEPGTPANSPSSTSQRISVELPVPI

Signal sequence.
amino acids 1-28
Transmembrane domains.
amino acids 517-537, 555-575, 1261-1281
N-glycosylation sites.
amino acids 53-56, 338-341, 374-377, 381-384, 607-610, 747-750, 798-801,
846-849, 939-942, 986-989, 1027-1030, 1082-1085, 1147-1150, 1223-1226
Tyrosine kinase phosphorylation sites.
amino acids 287-295, 1125-1132
N-myristoylation sites.
amino acids 102-107, 145-150, 195-200, 254-259, 305-310, 336-341, 349-354,
388-393, 480-485, 555-560, 573-578, 656-661, 709-714, 746-751, 792-797, 814-819,
828-833, 840-845, 844-849, 845-850, 897-902, 901-906, 933-938, 938-943, 953-958,
984-989, 1015-1020, 1030-1035, 1130-1135, 1222-1227, 1276-1281, 1315-1320
Immunoglobulin domains.
amino acids 51-108, 145-201, 241-298, 336-394, 434-486, 605-662, 696-752,
792-851, 888-944, 984-1040, 1080-1136, 1176-1228

FIGURE 34

```
MAPEPAPGRTMVPLVPALVMLGLVAGAHGDSKPVFIKVPEDQTGLSGGVASFVCQATGEPKPRITWMKKGKKVSSQR
FEVIEFDDGAGSVLRIQPLRVQRDEAIYECTATNSLGEINTSAKLSVLEEEQLPPGFPSIDMGPQLKVVEKARTATM
LCAAGGNPDPEISWFKDFLPVDPATSNGRIKQLRSGALQIESSEESDQGKYECVATNSAGTRYSAPANLYVRVRRVA
PRFSIPPSSQEVMPGGSVNLTCVAVGAPMPYVKWMMGAEELTKEDEMPVGRNVLELSNVVRSANYTCVAISSLGMIE
ATAQVTVKALPKPPIDLVVTETTATSVTLTWDSGNSEPVTYYGIQYRAAGTEGPFQEVDGVATTRYSIGGLSPFSEY
AFRVLAVNSIGRGPPSEAVRARTGEQAPSSPPRRVQARMLSASTMLVQWEPPEEPNGLVRGYRVYYTPDSRRPPNAW
HKHNTDAGLLTTVGSLLPGITYSLRVLAFTAVGDGPPSPTIQVKTQQGVPAQPADFQAEVESDTRIQLSWLLPPQER
IIMYELVYWAAEDEDQQHKVTFDPTSSYTLEDLKPDTLYRFQLAARSDMGVGVFTPTIEARTAQSTPSAPPQKVMCV
SMGSTTVRVSWVPPPADSRNGVITQYSVAHEAVDGEDRGRHVVDGISREHSSWDLVGLEKWTEYRVWVRAHTDVGPG
PESSPVLVRTDEDVPSGPPRKVEVEPLNSTAVHVYWKLPVPSKQHGQIRGYQVTYVRLENGEPRGLPIIQDVMLAEA
QWRPEESEDYETTISGLTPETTYSVTVAAYTTKGDGARSKPKIVTTTGAVPGRPTMMISTTAMNTALLQWHPPKELP
GELLGYRLQYCRADEARPNTIDFGKDDQHFTVTGLHKGTTYIFRLAAKNRAGLGEEFEKEIRTPEDLPSGFPQNLHV
TGLTTSTTELAWDPPVLAERNGRIISYTVVFRDINSQQELQNITTDTRFTLTGLKPDTTYDIKVRAWTSKGSGPLSP
SIQSRTMPVEQVFAKNFRVAAAMKTSVLLSWEVPDSYKSAVPFKILYNGQSVEVDGHSMRKLIADLQPNTEYSFVLM
NRGSSAGGLQHLVSIRTAPDLLPHKPLPASAYIEDGRFDLSMPHVQDPSLVRWFYIVVVPIDRVGGSMLTPRWSTPE
ELELDELLEAIEQGGEEQRRRRRQAERLKPYVAAQLDVLPETFTLGDKKNYRGFYNRPLSPDLSYQCFVLASLKEPM
DQKRYASSPYSDEIVVQVTPAQQQEEPEMLWVTGPVLAVILIILIVIAILLFKRKRTHSPSSKDEQSIGLKDSLLAH
SSDPVEMRRLNYQTPGMRDHPPIPITDLADNIERLKANDGLKFSQEYESIDPGQQFTWENSNLEVNKPKNRYANVIA
YDHSRVILTSIDGVPGSDYINANYIDGYRKQNAYIATQGPLPETMGDFWRMVWEQRTATVVMMTRLEEKSRVKCDQY
WPARGTETCGLIQVTLLDTVELATYTVRTFALHKSGSSEKRELRQFQFMAWPDHGVPEYPTPILAFLRRVKACNPLD
AGPMVVHCSAGVGRTGCFIVIDAMLERMKHEKTVDIYGHVTCMRSQRNYMVQTEDQYVFIHEALLEAATCGHTEVPA
RNLYAHIQKLGQVPPGESVTAMELEFKLLASSKAHTSRFISANLPCNKFKNRLVNIMPYELTRVCLQPIRGVEGSDY
INASFLDGYRQQKAYIATQGPLAESTEDFWRMLWEHNSTIIVMLTKLREMGREKCHQYWPAERSARYQYFVVDPMAE
YNMPQYILREFKVTDARDGQSRTIRQFQFTDWPEQGVPKTGEGFIDFIGQVHKTKEQFGQDGPITVHCSAGVGRTGV
FITLSIVLERMRYEGVVDMFQTVKTLRTQRPAMVQTEDQYQLCYRAALEYLGSFDHYAT
```

Signal sequence.
amino acids 1-29
Transmembrane domain.
amino acids 1262-1282
N-glycosylation sites.
amino acids 117-120, 250-253, 295-298, 721-724, 966-969, 1696-1699, 1731-1734
cAMP- and cGMP-dependent protein kinase phosphorylation site.
amino acids 71-74, 1286-1289
Tyrosine kinase phosphorylation sites.
amino acids 97-105, 773-780, 1229-1237, 1687-1694
N-myristoylation sites.
amino acids 22-27, 44-49, 47-52, 214-219, 246-251, 305-310, 368-373, 442-447,
470-475, 481-486, 739-744, 818-823, 881-886, 926-931, 1081-1084, 1301-1306,
1349-1354, 1362-1367, 1399-1404, 1468-1473, 1551-1556, 1688-1693, 1790-1795,
1807-1812, 1842-1847, 1847-1852
Amidation site.
amino acids 69-72
Leucine zipper pattern.
amino acids 1262-1283
Myb DNA-binding domain repeat signature 1.
amino acids 1151-1159
Tyrosine specific protein phosphatases active sites.
amino acids 1546-1558, 1837-1849
Immunoglobulin domains.
amino acids 47-109, 149-209, 246-300
Fibronectin type III domains.
amino acids 319-401, 413-500, 512-594, 606-696, 708-809, 821-904, 915-1000
Protein-tyrosine phosphatase homology.
amino acids 1375-1606, 1664-1897

FIGURE 35

MRRAALWLWLCALALSLQLALPQIVATNLPPEDQDGSGDDSDNFSGSGAGALQDITLSQQTPSTWKDTQLLTAIPTS
PEPTGLEATAASTSTLPAGEGPKEGEAVVLPEVEPGLTAREQEATPRPRETTQLPTTHQASTTTATTAQEPATSHPH
RDMQPGHHETSTPAGPSQADLHTPHTEDGGPSATERAAEDGASSQLPAAEGSGEQDFTFETSGENTAVVAVEPDRRN
QSPVDQGATGASQGLLDRKEVLGGVIAGGLVGLIFAVCLVGFMLYRMKKKDEGSYSLEEPKQANGGAYQKPTKQEEFYA

Signal sequence.
amino acids 1-22

Transmembrane domain.
amino acids 252-272

N-glycosylation site.
amino acids 43-46

Glycosaminoglycan attachment sites.
amino acids 45-48, 47-50

Tyrosine kinase phosphorylation site.
amino acids 279-286

N-myristoylation sites.
amino acids 46-51, 82-87, 183-188, 238-243, 241-246, 254-259, 255-260, 259-264, 263-268

Syndecans signature.
amino acids 276-289

Syndecan domain.
amino acids 3-308

FIGURE 36

MKIFLPVLLAALLGVERASSLMCFSCLNQKSNLYCLKPTICSDQDNYCVTVSASAGIGNLVTFGHSLSKTCSPACPI
PEGVNVGVASMGISCCQSFLCNFSAADGGLRASVTLLGAGLLLSLLPALLRFGP

Signal sequence.
amino acids 1-20

Transmembrane domain.
amino acids 108-128

N-glycosylation site.
amino acids 99-102

N-myristoylation sites.
amino acids 14-19, 58-63, 80-85, 89-94, 105-110, 106-111, 117-122 u-PAR/Ly-6 domain.
amino acids 21-100

FIGURE 37

MDGKKCSVWMFLPLVFTLFTSAGLWIVYFIAVEDDKILPLNSAERKPGVKHAPYISIAGDDPPASCVFSQVMNMAAF
LALVVAVLRFIQLKPKVLNPWLNISGLVALCLASFGMTLLGNFQLTNDEEIHNVGTSLTFGFGTLTCWIQAALTLKV
NIKNEGRRVGIPRVILSASITLCVVLYFILMAQSIHMYAARVQWGLVMCFLSYFGTFAVEFRHYRYEIVCSEYQENF
LSFSESLSEASEYQTDQV

Transmembrane domains.
amino acids 7-27, 65-85, 97-117, 131-151, 166-186

N-glycosylation site.
amino acids 100-103 cAMP- and cGMP-dependent protein kinase phosphorylation site.
amino acids 4-7

N-myristoylation sites.
amino acids 132-137, 140-145, 199-201

Amidation sites.
amino acids 2-5, 159-162

FIGURE 38

MELALLCGLVVMAGVIPIQGGILNLNKMVKQVTGKMPILSYWPYGCHCGLGGRGQPKDATDWCCQTHDCCYDHLKTQ
GCGIYKDYYRYNFSQGNIHCSDKGSWCEQQLCACDKEVAFCLKRNLDTYQKRLRFYWRPHCRGQTPGC

Signal sequence.
amino acids 1-17

N-glycosylation site.
amino acids 89-92

N-myristoylation sites.
amino acids 20-25, 45-50, 93-98, 140-145

Phospholipase A2 histidine active site.
amino acids 63-70

Phospholipase A2 aspartic acid active site.
amino acids 108-118

Phospholipase A2 homology.
amino acids 21-145

FIGURE 39

```
MYIRVSYDTKPDSLLHLMVKDWQLELPKLLISVHGGLQNFEMQPKLKQVFGKGLIKAAMTTGAWIFTGGVSTGVISH
VGDALKDHSSKSRGRVCAIGIAPWGIVENKEDLVGKDVTRVYQTMSNPLSKLSVLNNSHTHFILADNGTLGKYGAEV
KLRRLLEKHISLQKINTRLGQGVPLVGLVVEGGPNVVSIVLEYLQEEPPIPVVICDGSGRASDILSFAHKYCEEGGI
INESLREQLLVTIQKTFNYNKAQSHQLFAIIMECMKKKELVTVFRMGSEGQQDIEMAILTALLKGTNVSAPDQLSLA
LAWNRVDIARSQIFVFGPHWTPLGSLAPPTDSKATEKEKKPPMATTKGGRGKGKGKKKGKVKEEVEEETDPRKIELL
NWVNALEQAMLDALVLDRVDFVKLLIENGVNMQHFLTIPRLEELYNTRLGPPNTLHLLVRDVKKSNLPPDYHISLID
IGLVLEYLMGGAYRCNYTRKNFRTLYNNLFGPKRPKALKLLGMEDDEPPAKGKKKKKKKKEEEIDIDVDDPAVSRFQ
YPFHELMVWAVLMKRQKMAVFLWQRGEESMAKALVACKLYKAMAHESSESDLVDDISQDLDNNSKDFGQLALELLDQ
SYKHDEQIAMKLLTYELKNWSNSTCLKLAVAAKHRDFIAHTCSQMLLTDMWMGRLRMRKNPGLKVIMGILLPPTILF
LEFRTYDDFSYQTSKENEDGKEKEEENTDANADAGSRKGDEENEHKKQRSIPIGTKICEFYNAPIVKFWFYTISYLG
YLLLFNYVILVRMDGWPSLQEWIVISYIVSLALEKIREILMSEPGKLSQKIKVWLQEYWNITDLVAISTFMIGAILR
LQNQPYMGYGRVIYCVDIIFWYIRVLDIFGVNKYLGPYVMMIGKMMIDMLYFVVIMLVVLMSFGVARQAILHPEEKP
SWKLARNIFYMPYWMIYGEVFADQIDLYAMEINPPCGENLYDEEGKRLPPCIPGAWLTPALMACYLLVANILLVNLL
IAVFNNTFFEVKSISNQVWKFQRYQLIMTFHDRPVLPPPMIILSHIYIIIMRLSGRCRKKREGDQEERDRGLKLFLS
DEELKRLHEFEEQCVQEHFREKEDEQQSSSDERIRVTSERVENMSMRLEEINERETFMKTSLQTVDLRLAQLEELSN
RMVNALENLAGIDRSDLIQARSRASSECEATYLLRQSSINSADGYSLYRYHFNGEELLFEDTSLSTSPGTGVRKKTC
SFRIKEEKDVKTHLVPECQNSLHLSLGTSTSATPDGSHLAVDDLKNAEESKLGPDIGISKEDDERQTDSKKEETISP
SLNKTDVIHGQDKSDVQNTQLTVETTNIEGTISYPLEETKITRYFPDETINACKTMKSRSFVYSRGRKLVGGVNQDV
EYSSITDQQLTTEWQCQVQKITRSHSTDIPYIVSEAAVQAEQKEQFADMQDEHHVAEAIPRIPRLSLTITDRNGMEN
LLSVKPDQTLGFPSLRSKSLHGHPRNVKSIQGKLDRSGHASSVSSLVIVSGMTAEEKKVKKEKASTETEC
```

Transmembrane domains.

amino acids 759-779, 828-848, 857-877, 893-913, 976-996, 992-1012, 1031-1051

N-glycosylation sites.

amino acids 133-136, 144-147, 233-236, 298-301, 478-481, 601-604, 635-638, 638-641, 830-833, 1006-1009, 1121-1124, 1312-1315 cAMP- and cGMP-dependent protein kinase phosphorylation site.

amino acids 1228-1231

Tyrosine kinase phosphorylation sites.

amino acids 697-704, 891-898

N-myristoylation sites.

amino acids 35-40, 53-58, 68-73, 69-74, 102-107, 211-216, 229-234, 296-301, 473-478, 728-733, 747-752, 1166-1171, 1259-1264, 1268-1273, 1319-1324

Amidation sites.

amino acids 362-365, 513-516, 968-971, 1374-1377

Ion transport protein homology.

amino acids 789-1005

FIGURE 40

MSTEKVDQKEEAGEKEVCGDQIKGPDKEEEPPAAASHGQGWRPGGRAARNARPEPGARHPALPAMVNDPPVPALLWA
QEVGQVLAGRARRLLLQFGVLFCTILLLLWVSVFLYGSFYYSYMPTVSHLSPVHFYYRTDCDSSTTSLCSFPVANVS
LTKGGRDRVLMYGQPYRVTLELELPESPVNQDLGMFLVTISCYTRGGRIISTSSRSVMLHYRSDLLQMLDTLVFSSL
LLFGFAEQKQLLEVELYADYRENSYVPTTGAIIEIHSKRIQLYGAYLRIHAHFTGLRYLLYNFPMTCAFIGVASNFT
FLSVIVLFSYMQWVWGGIWPRHRFSLQVNIRKRDNSRKEVQRRISAHQPGPEGQEESTPQSDVTEDGESPEDPSGTE
GQLSEEEKPDQQPLSGEEELEPEASDGSGSWEDAALLTEANLPAPAPASASAPVLETLGSSEPAGGALRQRPTCSSS

Transmembrane domains.
amino acids 94-114, 134-154, 292-312, 308-328

N-glycosylation sites.
amino acids 152-155, 306-309 cAMP- and cGMP-dependent protein kinase phosphorylation site.
amino acids 350-353

Tyrosine kinase phosphorylation site.
amino acids 240-248

N-myristoylation sites.
amino acids 44-49, 81-86, 96-101, 302-307, 361-366

Leucine zipper patterns.
amino acids 84-105, 91-112

FIGURE 41

MGPPLPLLLLLLLLLLPPRVLPAAPSSVPRGRQLPGRLGCLLEEGLCGASEACVNDGVFGRCQKVPAMDFYRYEVSPV
ALQRLRVALQKLSGTGFTWQDDYTQYVMDQELADLPKTYLRRPEASSPARPSKHSVGSERRYSREGGAALANALRRH
LPFLEALSQAPASDVLARTHTAQDRPPAEGDDRFSESILTYVAHTSALTYPPGPRTQLREDLLPRTLGQLQPDELSP
KVDSGVDRHHLMAALSAYAAQRPPAPPGEGSLEPQYLLRAPSRMPRPLLAPAAPQKWPSPLGDSEDPSSTGDGARIH
TLLKDLQRQPAEVRGLSGLELDGMAELMAGLMQGVDHGVARGSPGRAALGESGEQADGPKATLRGDSFPDDGVQDDD
DRLYQEVHRLSATLGGLLQDHGSRLLPGALPFARPLDMERKKSEHPESSLSSEEETAGVENVKSQTYSKDLLGQQPH
SEPGAAAFGELQNQMPGPSKEEQSLPAGAQEALSDGLQLEVQPSEEEARGYIVTDRDPLRPEEGRRLVEDVARLLQV
PSSAFADVEVLGPAVTFKVSANVQNVTTEDVEKATVDNKDKLEETSGLKILQTGVGSKSKLKFLPPQAEQEDSTKFI
ALTLVSLACILGVLLASGLIYCLRHSSQHRLKEKLSGLGGDPGADATAAYQELCRQRMATRPPDRPEGPHTSRISSV
SSQFSDGPIPSPSARSSASSWSEEPVQSNMDISTGHMILSYMEDHLKNKNRLEKEWEALCAYQAEPNSSFVAQREEN
VPKNRSLAVLTYDHSRVLLKAENSHSHSDYINASPIMDHDPRNPAYIATQGPLPATVADFWQMVWESGCVVIVMLTP
LAENGVRQCYHYWPDEGSNLYHIYEVNLVSEHIWCEDFLVRSFYLKNLQTNETRTVTQFHFLSWYDRGVPSSSRSLL
DFRRKVNKCYRGRSCPIIVHCSDGAGRSGTYVLIDMVLNKMAKGAKEIDIAATLEHLRDQRPGMVQTKEQFEFALTA
VAEEVNAILKALPQ

Signal sequence.
amino acids 1-21
Transmembrane domain.
amino acids 616-636
N-glycosylation sites.
amino acids 564-567, 760-763, 774-777, 898-901
Glycosaminoglycan attachment sites.
amino acids 90-93, 652-655
cAMP- and cGMP-dependent protein kinase phosphorylation sites.
amino acids 137-140, 425-428
N-myristoylation sites.
amino acids 44-49, 47-52, 91-96, 144-149, 338-343, 342-347, 346-351, 490-495,
628-633, 634-639, 655-660, 659-664, 852-857, 915-920, 948-953, 987-992
Amidation site.
amino acids 525-528
Cell attachment sequence.
amino acids 372-374
Tyrosine specific protein phosphatases active site.
amino acids 943-955
Protein-tyrosine phosphatase.
amino acids 770-1004

FIGURE 42

MQPPPSLCGRALVALVLACGLSRIWGEERGFPPDRATPLLQTAEIMTPPTKTLWPKGSNASLARSLAPAEVPKGDRT
AGSPPRTISPPPCQGPIEIKETFKYINTVVSCLVFVLGIIGNSTLLRIIYKNKCMRNGPNILIASLALGDLLHIVID
IPINVYKLLAEDWPFGAEMCKLVPFIQKASVGITVLSLCALSIDRYRAVASWSRIKGIGVPKWTAVEIVLIWVVSVV
LAVPEAIGFDIITMDYKGSYLRICLLHPVQKTAFMQFYKTAKDWWLFSFYFCLPLAITAFFYTLMTCEMLRKKSGMQ
IALNDHLKQRREVAKTVFCLVLVFALCWLPLHLSRILKLTLYNQNDPNRCELLSFLLVLDYIGINMASLNSCINPIA
LYLVSKRFKNCFKSCLCCWCQSFEEKQSLEEKQSCLKFKANDHGYDNFRSSNKYSSS

Transmembrane domains.
amino acids 1-19, 101-121, 137-157, 177-197, 216-236, 275-295, 323-343, 362-382

N-glycosylation sites.
amino acids 59-62, 119-122 cAMP- and cGMP-dependent protein kinase phosphorylation site.
amino acids 302-305

Tyrosine kinase phosphorylation site.
amino acids 424-430

N-myristoylation sites.
amino acids 57-62, 115-120, 170-175, 306-311, 371-376

7 transmembrane receptor homology.
amino acids 118-386

COMPOSITIONS AND METHODS FOR THE DIAGNOSIS AND TREATMENT OF TUMOR

This is a continuation of Ser. No. 11/486,298, filed 13 Jul. 2006 which is a continuation of U.S. non-provisional application Ser. No. 10/712,892, filed 13 Nov. 2003 which claims the benefit under 35 USC §119(e) of U.S. Provisional Application Ser. Nos. 60/437,344 filed on 31 Dec. 2002, 60/431,250 filed on 6 Dec. 2002, and 60/426,847 filed on 15 Nov. 2002, all of which are incorporated by reference in their entirety.

FIELD OF THE INVENTION

The present invention is directed to compositions of matter useful for the diagnosis and treatment of tumor in mammals and to methods of using those compositions of matter for the same.

BACKGROUND OF THE INVENTION

Malignant tumors (cancers) are the second leading cause of death in the United States, after heart disease (Boring et al., *CA Cancel J. Clin.* 43:7 (1993)). Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites via a process called metastasis. In a cancerous state, a cell proliferates under conditions in which normal cells would not grow. Cancer manifests itself in a wide variety of forms, characterized by different degrees of invasiveness and aggressiveness.

In attempts to discover effective cellular targets for cancer diagnosis and therapy, researchers have sought to identify transmembrane or otherwise membrane-associated polypeptides that are specifically expressed on the surface of one or more particular type(s) of cancer cell as compared to on one or more normal non-cancerous cell(s). Often, such membrane-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies. In this regard, it is noted that antibody-based therapy has proved very effective in the treatment of certain cancers. For example, HERCEPTIN® and RITUXAN® (both from Genentech Inc., South San Francisco, Calif.) are antibodies that have been used successfully to treat breast cancer and non-Hodgkin's lymphoma, respectively. More specifically, HERCEPTIN® is a recombinant DNA-derived humanized monoclonal antibody that selectively binds to the extracellular domain of the human epidermal growth factor receptor 2 (HER2) proto-oncogene. HER2 protein overexpression is observed in 25-30% of primary breast cancers. RITUXAN® is a genetically engineered chimeric murine/human monoclonal antibody directed against the CD20 antigen found on the surface of normal and malignant B lymphocytes. Both these antibodies are recombinantly produced in CHO cells.

In other attempts to discover effective cellular targets for cancer diagnosis and therapy, researchers have sought to identify (1) non-membrane-associated polypeptides that are specifically produced by one or more particular type(s) of cancer cell(s) as compared to by one or more particular type(s) of non-cancerous normal cell(s), (2) polypeptides that are produced by cancer cells at an expression level that is significantly higher than that of one or more normal non-cancerous cell(s), or (3) polypeptides whose expression is specifically limited to only a single (or very limited number of different) tissue type(s) in both the cancerous and non-cancerous state (e.g., normal prostate and prostate tumor tissue). Such polypeptides may remain intracellularly located or may be secreted by the cancer cell. Moreover, such polypeptides may be expressed not by the cancer cell itself, but rather by cells which produce and/or secrete polypeptides having a potentiating or growth-enhancing effect on cancer cells. Such secreted polypeptides are often proteins that provide cancer cells with a growth advantage over normal cells and include such things as, for example, angiogenic factors, cellular adhesion factors, growth factors, and the like. Identification of antagonists of such non-membrane associated polypeptides would be expected to serve as effective therapeutic agents for the treatment of such cancers. Furthermore, identification of the expression pattern of such polypeptides would be useful for the diagnosis of particular cancers in mammals.

Despite the above identified advances in mammalian cancer therapy, there is a great need for additional diagnostic and therapeutic agents capable of detecting the presence of tumor in a mammal and for effectively inhibiting neoplastic cell growth, respectively. Accordingly, it is an objective of the present invention to identify: (1) cell membrane-associated polypeptides that are more abundantly expressed on one or more type(s) of cancer cell(s) as compared to on normal cells or on other different cancer cells, (2) non-membrane-associated polypeptides that are specifically produced by one or more particular type(s) of cancer cell(s) (or by other cells that produce polypeptides having a potentiating effect on the growth of cancer cells) as compared to by one or more particular type(s) of non-cancerous normal cell(s), (3) non-membrane-associated polypeptides that are produced by cancer cells at an expression level that is significantly higher than that of one or more normal non-cancerous cell(s), or (4) polypeptides whose expression is specifically limited to only a single (or very limited number of different) tissue type(s) in both a cancerous and non-cancerous state (e.g., normal prostate and prostate tumor tissue), and to use those polypeptides, and their encoding nucleic acids, to produce compositions of matter useful in the therapeutic treatment and diagnostic detection of cancer in mammals. It is also an objective of the present invention to identify cell membrane-associated, secreted or intracellular polypeptides whose expression is limited to a single or very limited number of tissues, and to use those polypeptides, and their encoding nucleic acids, to produce compositions of matter useful in the therapeutic treatment and diagnostic detection of cancer in mammals.

SUMMARY OF THE INVENTION

A. Embodiments

In the present specification, Applicants describe for the first time the identification of various cellular polypeptides (and their encoding nucleic acids or fragments thereof) which are expressed to a greater degree on the surface of or by one or more types of cancer cell(s) as compared to on the surface of or by one or more types of normal non-cancer cells. Alternatively, such polypeptides are expressed by cells which produce and/or secrete polypeptides having a potentiating or growth-enhancing effect on cancer cells. Again alternatively, such polypeptides may not be overexpressed by tumor cells as compared to normal cells of the same tissue type, but rather may be specifically expressed by both tumor cells and normal cells of only a single or very limited number of tissue types (preferably tissues which are not essential for life, e.g., prostate, etc.). All of the above polypeptides are herein referred to as Tumor-associated Antigenic Target polypeptides ("TAT" polypeptides) and are expected to serve as effective targets for cancer therapy and diagnosis in mammals.

Accordingly, in one embodiment of the present invention, the invention provides an isolated nucleic acid molecule having a nucleotide sequence that encodes a tumor-associated antigenic target polypeptide or fragment thereof (a "TAT" polypeptide).

In certain aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule encoding a full-length TAT polypeptide having an amino acid sequence as disclosed herein, a TAT polypeptide amino acid sequence lacking the signal peptide as disclosed herein, an extracellular domain of a transmembrane TAT polypeptide, with or without the signal peptide, as disclosed herein or any other specifically defined fragment of a full-length TAT polypeptide amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule comprising the coding sequence of a full-length TAT polypeptide cDNA as disclosed herein, the coding sequence of a TAT polypeptide lacking the signal peptide as disclosed herein, the coding sequence of an extracellular domain of a transmembrane TAT polypeptide, with or without the signal peptide, as disclosed herein or the coding sequence of any other specifically defined fragment of the full-length TAT polypeptide amino acid sequence as disclosed herein, or (b) the complement of the DNA molecule of (a).

In further aspects, the invention concerns an isolated nucleic acid molecule comprising a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule that encodes the same mature polypeptide encoded by the full-length coding region of any of the human protein cDNAs deposited with the ATCC as disclosed herein, or (b) the complement of the DNA molecule of (a).

Another aspect of the invention provides an isolated nucleic acid molecule comprising a nucleotide sequence encoding a TAT polypeptide which is either transmembrane domain-deleted or transmembrane domain-inactivated, or is complementary to such encoding nucleotide sequence, wherein the transmembrane domain(s) of such polypeptide(s) are disclosed herein. Therefore, soluble extracellular domains of the herein described TAT polypeptides are contemplated.

In other aspects, the present invention is directed to isolated nucleic acid molecules which hybridize to (a) a nucleotide sequence encoding a TAT polypeptide having a full-length amino acid sequence as disclosed herein, a TAT polypeptide amino acid sequence lacking the signal peptide as disclosed herein, an extracellular domain of a transmembrane TAT polypeptide, with or without the signal peptide, as disclosed herein or any other specifically defined fragment of a full-length TAT polypeptide amino acid sequence as disclosed herein, or (b) the complement of the nucleotide sequence of (a). In this regard, an embodiment of the present invention is directed to fragments of a full-length TAT polypeptide coding sequence, or the complement thereof, as disclosed herein, that may find use as, for example, hybridization probes useful as, for example, diagnostic probes, antisense oligonucleotide probes, or for encoding fragments of a full-length TAT polypeptide that may optionally encode a polypeptide comprising a binding site for an anti-TAT polypeptide antibody, a TAT binding oligopeptide or other small organic molecule that binds to a TAT polypeptide. Such nucleic acid fragments are usually at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length. It is noted that novel fragments of a TAT polypeptide-encoding nucleotide sequence may be determined in a routine manner by aligning the TAT polypeptide-encoding nucleotide sequence with other known nucleotide sequences using any of a number of well known sequence alignment programs and determining which TAT polypeptide-encoding nucleotide sequence fragment(s) are novel. All of such novel fragments of TAT polypeptide-encoding nucleotide sequences are contemplated herein. Also contemplated are the TAT polypeptide fragments encoded by these nucleotide molecule fragments, preferably those TAT polypeptide fragments that comprise a binding site for an anti-TAT antibody, a TAT binding oligopeptide or other small organic molecule that binds to a TAT polypeptide.

In another embodiment, the invention provides isolated TAT polypeptides encoded by any of the isolated nucleic acid sequences hereinabove identified.

In a certain aspect, the invention concerns an isolated TAT polypeptide, comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% amino acid sequence identity, to a TAT polypeptide having a full-length amino acid sequence as disclosed herein, a TAT polypeptide amino acid sequence lacking the signal peptide as disclosed herein, an extracellular domain of a transmembrane TAT polypeptide protein, with or without the signal peptide, as disclosed herein, an amino acid sequence encoded by any of the nucleic acid sequences disclosed herein or any other specifically defined fragment of a full-length TAT polypeptide amino acid sequence as disclosed herein.

In a further aspect, the invention concerns an isolated TAT polypeptide comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to an amino acid sequence encoded by any of the human protein cDNAs deposited with the ATCC as disclosed herein.

In a specific aspect, the invention provides an isolated TAT polypeptide without the N-terminal signal sequence and/or without the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the TAT polypeptide and recovering the TAT polypeptide from the cell culture.

Another aspect of the invention provides an isolated TAT polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the TAT polypeptide and recovering the TAT polypeptide from the cell culture.

In other embodiments of the present invention, the invention provides vectors comprising DNA encoding any of the herein described polypeptides. Host cells comprising any such vector are also provided. By way of example, the host cells may be CHO cells, E. coli cells, or yeast cells. A process for producing any of the herein described polypeptides is further provided and comprises culturing host cells under conditions suitable for expression of the desired polypeptide and recovering the desired polypeptide from the cell culture.

In other embodiments, the invention provides isolated chimeric polypeptides comprising any of the herein described TAT polypeptides fused to a heterologous (non-TAT) polypeptide. Example of such chimeric molecules comprise any of the herein described TAT polypeptides fused to a heterologous polypeptide such as, for example, an epitope tag sequence or a Fc region of an immunoglobulin.

In another embodiment, the invention provides an antibody which binds, preferably specifically, to any of the above or below described polypeptides. Optionally, the antibody is a monoclonal antibody, antibody fragment, chimeric antibody, humanized antibody, single-chain antibody or antibody that competitively inhibits the binding of an anti-TAT polypeptide antibody to its respective antigenic epitope. Antibodies of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies of the present invention may optionally be produced in CHO cells or bacterial cells and preferably induce death of a cell to which they bind. For diagnostic purposes, the antibodies of the present invention may be detectably labeled, attached to a solid support, or the like.

In other embodiments of the present invention, the invention provides vectors comprising DNA encoding any of the herein described antibodies. Host cell comprising any such vector are also provided. By way of example, the host cells may be CHO cells, E. coli cells, or yeast cells. A process for producing any of the herein described antibodies is further provided and comprises culturing host cells under conditions suitable for expression of the desired antibody and recovering the desired antibody from the cell culture.

In another embodiment, the invention provides oligopeptides ("TAT binding oligopeptides") which bind, preferably specifically, to any of the above or below described TAT polypeptides. Optionally, the TAT binding oligopeptides of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The TAT binding oligopeptides of the present invention may optionally be produced in CHO cells or bacterial cells and preferably induce death of a cell to which they bind. For diagnostic purposes, the TAT binding oligopeptides of the present invention may be detectably labeled, attached to a solid support, or the like.

In other embodiments of the present invention, the invention provides vectors comprising DNA encoding any of the herein described TAT binding oligopeptides. Host cell comprising any such vector are also provided. By way of example, the host cells may be CHO cells, E. coli cells, or yeast cells. A process for producing any of the herein described TAT binding oligopeptides is further provided and comprises culturing host cells under conditions suitable for expression of the desired oligopeptide and recovering the desired oligopeptide from the cell culture.

In another embodiment, the invention provides small organic molecules ("TAT binding organic molecules") which bind, preferably specifically, to any of the above or below described TAT polypeptides. Optionally, the TAT binding organic molecules of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The TAT binding organic molecules of the present invention preferably induce death of a cell to which they bind. For diagnostic purposes, the TAT binding organic molecules of the present invention may be detectably labeled, attached to a solid support, or the like.

In a still further embodiment, the invention concerns a composition of matter comprising a TAT polypeptide as described herein, a chimeric TAT polypeptide as described herein, an anti-TAT antibody as described herein, a TAT binding oligopeptide as described herein, or a TAT binding organic molecule as described herein, in combination with a carrier. Optionally, the carrier is a pharmaceutically acceptable carrier.

In yet another embodiment, the invention concerns an article of manufacture comprising a container and a composition of matter contained within the container, wherein the composition of matter may comprise a TAT polypeptide as described herein, a chimeric TAT polypeptide as described herein, an anti-TAT antibody as described herein, a TAT binding oligopeptide as described herein, or a TAT binding organic molecule as described herein. The article may further optionally comprise a label affixed to the container, or a package insert included with the container, that refers to the use of the composition of matter for the therapeutic treatment or diagnostic detection of a tumor.

Another embodiment of the present invention is directed to the use of a TAT polypeptide as described herein, a chimeric TAT polypeptide as described herein, an anti-TAT polypeptide antibody as described herein, a TAT binding oligopeptide as described herein, or a TAT binding organic molecule as described herein, for the preparation of a medicament useful in the treatment of a condition which is responsive to the TAT polypeptide, chimeric TAT polypeptide, anti-TAT polypeptide antibody, TAT binding oligopeptide, or TAT binding organic molecule.

B. Additional Embodiments

Another embodiment of the present invention is directed to a method for inhibiting the growth of a cell that expresses a TAT polypeptide, wherein the method comprises contacting the cell with an antibody, an oligopeptide or a small organic molecule that binds to the TAT polypeptide, and wherein the binding of the antibody, oligopeptide or organic molecule to the TAT polypeptide causes inhibition of the growth of the cell expressing the TAT polypeptide. In preferred embodiments, the cell is a cancer cell and binding of the antibody, oligopeptide or organic molecule to the TAT polypeptide causes death of the cell expressing the TAT polypeptide. Optionally, the antibody is a monoclonal antibody, antibody fragment, chimeric antibody, humanized antibody, or single-chain antibody. Antibodies, TAT binding oligopeptides and TAT binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and TAT binding oligopeptides employed in the methods of the present invention may optionally be produced in CHO cells or bacterial cells.

Yet another embodiment of the present invention is directed to a method of therapeutically treating a mammal having a cancerous tumor comprising cells that express a TAT polypeptide, wherein the method comprises administering to the mammal a therapeutically effective amount of an antibody, an oligopeptide or a small organic molecule that binds to the TAT polypeptide, thereby resulting in the effective therapeutic treatment of the tumor. Optionally, the antibody is a monoclonal antibody, antibody fragment, chimeric antibody, humanized antibody, or single-chain antibody. Antibodies, TAT binding oligopeptides and TAT binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and oligopeptides employed in the methods of the present invention may optionally be produced in CHO cells or bacterial cells.

Yet another embodiment of the present invention is directed to a method of determining the presence of a TAT polypeptide in a sample suspected of containing the TAT polypeptide, wherein the method comprises exposing the sample to an antibody, oligopeptide or small organic molecule that binds to the TAT polypeptide and determining binding of the antibody, oligopeptide or organic molecule to the TAT polypeptide in the sample, wherein the presence of such binding is indicative of the presence of the TAT polypeptide in the sample. Optionally, the sample may contain cells (which may be cancer cells) suspected of expressing the TAT polypeptide. The antibody, TAT binding oligopeptide or TAT binding organic molecule employed in the method may optionally be detectably labeled, attached to a solid support, or the like.

A further embodiment of the present invention is directed to a method of diagnosing the presence of a tumor in a mammal, wherein the method comprises detecting the level of expression of a gene encoding a TAT polypeptide (a) in a test sample of tissue cells obtained from said mammal, and (b) in a control sample of known normal non-cancerous cells of the same tissue origin or type, wherein a higher level of expression of the TAT polypeptide in the test sample, as compared to the control sample, is indicative of the presence of tumor in the mammal from which the test sample was obtained.

Another embodiment of the present invention is directed to a method of diagnosing the presence of a tumor in a mammal, wherein the method comprises (a) contacting a test sample comprising tissue cells obtained from the mammal with an antibody, oligopeptide or small organic molecule that binds to a TAT polypeptide and (b) detecting the formation of a complex between the antibody, oligopeptide or small organic molecule and the TAT polypeptide in the test sample, wherein the formation of a complex is indicative of the presence of a tumor in the mammal. Optionally, the antibody, TAT binding oligopeptide or TAT binding organic molecule employed is detectably labeled, attached to a solid support, or the like, and/or the test sample of tissue cells is obtained from an individual suspected of having a cancerous tumor.

Yet another embodiment of the present invention is directed to a method for treating or preventing a cell proliferative disorder associated with altered, preferably increased, expression or activity of a TAT polypeptide, the method comprising administering to a subject in need of such treatment an effective amount of an antagonist of a TAT polypeptide. Preferably, the cell proliferative disorder is cancer and the antagonist of the TAT polypeptide is an anti-TAT polypeptide antibody, TAT binding oligopeptide, TAT binding organic molecule or antisense oligonucleotide. Effective treatment or prevention of the cell proliferative disorder may be a result of direct killing or growth inhibition of cells that express a TAT polypeptide or by antagonizing the cell growth potentiating activity of a TAT polypeptide.

Yet another embodiment of the present invention is directed to a method of binding an antibody, oligopeptide or small organic molecule to a cell that expresses a TAT polypeptide, wherein the method comprises contacting a cell that expresses a TAT polypeptide with said antibody, oligopeptide or small organic molecule under conditions which are suitable for binding of the antibody, oligopeptide or small organic molecule to said TAT polypeptide and allowing binding therebetween.

Other embodiments of the present invention are directed to the use of (a) a TAT polypeptide, (b) a nucleic acid encoding a TAT polypeptide or a vector or host cell comprising that nucleic acid, (c) an anti-TAT polypeptide antibody, (d) a TAT-binding oligopeptide, or (e) a TAT-binding small organic molecule in the preparation of a medicament useful for (i) the therapeutic treatment or diagnostic detection of a cancer or tumor, or (ii) the therapeutic treatment or prevention of a cell proliferative disorder.

Another embodiment of the present invention is directed to a method for inhibiting the growth of a cancer cell, wherein the growth of said cancer cell is at least in part dependent upon the growth potentiating effect(s) of a TAT polypeptide (wherein the TAT polypeptide may be expressed either by the cancer cell itself or a cell that produces polypeptide(s) that have a growth potentiating effect on cancer cells), wherein the method comprises contacting the TAT polypeptide with an antibody, an oligopeptide or a small organic molecule that binds to the TAT polypeptide, thereby antagonizing the growth-potentiating activity of the TAT polypeptide and, in turn, inhibiting the growth of the cancer cell. Preferably the growth of the cancer cell is completely inhibited. Even more preferably, binding of the antibody, oligopeptide or small organic molecule to the TAT polypeptide induces the death of the cancer cell. Optionally, the antibody is a monoclonal antibody, antibody fragment, chimeric antibody, humanized antibody, or single-chain antibody. Antibodies, TAT binding oligopeptides and TAT binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and TAT binding oligopeptides employed in the methods of the present invention may optionally be produced in CHO cells or bacterial cells.

Yet another embodiment of the present invention is directed to a method of therapeutically treating a tumor in a mammal, wherein the growth of said tumor is at least in part dependent upon the growth potentiating effect(s) of a TAT polypeptide, wherein the method comprises administering to the mammal a therapeutically effective amount of an antibody, an oligopeptide or a small organic molecule that binds to the TAT polypeptide, thereby antagonizing the growth potentiating activity of said TAT polypeptide and resulting in the effective therapeutic treatment of the tumor. Optionally, the antibody is a monoclonal antibody, antibody fragment, chimeric antibody, humanized antibody, or single-chain antibody. Antibodies, TAT binding oligopeptides and TAT binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and oligopeptides employed in the methods of the present invention may optionally be produced in CHO cells or bacterial cells.

C. Further Additional Embodiments

In yet further embodiments, the invention is directed to the following set of potential claims for this application:

1. Isolated nucleic acid having a nucleotide sequence that has at least 80% nucleic acid sequence identity to:
   (a) a DNA molecule encoding the amino acid sequence shown in any one of FIGS. 22-42 (SEQ ID NOS:22-42);
   (b) a DNA molecule encoding the amino acid sequence shown in any one of FIGS. 22-42 (SEQ ID NOS:22-42), lacking its associated signal peptide;
   (c) a DNA molecule encoding an extracellular domain of the polypeptide shown in any one of FIGS. 22-42 (SEQ ID NOS:22-42), with its associated signal peptide;
   (d) a DNA molecule encoding an extracellular domain of the polypeptide shown in any one of FIGS. 22-42 (SEQ ID NOS:22-42), lacking its associated signal peptide;
   (e) the nucleotide sequence shown in any one of FIGS. 1-21 (SEQ ID NOS:1-21);
   (f) the full-length coding region of the nucleotide sequence shown in any one of FIGS. 1-21 (SEQ ID NOS:1-21); or
   (g) the complement of (a), (b), (c), (d), (e) or (f).

2. Isolated nucleic acid having:
   (a) a nucleotide sequence that encodes the amino acid sequence shown in any one of FIGS. 22-42 (SEQ ID NOS:22-42);
   (b) a nucleotide sequence that encodes the amino acid sequence shown in any one of FIGS. 22-42 (SEQ ID NOS:22-42), lacking its associated signal peptide;
   (c) a nucleotide sequence that encodes an extracellular domain of the polypeptide shown in any one of FIGS. 22-42 (SEQ ID NOS:22-42), with its associated signal peptide;
   (d) a nucleotide sequence that encodes an extracellular domain of the polypeptide shown in any one of FIGS. 22-42 (SEQ ID NOS:22-42), lacking its associated signal peptide;
   (e) the nucleotide sequence shown in any one of FIGS. 1-21 (SEQ ID NOS:1-21);
   (f) the full-length coding region of the nucleotide sequence shown in any one of FIGS. 1-21 (SEQ ID NOS:1-21); or
   (g) the complement of (a), (b), (c), (d), (e) or (f).

3. Isolated nucleic acid that hybridizes to:
   (a) a nucleic acid that encodes the amino acid sequence shown in any one of FIGS. 22-42 (SEQ ID NOS:22-42);
   (b) a nucleic acid that encodes the amino acid sequence shown in any one of FIGS. 22-42 (SEQ ID NOS:22-42), lacking its associated signal peptide;
   (c) a nucleic acid that encodes an extracellular domain of the polypeptide shown in any one of FIGS. 22-42 (SEQ ID NOS:22-42), with its associated signal peptide;
   (d) a nucleic acid that encodes an extracellular domain of the polypeptide shown in any one of FIGS. 22-42 (SEQ ID NOS:22-42), lacking its associated signal peptide;
   (e) the nucleotide sequence shown in any one of FIGS. 1-21 (SEQ ID NOS:1-21);
   (f) the full-length coding region of the nucleotide sequence shown in any one of FIGS. 1-21 (SEQ ID NOS:1-21); or
   (g) the complement of (a), (b), (c), (d), (e) or (f).

4. The nucleic acid of Claim 3, wherein the hybridization occurs under stringent conditions.

5. The nucleic acid of Claim 3 which is at least about 5 nucleotides in length.

6. An expression vector comprising the nucleic acid of Claim 1, 2 or 3.

7. The expression vector of Claim 6, wherein said nucleic acid is operably linked to control sequences recognized by a host cell transformed with the vector.

8. A host cell comprising the expression vector of Claim 7.

9. The host cell of Claim 8 which is a CHO cell, an *E. coli* cell or a yeast cell.

10. A process for producing a polypeptide comprising culturing the host cell of Claim 8 under conditions suitable for expression of said polypeptide and recovering said polypeptide from the cell culture.

11. An isolated polypeptide having at least 80% amino acid sequence identity to:
    (a) the polypeptide shown in any one of FIGS. 22-42 (SEQ ID NOS:22-42);
    (b) the polypeptide shown in any one of FIGS. 22-42 (SEQ ID NOS:22-42), lacking its associated signal peptide;
    (c) an extracellular domain of the polypeptide shown in any one of FIGS. 22-42 (SEQ ID NOS:22-42), with its associated signal peptide;
    (d) an extracellular domain of the polypeptide shown in any one of FIGS. 22-42 (SEQ ID NOS:22-42), lacking its associated signal peptide;
    (e) a polypeptide encoded by the nucleotide sequence shown in any one of FIGS. 1-21 (SEQ ID NOS:1-21); or
    (f) a polypeptide encoded by the full-length coding region of the nucleotide sequence shown in any one of FIGS. 1-21 (SEQ ID NOS:1-21).

12. An isolated polypeptide having:
    (a) the amino acid sequence shown in any one of FIGS. 22-42 (SEQ ID NOS:22-42);
    (b) the amino acid sequence shown in any one of FIGS. 22-42 (SEQ ID NOS:22-42), lacking its associated signal peptide sequence;
    (c) an amino acid sequence of an extracellular domain of the polypeptide shown in any one of FIGS. 22-42 (SEQ ID NOS:22-42), with its associated signal peptide sequence;
    (d) an amino acid sequence of an extracellular domain of the polypeptide shown in any one of FIGS. 22-42 (SEQ ID NOS:22-42), lacking its associated signal peptide sequence;
    (e) an amino acid sequence encoded by the nucleotide sequence shown in any one of FIGS. 1-21 (SEQ ID NOS:1-21); or
    (f) an amino acid sequence encoded by the full-length coding region of the nucleotide sequence shown in any one of FIGS. 1-21 (SEQ ID NOS:1-21).

13. A chimeric polypeptide comprising the polypeptide of Claim 11 or 12 fused to a heterologous polypeptide.

14. The chimeric polypeptide of Claim 13, wherein said heterologous polypeptide is an epitope tag sequence or an Fc region of an immunoglobulin.

15. An isolated antibody that binds to a polypeptide having at least 80% amino acid sequence identity to:
(a) the polypeptide shown in any one of FIGS. 22-42 (SEQ ID NOS:22-42);
(b) the polypeptide shown in any one of FIGS. 22-42 (SEQ ID NOS:22-42), lacking its associated signal peptide;
(c) an extracellular domain of the polypeptide shown in any one of FIGS. 22-42 (SEQ ID NOS:22-42), with its associated signal peptide;
(d) an extracellular domain of the polypeptide shown in any one of FIGS. 22-42 (SEQ ID NOS:22-42), lacking its associated signal peptide;
(e) a polypeptide encoded by the nucleotide sequence shown in any one of FIGS. 1-21 (SEQ ID NOS:1-21); or
(f) a polypeptide encoded by the full-length coding region of the nucleotide sequence shown in any one of FIGS. 1-21 (SEQ ID NOS:1-21).

16. An isolated antibody that binds to a polypeptide having:
(a) the amino acid sequence shown in any one of FIGS. 22-42 (SEQ ID NOS:22-42);
(b) the amino acid sequence shown in any one of FIGS. 22-42 (SEQ ID NOS:22-42), lacking its associated signal peptide sequence;
(c) an amino acid sequence of an extracellular domain of the polypeptide shown in any one of FIGS. 22-42 (SEQ ID NOS:22-42), with its associated signal peptide sequence;
(d) an amino acid sequence of an extracellular domain of the polypeptide shown in any one of FIGS. 22-42 (SEQ ID NOS:22-42), lacking its associated signal peptide sequence;
(e) an amino acid sequence encoded by the nucleotide sequence shown in any one of FIGS. 1-21 (SEQ ID NOS:1-21); or
(f) an amino acid sequence encoded by the full-length coding region of the nucleotide sequence shown in any one of FIGS. 1-21 (SEQ ID NOS:1-21).

17. The antibody of Claim 15 or 16 which is a monoclonal antibody.

18. The antibody of Claim 15 or 16 which is an antibody fragment.

19. The antibody of Claim 15 or 16 which is a chimeric or a humanized antibody.

20. The antibody of Claim 15 or 16 which is conjugated to a growth inhibitory agent.

21. The antibody of Claim 15 or 16 which is conjugated to a cytotoxic agent.

22. The antibody of Claim 21, wherein the cytotoxic agent is selected from the group consisting of toxins, antibiotics, radioactive isotopes and nucleolytic enzymes.

23. The antibody of Claim 21, wherein the cytotoxic agent is a toxin.

24. The antibody of Claim 23, wherein the toxin is selected from the group consisting of maytansinoid and calicheamicin.

25. The antibody of Claim 23, wherein the toxin is a maytansinoid.

26. The antibody of Claim 15 or 16 which is produced in bacteria.

27. The antibody of Claim 15 or 16 which is produced in CHO cells.

28. The antibody of Claim 15 or 16 which induces death of a cell to which it binds.

29. The antibody of Claim 15 or 16 which is detectably labeled.

30. An isolated nucleic acid having a nucleotide sequence that encodes the antibody of Claim 15 or 16.

31. An expression vector comprising the nucleic acid of Claim 30 operably linked to control sequences recognized by a host cell transformed with the vector.

32. A host cell comprising the expression vector of Claim 31.

33. The host cell of Claim 32 which is a CHO cell, an *E. coli* cell or a yeast cell.

34. A process for producing an antibody comprising culturing the host cell of Claim 32 under conditions suitable for expression of said antibody and recovering said antibody from the cell culture.

35. An isolated oligopeptide that binds to a polypeptide having at least 80% amino acid sequence identity to:
(a) the polypeptide shown in any one of FIGS. 22-42 (SEQ ID NOS:22-42);
(b) the polypeptide shown in any one of FIGS. 22-42 (SEQ ID NOS:22-42), lacking its associated signal peptide;
(c) an extracellular domain of the polypeptide shown in any one of FIGS. 22-42 (SEQ ID NOS:22-42), with its associated signal peptide;
(d) an extracellular domain of the polypeptide shown in any one of FIGS. 22-42 (SEQ ID NOS:22-42), lacking its associated signal peptide;
(e) a polypeptide encoded by the nucleotide sequence shown in any one of FIGS. 1-21 (SEQ ID NOS:1-21); or
(f) a polypeptide encoded by the full-length coding region of the nucleotide sequence shown in any one of FIGS. 1-21 (SEQ ID NOS:1-21).

36. An isolated oligopeptide that binds to a polypeptide having:
(a) the amino acid sequence shown in any one of FIGS. 22-42 (SEQ ID NOS:22-42);
(b) the amino acid sequence shown in any one of FIGS. 22-42 (SEQ ID NOS:22-42), lacking its associated signal peptide sequence;
(c) an amino acid sequence of an extracellular domain of the polypeptide shown in any one of FIGS. 22-42 (SEQ ID NOS:22-42), with its associated signal peptide sequence;
(d) an amino acid sequence of an extracellular domain of the polypeptide shown in any one of FIGS. 22-42 (SEQ ID NOS:22-42), lacking its associated signal peptide sequence;
(e) an amino acid sequence encoded by the nucleotide sequence shown in any one of FIGS. 1-21 (SEQ ID NOS:1-21); or
(f) an amino acid sequence encoded by the full-length coding region of the nucleotide sequence shown in any one of FIGS. 1-21 (SEQ ID NOS:1-21).

37. The oligopeptide of Claim 35 or 36 which is conjugated to a growth inhibitory agent.

38. The oligopeptide of Claim 35 or 36 which is conjugated to a cytotoxic agent.

39. The oligopeptide of Claim 38, wherein the cytotoxic agent is selected from the group consisting of toxins, antibiotics, radioactive isotopes and nucleolytic enzymes.

40. The oligopeptide of Claim 38, wherein the cytotoxic agent is a toxin.

41. The oligopeptide of Claim 40, wherein the toxin is selected from the group consisting of maytansinoid and calicheamicin.

42. The oligopeptide of Claim 40, wherein the toxin is a maytansinoid.

43. The oligopeptide of Claim 35 or 36 which induces death of a cell to which it binds.

44. The oligopeptide of Claim 35 or 36 which is detectably labeled.

45. A TAT binding organic molecule that binds to a polypeptide having at least 80% amino acid sequence identity to:
(a) the polypeptide shown in any one of FIGS. 22-42 (SEQ ID NOS:22-42);
(b) the polypeptide shown in any one of FIGS. 22-42 (SEQ ID NOS:22-42), lacking its associated signal peptide;
(c) an extracellular domain of the polypeptide shown in any one of FIGS. 22-42 (SEQ ID NOS:22-42), with its associated signal peptide;
(d) an extracellular domain of the polypeptide shown in any one of FIGS. 22-42 (SEQ ID NOS:22-42), lacking its associated signal peptide;
(e) a polypeptide encoded by the nucleotide sequence shown in any one of FIGS. 1-21 (SEQ ID NOS:1-21); or
(f) a polypeptide encoded by the full-length coding region of the nucleotide sequence shown in any one of FIGS. 1-21 (SEQ ID NOS:1-21).

46. The organic molecule of Claim 45 that binds to a polypeptide having:
(a) the amino acid sequence shown in any one of FIGS. 22-42 (SEQ ID NOS:22-42);
(b) the amino acid sequence shown in any one of FIGS. 22-42 (SEQ ID NOS:22-42), lacking its associated signal peptide sequence;
(c) an amino acid sequence of an extracellular domain of the polypeptide shown in any one of FIGS. 22-42 (SEQ ID NOS:22-42), with its associated signal peptide sequence;
(d) an amino acid sequence of an extracellular domain of the polypeptide shown in any one of FIGS. 22-42 (SEQ ID NOS:22-42), lacking its associated signal peptide sequence;
(e) an amino acid sequence encoded by the nucleotide sequence shown in any one of FIGS. 1-21 (SEQ ID NOS:1-21); or
(f) an amino acid sequence encoded by the full-length coding region of the nucleotide sequence shown in any one of FIGS. 1-21 (SEQ ID NOS:1-21).

47. The organic molecule of Claim 45 or 46 which is conjugated to a growth inhibitory agent.

48. The organic molecule of Claim 45 or 46 which is conjugated to a cytotoxic agent.

49. The organic molecule of Claim 48, wherein the cytotoxic agent is selected from the group consisting of toxins, antibiotics, radioactive isotopes and nucleolytic enzymes.

50. The organic molecule of Claim 48, wherein the cytotoxic agent is a toxin.

51. The organic molecule of Claim 50, wherein the toxin is selected from the group consisting of maytansinoid and calicheamicin.

52. The organic molecule of Claim 50, wherein the toxin is a maytansinoid.

53. The organic molecule of Claim 45 or 46 which induces death of a cell to which it binds.

54. The organic molecule of Claim 45 or 46 which is detectably labeled.

55. A composition of matter comprising:
(a) the polypeptide of Claim 11;
(b) the polypeptide of Claim 12;
(c) the chimeric polypeptide of Claim 13;
(d) the antibody of Claim 15;
(e) the antibody of Claim 16;
(f) the oligopeptide of Claim 35;
(g) the oligopeptide of Claim 36;
(h) the TAT binding organic molecule of Claim 45; or
(i) the TAT binding organic molecule of Claim 46; in combination with a carrier.

56. The composition of matter of Claim 55, wherein said carrier is a pharmaceutically acceptable carrier.

57. An article of manufacture comprising:
(a) a container; and
(b) the composition of matter of Claim 55 contained within said container.

58. The article of manufacture of Claim 57 further comprising a label affixed to said container, or a package insert included with said container, referring to the use of said composition of matter for the therapeutic treatment of or the diagnostic detection of a cancer.

59. A method of inhibiting the growth of a cell that expresses a protein having at least 80% amino acid sequence identity to:
(a) the polypeptide shown in any one of FIGS. 22-42 (SEQ ID NOS:22-42);
(b) the polypeptide shown in any one of FIGS. 22-42 (SEQ ID NOS:22-42), lacking its associated signal peptide;
(c) an extracellular domain of the polypeptide shown in any one of FIGS. 22-42 (SEQ ID NOS:22-42), with its associated signal peptide;
(d) an extracellular domain of the polypeptide shown in any one of FIGS. 22-42 (SEQ ID NOS:22-42), lacking its associated signal peptide;
(e) a polypeptide encoded by the nucleotide sequence shown in any one of FIGS. 1-21 (SEQ ID NOS:1-21); or
(f) a polypeptide encoded by the full-length coding region of the nucleotide sequence shown in any one of FIGS. 1-21 (SEQ ID NOS:1-21), said method comprising contacting said cell with an antibody, oligopeptide or organic molecule that binds to said protein, the binding of said antibody, oligopeptide or organic molecule to said protein thereby causing an inhibition of growth of said cell.

60. The method of Claim 59, wherein said antibody is a monoclonal antibody.

61. The method of Claim 59, wherein said antibody is an antibody fragment.

62. The method of Claim 59, wherein said antibody is a chimeric or a humanized antibody.

63. The method of Claim 59, wherein said antibody, oligopeptide or organic molecule is conjugated to a growth inhibitory agent.

64. The method of Claim 59, wherein said antibody, oligopeptide or organic molecule is conjugated to a cytotoxic agent.

65. The method of Claim 64, wherein said cytotoxic agent is selected from the group consisting of toxins, antibiotics, radioactive isotopes and nucleolytic enzymes.

66. The method of Claim 64, wherein the cytotoxic agent is a toxin.

67. The method of Claim 66, wherein the toxin is selected from the group consisting of maytansinoid and calicheamicin.

68. The method of Claim 66, wherein the toxin is a maytansinoid.

69. The method of Claim 59, wherein said antibody is produced in bacteria.

70. The method of Claim 59, wherein said antibody is produced in CHO cells.

71. The method of Claim 59, wherein said cell is a cancer cell.

72. The method of Claim 71, wherein said cancer cell is further exposed to radiation treatment or a chemotherapeutic agent.

73. The method of Claim 71, wherein said cancer cell is selected from the group consisting of a breast cancer cell, a colorectal cancer cell, a lung cancer cell, an ovarian cancer cell, a central nervous system cancer cell, a liver cancer cell, a bladder cancer cell, a pancreatic cancer cell, a cervical cancer cell, a melanoma cell and a leukemia cell.

74. The method of Claim 71, wherein said protein is more abundantly expressed by said cancer cell as compared to a normal cell of the same tissue origin.

75. The method of Claim 59 which causes the death of said cell.

76. The method of Claim 59, wherein said protein has:
(a) the amino acid sequence shown in any one of FIGS. 22-42 (SEQ ID NOS:22-42);
(b) the amino acid sequence shown in any one of FIGS. 22-42 (SEQ ID NOS:22-42), lacking its associated signal peptide sequence;
(c) an amino acid sequence of an extracellular domain of the polypeptide shown in any one of FIGS. 22-42 (SEQ ID NOS:22-42), with its associated signal peptide sequence;
(d) an amino acid sequence of an extracellular domain of the polypeptide shown in any one of FIGS. 22-42 (SEQ ID NOS:22-42), lacking its associated signal peptide sequence;
(e) an amino acid sequence encoded by the nucleotide sequence shown in any one of FIGS. 1-21 (SEQ ID NOS:1-21); or
(f) an amino acid sequence encoded by the full-length coding region of the nucleotide sequence shown in any one of FIGS. 1-21 (SEQ ID NOS:1-21).

77. A method of therapeutically treating a mammal having a cancerous tumor comprising cells that express a protein having at least 80% amino acid sequence identity to:
(a) the polypeptide shown in any one of FIGS. 22-42 (SEQ ID NOS:22-42);
(b) the polypeptide shown in any one of FIGS. 22-42 (SEQ ID NOS:22-42), lacking its associated signal peptide;
(c) an extracellular domain of the polypeptide shown in any one of FIGS. 22-42 (SEQ ID NOS:22-42), with its associated signal peptide;
(d) an extracellular domain of the polypeptide shown in any one of FIGS. 22-42 (SEQ ID NOS:22-42), lacking its associated signal peptide;
(e) a polypeptide encoded by the nucleotide sequence shown in any one of FIGS. 1-21 (SEQ ID NOS:1-21); or
(f) a polypeptide encoded by the full-length coding region of the nucleotide sequence shown in any one of FIGS. 1-21 (SEQ ID NOS:1-21), said method comprising administering to said mammal a therapeutically effective amount of an antibody, oligopeptide or organic molecule that binds to said protein, thereby effectively treating said mammal.

78. The method of Claim 77, wherein said antibody is a monoclonal antibody.

79. The method of Claim 77, wherein said antibody is an antibody fragment.

80. The method of Claim 77, wherein said antibody is a chimeric or a humanized antibody.

81. The method of Claim 77, wherein said antibody, oligopeptide or organic molecule is conjugated to a growth inhibitory agent.

82. The method of Claim 77, wherein said antibody, oligopeptide or organic molecule is conjugated to a cytotoxic agent.

83. The method of Claim 82, wherein said cytotoxic agent is selected from the group consisting of toxins, antibiotics, radioactive isotopes and nucleolytic enzymes.

84. The method of Claim 82, wherein the cytotoxic agent is a toxin.

85. The method of Claim 84, wherein the toxin is selected from the group consisting of maytansinoid and calicheamicin.

86. The method of Claim 84, wherein the toxin is a maytansinoid.

87. The method of Claim 77, wherein said antibody is produced in bacteria.

88. The method of Claim 77, wherein said antibody is produced in CHO cells.

89. The method of Claim 77, wherein said tumor is further exposed to radiation treatment or a chemotherapeutic agent.

90. The method of Claim 77, wherein said tumor is a breast tumor, a colorectal tumor, a lung tumor, an ovarian tumor, a central nervous system tumor, a liver tumor, a bladder tumor, a pancreatic tumor, or a cervical tumor.

91. The method of Claim 77, wherein said protein is more abundantly expressed by the cancerous cells of said tumor as compared to a normal cell of the same tissue origin.

92. The method of Claim 77, wherein said protein has:
(a) the amino acid sequence shown in any one of FIGS. 22-42 (SEQ ID NOS:22-42);
(b) the amino acid sequence shown in any one of FIGS. 22-42 (SEQ ID NOS:22-42), lacking its associated signal peptide sequence;
(c) an amino acid sequence of an extracellular domain of the polypeptide shown in any one of FIGS. 22-42 (SEQ ID NOS:22-42), with its associated signal peptide sequence;
(d) an amino acid sequence of an extracellular domain of the polypeptide shown in any one of FIGS. 22-42 (SEQ ID NOS:22-42), lacking its associated signal peptide sequence;
(e) an amino acid sequence encoded by the nucleotide sequence shown in any one of FIGS. 1-21 (SEQ ID NOS:1-21); or
(f) an amino acid sequence encoded by the full-length coding region of the nucleotide sequence shown in any one of FIGS. 1-21 (SEQ ID NOS:1-21).

93. A method of determining the presence of a protein in a sample suspected of containing said protein, wherein said protein has at least 80% amino acid sequence identity to:
(a) the polypeptide shown in any one of FIGS. 22-42 (SEQ ID NOS:22-42);
(b) the polypeptide shown in any one of FIGS. 22-42 (SEQ ID NOS:22-42), lacking its associated signal peptide;
(c) an extracellular domain of the polypeptide shown in any one of FIGS. 22-42 (SEQ ID NOS:22-42), with its associated signal peptide;
(d) an extracellular domain of the polypeptide shown in any one of FIGS. 22-42 (SEQ ID NOS:22-42), lacking its associated signal peptide;
(e) a polypeptide encoded by the nucleotide sequence shown in any one of FIGS. 1-21 (SEQ ID NOS:1-21); or
(f) a polypeptide encoded by the full-length coding region of the nucleotide sequence shown in any one of FIGS. 1-21 (SEQ ID NOS:1-21), said method comprising exposing said sample to an antibody, oligopeptide or organic molecule that binds to said protein and determining binding of said antibody, oligopeptide or organic molecule to said protein in said sample, wherein binding of the antibody, oligopeptide or organic molecule to said protein is indicative of the presence of said protein in said sample.

94. The method of Claim 93, wherein said sample comprises a cell suspected of expressing said protein.

95. The method of Claim 94, wherein said cell is a cancer cell.

96. The method of Claim 93, wherein said antibody, oligopeptide or organic molecule is detectably labeled.

97. The method of Claim 93, wherein said protein has:

(a) the amino acid sequence shown in any one of FIGS. 22-42 (SEQ ID NOS:22-42);

(b) the amino acid sequence shown in any one of FIGS. 22-42 (SEQ ID NOS:22-42), lacking its associated signal peptide sequence;

(c) an amino acid sequence of an extracellular domain of the polypeptide shown in any one of FIGS. 22-42 (SEQ ID NOS:22-42), with its associated signal peptide sequence;

(d) an amino acid sequence of an extracellular domain of the polypeptide shown in any one of FIGS. 22-42 (SEQ ID NOS:22-42), lacking its associated signal peptide sequence;

(e) an amino acid sequence encoded by the nucleotide sequence shown in any one of FIGS. 1-21 (SEQ ID NOS:1-21); or (f) an amino acid sequence encoded by the full-length coding region of the nucleotide sequence shown in any one of FIGS. 1-21 (SEQ ID NOS:1-21).

98. A method of diagnosing the presence of a tumor in a mammal, said method comprising determining the level of expression of a gene encoding a protein having at least 80% amino acid sequence identity to:

(a) the polypeptide shown in any one of FIGS. 22-42 (SEQ ID NOS:22-42);

(b) the polypeptide shown in any one of FIGS. 22-42 (SEQ ID NOS:22-42), lacking its associated signal peptide;

(c) an extracellular domain of the polypeptide shown in any one of FIGS. 22-42 (SEQ ID NOS:22-42), with its associated signal peptide;

(d) an extracellular domain of the polypeptide shown in any one of FIGS. 22-42 (SEQ ID NOS:22-42), lacking its associated signal peptide;

(e) a polypeptide encoded by the nucleotide sequence shown in any one of FIGS. 1-21 (SEQ ID NOS: 1-21); or (f) a polypeptide encoded by the full-length coding region of the nucleotide sequence shown in any one of FIGS. 1-21 (SEQ ID NOS:1-21), in a test sample of tissue cells obtained from said mammal and in a control sample of known normal cells of the same tissue origin, wherein a higher level of expression of said protein in the test sample, as compared to the control sample, is indicative of the presence of tumor in the mammal from which the test sample was obtained.

99. The method of Claim 98, wherein the step of determining the level of expression of a gene encoding said protein comprises employing an oligonucleotide in an in situ hybridization or RT-PCR analysis.

100. The method of Claim 98, wherein the step determining the level of expression of a gene encoding said protein comprises employing an antibody in an immunohistochemistry or Western blot analysis.

101. The method of Claim 98, wherein said protein has:

(a) the amino acid sequence shown in any one of FIGS. 22-42 (SEQ ID NOS:22-42);

(b) the amino acid sequence shown in any one of FIGS. 22-42 (SEQ ID NOS:22-42), lacking its associated signal peptide sequence;

(c) an amino acid sequence of an extracellular domain of the polypeptide shown in any one of FIGS. 22-42 (SEQ ID NOS:22-42), with its associated signal peptide sequence;

(d) an amino acid sequence of an extracellular domain of the polypeptide shown in any one of FIGS. 22-42 (SEQ ID NOS:22-42), lacking its associated signal peptide sequence;

(e) an amino acid sequence encoded by the nucleotide sequence shown in any one of FIGS. 1-21 (SEQ ID NOS:1-21); or (f) an amino acid sequence encoded by the full-length coding region of the nucleotide sequence shown in any one of FIGS. 1-21 (SEQ ID NOS:1-21).

102. A method of diagnosing the presence of a tumor in a mammal, said method comprising contacting a test sample of tissue cells obtained from said mammal with an antibody, oligopeptide or organic molecule that binds to a protein having at least 80% amino acid sequence identity to:

(a) the polypeptide shown in any one of FIGS. 22-42 (SEQ ID NOS:22-42);

(b) the polypeptide shown in any one of FIGS. 22-42 (SEQ ID NOS:22-42), lacking its associated signal peptide;

(c) an extracellular domain of the polypeptide shown in any one of FIGS. 22-42 (SEQ ID NOS:22-42), with its associated signal peptide;

(d) an extracellular domain of the polypeptide shown in any one of FIGS. 22-42 (SEQ ID NOS:22-42), lacking its associated signal peptide;

(e) a polypeptide encoded by the nucleotide sequence shown in any one of FIGS. 1-21 (SEQ ID NOS:1-21); or (f) a polypeptide encoded by the full-length coding region of the nucleotide sequence shown in any one of FIGS. 1-21 (SEQ ID NOS:1-21), and detecting the formation of a complex between said antibody, oligopeptide or organic molecule and said protein in the test sample, wherein the formation of a complex is indicative of the presence of a tumor in said mammal.

103. The method of Claim 102, wherein said antibody, oligopeptide or organic molecule is detectably labeled.

104. The method of Claim 102, wherein said test sample of tissue cells is obtained from an individual suspected of having a cancerous tumor.

105. The method of Claim 102, wherein said protein has:

(a) the amino acid sequence shown in any one of FIGS. 22-42 (SEQ ID NOS:22-42);

(b) the amino acid sequence shown in any one of FIGS. 22-42 (SEQ ID NOS:22-42), lacking its associated signal peptide sequence;

(c) an amino acid sequence of an extracellular domain of the polypeptide shown in any one of FIGS. 22-42 (SEQ ID NOS:22-42), with its associated signal peptide sequence;

(d) an amino acid sequence of an extracellular domain of the polypeptide shown in any one of FIGS. 22-42 (SEQ ID NOS:22-42), lacking its associated signal peptide sequence;

(e) an amino acid sequence encoded by the nucleotide sequence shown in any one of FIGS. 1-21 (SEQ ID NOS:1-21); or (f) an amino acid sequence encoded by the full-length coding region of the nucleotide sequence shown in any one of FIGS. 1-21 (SEQ ID NOS:1-21).

106. A method for treating or preventing a cell proliferative disorder associated with increased expression or activity of a protein having at least 80% amino acid sequence identity to:

(a) the polypeptide shown in any one of FIGS. 22-42 (SEQ ID NOS:22-42);

(b) the polypeptide shown in any one of FIGS. 22-42 (SEQ ID NOS:22-42), lacking its associated signal peptide;

(c) an extracellular domain of the polypeptide shown in any one of FIGS. 22-42 (SEQ ID NOS:22-42), with its associated signal peptide;

(d) an extracellular domain of the polypeptide shown in any one of FIGS. 22-42 (SEQ ID NOS:22-42), lacking its associated signal peptide;

(e) a polypeptide encoded by the nucleotide sequence shown in any one of FIGS. 1-21 (SEQ ID NOS:1-21); or (f) a polypeptide encoded by the full-length coding region of the nucleotide sequence shown in any one of FIGS. 1-21

(SEQ ID NOS:1-21), said method comprising administering to a subject in need of such treatment an effective amount of an antagonist of said protein, thereby effectively treating or preventing said cell proliferative disorder.

107. The method of Claim 106, wherein said cell proliferative disorder is cancer.

108. The method of Claim 106, wherein said antagonist is an anti-TAT polypeptide antibody, TAT binding oligopeptide, TAT binding organic molecule or antisense oligonucleotide.

109. A method of binding an antibody, oligopeptide or organic molecule to a cell that expresses a protein having at least 80% amino acid sequence identity to:
 (a) the polypeptide shown in any one of FIGS. 22-42 (SEQ ID NOS:22-42);
 (b) the polypeptide shown in any one of FIGS. 22-42 (SEQ ID NOS:22-42), lacking its associated signal peptide;
 (c) an extracellular domain of the polypeptide shown in any one of FIGS. 22-42 (SEQ ID NOS:22-42), with its associated signal peptide;
 (d) an extracellular domain of the polypeptide shown in any one of FIGS. 22-42 (SEQ ID NOS:22-42), lacking its associated signal peptide;
 (e) a polypeptide encoded by the nucleotide sequence shown in any one of FIGS. 1-21 (SEQ ID NOS:1-21); or
 (f) a polypeptide encoded by the full-length coding region of the nucleotide sequence shown in any one of FIGS. 1-21 (SEQ ID NOS:1-21), said method comprising contacting said cell with an antibody, oligopeptide or organic molecule that binds to said protein and allowing the binding of the antibody, oligopeptide or organic molecule to said protein to occur, thereby binding said antibody, oligopeptide or organic molecule to said cell.

110. The method of Claim 109, wherein said antibody is a monoclonal antibody.

111. The method of Claim 109, wherein said antibody is an antibody fragment.

112. The method of Claim 109, wherein said antibody is a chimeric or a humanized antibody.

113. The method of Claim 109, wherein said antibody, oligopeptide or organic molecule is conjugated to a growth inhibitory agent.

114. The method of Claim 109, wherein said antibody, oligopeptide or organic molecule is conjugated to a cytotoxic agent.

115. The method of Claim 114, wherein said cytotoxic agent is selected from the group consisting of toxins, antibiotics, radioactive isotopes and nucleolytic enzymes.

116. The method of Claim 114, wherein the cytotoxic agent is a toxin.

117. The method of Claim 116, wherein the toxin is selected from the group consisting of maytansinoid and calicheamicin.

118. The method of Claim 116, wherein the toxin is a maytansinoid.

119. The method of Claim 109, wherein said antibody is produced in bacteria.

120. The method of Claim 109, wherein said antibody is produced in CHO cells.

121. The method of Claim 109, wherein said cell is a cancer cell.

122. The method of Claim 121, wherein said cancer cell is further exposed to radiation treatment or a chemotherapeutic agent.

123. The method of Claim 121, wherein said cancer cell is selected from the group consisting of a breast cancer cell, a colorectal cancer cell, a lung cancer cell, an ovarian cancer cell, a central nervous system cancer cell, a liver cancer cell, a bladder cancer cell, a pancreatic cancer cell, a cervical cancer cell, a melanoma cell and a leukemia cell.

124. The method of Claim 123, wherein said protein is more abundantly expressed by said cancer cell as compared to a normal cell of the same tissue origin.

125. The method of Claim 109 which causes the death of said cell.

126. Use of a nucleic acid as claimed in any of Claims 1 to 5 or 30 in the preparation of a medicament for the therapeutic treatment or diagnostic detection of a cancer.

127. Use of a nucleic acid as claimed in any of Claims 1 to 5 or 30 in the preparation of a medicament for treating a tumor.

128. Use of a nucleic acid as claimed in any of Claims 1 to 5 or 30 in the preparation of a medicament for treatment or prevention of a cell proliferative disorder.

129. Use of an expression vector as claimed in any of Claims 6, 7 or 31 in the preparation of a medicament for the therapeutic treatment or diagnostic detection of a cancer.

130. Use of an expression vector as claimed in any of Claims 6, 7 or 31 in the preparation of medicament for treating a tumor.

131. Use of an expression vector as claimed in any of Claims 6, 7 or 31 in the preparation of a medicament for treatment or prevention of a cell proliferative disorder.

132. Use of a host cell as claimed in any of Claims 8, 9, 32, or 33 in the preparation of a medicament for the therapeutic treatment or diagnostic detection of a cancer.

133. Use of a host cell as claimed in any of Claims 8, 9, 32 or 33 in the preparation of a medicament for treating a tumor.

134. Use of a host cell as claimed in any of Claims 8, 9, 32 or 33 in the preparation of a medicament for treatment or prevention of a cell proliferative disorder.

135. Use of a polypeptide as claimed in any of Claims 11 to 14 in the preparation of a medicament for the therapeutic treatment or diagnostic detection of a cancer.

136. Use of a polypeptide as claimed in any of Claims 11 to 14 in the preparation of a medicament for treating a tumor.

137. Use of a polypeptide as claimed in any of Claims 11 to 14 in the preparation of a medicament for treatment or prevention of a cell proliferative disorder.

138. Use of an antibody as claimed in any of Claims 15 to 29 in the preparation of a medicament for the therapeutic treatment or diagnostic detection of a cancer.

139. Use of an antibody as claimed in any of Claims 15 to 29 in the preparation of a medicament for treating a tumor.

140. Use of an antibody as claimed in any of Claims 15 to 29 in the preparation of a medicament for treatment or prevention of a cell proliferative disorder.

141. Use of an oligopeptide as claimed in any of Claims 35 to 44 in the preparation of a medicament for the therapeutic treatment or diagnostic detection of a cancer.

142. Use of an oligopeptide as claimed in any of Claims 35 to 44 in the preparation of a medicament for treating a tumor.

143. Use of an oligopeptide as claimed in any of Claims 35 to 44 in the preparation of a medicament for treatment or prevention of a cell proliferative disorder.

144. Use of a TAT binding organic molecule as claimed in any of Claims 45 to 54 in the preparation of a medicament for the therapeutic treatment or diagnostic detection of a cancer.

145. Use of a TAT binding organic molecule as claimed in any of Claims 45 to 54 in the preparation of a medicament for treating a tumor.

146. Use of a TAT binding organic molecule as claimed in any of Claims 45 to 54 in the preparation of a medicament for treatment or prevention of a cell proliferative disorder.

147. Use of a composition of matter as claimed in any of Claims 55 or 56 in the preparation of a medicament for the therapeutic treatment or diagnostic detection of a cancer.

148. Use of a composition of matter as claimed in any of Claims 55 or 56 in the preparation of a medicament for treating a tumor.

149. Use of a composition of matter as claimed in any of Claims 55 or 56 in the preparation of a medicament for treatment or prevention of a cell proliferative disorder.

150. Use of an article of manufacture as claimed in any of Claims 57 or 58 in the preparation of a medicament for the therapeutic treatment or diagnostic detection of a cancer.

151. Use of an article of manufacture as claimed in any of Claims 57 or 58 in the preparation of a medicament for treating a tumor.

152. Use of an article of manufacture as claimed in any of Claims 57 or 58 in the preparation of a medicament for treatment or prevention of a cell proliferative disorder.

153. A method for inhibiting the growth of a cell, wherein the growth of said cell is at least in part dependent upon a growth potentiating effect of a protein having at least 80% amino acid sequence identity to:

(a) the polypeptide shown in any one of FIGS. 22-42 (SEQ ID NOS:22-42);

(b) the polypeptide shown in any one of FIGS. 22-42 (SEQ ID NOS:22-42), lacking its associated signal peptide;

(c) an extracellular domain of the polypeptide shown in any one of FIGS. 22-42 (SEQ ID NOS:22-42), with its associated signal peptide;

(d) an extracellular domain of the polypeptide shown in any one of FIGS. 22-42 (SEQ ID NOS:22-42), lacking its associated signal peptide;

(e) a polypeptide encoded by the nucleotide sequence shown in any one of FIGS. 1-21 (SEQ ID NOS:1-21); or (f) a polypeptide encoded by the full-length coding region of the nucleotide sequence shown in any one of FIGS. 1-21 (SEQ ID NOS:1-21), said method comprising contacting said protein with an antibody, oligopeptide or organic molecule that binds to said protein, there by inhibiting the growth of said cell.

154. The method of Claim 153, wherein said cell is a cancer cell.

155. The method of Claim 153, wherein said protein is expressed by said cell.

156. The method of Claim 153, wherein the binding of said antibody, oligopeptide or organic molecule to said protein antagonizes a cell growth-potentiating activity of said protein.

157. The method of Claim 153, wherein the binding of said antibody, oligopeptide or organic molecule to said protein induces the death of said cell.

158. The method of Claim 153, wherein said antibody is a monoclonal antibody.

159. The method of Claim 153, wherein said antibody is an antibody fragment.

160. The method of Claim 153, wherein said antibody is a chimeric or a humanized antibody.

161. The method of Claim 153, wherein said antibody, oligopeptide or organic molecule is conjugated to a growth inhibitory agent.

162. The method of Claim 153, wherein said antibody, oligopeptide or organic molecule is conjugated to a cytotoxic agent.

163. The method of Claim 162, wherein said cytotoxic agent is selected from the group consisting of toxins, antibiotics, radioactive isotopes and nucleolytic enzymes.

164. The method of Claim 162, wherein the cytotoxic agent is a toxin.

165. The method of Claim 164, wherein the toxin is selected from the group consisting of maytansinoid and calicheamicin.

166. The method of Claim 164, wherein the toxin is a maytansinoid.

167. The method of Claim 153, wherein said antibody is produced in bacteria.

168. The method of Claim 153, wherein said antibody is produced in CHO cells.

169. The method of Claim 153, wherein said protein has:

(a) the amino acid sequence shown in any one of FIGS. 22-42 (SEQ ID NOS:22-42);

(b) the amino acid sequence shown in any one of FIGS. 22-42 (SEQ ID NOS:22-42), lacking its associated signal peptide sequence;

(c) an amino acid sequence of an extracellular domain of the polypeptide shown in any one of FIGS. 22-42 (SEQ ID NOS:22-42), with its associated signal peptide sequence;

(d) an amino acid sequence of an extracellular domain of the polypeptide shown in any one of FIGS. 22-42 (SEQ ID NOS:22-42), lacking its associated signal peptide sequence;

(e) an amino acid sequence encoded by the nucleotide sequence shown in any one of FIGS. 1-21 (SEQ ID NOS:1-21); or (f) an amino acid sequence encoded by the full-length coding region of the nucleotide sequence shown in any one of FIGS. 1-21 (SEQ ID NOS:1-21).

170. A method of therapeutically treating a tumor in a mammal, wherein the growth of said tumor is at least in part dependent upon a growth potentiating effect of a protein having at least 80% amino acid sequence identity to:

(a) the polypeptide shown in any one of FIGS. 22-42 (SEQ ID NOS:22-42);

(b) the polypeptide shown in any one of FIGS. 22-42 (SEQ ID NOS:22-42), lacking its associated signal peptide;

(c) an extracellular domain of the polypeptide shown in any one of FIGS. 22-42 (SEQ ID NOS:22-42), with its associated signal peptide;

(d) an extracellular domain of the polypeptide shown in any one of FIGS. 22-42 (SEQ ID NOS:22-42), lacking its associated signal peptide;

(e) a polypeptide encoded by the nucleotide sequence shown in any one of FIGS. 1-21 (SEQ ID NOS:1-21); or (f) a polypeptide encoded by the full-length coding region of the nucleotide sequence shown in any one of FIGS. 1-21 (SEQ ID NOS:1-21), said method comprising contacting said protein with an antibody, oligopeptide or organic molecule that binds to said protein, thereby effectively treating said tumor.

171. The method of Claim 170, wherein said protein is expressed by cells of said tumor.

172. The method of Claim 170, wherein the binding of said antibody, oligopeptide or organic molecule to said protein antagonizes a cell growth-potentiating activity of said protein.

173. The method of Claim 170, wherein said antibody is a monoclonal antibody.

174. The method of Claim 170, wherein said antibody is an antibody fragment.

175. The method of Claim 170, wherein said antibody is a chimeric or a humanized antibody.

176. The method of Claim 170, wherein said antibody, oligopeptide or organic molecule is conjugated to a growth inhibitory agent.

177. The method of Claim 170, wherein said antibody, oligopeptide or organic molecule is conjugated to a cytotoxic agent.

178. The method of Claim 177, wherein said cytotoxic agent is selected from the group consisting of toxins, antibiotics, radioactive isotopes and nucleolytic enzymes.

179. The method of Claim 177, wherein the cytotoxic agent is a toxin.

180. The method of Claim 179, wherein the toxin is selected from the group consisting of maytansinoid and calicheamicin.

181. The method of Claim 179, wherein the toxin is a maytansinoid.

182. The method of Claim 170, wherein said antibody is produced in bacteria.

183. The method of Claim 170, wherein said antibody is produced in CHO cells.

184. The method of Claim 170, wherein said protein has:

(a) the amino acid sequence shown in any one of FIGS. 22-42 (SEQ ID NOS:22-42);

(b) the amino acid sequence shown in any one of FIGS. 22-42 (SEQ ID NOS:22-42), lacking its associated signal peptide sequence;

(c) an amino acid sequence of an extracellular domain of the polypeptide shown in any one of FIGS. 22-42 (SEQ ID NOS:22-42), with its associated signal peptide sequence;

(d) an amino acid sequence of an extracellular domain of the polypeptide shown in any one of FIGS. 22-42 (SEQ ID NOS:22-42), lacking its associated signal peptide sequence;

(e) an amino acid sequence encoded by the nucleotide sequence shown in any one of FIGS. 1-21 (SEQ ID NOS:1-21); or (f) an amino acid sequence encoded by the full-length coding region of the nucleotide sequence shown in any one of FIGS. 1-21 (SEQ ID NOS:1-21).

Yet further embodiments of the present invention will be evident to the skilled artisan upon a reading of the present specification.

BRIEF DESCRIPTION OF THE DRAWINGS

FIG. 1 shows a nucleotide sequence (SEQ ID NO:1) of a TAT400 cDNA, wherein SEQ ID NO:1 is a clone designated herein as "DNA225795".

FIG. 2 shows a nucleotide sequence (SEQ ID NO:2) of a TAT401 cDNA, wherein SEQ ID NO:2 is a clone designated herein as "DNA62814".

FIG. 3 shows a nucleotide sequence (SEQ ID NO:3) of a TAT402 cDNA, wherein SEQ ID NO:3 is a clone designated herein as "DNA334601".

FIG. 4 shows a nucleotide sequence (SEQ ID NO:4) of a TAT403 cDNA, wherein SEQ ID NO:4 is a clone designated herein as "DNA255030".

FIG. 5 shows a nucleotide sequence (SEQ ID NO:5) of a TAT404 cDNA, wherein SEQ ID NO:5 is a clone designated herein as "DNA257428".

FIG. 6 shows a nucleotide sequence (SEQ ID NO:6) of a TAT405 cDNA, wherein SEQ ID NO:6 is a clone designated herein as "DNA194132".

FIG. 7 shows a nucleotide sequence (SEQ ID NO:7) of a TAT406 cDNA, wherein SEQ ID NO:7 is a clone designated herein as "DNA255706".

FIG. 8 shows a nucleotide sequence (SEQ ID NO:8) of a TAT407 cDNA, wherein SEQ ID NO:8 is a clone designated herein as "DNA329863".

FIG. 9 shows a nucleotide sequence (SEQ ID NO:9) of a TAT408 cDNA, wherein SEQ ID NO:9 is a clone designated herein as "DNA22780".

FIG. 10 shows a nucleotide sequence (SEQ ID NO:10) of a TAT206 cDNA, wherein SEQ ID NO:10 is a clone designated herein as "DNA56041".

FIGS. 11A-B show a nucleotide sequence (SEQ ID NO:11) of a TAT409 cDNA, wherein SEQ ID NO:11 is a clone designated herein as "DNA220758".

FIGS. 12A-B show a nucleotide sequence (SEQ ID NO:12) of a TAT410 cDNA, wherein SEQ ID NO:12 is a clone designated herein as "DNA225549".

FIGS. 13A-B show a nucleotide sequence (SEQ ID NO:13) of a TAT411 cDNA, wherein SEQ ID NO:13 is a clone designated herein as "DNA225701".

FIG. 14 shows a nucleotide sequence (SEQ ID NO:14) of a TAT412 cDNA, wherein SEQ ID NO:14 is a clone designated herein as "DNA226115".

FIG. 15 shows a nucleotide sequence (SEQ ID NO:15) of a TAT413 cDNA, wherein SEQ ID NO:15 is a clone designated herein as "DNA227150".

FIG. 16 shows a nucleotide sequence (SEQ ID NO:16) of a TAT414 cDNA, wherein SEQ ID NO:16 is a clone designated herein as "DNA247426".

FIG. 17 shows a nucleotide sequence (SEQ ID NO:17) of a TAT415 cDNA, wherein SEQ ID NO:17 is a clone designated herein as "DNA84914".

FIGS. 18A-B show a nucleotide sequence (SEQ ID NO:18) of a TAT416 cDNA, wherein SEQ ID NO:18 is a clone designated herein as "DNA226751".

FIG. 19 shows a nucleotide sequence (SEQ ID NO:19) of a TAT417 cDNA, wherein SEQ ID NO:19 is a clone designated herein as "DNA151312".

FIGS. 20A-B show a nucleotide sequence (SEQ ID NO:20) of a TAT418 cDNA, wherein SEQ ID NO:20 is a clone designated herein as "DNA225703".

FIG. 21 shows a nucleotide sequence (SEQ ID NO:21) of a TAT419 cDNA, wherein SEQ ID NO:21 is a clone designated herein as "DNA96945".

FIG. 22 shows the amino acid sequence (SEQ ID NO:22) derived from the coding sequence of SEQ ID NO:1 shown in FIG. 1.

FIG. 23 shows the amino acid sequence (SEQ ID NO:23) derived from the coding sequence of SEQ ID NO:2 shown in FIG. 2.

FIG. 24 shows the amino acid sequence (SEQ ID NO:24) derived from the coding sequence of SEQ ID NO:3 shown in FIG. 3.

FIG. 25 shows the amino acid sequence (SEQ ID NO:25) derived from the coding sequence of SEQ ID NO:4 shown in FIG. 4.

FIG. 26 shows the amino acid sequence (SEQ ID NO:26) derived from the coding sequence of SEQ ID NO:5 shown in FIG. 5.

FIG. 27 shows the amino acid sequence (SEQ ID NO:27) derived from the coding sequence of SEQ ID NO:6 shown in FIG. 6.

FIG. 28 shows the amino acid sequence (SEQ ID NO:28) derived from the coding sequence of SEQ ID NO:7 shown in FIG. 7.

FIG. 29 shows the amino acid sequence (SEQ ID NO:29) derived from the coding sequence of SEQ ID NO:8 shown in FIG. 8.

FIG. 30 shows the amino acid sequence (SEQ ID NO:30) derived from the coding sequence of SEQ ID NO:9 shown in FIG. 9.

FIG. 31 shows the amino acid sequence (SEQ ID NO:31) derived from the coding sequence of SEQ ID NO:10 shown in FIG. 10.

FIG. 32 shows the amino acid sequence (SEQ ID NO:32) derived from the coding sequence of SEQ ID NO:11 shown in FIGS. 11A-B.

FIG. 33 shows the amino acid sequence (SEQ ID NO:33) derived from the coding sequence of SEQ ID NO:12 shown in FIGS. 12A-B.

FIG. 34 shows the amino acid sequence (SEQ ID NO:34) derived from the coding sequence of SEQ ID NO:13 shown in FIGS. 13A-B.

FIG. 35 shows the amino acid sequence (SEQ ID NO:35) derived from the coding sequence of SEQ ID NO:14 shown in FIG. 14.

FIG. 36 shows the amino acid sequence (SEQ ID NO:36) derived from the coding sequence of SEQ ID NO:15 shown in FIG. 15.

FIG. 37 shows the amino acid sequence (SEQ ID NO:37) derived from the coding sequence of SEQ ID NO:16 shown in FIG. 16.

FIG. 38 shows the amino acid sequence (SEQ ID NO:38) derived from the coding sequence of SEQ ID NO:17 shown in FIG. 17.

FIG. 39 shows the amino acid sequence (SEQ ID NO:39) derived from the coding sequence of SEQ ID NO:18 shown in FIGS. 18A-B.

FIG. 40 shows the amino acid sequence (SEQ ID NO:40) derived from the coding sequence of SEQ ID NO:19 shown in FIG. 19.

FIG. 41 shows the amino acid sequence (SEQ ID NO:41) derived from the coding sequence of SEQ ID NO:20 shown in FIGS. 20A-B.

FIG. 42 shows the amino acid sequence (SEQ ID NO:42) derived from the coding sequence of SEQ ID NO:21 shown in FIG. 21.

DETAILED DESCRIPTION OF THE PREFERRED EMBODIMENTS

I. Definitions

The terms "TAT polypeptide" and "TAT" as used herein and when immediately followed by a numerical designation, refer to various polypeptides, wherein the complete designation (i.e., TAT/number) refers to specific polypeptide sequences as described herein. The terms "TAT/number polypeptide" and "TAT/number" wherein the term "number" is provided as an actual numerical designation as used herein encompass native sequence polypeptides, polypeptide variants and fragments of native sequence polypeptides and polypeptide variants (which are further defined herein). The TAT polypeptides described herein may be isolated from a variety of sources, such as from human tissue types or from another source, or prepared by recombinant or synthetic methods. The term "TAT polypeptide" refers to each individual TAT/number polypeptide disclosed herein. All disclosures in this specification which refer to the "TAT polypeptide" refer to each of the polypeptides individually as well as jointly. For example, descriptions of the preparation of, purification of, derivation of, formation of antibodies to or against, formation of TAT binding oligopeptides to or against, formation of TAT binding organic molecules to or against, administration of, compositions containing, treatment of a disease with, etc., pertain to each polypeptide of the invention individually. The term "TAT polypeptide" also includes variants of the TAT/number polypeptides disclosed herein.

A "native sequence TAT polypeptide" comprises a polypeptide having the same amino acid sequence as the corresponding TAT polypeptide derived from nature. Such native sequence TAT polypeptides can be isolated from nature or can be produced by recombinant or synthetic means. The term "native sequence TAT polypeptide" specifically encompasses naturally-occurring truncated or secreted forms of the specific TAT polypeptide (e.g., an extracellular domain sequence), naturally-occurring variant forms (e.g., alternatively spliced forms) and naturally-occurring allelic variants of the polypeptide. In certain embodiments of the invention, the native sequence TAT polypeptides disclosed herein are mature or full-length native sequence polypeptides comprising the full-length amino acids sequences shown in the accompanying figures. Start and stop codons (if indicated) are shown in bold font and underlined in the figures. Nucleic acid residues indicated as "N" or "X" in the accompanying figures are any nucleic acid residue. However, while the TAT polypeptides disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the TAT polypeptides.

The TAT polypeptide "extracellular domain" or "ECD" refers to a form of the TAT polypeptide which is essentially free of the transmembrane and cytoplasmic domains. Ordinarily, a TAT polypeptide ECD will have less than 1% of such transmembrane and/or cytoplasmic domains and preferably, will have less than 0.5% of such domains. It will be understood that any transmembrane domains identified for the TAT polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a TAT polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various TAT polypeptides disclosed herein may be shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., Prot. Eng. 10:1-6 (1997) and von Heinje et al., Nucl. Acids. Res. 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"TAT polypeptide variant" means a TAT polypeptide, preferably an active TAT polypeptide, as defined herein having at least about 80% amino acid sequence identity with a full-length native sequence TAT polypeptide sequence as disclosed herein, a TAT polypeptide sequence lacking the signal peptide as disclosed herein, an extracellular domain of a TAT polypeptide, with or without the signal peptide, as disclosed herein or any other fragment of a full-length TAT polypeptide sequence as disclosed herein (such as those encoded by a nucleic acid that represents only a portion of the complete coding sequence for a full-length TAT polypeptide). Such TAT polypeptide variants include, for instance, TAT polypeptides wherein one or more amino acid residues are added, or deleted, at the N- or C-terminus of the full-length native amino acid sequence. Ordinarily, a TAT polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence TAT polypeptide sequence as disclosed herein, a TAT polypeptide sequence lacking the signal peptide as disclosed herein, an extracellular domain of a TAT polypeptide, with or without the signal peptide, as disclosed herein or any other specifically defined fragment of a full-length TAT polypeptide sequence as disclosed herein. Ordinarily, TAT variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, TAT variant polypeptides will have no more than one conservative amino acid substitution as compared to the native TAT polypeptide sequence, alternatively no more than 2, 3, 4, 5, 6, 7, 8, 9, or 10 conservative amino acid substitution as compared to the native TAT polypeptide sequence.

"Percent (%) amino acid sequence identity" with respect to the TAT polypeptide sequences identified herein is defined as the percentage of amino acid residues in a candidate sequence that are identical with the amino acid residues in the specific TAT polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "TAT", wherein "TAT" represents the amino acid sequence of a hypothetical TAT polypeptide of interest, "Comparison Protein" represents the amino acid sequence of a polypeptide against which the "TAT" polypeptide of interest is being compared, and "X", "Y" and "Z" each represent different hypothetical amino acid residues. Unless specifically stated otherwise, all % amino acid sequence identity values used herein are obtained as described in the immediately preceding paragraph using the ALIGN-2 computer program.

"TAT variant polynucleotide" or "TAT variant nucleic acid sequence" means a nucleic acid molecule which encodes a TAT polypeptide, preferably an active TAT polypeptide, as defined herein and which has at least about 80% nucleic acid sequence identity with a nucleotide acid sequence encoding a full-length native sequence TAT polypeptide sequence as disclosed herein, a full-length native sequence TAT polypeptide sequence lacking the signal peptide as disclosed herein, an extracellular domain of a TAT polypeptide, with or without the signal peptide, as disclosed herein or any other fragment of a full-length TAT polypeptide sequence as disclosed herein (such as those encoded by a nucleic acid that represents only a portion of the complete coding sequence for a full-length TAT polypeptide). Ordinarily, a TAT variant polynucleotide will have at least about 80% nucleic acid sequence identity, alternatively at least about 8%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence TAT polypeptide sequence as disclosed herein, a full-length native sequence TAT polypeptide sequence lacking the signal peptide as disclosed herein, an extracellular domain of a TAT polypeptide, with or without the signal sequence, as disclosed herein or any other fragment of a full-length TAT polypeptide sequence as disclosed herein. Variants do not encompass the native nucleotide sequence.

Ordinarily, TAT variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to TAT-encoding nucleic acid sequences identified herein is defined as the percentage of nucleotides in a candidate sequence that are identical with the nucleotides in the TAT nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "TAT-DNA", wherein "TAT-DNA" represents a hypothetical TAT-encoding nucleic acid sequence of interest, "Comparison DNA" represents the nucleotide sequence of a nucleic acid molecule against which the "TAT-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

In other embodiments, TAT variant polynucleotides are nucleic acid molecules that encode a TAT polypeptide and which are capable of hybridizing, preferably under stringent hybridization and wash conditions, to nucleotide sequences encoding a full-length TAT polypeptide as disclosed herein. TAT variant polypeptides may be those that are encoded by a TAT variant polynucleotide.

The term "full-length coding region" when used in reference to a nucleic acid encoding a TAT polypeptide refers to the sequence of nucleotides which encode the full-length TAT polypeptide of the invention (which is often shown between start and stop codons, inclusive thereof, in the accompanying figures). The term "full-length coding region" when used in reference to an ATCC deposited nucleic acid refers to the TAT polypeptide-encoding portion of the cDNA that is inserted into the vector deposited with the ATCC (which is often shown between start and stop codons, inclusive thereof, in the accompanying figures).

"Isolated," when used to describe the various TAT polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the TAT polypeptide natural environment will not be present. Ordinarily, however, isolated polypeptide will be prepared by at least one purification step.

An "isolated" TAT polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a TAT polypeptide or anti-TAT antibody fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a TAT polypeptide which retain a biological and/or an immunological activity of native or naturally-occurring TAT, wherein "biological" activity refers to a biological function (either inhibitory or stimulatory) caused by a native or naturally-occurring TAT other than the ability to induce the production of an antibody against an antigenic epitope possessed by a native or naturally-occurring TAT and an "immunological" activity refers to the ability to induce the production of an antibody against an antigenic epitope possessed by a native or naturally-occurring TAT.

The term "antagonist" is used in the broadest sense, and includes any molecule that partially or fully blocks, inhibits, or neutralizes a biological activity of a native TAT polypeptide disclosed herein. In a similar manner, the term "agonist" is used in the broadest sense and includes any molecule that mimics a biological activity of a native TAT polypeptide disclosed herein. Suitable agonist or antagonist molecules specifically include agonist or antagonist antibodies or antibody fragments, fragments or amino acid sequence variants of native TAT polypeptides, peptides, antisense oligonucleotides, small organic molecules, etc. Methods for identifying agonists or antagonists of a TAT polypeptide may comprise contacting a TAT polypeptide with a candidate agonist or antagonist molecule and measuring a detectable change in one or more biological activities normally associated with the TAT polypeptide.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a TAT polypeptide-expressing cancer if, after receiving a therapeutic amount of an anti-TAT antibody, TAT binding oligopeptide or TAT binding organic molecule according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-TAT antibody or TAT binding oligopeptide may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

For bladder cancer, which is a more localized cancer, methods to determine progress of disease include urinary cytologic evaluation by cystoscopy, monitoring for presence of blood in the urine, visualization of the urothelial tract by sonography or an intravenous pyelogram, computed tomography (CT) and magnetic resonance imaging (MRI). The presence of distant metastases can be assessed by CT of the abdomen, chest x-rays, or radionuclide imaging of the skeleton.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of or diagnosis of a cancer refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which an antibody, TAT binding oligopeptide or TAT binding organic molecule of the present invention can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a TAT polypeptide, an antibody thereto or a TAT binding oligopeptide) to a mammal. The components of the liposome are commonly arranged in a bilayer formation, similar to the lipid arrangement of biological membranes.

A "small" molecule or "small" organic molecule is defined herein to have a molecular weight below about 500 Daltons.

An "effective amount" of a polypeptide, antibody, TAT binding oligopeptide, TAT binding organic molecule or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an antibody, polypeptide, TAT binding oligopeptide, TAT binding organic molecule or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

A "growth inhibitory amount" of an anti-TAT antibody, TAT polypeptide, TAT binding oligopeptide or TAT binding organic molecule is an amount capable of inhibiting the growth of a cell, especially tumor, e.g., cancer cell, either in vitro or in vivo. A "growth inhibitory amount" of an anti-TAT antibody, TAT polypeptide, TAT binding oligopeptide or TAT binding organic molecule for purposes of inhibiting neoplastic cell growth may be determined empirically and in a routine manner.

A "cytotoxic amount" of an anti-TAT antibody, TAT polypeptide, TAT binding oligopeptide or TAT binding organic molecule is an amount capable of causing the destruction of a cell, especially tumor, e.g., cancer cell, either in vitro or in vivo. A "cytotoxic amount" of an anti-TAT antibody, TAT polypeptide, TAT binding oligopeptide or TAT binding organic molecule for purposes of inhibiting neoplastic cell growth may be determined empirically and in a routine manner.

The term "antibody" is used in the broadest sense and specifically covers, for example, single anti-TAT monoclonal antibodies (including agonist, antagonist, and neutralizing antibodies), anti-TAT antibody compositions with poly-epitopic specificity, polyclonal antibodies, single chain anti-TAT antibodies, and fragments of anti-TAT antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature*, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains may be native sequence constant domains e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

A "TAT binding oligopeptide" is an oligopeptide that binds, preferably specifically, to a TAT polypeptide as described herein. TAT binding oligopeptides may be chemically synthesized using known oligopeptide synthesis methodology or may be prepared and purified using recombinant technology. TAT binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a TAT polypeptide as described herein. TAT binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833, 092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

A "TAT binding organic molecule" is an organic molecule other than an oligopeptide or antibody as defined herein that binds, preferably specifically, to a TAT polypeptide as described herein. TAT binding organic molecules may be identified and chemically synthesized using known methodology (see, e.g., PCT Publication Nos. WO00/00823 and WO00/39585). TAT binding organic molecules are usually less than about 2000 daltons in size, alternatively less than about 1500, 750, 500, 250 or 200 daltons in size, wherein such organic molecules that are capable of binding, preferably specifically, to a TAT polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is useful as a diagnostic and/or therapeutic agent in targeting a cell or tissue expressing the antigen, and does not significantly cross-react with other proteins. In such embodiments, the extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

An antibody, oligopeptide or other organic molecule that "inhibits the growth of tumor cells expressing a TAT polypeptide" or a "growth inhibitory" antibody, oligopeptide or other organic molecule is one which results in measurable growth inhibition of cancer cells expressing or overexpressing the appropriate TAT polypeptide. The TAT polypeptide may be a transmembrane polypeptide expressed on the surface of a cancer cell or may be a polypeptide that is produced and secreted by a cancer cell. Preferred growth inhibitory anti-TAT antibodies, oligopeptides or organic molecules inhibit growth of TAT-expressing tumor cells by greater than 20%, preferably from about 20% to about 50%, and even more preferably, by greater than 50% (e.g., from about 50% to about 100%) as compared to the appropriate control, the control typically being tumor cells not treated with the antibody, oligopeptide or other organic molecule being tested. In one embodiment, growth inhibition can be measured at an antibody concentration of about 0.1 to 30 μg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-TAT antibody at about 1 μg/kg to about 100 mg/kg body weight results in reduction in tumor size or tumor cell proliferation within about 5 days to 3 months from the first administration of the antibody, preferably within about 5 to 30 days.

An antibody, oligopeptide or other organic molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses a TAT polypeptide. Preferably the cell is a tumor cell, e.g., a prostate, breast, ovarian, stomach, endometrial, lung, kidney, colon, bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express Fc γRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *Immunol. Methods* 202:163 (1996), may be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues.

An antibody, oligopeptide or other organic molecule which "induces cell death" is one which causes a viable cell to become nonviable. The cell is one which expresses a TAT polypeptide, preferably a cell that overexpresses a TAT polypeptide as compared to a normal cell of the same tissue type. The TAT polypeptide may be a transmembrane polypeptide expressed on the surface of a cancer cell or may be a polypeptide that is produced and secreted by a cancer cell. Preferably, the cell is a cancer cell, e.g., a breast, ovarian, stomach, endometrial, salivary gland, lung, kidney, colon, thyroid, pancreatic or bladder cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody, oligopeptide or other organic molecule is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies, oligopeptides or other organic molecules are those which induce PI uptake in the PI uptake assay in BT474 cells.

A "TAT-expressing cell" is a cell which expresses an endogenous or transfected TAT polypeptide either on the cell surface or in a secreted form. A "TAT-expressing cancer" is a cancer comprising cells that have a TAT polypeptide present on the cell surface or that produce and secrete a TAT polypeptide. A "TAT-expressing cancer" optionally produces sufficient levels of TAT polypeptide on the surface of cells thereof, such that an anti-TAT antibody, oligopeptide or other organic molecule can bind thereto and have a therapeutic effect with respect to the cancer. In another embodiment, a "TAT-expressing cancer" optionally produces and secretes sufficient levels of TAT polypeptide, such that an anti-TAT antibody, oligopeptide or other organic molecule antagonist can bind thereto and have a therapeutic effect with respect to the cancer. With regard to the latter, the antagonist may be an antisense oligonucleotide which reduces, inhibits or prevents production and secretion of the secreted TAT polypeptide by tumor cells. A cancer which "overexpresses" a TAT polypeptide is one which has significantly higher levels of TAT polypeptide at the cell surface thereof, or produces and secretes, compared to a noncancerous cell of the same tissue type. Such overexpression may be caused by gene amplification or by increased transcription or translation. TAT polypeptide overexpression may be determined in a diagnostic or prognostic assay by evaluating increased levels of the TAT protein present on the surface of a cell, or secreted by the cell (e.g., via an immunohistochemistry assay using anti-TAT antibodies prepared against an isolated TAT polypeptide which may be prepared using recombinant DNA technology from an isolated nucleic acid encoding the TAT polypeptide; FACS analysis, etc.). Alternatively, or additionally, one may measure levels of TAT polypeptide-encoding nucleic acid or mRNA in the cell, e.g., via fluorescent in situ hybridization using a nucleic acid based probe corresponding to a TAT-encoding nucleic acid or the complement thereof; (FISH; see WO98/45479 published October, 1998), Southern blotting, Northern blotting, or polymerase chain reaction (PCR) techniques, such as real time quantitative PCR(RT-PCR). One may also study TAT polypeptide overexpression by measuring shed antigen in a biological fluid such as serum, e.g, using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., *J. Immunol. Methods* 132:73-80 (1990)). Aside from the above assays, various in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody, oligopeptide or other organic molecule so as to generate a "labeled" antibody, oligopeptide or other organic molecule. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "growth inhibitory agent" when used herein refers to a compound or composition which inhibits growth of a cell, especially a TAT-expressing cancer cell, either in vitro or in vivo. Thus, the growth inhibitory agent may be one which significantly reduces the percentage of TAT-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3, 6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon -α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

TABLE 1

```
/*
*
* C-C increased from 12 to 15
* Z is average of EQ
* B is average of ND
* match with stop is _M; stop-stop = 0; J (joker) match = 0
*/
#define    _M      -8      /* value of a match with a stop */
int       _day[26][26] = {
/* A     B C D E F G H I J K L M N O P Q R S T U V W X Y Z */
/* A */  { 2, 0,-2, 0, 0,-4, 1,-1,-1, 0,-1,-2,-1, 0,_M, 1, 0,-2, 1, 1, 0, 0,-6, 0,-3, 0},
/* B */  { 0, 3,-4, 3, 2,-5, 0, 1,-2, 0, 0,-3,-2, 2,_M,-1, 1, 0, 0, 0, 0,-2,-5, 0,-3, 1},
/* C */  {-2,-4,15,-5,-5,-4,-3,-3,-2, 0,-5,-6,-5,-4,_M,-3,-5,-4, 0,-2, 0,-2,-8, 0, 0,-5},
```

TABLE 1-continued

```
/* D */    { 0, 3,-5, 4, 3,-6, 1, 1,-2, 0, 0,-4,-3, 2,_M,-1, 2,-1, 0, 0, 0,-2,-7, 0,-4, 2},
/* E */    { 0, 2,-5, 3, 4,-5, 0, 1,-2, 0, 0,-3,-2, 1,_M,-1, 2,-1, 0, 0, 0,-2,-7, 0,-4, 3},
/* F */    {-4,-5,-4,-6,-5, 9,-5,-2, 1, 0,-5, 2, 0,-4,_M,-5,-5,-4,-3,-3, 0,-1, 0, 0, 7,-5},
/* G */    { 1, 0,-3, 1, 0,-5, 5,-2,-3, 0,-2,-4,-3, 0,_M,-1,-1,-3, 1, 0, 0,-1,-7, 0,-5, 0},
/* H */    {-1, 1,-3, 1, 1,-2,-2, 6,-2, 0, 0,-2,-2, 2,_M, 0, 3, 2,-1,-1, 0,-2,-3, 0, 0, 2},
/* I */    {-1,-2,-2,-2,-2, 1,-3,-2, 5, 0,-2, 2, 2,-2,_M,-2,-2,-2,-1, 0, 0, 4,-5, 0,-1,-2},
/* J */    { 0, 0, 0, 0, 0, 0, 0, 0, 0, 0, 0, 0, 0, 0,_M, 0, 0, 0, 0, 0, 0, 0, 0, 0, 0, 0},
/* K */    {-1, 0,-5, 0, 0,-5,-2, 0,-2, 0, 5,-3, 0, 1,_M,-1, 1, 3, 0, 0, 0,-2,-3, 0,-4, 0},
/* L */    {-2,-3,-6,-4,-3, 2,-4,-2, 2, 0,-3, 6, 4,-3,_M,-3,-2,-3,-3,-1, 0, 2,-2, 0,-1,-2},
/* M */    {-1,-2,-5,-3,-2, 0,-3,-2, 2, 0, 0, 4, 6,-2,_M,-2,-1, 0,-2,-1, 0, 2,-4, 0,-2,-1},
/* N */    { 0, 2,-4, 2, 1,-4, 0, 2,-2, 0, 1,-3,-2, 2,_M,-1, 1, 0, 1, 0, 0,-2,-4, 0,-2, 1},
/* O */    {_M,_M,_M,_M,_M,_M,_M,_M,_M,_M,_M,_M,_M,_M,_M, 0,_M,_M,_M,_M,_M,_M,_M,_M,_M,_M},
/* P */    { 1,-1,-3,-1,-1,-5,-1, 0,-2, 0,-1,-3,-2,-1,_M, 6, 0, 0, 1, 0,-1,-6, 0,-5, 0},
/* Q */    { 0, 1,-5, 2, 2,-5,-1, 3,-2, 0, 1,-2,-1, 1,_M, 0, 4, 1,-1,-1, 0,-2,-5, 0,-4, 3},
/* R */    {-2, 0,-4,-1,-1,-4,-3, 2,-2, 0, 3,-3, 0, 0,_M, 0, 1, 6, 0,-1, 0,-2, 2, 0,-4, 0},
/* S */    { 1, 0, 0, 0, 0,-3, 1,-1,-1, 0, 0,-3,-2, 1,_M, 1,-1, 0, 2, 1, 0,-1,-2, 0,-3, 0},
/* T */    { 1, 0,-2, 0, 0,-3, 0,-1, 0, 0, 0,-1,-1, 0,_M, 0,-1,-1, 1, 3, 0, 0,-5, 0,-3, 0},
/* U */    { 0, 0, 0, 0, 0, 0, 0, 0, 0, 0, 0, 0, 0, 0,_M, 0, 0, 0, 0, 0, 0, 0, 0, 0, 0, 0},
/* V */    { 0,-2,-2,-2,-2,-1,-1,-2, 4, 0,-2, 2, 2,-2,_M,-1,-2,-2,-1, 0, 0, 4,-6, 0,-2,-2},
/* W */    {-6,-5,-8,-7,-7, 0,-7,-3,-5, 0,-3,-2,-4,-4,_M,-6,-5, 2,-2,-5, 0,-6,17, 0, 0,-6},
/* X */    { 0, 0, 0, 0, 0, 0, 0, 0, 0, 0, 0, 0, 0, 0,_M, 0, 0, 0, 0, 0, 0, 0, 0, 0, 0, 0},
/* Y */    {-3,-3, 0,-4,-4, 7,-5, 0,-1, 0,-4,-1,-2,-2,_M,-5,-4,-4,-3,-3, 0,-2, 0, 0,10,-4},
/* Z */    { 0, 1,-5, 2, 3,-5, 0, 2,-2, 0, 0,-2,-1, 1,_M, 0, 3, 0, 0, 0, 0,-2,-6, 0,-4, 4}
};
/*
*/
#include <stdio.h>
#include <ctype.h>
#define   MAXJMP     16        /* max jumps in a diag */
#define   MAXGAP     24        /* don't continue to penalize gaps larger than this */
#define   JMPS       1024      /* max jmps in an path */
#define   MX         4         /* save if there's at least MX-1 bases since last jmp */
#define   DMAT       3         /* value of matching bases */
#define   DMIS       0         /* penalty for mismatched bases */
#define   DINS0      8         /* penalty for a gap */
#define   DINS1      1         /* penalty per base */
#define   PINS0      8         /* penalty for a gap */
#define   PINS1      4         /* penalty per residue */
struct jmp {
          short         n[MAXJMP];          /* size of jmp (neg for dely) */
          unsigned short x[MAXJMP];         /* base no. of jmp in seq x */
};                                          /* limits seq to 2 16 -1 */
struct diag {
          int           score;              /* score at last jmp */
          long          offset;             /* offset of prev block */
          short         ijmp;               /* current jmp index */
          struct        jmp jp;             /* list of jmps */
};
struct path {
          int           spc;                /* number of leading spaces */
          short         n[JMPS];            /* size of jmp (gap) */
          int           x[JMPS];            /* loc of jmp (last elem before gap) */
};
char              *ofile;                   /* output file name */
char              *namex[2];                /* seq names: getseqs( ) */
char              *prog;                    /* prog name for err msgs */
char              *seqx[2];                 /* seqs: getseqs( ) */
int               dmax;                     /* best diag: nw( ) */
int               dmax0;                    /* final diag */
int               dna;                      /* set if dna: main( ) */
int               endgaps;                  /* set if penalizing end gaps */
int               gapx, gapy;               /* total gaps in seqs */
int               len0, len1;               /* seq lens */
int               ngapx, ngapy;             /* total size of gaps */
int               smax;                     /* max score: nw( ) */
int               *xbm;                     /* bitmap for matching */
long              offset;                   /* current offset in jmp file */
struct   diag     *dx;                      /* holds diagonals */
struct   path     pp[2];                    /* holds path for seqs */
char              *calloc( ), *malloc( ), *index( ), *strcpy( );
char              *getseq( ), *g_calloc( );
/* Needleman-Wunsch alignment program
*
* usage: progs file1 file2
* where file1 and file2 are two dna or two protein sequences.
* The sequences can be in upper- or lower-case an may contain ambiguity
* Any lines beginning with ';', '>' or '<' are ignored
* Max file length is 65535 (limited by unsigned short x in the jmp struct)
* A sequence with ⅓ or more of its elements ACGTU is assumed to be DNA
* Output is in the file "align.out"
```

TABLE 1-continued

```
*
* The program may create a tmp file in /tmp to hold info about traceback.
* Original version developed under BSD 4.3 on a vax 8650
*/
#include "nw.h"
#include "day.h"
static      _dbval[26] = {
        1,14,2,13,0,0,4,11,0,0,12,0,3,15,0,0,0,5,6,8,8,7,9,0,10,0
};
static      _pbval[26] = {
        1, 2|(1<<('D'-'A'))|(1<<('N'-'A')), 4, 8, 16, 32, 64,
        128, 256, 0xFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};
main(ac, av)                                                                                  main
        int     ac;
        char    *av[ ];
{ prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;
        endgaps = 0;                    /* 1 to penalize endgaps */
        ofile = "align.out";            /* output file */
        nw( );                          /* fill in the matrix, get the possible jmps */
        readjmps( );                    /* get the actual jmps */
        print( );                       /* print stats, alignment */
        cleanup(0);                     /* unlink any tmp files */}
/* do the alignment, return best score: main( )
* dna: values in Fitch and Smith, PNAS, 80, 1382-1386, 1983
* pro: PAM 250 values
* When scores are equal, we prefer mismatches to any gap, prefer
* a new gap to extending an ongoing gap, and prefer a gap in seqx
* to a gap in seq y.
*/
nw( )                                                                                         nw
{
        char            *px, *py;               /* seqs and ptrs */
        int             *ndely, *dely;          /* keep track of dely */
        int             ndelx, delx;            /* keep track of delx */
        int             *tmp;                   /* for swapping row0, row1 */
        int             mis;                    /* score for each type */
        int             ins0, ins1;             /* insertion penalties */
        register        id;                     /* diagonal index */
        register        ij;                     /* jmp index */
        register        *col0, *col1;           /* score for curr, last row */
        register        xx, yy;                 /* index into seqs */
        dx = (struct diag *)g_calloc("to get diags", len0+len1+1, sizeof(struct diag));
        ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;
        smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;            /* Waterman Bull Math Biol 84 */
        }
        else
                for (yy = 1; yy <= len1; yy++)
                        dely[yy] = -ins0;
        /* fill in match matrix
        */
        for (px = seqx[0], xx = 1; xx <= len0; px++, xx++) {
                /* initialize first entry in col
```

TABLE 1-continued

```
            */
            if (endgaps) {
                    if (xx == 1)
                            col1[0] = delx = -(ins0+ins1);
                    else
                            col1[0] = delx = col0[0] - ins1;
                    ndelx = xx;
            }
            else {
                    col1[0] = 0;
                    delx = -ins0;
                    ndelx = 0;
            }
                                                                                                        ...nw
    for (py = seqx[1], yy = 1; yy <= len1; py++, yy++) {
            mis = col0[yy-1];
            if (dna)
                    mis += (xbm[*px-'A']&xbm[*py-'A'])? DMAT : DMIS;
            else
                    mis += __day[*px-'A'][*py-'A'];
            /* update penalty for del in x seq;
             * favor new del over ongong del
             * ignore MAXGAP if weighting endgaps
             */
            if (endgaps || ndely[yy] < MAXGAP) {
                    if (col0[yy] - ins0 >= dely[yy]) {
                            dely[yy] = col0[yy] - (ins0+ins1);
                            ndely[yy] = 1;
                    } else {
                            dely[yy] -= ins1;
                            ndely[yy]++;
                    }
            } else {
                    if (col0[yy] - (ins0+ins1) >= dely[yy]) {
                            dely[yy] = col0[yy] - (ins0+ins1);
                            ndely[yy] = 1;
                    } else
                            ndely[yy]++;
            }
            /* update penalty for del in y seq;
             * favor new del over ongong del
             */
            if (endgaps || ndelx < MAXGAP) {
                    if (col1[yy-1] - ins0 >= delx) {
                            delx = col1[yy-1] - (ins0+ins1);
                            ndelx = 1;
                    } else {
                            delx -= ins1;
                            ndelx++;
                    }
            } else {
                    if (col1[yy-1] - (ins0+ins1) >= delx) {
                            delx = col1[yy-1] - (ins0+ins1);
                            ndelx = 1;
                    } else
                            ndelx++;
            }
            /* pick the maximum score; we're favoring
             * mis over any del and delx over dely
             */
                                                                                                        ...nw
            id = xx - yy + len1 - 1;
            if (mis >= delx && mis >= dely[yy])
                    col1[yy] = mis;
            else if (delx >= dely[yy]) {
                    col1[yy] = delx;
                    ij = dx[id].ijmp;
                    if (dx[id].jp.n[0] && (!dna || (ndelx >= MAXJMP
                            && xx > dx[id].jp.x[ij]+MX) || mis > dx[id].score+DINS0)) {
                            dx[id].ijmp++;
                            if (++ij >= MAXJMP) {
                                    writejmps(id);
                                    ij = dx[id].ijmp = 0;
                                    dx[id].offset = offset;
                                    offset += sizeof(struct jmp) + sizeof(offset);
                            }
                    }
                    dx[id].jp.n[ij] = ndelx;
                    dx[id].jp.x[ij] = xx;
                    dx[id].score = delx;
```

TABLE 1-continued

```
                }
                else {
                        col1[yy] = dely[yy];
                        ij = dx[id].ijmp;
if (dx[id].jp.n[0] && (!dna || (ndely[yy] >= MAXJMP
                                && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = –ndely[yy];
                        dx[id].jp.x[ij] = xx;
                        dx[id].score = dely[yy];
                }
                if (xx == len0 && yy < len1) {
                        /* last col
                         */
                        if (endgaps)
                                col1[yy] –= ins0+ins1*(len1–yy);
                        if (col1[yy] > smax) {
                                smax = col1[yy];
                                dmax = id;
                        }
                }
        }
        if (endgaps && xx < len0)
                col1[yy–1] –= ins0+ins1*(len0–xx);
        if (col1[yy–1] > smax) {
                smax = col1[yy–1];
                dmax = id;
        }
        tmp = col0; col0 = col1; col1 = tmp;              }
(void) free((char *)ndely);
(void) free((char *)dely);
(void) free((char *)col0);
(void) free((char *)col1);                                 }
/*
*
* print( ) -- only routine visible outside this module
*
* static:
* getmat( ) -- trace back best path, count matches: print( )
* pr_align( ) -- print alignment of described in array p[ ]: print( )
* dumpblock( ) -- dump a block of lines with numbers, stars: pr_align( )
* nums( ) -- put out a number line: dumpblock( )
* putline( ) -- put out a line (name, [num], seq, [num]): dumpblock( )
* stars( ) -- -put a line of stars: dumpblock( )
* stripname( ) -- strip any path and prefix from a seqname
*/
#include "nw.h"
#define SPC        3
#define P_LINE     256      /* maximum output line */
#define P_SPC      3        /* space between name or num and seq */
extern     _day[26][26];
int        olen;            /* set output line length */
FILE       *fx;             /* output file */
print( )                                                                                         print
{
        int     lx, ly, firstgap, lastgap;      /* overlap */
        if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 – 1) {          /* leading gap in x */
                pp[0].spc = firstgap = len1 – dmax – 1;
                ly –= pp[0].spc;
        }
        else if (dmax > len1 – 1) {     /* leading gap in y */
                pp[1].spc = firstgap = dmax – (len1 – 1);
                lx –= pp[1].spc;
```

TABLE 1-continued

```
                }
                if (dmax0 < len0 – 1) {        /* trailing gap in x */
                        lastgap = len0 – dmax0 –1;
                        lx –= lastgap;
                }
                else if (dmax0 > len0 – 1) {              /* trailing gap in y */
                        lastgap = dmax0 – (len0 – 1);
                        ly –= lastgap;
                }
                getmat(lx, ly, firstgap, lastgap);
                pr_align( );              }
/*
* trace back the best path, count matches
*/
static
getmat(lx, ly, firstgap, lastgap)                                                                                        getmat
        int       lx, ly;                      /* "core" (minus endgaps) */
        int       firstgap, lastgap;           /* leading trailing overlap */
{
        int              nm, i0, i1, siz0, siz1;
        char             outx[32];
        double           pct;
        register         n0, n1;
        register         char *p0, *p1;
        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }
        /* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
        fprintf(fx, "<gaps in first sequence: %d", gapx);                                                                 ...getmat
        if (gapx) {
                (void) sprintf(outx, " (%d %s%s)",
                        ngapx, (dna)? "base":"residue", (ngapx == 1)? "":"s");
                fprintf(fx,"%s", outx);
        }
        fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                        "\n<score: %d (match = %d, mismatch = %d, gap penalty = %d + %d per base)\n",
```

TABLE 1-continued

```
                       smax, DMAT, DMIS, DINS0, DINS1);
        else
                    fprintf(fx,
                    "\n<score: %d (Dayhoff PAM 250 matrix, gap penalty = %d + %d per residue)\n",
                    smax, PINS0, PINS1);
        if (endgaps)
                    fprintf(fx,
                    "<endgaps penalized. left endgap: %d %s%s, right endgap: %d %s%s\n",
                    firstgap, (dna)? "base" : "residue", (firstgap == 1)? "" : "s",
                    lastgap, (dna)? "base" : "residue", (lastgap == 1)? "" : "s");
        else
                    fprintf(fx, "<endgaps not penalized\n");
}
static           nm;            /* matches in core -- for checking */
static           lmax;          /* lengths of stripped file names */
static           ij[2];         /* jmp index for a path */
static           nc[2];         /* number at start of current line */
static           ni[2];         /* current elem number -- for gapping */
static           siz[2];
static char      *ps[2];        /* ptr to current element */
static char      *po[2];        /* ptr to next output char slot */
static char      out[2][P_LINE];/* output line */
static char      star[P_LINE];  /* set by stars( ) */
/*
 * print alignment of described in struct path pp[ ]
 */
static
pr_align( )                                                                                         pr_align
{
        int           nn;        /* char count */
        int           more;
        register      i;
        for (i = 0, lmax = 0; i < 2; i++) {
                    nn = stripname(namex[i]);
                    if (nn > lmax)
                              lmax = nn;
                    nc[i] = 1;
                    ni[i] = 1;
                    siz[i] = ij[i] = 0;
                    ps[i] = seqx[i];
                    po[i] = out[i];                       }
        for (nn = nm = 0, more = 1; more; ) {                                                       ...pr_align
                    for (i = more = 0; i < 2; i++) {
                              /*
                               * do we have more of this sequence?
                               */
                              if (!*ps[i])
                                        continue;
                              more++;
                              if (pp[i].spc) {     /* leading space */
                                        *po[i]++ = ' ';
                                        pp[i].spc--;
                              }
                              else if (siz[i]) {   /* in a gap */
                                        *po[i]++ = '-';
                                        siz[i]--;
                              }
                              else {                /* we're putting a seq element
                                                     */
                                        *po[i] = *ps[i];
                                        if (islower(*ps[i]))
                                                  *ps[i] = toupper(*ps[i]);
                                        po[i]++;
                                        ps[i]++;
                                        /*
                                         * are we at next gap for this seq?
                                         */
                                        if (ni[i] == pp[i].x[ij[i]]) {
                                                  /*
                                                   * we need to merge all gaps
                                                   * at this location
                                                   */
                                                  siz[i] = pp[i].n[ij[i]++];
                                                  while (ni[i] == pp[i].x[ij[i]])
                                                            siz[i] += pp[i].n[ij[i]++];
                                        }
                                        ni[i]++;
                              }
                    }
                    if (++nn == olen || !more && nn) {
```

TABLE 1-continued

```
                    dumpblock( );
                    for (i = 0; i < 2; i++)
                              po[i] = out[i];
                    nn = 0;
          }
     }
}
/*
* dump a block of lines, including numbers, stars: pr_align( )
*/
static
dumpblock( )                                                                                    dumpblock
{
     register i;
     for (i = 0; i < 2; i++)
               *po[i]-- = '\0';                                                                 ...dumpblock
     (void) putc('\n', fx);
     for (i = 0; i < 2; i++) {
               if (*out[i] && (*out[i] != ' ' || *(po[i]) != ' ')) {
                         if (i == 0)
                                   nums(i);
                         if (i == 0 && *out[1])
                                   stars( );
                         putline(i);
                         if (i == 0 && *out[1])
                                   fprintf(fx, star);
                         if (i == 1)
                                   nums(i);
               }
     }
}
/*
* put out a number line: dumpblock( )
*/
static
nums(ix)                                                                                        nums
     int       ix;          /* index in out[ ] holding seq line */
{
     char           nline[P_LINE];
     register       i, j;
     register char  *pn, *px, *py;
     for (pn = nline, i = 0; i < lmax+P_SPC; i++, pn++)
               *pn = ' ';
     for (i = nc[ix], py = out[ix]; *py; py++, pn++) {
               if (*py == ' ' || *py == '-')
                         *pn = ' ';
               else {
                         if (i%10 == 0 || (i == 1 && nc[ix] != 1)) {
                                   j = (i < 0)? -i : i;
                                   for (px = pn; j; j /= 10, px--)
                                             *px = j%10 + '0';
                                   if (i < 0)
                                             *px = '-';
                         }
                         else
                                   *pn = ' ';
                         i++;
               }
     }
     *pn = '\0';
     nc[ix] = i;
     for (pn = nline; *pn; pn++)
               (void) putc(*pn, fx);
     (void) putc('\n', fx);
}
/*
* put out a line (name, [num], seq, [num]): dumpblock( )
*/
static
putline(ix)                                                                                     putline
     int       ix;                    {                                                         ...putline
     int            i;
     register char  *px;
     for (px = namex[ix], i = 0; *px && *px != ':'; px++, i++)
               (void) putc(*px, fx);
     for (; i < lmax+P_SPC; i++)
               (void) putc(' ', fx);
     /* these count from 1:
```

TABLE 1-continued

```
         * ni[ ] is current element (from 1)
         * nc[ ] is number at start of current line
         */
        for (px = out[ix]; *px; px++)
                (void) putc(*px&0x7F, fx);
        (void) putc('\n', fx);
}
/*
* put a line of stars (seqs always in out[0], out[1]): dumpblock( )
*/
static
stars( )                                                                                                                stars
{
        int             i;
        register char   *p0, *p1, cx, *px;
        if (!*out[0] || (*out[0] == ' ' && *(po[0]) == ' ') ||
           !*out[1] || (*out[1] == ' ' && *(po[1]) == ' '))
                return;
        px = star;
        for (i = lmax+P_SPC; i; i--)
                *px++ = ' ';
        for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && __day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
/*
* strip path or prefix from pn, return len: pr_align( )
*/
static
stripname(pn)                                                                                                           stripname
        char    *pn;     /* file name (may be path) */
{
        register char   *px, *py;
        py = 0;
        for (px = pn; *px; px++)
                if (*px == '/')
                        py = px + 1;
        if (py)
                (void) strcpy(pn, py);
        return(strlen(pn));
}
/*
* cleanup( ) -- cleanup any tmp file
* getseq( ) -- read in seq, set dna, len, maxlen
* g_calloc( ) -- calloc( ) with error checkin
* readjmps( ) -- get the good jmps, from tmp file if necessary
* writejmps( ) -- write a filled array of jmps to a tmp file: nw( )
*/
#include "nw.h"
#include <sys/file.h>
char    *jname = "/tmp/homgXXXXXX";             /* tmp file for jmps */
FILE    *fj;
int     cleanup( );                             /* cleanup tmp file */
long    lseek( );
/*
* remove any tmp file if we blow
*/
cleanup(i)                                                                                                              cleanup
        int     i;
{
        if (fj)
                (void) unlink(jname);
        exit(i);
}
/*
* read, return ptr to seq, set dna, len, maxlen
```

TABLE 1-continued

```
 * skip lines starting with ';', '<', or '>'
 * seq in upper or lower case
 */
char    *
getseq(file, len)                                                                                    getseq
        char    *file;  /* file name */
        int     *len;   /* seq len */
{
        char            line[1024], *pseq;
        register char   *px, *py;
        int             natgc, tlen;
        FILE            *fp;
        if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc( ) failed to get %d bytes for %s\n", prog, tlen+6, file);
                exit(1);
        }
        pseq[0] = pseq[1] = pseq[2] = pseq[3] = '\0';
                                                                                                     ...getseq
        py = pseq + 4;
        *len = tlen;
        rewind(fp);
        while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
}
char    *
g_calloc(msg, nx, sz)                                                                                g_calloc
        char    *msg;           /* program, calling routine */
        int     nx, sz;         /* number and size of elements */
{
        char            *px, *calloc( );
        if ((px = calloc((unsigned)nx, (unsigned)sz)) == 0) {
                if (*msg) {
                        fprintf(stderr, "%s: g_calloc( ) failed %s (n=%d, sz=%d)\n", prog, msg, nx, sz);
                        exit(1);
                }
        }
        return(px);
}
/*
 * get final jmps from dx[ ] or tmp file, set pp[ ], reset dmax: main( )
 */
readjmps( )                                                                                          readjmps
{
        int             fd = -1;
        int             siz, i0, i1;
        register i, j, xx;
        if (fj) {
                (void) fclose(fj);
                if ((fd = open(jname, O_RDONLY, 0)) < 0) {
                        fprintf(stderr, "%s: can't open( ) %s\n", prog, jname);
                        cleanup(1);
                }
        }
```

TABLE 1-continued

```
            for (i = i0 = i1 = 0, dmax0 = dmax, xx = len0; ; i++) {
                    while (1) {
                            for (j = dx[dmax].ijmp; j >= 0 && dx[dmax].jp.x[j] >= xx; j--)
                                    ;
                                                                                                        ...readjmps
                            if (j < 0 && dx[dmax].offset && fj) {
                                    (void) lseek(fd, dx[dmax].offset, 0);
                                    (void) read(fd, (char *)&dx[dmax].jp, sizeof(struct jmp));
                                    (void) read(fd, (char *)&dx[dmax].offset, sizeof(dx[dmax].offset));
                                    dx[dmax].ijmp = MAXJMP-1;                             }
                            else
                                    break;              }
                    if (i >= JMPS) {
                            fprintf(stderr, "%s: too many gaps in alignment\n", prog);
                            cleanup(1);
                    }
                    if (j >= 0) {
                            siz = dx[dmax].jp.n[j];
                            xx = dx[dmax].jp.x[j];
                            dmax += siz;
                            if (siz < 0) {                      /* gap in second seq */
                                    pp[1].n[i1] = -siz;
                                    xx += siz;
                                    /* id = xx - yy + len1 - 1                     */
                                    pp[1].x[i1] = xx - dmax + len1 - 1;
                                    gapy++;
                                    ngapy -= siz;
/* ignore MAXGAP when doing endgaps */
                                    siz = (-siz < MAXGAP || endgaps)? -siz : MAXGAP;
                                    i1++;
                            }
                            else if (siz > 0) { /* gap in first seq */
                                    pp[0].n[i0] = siz;
                                    pp[0].x[i0] = xx;
                                    gapx++;
                                    ngapx += siz;
/* ignore MAXGAP when doing endgaps */
                                    siz = (siz < MAXGAP || endgaps)? siz : MAXGAP;
                                    i0++;
                            }
                    }
                    else
                            break;
            }
            /* reverse the order of jmps           */
            for (j = 0, i0--; j < i0; j++, i0--) {
                    i = pp[0].n[j]; pp[0].n[j] = pp[0].n[i0]; pp[0].n[i0] = i;
                    i = pp[0].x[j]; pp[0].x[j] = pp[0].x[i0]; pp[0].x[i0] = i;
            }
            for (j = 0, i1--; j < i1; j++, i1--) {
                    i = pp[1].n[j]; pp[1].n[j] = pp[1].n[i1]; pp[1].n[i1] = i;
                    i = pp[1].x[j]; pp[1].x[j] = pp[1].x[i1]; pp[1].x[i1] = i;
            }
            if (fd >= 0)
                    (void) close(fd);
            if (fj) {
                    (void) unlink(jname);
                    fj = 0;
                    offset = 0;
            }                       }
/*
 * write a filled jmp struct offset of the prev one (if any): nw( )
 */
writejmps(ix)                                                                                           writejmps
            int     ix;
{
            char    *mktemp( );
            if (!fj) {
                    if (mktemp(jname) < 0) {
                            fprintf(stderr, "%s: can't mktemp( ) %s\n", prog, jname);
                            cleanup(1);
                    }
                    if ((fj = fopen(jname, "w")) == 0) {
                            fprintf(stderr, "%s: can't write %s\n", prog, jname);
                            exit(1);
```

TABLE 1-continued

```
            }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| TAT | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the TAT polypeptide) = 5 divided by 15 = 33.3%

TABLE 3

| TAT | XXXXXXXXXX | (Length = 10 amino acids) |
|---|---|---|
| Comparison Protein | XXXXXYYYYYZZYZ | (Length = 15 amino acids) |

% amino acid sequence identity = (the number of identically matching amino acid residues between the two polypeptide sequences as determined by ALIGN-2) divided by (the total number of amino acid residues of the TAT polypeptide) = 5 divided by 10 = 50%

TABLE 4

| TAT-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the TAT-DNA nucleic acid sequence) = 6 divided by 14 = 42.9%

TABLE 5

| TAT-DNA | NNNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the TAT-DNA nucleic acid sequence) = 4 divided by 12 = 33.3%

II. Compositions and Methods of the Invention

A. Anti-TAT Antibodies

In one embodiment, the present invention provides anti-TAT antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl. Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-TAT antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-TAT antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggemann et al., *Year in Immuno.* 7:33 (1993); U.S. Pat. Nos. 5,545,806, 5,569,825, 5,591,669 (all of GenPharm); 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a TAT protein as described herein. Other such antibodies may combine a TAT binding site with a binding site for another protein. Alternatively, an anti-TAT arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the TAT-expressing cell. Bispecific antibodies may also be used to localize cytotoxic agents to cells which express TAT. These antibodies possess a TAT-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fc α antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)).

Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH$_1$-Fc region chain; or VH-CH$_1$-VH-CH$_1$-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced antitumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

In one preferred embodiment, an anti-TAT antibody (full length or fragments) of the invention is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA. 1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-TAT Polypeptide Antibody-maytansinoid Conjugates (Immunoconjugates)

Anti-TAT antibody-maytansinoid conjugates are prepared by chemically linking an anti-TAT antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another immunoconjugate of interest comprises an anti-TAT antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$, (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-TAT antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-TAT antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as tc$^{99m}$ or I$^{123}$, Re$^{186}$, Re$^{188}$ and In$^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as his (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

Alternatively, a fusion protein comprising the anti-TAT antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-TAT antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

B. TAT Binding Oligopeptides

TAT binding oligopeptides of the present invention are oligopeptides that bind, preferably specifically, to a TAT polypeptide as described herein. TAT binding oligopeptides may be chemically synthesized using known oligopeptide synthesis methodology or may be prepared and purified using recombinant technology. TAT binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a TAT polypeptide as described herein. TAT binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) Science 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363) libraries on phage have been used for screening millions of polypeptides or oligopeptides for ones with specific binding properties (Smith, G. P. (1991) Current Opin. Biotechnol., 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., Gene, 215: 439 (1998); Zhu et al., Cancer Research, 58(15): 3209-3214 (1998); Jiang et al., Infection & Immunity, 65(11): 4770-4777 (1997); Ren et al., Gene, 195(2):303-311 (1997); Ren, Protein Sci., 5: 1833 (1996); Efimov et al., Virus Genes, 10: 173 (1995)) and T7 phage display systems (Smith and Scott, Methods in Enzymology, 217: 228-257 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al. (1998) Mol. Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. TAT Binding Organic Molecules

TAT binding organic molecules are organic molecules other than oligopeptides or antibodies as defined herein that bind, preferably specifically, to a TAT polypeptide as described herein. TAT binding organic molecules may be identified and chemically synthesized using known methodology (see, e.g., PCT Publication Nos. WO00/00823 and WO00/39585). TAT binding organic molecules are usually less than about 2000 daltons in size, alternatively less than about 1500, 750, 500, 250 or 200 daltons in size, wherein such organic molecules that are capable of binding, preferably specifically, to a TAT polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585). TAT binding organic molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

D. Screening for Anti-TAT Antibodies, TAT Binding Oligopeptides and TAT Binding Organic Molecules with the Desired Properties Techniques for generating antibodies, oligopeptides and organic molecules that bind to TAT polypeptides have been described above. One may further select antibodies, oligopeptides or other organic molecules with certain biological characteristics, as desired.

The growth inhibitory effects of an anti-TAT antibody, oligopeptide or other organic molecule of the invention may be assessed by methods known in the art, e.g., using cells which express a TAT polypeptide either endogenously or following transfection with the TAT gene. For example, appropriate tumor cell lines and TAT-transfected cells may treated with an anti-TAT monoclonal antibody, oligopeptide or other organic molecule of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-TAT antibody, TAT binding oligopeptide or TAT binding organic molecule of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. Preferably, the tumor cell is one that overexpresses a TAT polypeptide. Preferably, the anti-TAT antibody, TAT binding oligopeptide or TAT binding organic molecule will inhibit cell proliferation of a TAT-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 μg/ml. Growth inhibition can be measured at an antibody concentration of about 0.5 to 30 μg/ml or about 0.5 nM to 200 nM in cell culture, where the growth inhibition is determined 1-10 days after exposure of the tumor cells to the antibody. The antibody is growth inhibitory in vivo if administration of the anti-TAT antibody at about 1 μg/kg to about 100 mg/kg body weight results in reduction in tumor size or reduction of tumor cell proliferation within about 5 days to 3 months from the first administration of the antibody, preferably within about 5 to 30 days.

To select for an anti-TAT antibody, TAT binding oligopeptide or TAT binding organic molecule which induces cell death, loss of membrane integrity as indicated by, e.g., propidium iodide (PI), trypan blue or 7AAD uptake may be assessed relative to control. A PI uptake assay can be performed in the absence of complement and immune effector cells. TAT polypeptide-expressing tumor cells are incubated with medium alone or medium containing the appropriate anti-TAT antibody (e.g, at about 10 μg/ml), TAT binding oligopeptide or TAT binding organic molecule. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 μg/ml). Samples may be analyzed using a FACSCAN® flow cytometer and FACSCONVERT® CellQuest software (Becton Dickinson). Those anti-TAT antibodies, TAT binding oligopeptides or TAT binding organic molecules that induce statistically significant levels of cell death as determined by PI uptake may be selected as cell death-inducing anti-TAT antibodies, TAT binding oligopeptides or TAT binding organic molecules.

To screen for antibodies, oligopeptides or other organic molecules which bind to an epitope on a TAT polypeptide bound by an antibody of interest, a routine cross-blocking assay such as that described in *Antibodies, A Laboratory Manual*, Cold Spring Harbor Laboratory, Ed Harlow and David Lane (1988), can be performed. This assay can be used to determine if a test antibody, oligopeptide or other organic molecule binds the same site or epitope as a known anti-TAT antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a TAT polypeptide can be used in competition assays with the test antibodies or with a test antibody and an antibody with a characterized or known epitope.

E. Antibody Dependent Enzyme Mediated Prodrug Therapy (ADEPT)

The antibodies of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 (1987)). Antibody-abzyme conjugates can be prepared as described herein for delivery of the abzyme to a tumor cell population.

The enzymes of this invention can be covalently bound to the anti-TAT antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604-608 (1984)).

F. Full-Length TAT Polypeptides

The present invention also provides newly identified and isolated nucleotide sequences encoding polypeptides referred to in the present application as TAT polypeptides. In particular, cDNAs (partial and full-length) encoding various TAT polypeptides have been identified and isolated, as disclosed in further detail in the Examples below.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the TAT polypeptides and encoding nucleic acids described herein, in some cases, Applicants have identified what is believed to be the reading frame best identifiable with the sequence information available at the time.

G. Anti-TAT Antibody and TAT Polypeptide Variants

In addition to the anti-TAT antibodies and full-length native sequence TAT polypeptides described herein, it is contemplated that anti-TAT antibody and TAT polypeptide variants can be prepared. Anti-TAT antibody and TAT polypeptide variants can be prepared by introducing appropriate nucleotide changes into the encoding DNA, and/or by synthesis of the desired antibody or polypeptide. Those skilled in the art will appreciate that amino acid changes may alter post-translational processes of the anti-TAT antibody or TAT polypeptide, such as changing the number or position of glycosylation sites or altering the membrane anchoring characteristics.

Variations in the anti-TAT antibodies and TAT polypeptides described herein, can be made, for example, using any of the techniques and guidelines for conservative and non-conservative mutations set forth, for instance, in U.S. Pat. No. 5,364,934. Variations may be a substitution, deletion or insertion of one or more codons encoding the antibody or polypeptide that results in a change in the amino acid sequence as compared with the native sequence antibody or polypeptide. Optionally the variation is by substitution of at least one amino acid with any other amino acid in one or more of the domains of the anti-TAT antibody or TAT polypeptide. Guidance in determining which amino acid residue may be inserted, substituted or deleted without adversely affecting the desired activity may be found by comparing the sequence of the anti-TAT antibody or TAT polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Anti-TAT antibody and TAT polypeptide fragments are provided herein. Such fragments may be truncated at the N-terminus or C-terminus, or may lack internal residues, for example, when compared with a full length native antibody or protein. Certain fragments lack amino acid residues that are not essential for a desired biological activity of the anti-TAT antibody or TAT polypeptide.

Anti-TAT antibody and TAT polypeptide fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-TAT antibody and TAT polypeptide fragments share at least one biological and/or immunological activity with the native anti-TAT antibody or TAT polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the anti-TAT antibody or TAT polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the anti-TAT antibody or TAT polypeptide variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244:1081-1085 (1989)]. Alanine is also typically preferred because it is the most common amino acid. Further, it is frequently found in both buried and exposed positions [Creighton, The Proteins, (W.H. Freeman & Co., N.Y.); Chothia, J. Mol. Biol., 150:1 (1976)]. If alanine substitution does not yield adequate amounts of variant, an isoteric amino acid can be used.

Any cysteine residue not involved in maintaining the proper conformation of the anti-TAT antibody or TAT polypeptide also may be substituted, generally with serine, to improve the oxidative stability of the molecule and prevent aberrant crosslinking. Conversely, cysteine bond(s) may be added to the anti-TAT antibody or TAT polypeptide to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human TAT polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the anti-TAT antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-TAT antibody.

H. Modifications of Anti-TAT Antibodies and TAT Polypeptides

Covalent modifications of anti-TAT antibodies and TAT polypeptides are included within the scope of this invention. One type of covalent modification includes reacting targeted amino acid residues of an anti-TAT antibody or TAT polypeptide with an organic derivatizing agent that is capable of reacting with selected side chains or the N- or C-terminal residues of the anti-TAT antibody or TAT polypeptide. Derivatization with bifunctional agents is useful, for instance, for crosslinking anti-TAT antibody or TAT polypeptide to a water-insoluble support matrix or surface for use in the method for purifying anti-TAT antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the $\alpha$-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the anti-TAT antibody or TAT polypeptide included within the scope of this invention comprises altering the native glycosylation pattern of the antibody or polypeptide. "Altering the native glycosylation pattern" is intended for purposes herein to mean deleting one or more carbohydrate moieties found in native sequence anti-TAT antibody or TAT polypeptide (either by removing the underlying glycosylation site or by deleting the glycosylation by chemical and/or enzymatic means), and/or adding one or more glycosylation sites that are not present in the native sequence anti-TAT antibody or TAT polypeptide. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the anti-TAT antibody or TAT polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-TAT antibody or TAT polypeptide (for O-linked glycosylation sites). The anti-TAT antibody or TAT polypeptide amino acid sequence may optionally be altered through changes at the DNA level, particularly by mutating the DNA encoding the anti-TAT antibody or TAT polypeptide at preselected bases such that codons are generated that will translate into the desired amino acids.

Another means of increasing the number of carbohydrate moieties on the anti-TAT antibody or TAT polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the anti-TAT antibody or TAT polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of anti-TAT antibody or TAT polypeptide comprises linking the antibody or polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

The anti-TAT antibody or TAT polypeptide of the present invention may also be modified in a way to form chimeric molecules comprising an anti-TAT antibody or TAT polypeptide fused to another, heterologous polypeptide or amino acid sequence.

In one embodiment, such a chimeric molecule comprises a fusion of the anti-TAT antibody or TAT polypeptide with a tag polypeptide which provides an epitope to which an anti-tag antibody can selectively bind. The epitope tag is generally placed at the amino- or carboxyl-terminus of the anti-TAT antibody or TAT polypeptide. The presence of such epitope-tagged forms of the anti-TAT antibody or TAT polypeptide can be detected using an antibody against the tag polypeptide. Also, provision of the epitope tag enables the anti-TAT antibody or TAT polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.* 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the anti-TAT antibody or TAT polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-TAT antibody or TAT polypeptide in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule. For the production of immunoglobulin fusions see also U.S. Pat. No. 5,428,130 issued Jun. 27, 1995.

I. Preparation of Anti-TAT Antibodies and TAT Polypeptides

The description below relates primarily to production of anti-TAT antibodies and TAT polypeptides by culturing cells transformed or transfected with a vector containing anti-TAT antibody- and TAT polypeptide-encoding nucleic acid. It is, of course, contemplated that alternative methods, which are well known in the art, may be employed to prepare anti-TAT antibodies and TAT polypeptides. For instance, the appropriate amino acid sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the anti-TAT antibody or TAT polypeptide may be chemically synthesized separately and combined using chemical or enzymatic methods to produce the desired anti-TAT antibody or TAT polypeptide.

1. Isolation of DNA Encoding Anti-TAT Antibody or TAT Polypeptide

DNA encoding anti-TAT antibody or TAT polypeptide may be obtained from a cDNA library prepared from tissue believed to possess the anti-TAT antibody or TAT polypeptide mRNA and to express it at a detectable level. Accordingly, human anti-TAT antibody or TAT polypeptide DNA can be conveniently obtained from a cDNA library prepared from human tissue. The anti-TAT antibody- or TAT polypeptide-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding anti-TAT antibody or TAT polypeptide is to use PCR methodology [Sambrook et al., supra; Dieffenbach et al., *PCR Primer: A Laboratory Manual* (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-TAT antibody or TAT polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach* M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT kan$^r$ *E. coli* W3110 strain 37D6, which has the complete genotype tonA ptr3 phoA E15 (argF-lac) 169 degP ompT rbs7 ilvG kan$^r$ *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation regio (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g, in CHO cells.

In addition to prokaryotes, eukaryotic microbes such as filamentous fungi or yeast are suitable cloning or expression hosts for anti-TAT antibody- or TAT polypeptide-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2): 737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus*; *yarrowia* (EP 402,226); *Pichia pastoris* (EP 183,070; Sreekrishna et al., *J. Basic Microbiol.*, 28:265-278 [1988]); *Candida*; *Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis*(EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated anti-TAT antibody or TAT polypeptide are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR(CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV 1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for anti-TAT antibody or TAT polypeptide production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding anti-TAT antibody or TAT polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The TAT may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-TAT antibody- or TAT polypeptide-encoding DNA that is inserted into the vector. The signal sequence may be a prokaryotic signal sequence selected, for example, from the group of the alkaline phosphatase, penicillinase, 1pp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the anti-TAT antibody- or TAT polypeptide-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is therp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the anti-TAT antibody- or TAT polypeptide-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding anti-TAT antibody or TAT polypeptide.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Anti-TAT antibody or TAT polypeptide transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the anti-TAT antibody or TAT polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the anti-TAT antibody or TAT polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-TAT antibody or TAT polypeptide.

Still other methods, vectors, and host cells suitable for adaptation to the synthesis of anti-TAT antibody or TAT polypeptide in recombinant vertebrate cell culture are described in Gething et al., *Nature,* 293:620-625 (1981); Mantei et al., *Nature,* 281:40-46 (1979); EP 117,060; and EP 117,058.

4. Culturing the Host Cells

The host cells used to produce the anti-TAT antibody or TAT polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102: 255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence TAT polypeptide or against a synthetic peptide based on the DNA sequences provided herein or against exogenous sequence fused to TAT DNA and encoding a specific antibody epitope.

6. Purification of Anti-TAT Antibody and TAT Polypeptide

Forms of anti-TAT antibody and TAT polypeptide may be recovered from culture medium or from host cell lysates. If membrane-bound, it can be released from the membrane using a suitable detergent solution (e.g. Triton-X 100) or by enzymatic cleavage. Cells employed in expression of anti-TAT antibody and TAT polypeptide can be disrupted by various physical or chemical means, such as freeze-thaw cycling, sonication, mechanical disruption, or cell lysing agents.

It may be desired to purify anti-TAT antibody and TAT polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-TAT antibody and TAT polypeptide. Various methods of protein purification may be employed and such methods are known in the art and described for example in Deutscher, *Methods in Enzymology,* 182 (1990); Scopes, *Protein Purification: Principles and Practice,* Springer-Verlag, New York (1982). The purification step(s) selected will depend, for example, on the nature of the production process used and the particular anti-TAT antibody or TAT polypeptide produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

J. Pharmaceutical Formulations

Therapeutic formulations of the anti-TAT antibodies, TAT binding oligopeptides, TAT binding organic molecules and/or TAT polypeptides used in accordance with the present invention are prepared for storage by mixing the antibody, polypeptide, oligopeptide or organic molecule having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). The antibody preferably comprises the antibody at a concentration of between 5-200 mg/ml, preferably between 10-100 mg/ml.

The formulations herein may also contain more than one active compound as necessary for the particular indication being treated, preferably those with complementary activities that do not adversely affect each other. For example, in addition to an anti-TAT antibody, TAT binding oligopeptide, or TAT binding organic molecule, it may be desirable to include in the one formulation, an additional antibody, e.g., a second anti-TAT antibody which binds a different epitope on the TAT polypeptide, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences,* 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

K. Diagnosis and Treatment with Anti-TAT Antibodies, TAT Binding Oligopeptides and TAT Binding Organic Molecules To determine TAT expression in the cancer, various diagnostic assays are available. In one embodiment, TAT polypeptide overexpression may be analyzed by immunohistochemistry (IHC). Parrafin embedded tissue sections from a tumor biopsy may be subjected to the IHC assay and accorded a TAT protein staining intensity criteria as follows:

Score 0—no staining is observed or membrane staining is observed in less than 10% of tumor cells.

Score 1+—a faint/barely perceptible membrane staining is detected in more than 10% of the tumor cells. The cells are only stained in part of their membrane.

Score 2+—a weak to moderate complete membrane staining is observed in more than 10% of the tumor cells.

Score 3+—a moderate to strong complete membrane staining is observed in more than 10% of the tumor cells.

Those tumors with 0 or 1+ scores for TAT polypeptide expression may be characterized as not overexpressing TAT, whereas those tumors with 2+ or 3+ scores may be characterized as overexpressing TAT.

Alternatively, or additionally, FISH assays such as the INFORM® (sold by Ventana, Arizona) or PATHVISION® (Vysis, Illinois) may be carried out on formalin-fixed, paraffin-embedded tumor tissue to determine the extent (if any) of TAT overexpression in the tumor.

TAT overexpression or amplification may be evaluated using an in vivo diagnostic assay, e.g., by administering a molecule (such as an antibody, oligopeptide or organic molecule) which binds the molecule to be detected and is tagged with a detectable label (e.g., a radioactive isotope or a fluorescent label) and externally scanning the patient for localization of the label.

As described above, the anti-TAT antibodies, oligopeptides and organic molecules of the invention have various non-therapeutic applications. The anti-TAT antibodies, oligopeptides and organic molecules of the present invention can be useful for diagnosis and staging of TAT polypeptide-expressing cancers (e.g., in radioimaging). The antibodies, oligopeptides and organic molecules are also useful for purification or immunoprecipitation of TAT polypeptide from cells, for detection and quantitation of TAT polypeptide in vitro, e.g., in an ELISA or a Western blot, to kill and eliminate TAT-expressing cells from a population of mixed cells as a step in the purification of other cells.

Currently, depending on the stage of the cancer, cancer treatment involves one or a combination of the following therapies: surgery to remove the cancerous tissue, radiation therapy, and chemotherapy. Anti-TAT antibody, oligopeptide or organic molecule therapy may be especially desirable in elderly patients who do not tolerate the toxicity and side effects of chemotherapy well and in metastatic disease where radiation therapy has limited usefulness. The tumor targeting anti-TAT antibodies, oligopeptides and organic molecules of the invention are useful to alleviate TAT-expressing cancers upon initial diagnosis of the disease or during relapse. For therapeutic applications, the anti-TAT antibody, oligopeptide or organic molecule can be used alone, or in combination therapy with, e.g., hormones, antiangiogens, or radiolabelled compounds, or with surgery, cryotherapy, and/or radiotherapy. Anti-TAT antibody, oligopeptide or organic molecule treatment can be administered in conjunction with other forms of conventional therapy, either consecutively with, pre- or post-conventional therapy. Chemotherapeutic drugs such as TAXOTERE® (docetaxel), TAXOL® (palictaxel), estramustine and mitoxantrone are used in treating cancer, in particular, in good risk patients. In the present method of the invention for treating or alleviating cancer, the cancer patient can be administered anti-TAT antibody, oligopeptide or organic molecule in conjunction with treatment with the one or more of the preceding chemotherapeutic agents. In particular, combination therapy with palictaxel and modified derivatives (see, e.g., EP0600517) is contemplated. The anti-TAT antibody, oligopeptide or organic molecule will be administered with a therapeutically effective dose of the chemotherapeutic agent. In another embodiment, the anti-TAT antibody, oligopeptide or organic molecule is administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, a conjugate comprising an anti-TAT antibody, oligopeptide or organic molecule conjugated with a cytotoxic agent is administered to the patient. Preferably, the immunoconjugate bound to the TAT protein is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The anti-TAT antibodies, oligopeptides, organic molecules or toxin conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody, oligopeptide or organic molecule is preferred.

Other therapeutic regimens may be combined with the administration of the anti-TAT antibody, oligopeptide or organic molecule. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-TAT antibody or antibodies, oligopeptides or organic molecules, with administration of an antibody directed against another tumor antigen associated with the particular cancer.

In another embodiment, the therapeutic treatment methods of the present invention involves the combined administration of an anti-TAT antibody (or antibodies), oligopeptides or organic molecules and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M.C. Perry, Williams & Wilkins, Baltimore, Md. (1992).

The antibody, oligopeptide or organic molecule may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-TAT antibody, oligopeptide or organic molecule (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody, oligopeptide or organic molecule therapy. Suitable dosages for any of the above co-administered agents are those presently used and may be lowered due to the combined action (synergy) of the agent and anti-TAT antibody, oligopeptide or organic molecule.

For the prevention or treatment of disease, the dosage and mode of administration will be chosen by the physician according to known criteria. The appropriate dosage of antibody, oligopeptide or organic molecule will depend on the type of disease to be treated, as defined above, the severity and course of the disease, whether the antibody, oligopeptide or organic molecule is administered for preventive or therapeutic purposes, previous therapy, the patient's clinical history and response to the antibody, oligopeptide or organic molecule, and the discretion of the attending physician. The antibody, oligopeptide or organic molecule is suitably administered to the patient at one time or over a series of treatments. Preferably, the antibody, oligopeptide or organic molecule is administered by intravenous infusion or by subcutaneous injections. Depending on the type and severity of the disease, about 1 µg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-TAT antibody. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., *Science* 256:808-813 (1992). See also WO 93/25673 and the references cited therein.

The anti-TAT antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies an antibody sequence is fused to a heterologous polypeptide sequence. The antibodies can be modified in the Fc region to provide desired effector functions. As discussed in more detail in the sections herein, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody competes for binding or bind substantially to, the same epitope as the antibodies of the invention. Antibodies having the biological characteristics of the present anti-TAT antibodies of the invention are also contemplated, specifically including the in vivo tumor targeting and any cell proliferation inhibition or cytotoxic characteristics.

Methods of producing the above antibodies are described in detail herein.

The present anti-TAT antibodies, oligopeptides and organic molecules are useful for treating a TAT-expressing cancer or alleviating one or more symptoms of the cancer in a mammal. Such a cancer includes prostate cancer, cancer of the urinary tract, lung cancer, breast cancer, colon cancer and ovarian cancer, more specifically, prostate adenocarcinoma, renal cell carcinomas, colorectal adenocarcinomas, lung adenocarcinomas, lung squamous cell carcinomas, and pleural mesothelioma. The cancers encompass metastatic cancers of any of the preceding. The antibody, oligopeptide or organic molecule is able to bind to at least a portion of the cancer cells that express TAT polypeptide in the mammal. In a preferred embodiment, the antibody, oligopeptide or organic molecule is effective to destroy or kill TAT-expressing tumor cells or inhibit the growth of such tumor cells, in vitro or in vivo, upon binding to TAT polypeptide on the cell. Such an antibody includes a naked anti-TAT antibody (not conjugated to any agent). Naked antibodies that have cytotoxic or cell growth inhibition properties can be further harnessed with a cytotoxic agent to render them even more potent in tumor cell destruction. Cytotoxic properties can be conferred to an anti-TAT antibody by, e.g., conjugating the antibody with a cytotoxic agent, to form an immunoconjugate as described herein. The cytotoxic agent or a growth inhibitory agent is preferably a small molecule. Toxins such as calicheamicin or a maytansinoid and analogs or derivatives thereof, are preferable.

The invention provides a composition comprising an anti-TAT antibody, oligopeptide or organic molecule of the invention, and a carrier. For the purposes of treating cancer, compositions can be administered to the patient in need of such treatment, wherein the composition can comprise one or more anti-TAT antibodies present as an immunoconjugate or as the naked antibody. In a further embodiment, the compositions can comprise these antibodies, oligopeptides or organic molecules in combination with other therapeutic agents such as cytotoxic or growth inhibitory agents, including chemotherapeutic agents. The invention also provides formulations comprising an anti-TAT antibody, oligopeptide or organic molecule of the invention, and a carrier. In one embodiment, the formulation is a therapeutic formulation comprising a pharmaceutically acceptable carrier.

Another aspect of the invention is isolated nucleic acids encoding the anti-TAT antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a TAT polypeptide-expressing cancer or alleviating one or more symptoms of the cancer in a mammal, comprising administering a therapeutically effective amount of an anti-TAT antibody, oligopeptide or organic molecule to the mammal. The antibody, oligopeptide or organic molecule therapeutic compositions can be administered short term (acute) or chronic, or intermittent as directed by physician. Also provided are methods of inhibiting the growth of, and killing a TAT polypeptide-expressing cell.

The invention also provides kits and articles of manufacture comprising at least one anti-TAT antibody, oligopeptide or organic molecule. Kits containing anti-TAT antibodies, oligopeptides or organic molecules find use, e.g., for TAT cell killing assays, for purification or immunoprecipitation of TAT polypeptide from cells. For example, for isolation and purification of TAT, the kit can contain an anti-TAT antibody, oligopeptide or organic molecule coupled to beads (e.g., sepharose beads). Kits can be provided which contain the antibodies, oligopeptides or organic molecules for detection and quantitation of TAT in vitro, e.g., in an ELISA or a Western blot. Such antibody, oligopeptide or organic molecule useful for detection may be provided with a label such as a fluorescent or radiolabel.

L. Articles of Manufacture and Kits

Another embodiment of the invention is an article of manufacture containing materials useful for the treatment of anti-TAT expressing cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the cancer condition and may have a sterile access port (for example the container may be an intravenous solution bag or a vial having a stopper pierceable by a hypodermic injection needle). At least one active agent in the composition is an anti-TAT antibody, oligopeptide or organic molecule of the invention. The label or package insert indicates that the composition is used for treating cancer. The label or package insert will further comprise instructions for administering the antibody, oligopeptide or organic molecule composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for TAT-expressing cell killing assays, for purification or immunoprecipitation of TAT polypeptide from cells. For isolation and purification of TAT polypeptide, the kit can contain an anti-TAT antibody, oligopeptide or organic molecule coupled to beads (e.g., sepharose beads). Kits can be provided which contain the antibodies, oligopeptides or organic molecules for detection and quantitation of TAT polypeptide in vitro, e.g., in an ELISA or a Western blot. As with the article of manufacture, the kit comprises a container and a label or package insert on or associated with the container. The container holds a composition comprising at least one anti-TAT antibody, oligopeptide or organic molecule of the invention. Additional containers may be included that contain, e.g., diluents and buffers, control antibodies. The label or package insert may provide a description of the composition as well as instructions for the intended in vitro or diagnostic use.

M. Uses for TAT Polypeptides and TAT-Polypeptide Encoding Nucleic Acids

Nucleotide sequences (or their complement) encoding TAT polypeptides have various applications in the art of molecular biology, including uses as hybridization probes, in chromosome and gene mapping and in the generation of anti-sense RNA and DNA probes. TAT-encoding nucleic acid will also be useful for the preparation of TAT polypeptides by the recombinant techniques described herein, wherein those TAT polypeptides may find use, for example, in the preparation of anti-TAT antibodies as described herein.

The full-length native sequence TAT gene, or portions thereof, may be used as hybridization probes for a cDNA library to isolate the full-length TAT cDNA or to isolate still other cDNAs (for instance, those encoding naturally-occurring variants of TAT or TAT from other species) which have a desired sequence identity to the native TAT sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence TAT. By way of example, a screening method will comprise isolating the coding region of the TAT gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the TAT gene of the present invention can be used to screen libraries of human cDNA, genomic DNA or mRNA to determine which members of such libraries the probe hybridizes to. Hybridization techniques are described in further detail in the Examples below. Any EST sequences disclosed in the present application may similarly be employed as probes, using the methods disclosed herein.

Other useful fragments of the TAT-encoding nucleic acids include antisense or sense oligonucleotides comprising a singe-stranded nucleic acid sequence (either RNA or DNA) capable of binding to target TAT mRNA (sense) or TAT DNA (antisense) sequences. Antisense or sense oligonucleotides, according to the present invention, comprise a fragment of the coding region of TAT DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The antisense oligonucleotides thus may be used to block expression of TAT proteins, wherein those TAT proteins may play a role in the induction of cancer in mammals. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Preferred intragenic sites for antisense binding include the region incorporating the translation initiation/start codon (5'-AUG/5'-ATG) or termination/stop codon (5'-UAA, 5'-UAG and 5-UGA/5'-TAA, 5'-TAG and 5'-TGA) of the open reading frame (ORF) of the gene. These regions refer to a portion of the mRNA or gene that encompasses from about 25 to about 50 contiguous nucleotides in either direction (i.e., 5' or 3') from a translation initiation or termination codon. Other preferred regions for antisense binding include: introns; exons; intron-exon junctions; the open reading frame (ORF) or "coding region," which is the region between the translation initiation codon and the translation termination codon; the 5' cap of an mRNA which comprises an N7-methylated guanosine residue joined to the 5'-most residue of the mRNA via a 5'-5' triphosphate linkage and includes 5' cap structure itself as well as the first 50 nucleotides adjacent to the cap; the 5' untranslated region (5'UTR), the portion of an mRNA in the 5' direction from the translation initiation codon, and thus including nucleotides between the 5' cap site and the translation initiation codon of an mRNA or corresponding nucleotides on the gene; and the 3' untranslated region (3'UTR), the portion of an mRNA in the 3' direction from the translation termination codon, and thus including nucleotides between the translation termination codon and 3' end of an mRNA or corresponding nucleotides on the gene.

Specific examples of preferred antisense compounds useful for inhibiting expression of TAT proteins include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of such oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred antisense oligonucleotides, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Preferred antisense oligonucleotides incorporate phosphorothioate backbones and/or heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] described in the above referenced U.S. Pat. No. 5,489,677, and the amide backbones of the above referenced U.S. Pat. No. 5,602,240. Also preferred are antisense oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-alkyl, S-alkyl, or N-alkyl; O-alkenyl, S-alkenyl, or N-alkenyl; O-alkynyl, S-alkynyl or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$$OCH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. Other preferred antisense oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy(2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$).

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—CH$_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy(2'-O—CH$_3$), 2'-aminopropoxy(2'-OCH$_2$CH$_2$CH$_2$NH$_2$), 2'-allyl(2'-CH$_2$—CH=CH$_2$), 2'-O-allyl(2'-O—CH$_2$—CH=CH$_2$) and 2'-fluoro(2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$ or —CH$_2$—C≡CH) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi et al, Antisense Research and Applications, CRC Press, Boca Raton, 1993, pp. 276-278) and are preferred base substitutions, even more particularly when combined with 2'-O-methoxyethyl sugar modifications. Representative United States patents that teach the preparation of modified nucleobases include, but are not limited to: U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941 and 5,750,692, each of which is herein incorporated by reference.

Another modification of antisense oligonucleotides chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, cation lipids, phospholipids, cationic phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) and U.S. Pat. Nos.: 4,828, 979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Preferred chimeric antisense oligonucleotides incorporate at least one 2' modified sugar (preferably 2'-O-$(CH_2)_2$O—$CH_3$) at the 3' terminal to confer nuclease resistance and a region with at least 4 contiguous 2'-H sugars to confer RNase H activity. Such compounds have also been referred to in the art as hybrids or gapmers. Preferred gapmers have a region of 2' modified sugars (preferably 2'-O—$(CH_2)_2$—O—$CH_3$) at the 3'-terminal and at the 5' terminal separated by at least one region having at least 4 contiguous 2'-H sugars and preferably incorporate phosphorothioate backbone linkages. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521, 291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $Ca_4PO$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

The probes may also be employed in PCR techniques to generate a pool of sequences for identification of closely related TAT coding sequences.

Nucleotide sequences encoding a TAT can also be used to construct hybridization probes for mapping the gene which encodes that TAT and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for TAT encode a protein which binds to another protein (example, where the TAT is a receptor), the TAT can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor TAT can be used to isolate correlative ligand(s). Screening assays can be designed to find lead compounds that mimic the biological activity of a native TAT or a receptor for TAT. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode TAT or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding TAT can be used to clone genomic DNA encoding TAT in accordance with established techniques and the genomic sequences used to generate transgenic animals that contain cells which express DNA encoding TAT. Methods for generating transgenic animals, particularly animals such as mice or rats, have become conventional in the art and are described, for example, in U.S. Pat. Nos. 4,736,866 and 4,870,009. Typically, particular cells would be targeted for TAT transgene incorporation with tissue-specific enhancers. Transgenic animals that include a copy of a transgene encoding TAT introduced into the germ line of the animal at an embryonic stage can be used to examine the effect of increased expression of DNA encoding TAT. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of TAT can be used to construct a TAT "knock out" animal which has a defective or altered gene encoding TAT as a result of homologous recombination between the endogenous gene encoding TAT and altered genomic DNA encoding TAT introduced into an embryonic stem cell of the animal. For example, cDNA encoding TAT can be used to clone genomic DNA encoding TAT in accordance with established techniques. A portion of the genomic DNA encoding TAT can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the TAT polypeptide.

Nucleic acid encoding the TAT polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The nucleic acid molecules encoding the TAT polypeptides or fragments thereof described herein are useful for chromosome identification. In this regard, there exists an ongoing need to identify new chromosome markers, since relatively few chromosome marking reagents, based upon actual sequence data are presently available. Each TAT nucleic acid molecule of the present invention can be used as a chromosome marker.

The TAT polypeptides and nucleic acid molecules of the present invention may also be used diagnostically for tissue typing, wherein the TAT polypeptides of the present invention may be differentially expressed in one tissue as compared to another, preferably in a diseased tissue as compared to a normal tissue of the same tissue type. TAT nucleic acid molecules will find use for generating probes for PCR, Northern analysis, Southern analysis and Western analysis.

This invention encompasses methods of screening compounds to identify those that mimic the TAT polypeptide (agonists) or prevent the effect of the TAT polypeptide (antagonists). Screening assays for antagonist drug candidates are designed to identify compounds that bind or complex with the TAT polypeptides encoded by the genes identified herein, or otherwise interfere with the interaction of the encoded polypeptides with other cellular proteins, including e.g., inhibiting the expression of TAT polypeptide from cells. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a TAT polypeptide encoded by a nucleic acid identified herein under conditions and for a time sufficient to allow these two components to interact.

In binding assays, the interaction is binding and the complex formed can be isolated or detected in the reaction mixture. In a particular embodiment, the TAT polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the TAT polypeptide and drying. Alternatively, an immobilized antibody, e.g., a monoclonal antibody, specific for the TAT polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular TAT polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a TAT polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the TAT polypeptide may be added to a cell along with the compound to be screened for a particular activity and the ability of the compound to inhibit the activity of interest in the presence of the TAT polypeptide indicates that the compound is an antagonist to the TAT polypeptide. Alternatively, antagonists may be detected by combining the TAT polypeptide and a potential antagonist with membrane-bound TAT polypeptide receptors or recombinant receptors under appropriate conditions for a competitive inhibition assay. The TAT polypeptide can be labeled, such as by radioactivity, such that the number of TAT polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the TAT polypeptide and a cDNA library created from this RNA is divided into pools and used to transfect COS cells or other cells that are not responsive to the TAT polypeptide. Transfected cells that are grown on glass slides are exposed to labeled TAT polypeptide. The TAT polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled TAT polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled TAT polypeptide in the presence of the candidate compound. The ability of the compound to enhance or block this interaction could then be measured.

More specific examples of potential antagonists include an oligonucleotide that binds to the fusions of immunoglobulin with TAT polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the TAT polypeptide that recognizes the receptor but imparts no effect, thereby competitively inhibiting the action of the TAT polypeptide.

Another potential TAT polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature TAT polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the TAT polypeptide. The antisense RNA oligonucleotide hybridizes to the mRNA in vivo and blocks translation of the mRNA molecule into the TAT polypeptide (antisense —Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the TAT polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the TAT polypeptide, thereby blocking the normal biological activity of the TAT polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Isolated TAT polypeptide-encoding nucleic acid can be used herein for recombinantly producing TAT polypeptide using techniques well known in the art and as described herein. In turn, the produced TAT polypeptides can be employed for generating anti-TAT antibodies using techniques well known in the art and as described herein.

Antibodies specifically binding a TAT polypeptide identified herein, as well as other molecules identified by the screening assays disclosed hereinbefore, can be administered for the treatment of various disorders, including cancer, in the form of pharmaceutical compositions.

If the TAT polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Tissue Expression Profiling Using GeneExpress®

A proprietary database containing gene expression information (GeneExpress®, Gene Logic Inc., Gaithersburg, Md.) was analyzed in an attempt to identify polypeptides (and their encoding nucleic acids) whose expression is significantly upregulated in a particular tumor tissue(s) of interest as compared to other tumor(s) and/or normal tissues. Specifically, analysis of the GeneExpress® database was conducted using either software available through Gene Logic Inc., Gaithersburg, Md., for use with the GeneExpress® database or with proprietary software written and developed at Genentech, Inc. for use with the GeneExpress® database. The rating of positive hits in the analysis is based upon several criteria including, for example, tissue specificity, tumor specificity and expression level in normal essential and/or normal proliferating tissues. The following is a list of molecules whose tissue expression profile as determined from an analysis of the GeneExpress® database evidences high tissue expression and significant upregulation of expression in a specific tumor or tumors as compared to other tumor(s) and/or normal tissues and optionally relatively low expression in normal essential and/or normal proliferating tissues. As such, the molecules listed below are excellent polypeptide targets for the diagnosis and therapy of cancer in mammals.

| Molecule | upregulation of expression in: | as compared to: |
| --- | --- | --- |
| DNA225795 (TAT400) | brain tumor | normal brain tissue |
| DNA225795 (TAT400) | breast tumor | normal breast tissue |
| DNA225795 (TAT400) | bone tumor | normal bone tissue |
| DNA225795 (TAT400) | colon tumor | normal colon tissue |
| DNA225795 (TAT400) | kidney tumor | normal kidney tissue |
| DNA225795 (TAT400) | pancreatic tumor | normal pancreatic tissue |
| DNA225795 (TAT400) | soft tissue tumor | normal soft tissue |
| DNA62814 (TAT401) | lung tumor | normal lung tissue |
| DNA62814 (TAT401) | thyroid tumor | normal thyroid tissue |
| DNA62814 (TAT401) | bladder tumor | normal bladder tissue |
| DNA62814 (TAT401) | uterine tumor | normal uterine tissue |
| DNA62814 (TAT401) | ovarian tumor | normal ovarian tissue |
| DNA62814 (TAT401) | colon tumor | normal colon tissue |
| DNA62814 (TAT401) | brain tumor | normal brain tissue |
| DNA62814 (TAT401) | pancreatic tumor | normal pancreatic tissue |
| DNA334601 (TAT402) | breast tumor | normal breast tissue |
| DNA334601 (TAT402) | uterine tumor | normal uterine tissue |
| DNA334601 (TAT402) | ovarian tumor | normal ovarian tissue |
| DNA334601 (TAT402) | colon tumor | normal colon tissue |
| DNA255030 (TAT403) | prostate tumor | normal prostate tissue |
| DNA255030 (TAT403) | uterine tumor | normal uterine tissue |
| DNA255030 (TAT403) | breast tumor | normal breast tissue |
| DNA257428 (TAT404) | breast tumor | normal breast tissue |
| DNA257428 (TAT404) | ovarian tumor | normal ovarian tissue |
| DNA257428 (TAT404) | kidney tumor | normal kidney tissue |
| DNA257428 (TAT404) | uterine tumor | normal uterine tissue |
| DNA257428 (TAT404) | testis tumor | normal testis tissue |
| DNA257428 (TAT404) | adrenal tumor | normal adrenal tissue |
| DNA194132 (TAT405) | breast tumor | normal breast tissue |
| DNA194132 (TAT405) | lung tumor | normal lung tissue |
| DNA194132 (TAT405) | ovarian tumor | normal ovarian tissue |
| DNA22780 (TAT408) | kidney tumor | normal kidney tissue |
| DNA220758 (TAT409) | colon tumor | normal colon tissue |
| DNA220758 (TAT409) | uterine tumor | normal uterine tissue |
| DNA220758 (TAT409) | prostate tumor | normal prostate tissue |
| DNA220758 (TAT409) | breast tumor | normal breast tissue |
| DNA220758 (TAT409) | pancreatic tumor | normal pancreatic tissue |
| DNA220758 (TAT409) | bladder tumor | normal bladder tissue |
| DNA220758 (TAT409) | kidney tumor | normal kidney tissue |
| DNA220758 (TAT409) | lung tumor | normal lung tissue |
| DNA220758 (TAT409) | fallopian tube tumor | normal fallopian tube tissue |
| DNA220758 (TAT409) | head and neck tumor | normal head and neck tissue |
| DNA220758 (TAT409) | ovarian tumor | normal ovarian tissue |
| DNA220758 (TAT409) | esophageal tumor | normal esophageal tissue |

-continued

| Molecule | upregulation of expression in: | as compared to: |
|---|---|---|
| DNA220758 (TAT409) | stomach tumor | normal stomach tissue |
| DNA220758 (TAT409) | urinary system tumor | normal urinary system tissue |
| DNA225549 (TAT410) | prostate tumor | normal prostate tissue |
| DNA225549 (TAT410) | uterine tumor | normal uterine tissue |
| DNA225549 (TAT410) | breast tumor | normal breast tissue |
| DNA225549 (TAT410) | pancreatic tumor | normal pancreatic tissue |
| DNA225549 (TAT410) | thyroid tumor | normal thyroid tissue |
| DNA225701 (TAT411) | ovarian tumor | normal ovarian tissue |
| DNA225701 (TAT411) | breast tumor | normal breast tissue |
| DNA225701 (TAT411) | urinary tumor | normal urinary tissue |
| DNA226115 (TAT412) | lung tumor | normal lung tissue |
| DNA226115 (TAT412) | colon tumor | normal colon tissue |
| DNA226115 (TAT412) | bladder tumor | normal bladder tissue |
| DNA226115 (TAT412) | breast tumor | normal breast tissue |
| DNA226115 (TAT412) | prostate tumor | normal prostate tissue |
| DNA226115 (TAT412) | kidney tumor | normal kidney tissue |
| DNA226115 (TAT412) | pancreatic tumor | normal pancreatic tissue |
| DNA226115 (TAT412) | liver tumor | normal liver tissue |
| DNA226115 (TAT412) | uterine tumor | normal uterine tissue |
| DNA227150 (TAT413) | breast tumor | normal breast tissue |
| DNA227150 (TAT413) | brain tumor | normal brain tissue |
| DNA227150 (TAT413) | lung tumor | normal lung tissue |
| DNA227150 (TAT413) | uterine tumor | normal uterine tissue |
| DNA227150 (TAT413) | ovarian tumor | normal ovarian tissue |
| DNA227150 (TAT413) | fallopian tube tumor | normal fallopian tube tissue |
| DNA227150 (TAT413) | kidney tumor | normal kidney tissue |
| DNA227150 (TAT413) | testis tumor | normal testis tissue |
| DNA227150 (TAT413) | pancreatic tumor | normal pancreatic tissue |
| DNA247426 (TAT414) | breast tumor | normal breast tissue |
| DNA84914 (TAT415) | lung tumor | normal lung tissue |
| DNA84914 (TAT415) | breast tumor | normal breast tissue |
| DNA84914 (TAT415) | uterine tumor | normal uterine tissue |
| DNA84914 (TAT415) | lymphoid tumor | normal lymphoid tissue |
| DNA226751 (TAT416) | skin tumor | normal skin tissue |
| DNA226751 (TAT416) | melanoma tumor | normal associated tissue |
| DNA151312 (TAT417) | lung tumor | normal lung tissue |
| DNA151312 (TAT417) | non small cell lung tumor | normal lung tissue |
| DNA151312 (TAT417) | uterine tumor | normal uterine tissue |
| DNA151312 (TAT417) | breast tumor | normal breast tissue |
| DNA151312 (TAT417) | kidney tumor | normal kidney tissue |
| DNA151312 (TAT417) | adrenal tumor | normal adrenal tissue |
| DNA151312 (TAT417) | lymphoid tumor | normal lymphoid tissue |
| DNA225703 (TAT418) | prostate tumor | normal prostate tissue |
| DNA96945 (TAT419) | skin tumor | normal skin tissue |
| DNA96945 (TAT419) | melanoma tumor | normal associated tissue |
| DNA96945 (TAT419) | kidney tumor | normal kidney tissue |
| DNA96945 (TAT419) | ovarian tumor | normal ovarian tissue |
| DNA96945 (TAT419) | stomach tumor | normal stomach tissue |
| DNA96945 (TAT419) | pancreatic tumor | normal pancreatic tissue |

Example 2

Quantitative Analysis of TAT mRNA Expression

In this assay, a 5' nuclease assay (for example, TaqMan®) and real-time quantitative PCR (for example, ABI Prizm 7700 Sequence Detection System® (Perkin Elmer, Applied Biosystems Division, Foster City, Calif.)), were used to find genes that are significantly overexpressed in a cancerous tumor or tumors as compared to other cancerous tumors or normal non-cancerous tissue. The 5' nuclease assay reaction is a fluorescent PCR-based technique which makes use of the 5' exonuclease activity of Taq DNA polymerase enzyme to monitor gene expression in real time. Two oligonucleotide primers (whose sequences are based upon the gene or EST sequence of interest) are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the PCR amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI Prism 7700™ Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

The starting material for the screen was mRNA isolated from a variety of different cancerous tissues. The mRNA is quantitated precisely, e.g., fluorometrically. As a negative control, RNA was isolated from various normal tissues of the same tissue type as the cancerous tissues being tested.

5' nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample when comparing cancer mRNA results to normal human mRNA results. As one Ct unit corresponds to 1 PCR cycle or approximately a 2-fold relative increase relative to normal, two units corresponds to a 4-fold relative increase, 3 units corresponds to an 8-fold relative increase and so on, one can quantitatively measure the relative fold increase in mRNA expression between two or more different tissues. Using this technique, the molecules listed below have been identified as being significantly overexpressed (i.e., at least 2 fold) in a particular tumor(s) as compared to their normal non-cancerous counterpart tissue(s) (from both the same and different tissue donors) and thus, represent excellent polypeptide targets for the diagnosis and therapy of cancer in mammals.

| Molecule | upregulation of expression in: | as compared to: |
| --- | --- | --- |
| DNA225795 (TAT400) | brain tumor | normal brain tissue |
| DNA225795 (TAT400) | breast tumor | normal breast tissue |
| DNA225795 (TAT400) | bone tumor | normal bone tissue |
| DNA225795 (TAT400) | colon tumor | normal colon tissue |
| DNA225795 (TAT400) | kidney tumor | normal kidney tissue |
| DNA225795 (TAT400) | pancreatic tumor | normal pancreatic tissue |
| DNA225795 (TAT400) | soft tissue tumor | normal soft tissue |
| DNA22780 (TAT408) | kidney tumor | normal kidney tissue |
| DNA220758 (TAT409) | ovarian tumor | normal ovarian tissue |
| DNA227150 (TAT413) | breast tumor | normal breast tissue |

Example 3

In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision* 1:169-176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A [$^{33}$-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 µl (125 mCi) of $^{33}$P-UTP (Amersham BF 1002, SA<2000 Ci/mmol) were speed vac dried. To each tube containing dried $^{33}$P-UTP, the following ingredients were added:

2.0 µl 5× transcription buffer
1.0 µl DTT (100 mM)
2.0 µl NTP mix (2.5 mM: 10 µl; each of 10 mM GTP, CTP & ATP+10 µl H$_2$O)
1.0 µl UTP (50 µM)
1.0 µl Rnasin
1.0 µl DNA template (1 µg)
1.0 µl H$_2$O
1.0 µl RNA polymerase (for PCR products T3 AS, T7=S, usually)

The tubes were incubated at 37° C. for one hour. 1.0 µl RQ1 DNase were added, followed by incubation at 37° C. for 15 minutes. 90 µl TE (10 mM Tris pH 7.6/1 nM EDTA pH 8.0) were added, and the mixture was pipetted onto DE81 paper. The remaining solution was loaded in a Microcon-50 ultra-filtration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1-3 µl of the probe or 5111 of RNA Mrk III were added to 3 µl of loading buffer. After heating on a 95° C. heat block for three minutes, the probe was immediately placed on ice. The wells of gel were flushed, the sample loaded, and run at 180-250 volts for 45 minutes. The gel was wrapped in saran wrap and exposed to XAR film with an intensifying screen in −70° C. freezer one hour to overnight.

$^{33}$P-Hybridization

A. Pretreatment of Frozen Sections

The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+975 ml SQ H$_2$O). After deproteination in 0.5 µg/ml proteinase K for 10 minutes at 37° C. (12.5 µl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

B. Pretreatment of Paraffin-Embedded Sections

The slides were deparaffinized, placed in SQ H$_2$O, and rinsed twice in 2×SSC at room temperature, for 5 minutes each time. The sections were deproteinated in 20 µg/ml proteinase K (500 µl of 10 mg/ml in 250 ml RNase-free RNase buffer; 37° C., 15 minutes)—human embryo, or 8× proteinase K (100 µl in 250 ml Rnase buffer, 37° C., 30 minutes)—formalin tissues. Subsequent rinsing in 0.5×SSC and dehydration were performed as described above.

C. Prehybridization

The slides were laid out in a plastic box lined with Box buffer (4×SSC, 50% form amide)—saturated filter paper.

D. Hybridization 1.0×10$^6$ cpm probe and 1.0 µl tRNA (50 mg/ml stock) per slide were heated at 95° C. for 3 minutes. The slides were cooled on ice, and 48 µl hybridization buffer were added per slide. After vortexing, 50 µl $^{33}$P mix were added to 50 µl prehybridization on slide. The slides were incubated overnight at 55° C.

E. Washes

Washing was done 2×10 minutes with 2×SSC, EDTA at room temperature (400 ml 20×SSC+16 ml 0.25M EDTA, V$_f$=4 L), followed by RNaseA treatment at 37° C. for 30 minutes (500 µl of 10 mg/ml in 250 ml Rnase buffer=20 µg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, V$_f$=4 L).

F. Oligonucleotides

In situ analysis was performed on a variety of DNA sequences disclosed herein. The oligonucleotides employed for these analyses were obtained so as to be complementary to the nucleic acids (or the complements thereof) as shown in the accompanying figures.

G. Results

In situ analysis was performed on a variety of DNA sequences disclosed herein. The results from these analyses are as follows.

(1) DNA225795 (TAT400)

1/1 breast carcinomas shows a positive signal in tumor cells and stroma. 1/1 NSCLC shows a very strong signal in tumor stroma, but is negative in malignant epithelium. 2/2 colorectal carcinomas and 1/1 chondrosarcoma is strongly positive. 2/2 leiomyosarcomas are also positive for expression.

Example 4

Verification and Analysis of Differential TAT Polypeptide Expression by GEPIS

TAT polypeptides which may have been identified as a tumor antigen as described in one or more of the above Examples were analyzed and verified as follows. An expressed sequence tag (EST) DNA database (LIFESEQ®, Incyte Pharmaceuticals, Palo Alto, Calif.) was searched and interesting EST sequences were identified by GEPIS. Gene expression profiling in silico (GEPIS) is a bioinformatics tool developed at Genentech, Inc. that characterizes genes of interest for new cancer therapeutic targets. GEPIS takes advantage of large amounts of EST sequence and library information to determine gene expression profiles. GEPIS is capable of determining the expression profile of a gene based upon its proportional correlation with the number of its occurrences in EST databases, and it works by integrating the LIFESEQ® EST relational database and Genentech proprietary information in a stringent and statistically meaningful way. In this example, GEPIS is used to identify and cross-validate novel tumor antigens, although GEPIS can be configured to perform either very specific analyses or broad screening tasks. For the initial screen, GEPIS is used to identify EST sequences from the LIFESEQ® database that correlate to expression in a particular tissue or tissues of interest (often a tumor tissue of interest). The EST sequences identified in this initial screen (or consensus sequences obtained from aligning multiple related and overlapping EST sequences obtained from the initial screen) were then subjected to a screen intended to identify the presence of at least one transmembrane domain in the encoded protein. Finally, GEPIS was employed to generate a complete tissue expression profile for the various sequences of interest. Using this type of screening bioinformatics, various TAT polypeptides (and their encoding nucleic acid molecules) were identified as being significantly overexpressed in a particular type of cancer or certain cancers as compared to other cancers and/or normal non-cancerous tissues. The rating of GEPIS hits is based upon several criteria including, for example, tissue specificity, tumor specificity and expression level in normal essential and/or normal proliferating tissues. The following is a list of molecules whose tissue expression profile as determined by GEPIS evidences high tissue expression and significant upregulation of expression in a specific tumor or tumors as compared to other tumor(s) and/or normal tissues and optionally relatively low expression in normal essential and/or normal proliferating tissues. As such, the molecules listed below are excellent polypeptide targets for the diagnosis and therapy of cancer in mammals.

| Molecule | upregulation of expression in: | as compared to: |
| --- | --- | --- |
| DNA225795 (TAT400) | brain tumor | normal brain tissue |
| DNA225795 (TAT400) | breast tumor | normal breast tissue |
| DNA225795 (TAT400) | bone tumor | normal bone tissue |
| DNA225795 (TAT400) | colon tumor | normal colon tissue |
| DNA225795 (TAT400) | kidney tumor | normal kidney tissue |
| DNA225795 (TAT400) | pancreatic tumor | normal pancreatic tissue |
| DNA225795 (TAT400) | soft tissue tumor | normal soft tissue |
| DNA62814 (TAT401) | lung tumor | normal lung tissue |
| DNA62814 (TAT401) | thyroid tumor | normal thyroid tissue |
| DNA62814 (TAT401) | bladder tumor | normal bladder tissue |
| DNA62814 (TAT401) | uterine tumor | normal uterine tissue |
| DNA62814 (TAT401) | ovarian tumor | normal ovarian tissue |
| DNA62814 (TAT401) | colon tumor | normal colon tissue |
| DNA62814 (TAT401) | brain tumor | normal brain tissue |
| DNA62814 (TAT401) | pancreatic tumor | normal pancreatic tissue |
| DNA334601 (TAT402) | breast tumor | normal breast tissue |
| DNA334601 (TAT402) | uterine tumor | normal uterine tissue |
| DNA334601 (TAT402) | ovarian tumor | normal ovarian tissue |
| DNA334601 (TAT402) | colon tumor | normal colon tissue |
| DNA255030 (TAT403) | prostate tumor | normal prostate tissue |
| DNA255030 (TAT403) | uterine tumor | normal uterine tissue |
| DNA255030 (TAT403) | breast tumor | normal breast tissue |
| DNA257428 (TAT404) | breast tumor | normal breast tissue |
| DNA257428 (TAT404) | ovarian tumor | normal ovarian tissue |
| DNA257428 (TAT404) | kidney tumor | normal kidney tissue |
| DNA257428 (TAT404) | uterine tumor | normal uterine tissue |
| DNA257428 (TAT404) | testis tumor | normal testis tissue |
| DNA257428 (TAT404) | adrenal tumor | normal adrenal tissue |
| DNA194132 (TAT405) | breast tumor | normal breast tissue |
| DNA194132 (TAT405) | lung tumor | normal lung tissue |
| DNA194132 (TAT405) | ovarian tumor | normal ovarian tissue |
| DNA22780 (TAT408) | kidney tumor | normal kidney tissue |
| DNA220758 (TAT409) | colon tumor | normal colon tissue |
| DNA220758 (TAT409) | uterine tumor | normal uterine tissue |
| DNA220758 (TAT409) | prostate tumor | normal prostate tissue |

-continued

| Molecule | upregulation of expression in: | as compared to: |
|---|---|---|
| DNA220758 (TAT409) | breast tumor | normal breast tissue |
| DNA220758 (TAT409) | pancreatic tumor | normal pancreatic tissue |
| DNA220758 (TAT409) | bladder tumor | normal bladder tissue |
| DNA220758 (TAT409) | kidney tumor | normal kidney tissue |
| DNA220758 (TAT409) | lung tumor | normal lung tissue |
| DNA220758 (TAT409) | fallopian tube tumor | normal fallopian tube tissue |
| DNA220758 (TAT409) | head and neck tumor | normal head and neck tissue |
| DNA220758 (TAT409) | ovarian tumor | normal ovarian tissue |
| DNA220758 (TAT409) | esophageal tumor | normal esophageal tissue |
| DNA220758 (TAT409) | stomach tumor | normal stomach tissue |
| DNA220758 (TAT409) | urinary system tumor | normal urinary system tissue |
| DNA225549 (TAT410) | prostate tumor | normal prostate tissue |
| DNA225549 (TAT410) | uterine tumor | normal uterine tissue |
| DNA225549 (TAT410) | breast tumor | normal breast tissue |
| DNA225549 (TAT410) | pancreatic tumor | normal pancreatic tissue |
| DNA225549 (TAT410) | thyroid tumor | normal thyroid tissue |
| DNA225701 (TAT411) | ovarian tumor | normal ovarian tissue |
| DNA225701 (TAT411) | breast tumor | normal breast tissue |
| DNA225701 (TAT411) | urinary tumor | normal urinary tissue |
| DNA226115 (TAT412) | lung tumor | normal lung tissue |
| DNA226115 (TAT412) | colon tumor | normal colon tissue |
| DNA226115 (TAT412) | bladder tumor | normal bladder tissue |
| DNA226115 (TAT412) | breast tumor | normal breast tissue |
| DNA226115 (TAT412) | prostate tumor | normal prostate tissue |
| DNA226115 (TAT412) | kidney tumor | normal kidney tissue |
| DNA226115 (TAT412) | pancreatic tumor | normal pancreatic tissue |
| DNA226115 (TAT412) | liver tumor | normal liver tissue |
| DNA226115 (TAT412) | uterine tumor | normal uterine tissue |
| DNA227150 (TAT413) | breast tumor | normal breast tissue |
| DNA227150 (TAT413) | brain tumor | normal brain tissue |
| DNA227150 (TAT413) | lung tumor | normal lung tissue |
| DNA227150 (TAT413) | uterine tumor | normal uterine tissue |
| DNA227150 (TAT413) | ovarian tumor | normal ovarian tissue |
| DNA227150 (TAT413) | fallopian tube tumor | normal fallopian tube tissue |
| DNA227150 (TAT413) | kidney tumor | normal kidney tissue |
| DNA227150 (TAT413) | testis tumor | normal testis tissue |
| DNA227150 (TAT413) | pancreatic tumor | normal pancreatic tissue |
| DNA247426 (TAT414) | breast tumor | normal breast tissue |
| DNA84914 (TAT415) | lung tumor | normal lung tissue |
| DNA84914 (TAT415) | breast tumor | normal breast tissue |
| DNA84914 (TAT415) | uterine tumor | normal uterine tissue |
| DNA84914 (TAT415) | lymphoid tumor | normal lymphoid tissue |
| DNA226751 (TAT416) | skin tumor | normal skin tissue |
| DNA226751 (TAT416) | melanoma tumor | normal associated tissue |
| DNA151312 (TAT417) | lung tumor | normal lung tissue |
| DNA151312 (TAT417) | non small cell lung tumor | normal lung tissue |
| DNA151312 (TAT417) | uterine tumor | normal uterine tissue |
| DNA151312 (TAT417) | breast tumor | normal breast tissue |
| DNA151312 (TAT417) | kidney tumor | normal kidney tissue |
| DNA151312 (TAT417) | adrenal tumor | normal adrenal tissue |
| DNA151312 (TAT417) | lymphoid tumor | normal lymphoid tissue |
| DNA225703 (TAT418) | prostate tumor | normal prostate tissue |
| DNA96945 (TAT419) | skin tumor | normal skin tissue |
| DNA96945 (TAT419) | melanoma tumor | normal associated tissue |
| DNA96945 (TAT419) | kidney tumor | normal kidney tissue |
| DNA96945 (TAT419) | ovarian tumor | normal ovarian tissue |
| DNA96945 (TAT419) | stomach tumor | normal stomach tissue |
| DNA96945 (TAT419) | pancreatic tumor | normal pancreatic tissue |

Example 5

Identification of TAT Polypeptides that are Specifically Expressed by B Cells

Using the GeneExpress®- and GEPIS-associated tissue expression analyses described in Examples 1 and 4 above, various TAT polypeptides have been identified as being specifically expressed on the surface of both normal and malignant B cells. By "specifically expressed" on a certain tissue or cell type, it is meant that the TAT polypeptide is expressed by that certain tissue or cell type and is not significantly expressed by any other tissue or cell type. TAT polypeptides that are specifically expressed on the surface of both normal and malignant B cells are excellent polypeptide targets for the treatment of B cell-associated cancers including, for example, high, intermediate and low grade lymphomas (including B cell lymphomas such as, for example, mucosa-associated-lymphoid tissue B cell lymphoma and non-Hodgkin's lymphoma, mantle cell lymphoma, Burkitt's lymphoma, marginal zone lymphoma, diffuse large cell lymphoma, follicular lymphoma, and Hodgkin's lymphoma) and leukemias (including chronic lymphocytic leukemia), multiple myeloma, and other hematological and/or B cell-associated cancers. In this regard, we note that RITUXAN® (Genentech Inc., South San Francisco, Calif.) is an antibody that binds to the CD20 antigen that is specifically expressed on the surface of both normal and malignant B cells and which has been used successfully to treat non-Hodgkin's lymphoma in humans. The following are TAT polypeptides that have been herein identified as being specifically expressed on the surface of both normal and malignant B-cells and, therefore, will serve as excellent polypeptide targets for the treatment of B-cell-associated cancers: TAT406 (DNA255706), TAT407 (DNA329863) and TAT206 (DNA56041).

Example 6

Use of TAT as a Hybridization Probe

The following method describes use of a nucleotide sequence encoding TAT as a hybridization probe for, i.e., diagnosis of the presence of a tumor in a mammal.

DNA comprising the coding sequence of full-length or mature TAT as disclosed herein can also be employed as a probe to screen for homologous DNAs (such as those encoding naturally-occurring variants of TAT) in human tissue cDNA libraries or human tissue genomic libraries.

Hybridization and washing of filters containing either library DNAs is performed under the following high stringency conditions. Hybridization of radiolabeled TAT-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence TAT can then be identified using standard techniques known in the art.

Example 7

Expression of TAT in E. coli

This example illustrates preparation of an unglycosylated form of TAT by recombinant expression in E. coli.

The DNA sequence encoding TAT is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the TAT coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized TAT protein can then be purified using a metal chelating column under conditions that allow tight binding of the protein.

TAT may be expressed in E. coli in a poly-His tagged form, using the following procedure. The DNA encoding TAT is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an E. coli host based on strain 52 (W3110 fuhA(tonA) lon galE rpoHts(htpRts) clpP(lacIq). Transformants are first grown in LB containing 50 mg/ml carbenicillin at 30° C. with shaking until an O.D. 600 of 3-5 is reached. Cultures are then diluted 50-100 fold into CRAP media (prepared by mixing 3.57 g $(NH_4)_2SO_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentrifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded TAT polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Certain of the TAT polypeptides disclosed herein have been successfully expressed and purified using this technique(s).

Example 8

Expression of TAT in Mammalian Cells

This example illustrates preparation of a potentially glycosylated form of TAT by recombinant expression in mammalian cells.

The vector, pRK5 (see EP 307,247, published Mar. 15, 1989), is employed as the expression vector. Optionally, the TAT DNA is ligated into pRK5 with selected restriction enzymes to allow insertion of the TAT DNA using ligation methods such as described in Sambrook et al., supra. The resulting vector is called pRK5-TAT.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-TAT DNA is mixed with about 1 µg DNA encoding the VA RNA gene [Thimmappaya et al., Cell, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of TAT polypeptide. The cultures containing transfected cells may undergo further incubation (in serum free medium) and the medium is tested in selected bioassays.

In an alternative technique, TAT may be introduced into 293 cells transiently using the dextran sulfate method described by Somparyrac et al., Proc. Natl. Acad. Sci., 12:7575 (1981). 293 cells are grown to maximal density in a spinner flask and 700 µg pRK5-TAT DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed TAT can then be concentrated and purified by any selected method, such as dialysis and/or column chromatography.

In another embodiment, TAT can be expressed in CHO cells. The pRK5-TAT can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of TAT polypeptide, the culture medium may be replaced with serum free medium. Preferably, the cultures are incubated for about 6 days, and then the conditioned medium is harvested. The medium containing the expressed TAT can then be concentrated and purified by any selected method.

Epitope-tagged TAT may also be expressed in host CHO cells. The TAT may be subcloned out of the pRK5 vector. The subclone insert can undergo PCR to fuse in frame with a selected epitope tag such as a poly-his tag into a Baculovirus expression vector. The poly-his tagged TAT insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged TAT can then be concentrated and purified by any selected method, such as by $Ni^{2+}$-chelate affinity chromatography.

TAT may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., Current Protocols of Molecular Biology, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., Nucl. Acids Res. 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al. supra. Approximately $3 \times 10^{7'}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Certain of the TAT polypeptides disclosed herein have been successfully expressed and purified using this technique(s).

Example 9

Expression of TAT in Yeast

The following method describes recombinant expression of TAT in yeast.

First, yeast expression vectors are constructed for intracellular production or secretion of TAT from the ADH2/GAPDH promoter. DNA encoding TAT and the promoter is inserted into suitable restriction enzyme sites in the selected plasmid to direct intracellular expression of TAT. For secretion, DNA encoding TAT can be cloned into the selected plasmid, together with DNA encoding the ADH2/GAPDH promoter, a native TAT signal peptide or other mammalian signal peptide, or, for example, a yeast alpha-factor or invertase secretory signal/leader sequence, and linker sequences (if needed) for expression of TAT.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant TAT can subsequently be isolated and purified by removing the yeast cells from the fermentation medium by centrifugation and then concentrating the medium using selected cartridge filters. The concentrate containing TAT may further be purified using selected column chromatography resins.

Certain of the TAT polypeptides disclosed herein have been successfully expressed and purified using this technique(s).

Example 10

Expression of TAT in Baculovirus-Infected Insect Cells

The following method describes recombinant expression of TAT in Baculovirus-infected insect cells.

The sequence coding for TAT is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding TAT or the desired portion of the coding sequence of TAT such as the sequence encoding an extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGoldvirus™ DNA (Pharmingen) into *Spodoptera frugiperda* ("Sf9") cells (ATCC CRL 1711) using lipofectin (commercially available from GIBCO-BRL). After 4-5 days of incubation at 28 C, the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged TAT can then be purified, for example, by $Ni^{2+}$-chelate affinity chromatography as follows. Extracts are prepared from recombinant virus-infected Sf9 cells as described by Rupert et al., *Nature,* 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $^{2+}$NNTA-conjugated to alkaline phosphatase (Qiagen). Fractions containing the eluted His$_{10}$-tagged TAT are pooled and dialyzed against loading buffer.

Alternatively, purification of the IgG tagged (or Fc tagged) TAT can be performed using known chromatography techniques, including for instance, Protein A or protein G column chromatography.

Certain of the TAT polypeptides disclosed herein have been successfully expressed and purified using this technique(s).

Example 11

Preparation of Antibodies that Bind TAT

This example illustrates preparation of monoclonal antibodies which can specifically bind TAT.

Techniques for producing the monoclonal antibodies are known in the art and are described, for instance, in Goding, supra. Immunogens that may be employed include purified TAT, fusion proteins containing TAT, and cells expressing recombinant TAT on the cell surface. Selection of the immunogen can be made by the skilled artisan without undue experimentation.

Mice, such as Balb/c, are immunized with the TAT immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-TAT antibodies.

After a suitable antibody titer has been detected, the animals "positive" for antibodies can be injected with a final intravenous injection of TAT. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against TAT. Determination of "positive" hybridoma cells secreting the desired monoclonal antibodies against TAT is within the skill in the art.

The positive hybridoma cells can be injected intraperitoneally into syngeneic Balb/c mice to produce ascites containing the anti-TAT monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Antibodies directed against certain of the TAT polypeptides disclosed herein have been successfully produced using this technique(s). More specifically, functional monoclonal antibodies that are capable of recognizing and binding to TAT protein (as measured by standard ELISA, FACS sorting analysis and/or immunohistochemistry analysis) have been successfully generated against the following TAT proteins as disclosed herein: TAT400 (DNA225795), TAT401 (DNA62814), TAT406 (DNA255706), TAT407 (DNA329863), TAT206 (DNA56041), TAT412 (DNA226115), TAT413 (DNA227150), TAT416 (DNA226751) and TAT419 (DNA96945).

Example 12

Purification of TAT Polypeptides Using Specific Antibodies

Native or recombinant TAT polypeptides may be purified by a variety of standard techniques in the art of protein purification. For example, pro-TAT polypeptide, mature TAT polypeptide, or pre-TAT polypeptide is purified by immunoaffinity chromatography using antibodies specific for the TAT polypeptide of interest. In general, an immunoaffinity column is constructed by covalently coupling the anti-TAT polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of TAT polypeptide by preparing a fraction from cells containing TAT polypeptide in a soluble form. This preparation is derived by solubilization of the whole cell or of a subcellular fraction obtained via differential centrifugation by the addition of detergent or by other methods well known in the art. Alternatively, soluble TAT polypeptide containing a signal sequence may be secreted in useful quantity into the medium in which the cells are grown.

A soluble TAT polypeptide-containing preparation is passed over the immunoaffinity column, and the column is washed under conditions that allow the preferential absorbance of TAT polypeptide (e.g., high ionic strength buffers in the presence of detergent). Then, the column is eluted under conditions that disrupt antibody/TAT polypeptide binding (e.g., a low pH buffer such as approximately pH 2-3, or a high concentration of a chaotrope such as urea or thiocyanate ion), and TAT polypeptide is collected.

Example 13

In Vitro Tumor Cell Killing Assay

Mammalian cells expressing the TAT polypeptide of interest may be obtained using standard expression vector and cloning techniques. Alternatively, many tumor cell lines expressing TAT polypeptides of interest are publicly available, for example, through the ATCC and can be routinely identified using standard ELISA or FACS analysis. Anti-TAT polypeptide monoclonal antibodies (and toxin conjugated derivatives thereof) may then be employed in assays to determine the ability of the antibody to kill TAT polypeptide expressing cells in vitro.

For example, cells expressing the TAT polypeptide of interest are obtained as described above and plated into 96 well dishes. In one analysis, the antibody/toxin conjugate (or naked antibody) is included throughout the cell incubation for a period of 4 days. In a second independent analysis, the cells are incubated for 1 hour with the antibody/toxin conjugate (or naked antibody) and then washed and incubated in the absence of antibody/toxin conjugate for a period of 4 days. Cell viability is then measured using the CellTiter-Glo Luminescent Cell Viability Assay from Promega (Cat# G7571). Untreated cells serve as a negative control.

Example 14

In Vivo Tumor Cell Killing Assay

To test the efficacy of conjugated or unconjugated anti-TAT polypeptide monoclonal antibodies, anti-TAT antibody is injected intraperitoneally into nude mice 24 hours prior to receiving tumor promoting cells subcutaneously in the flank. Antibody injections continue twice per week for the remainder of the study. Tumor volume is then measured twice per week.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A method of diagnosing in a mammal the presence of a tumor in which a nucleic acid encoding a protein is significantly upregulated, wherein the protein comprises an amino acid sequence having at least 95% amino acid sequence identity to:
   (a) the polypeptide of SEQ ID NO:30;
   (b) the polypeptide of SEQ ID NO:30, lacking its associated signal peptide; or
   (c) a polypeptide encoded by the nucleotide sequence of SEQ ID NO:9,
   the method comprising (i) determining the level of expression of the nucleic acid in a test sample of tissue cells obtained from the mammal and (ii) comparing the level of expression of (i) with the level of expression of the nucleic acid in a control sample, wherein a significantly higher level of expression of the nucleic acid encoding the protein in the test sample, as compared to the control sample, is indicative of the presence of a tumor in which the nucleic acid is significantly upregulated, wherein the tumor is a kidney tumor and the tissue cells are kidney tissue cells.

2. The method of claim 1, wherein determining the level of expression of the nucleic acid comprises employing an oligonucleotide in an in situ hybridization or RT-PCR analysis.

3. The method of claim 1, wherein the protein comprises:
   (a) the amino acid sequence of SEQ ID NO:30;
   (b) the amino acid sequence of SEQ ID NO:30, lacking its associated signal peptide sequence; or
   (c) an amino acid sequence encoded by the nucleotide sequence of SEQ ID NO:9.

* * * * *

```
                        SEQUENCE LISTING

<160> NUMBER OF SEQ ID NOS: 42

<210> SEQ ID NO 1
<211> LENGTH: 2625
<212> TYPE: DNA
<213> ORGANISM: Homo sapiens

<400> SEQUENCE: 1
cggcagccct gacgtgatga gctcaaccag cagagacatt ccatcccaag         50
agaggtctgc gtgacgcgtc cgggaggcca ccctcagcaa gaccaccgta        100
cagttggtgg aagggtgac agctgcattc tcctgtgcct accacgtaac         150
caaaaatgaa ggagaactac tgtttacaag ccgccctggt gtgcctgggc        200
atgctgtgcc acagccatgc ctttgcccca gagcggcggg ggcacctgcg        250
gccctccttc catgggcacc atgagaaggg caaggagggg caggtgctac        300
agcgctccaa gcgtggctgg gtctggaacc agttcttcgt gatagaggag        350
tacaccgggc ctgaccccgt gcttgtgggc aggcttcatt cagatattga        400
ctctggtgat gggaacatta aatacattct ctcaggggaa ggagctggaa        450 ccattttgt gattgatgac aaatcaggga acattcatgc caccaagacg         500
ttggatcgag aagagagagc ccagtacacg ttgatggctc aggcggtgga        550
cagggacacc aatcggccac tggagccacc gtcggaattc attgtcaagg        600
tccaggacat taatgacaac cctccggagt tcctgcacga gacctatcat        650
gccaacgtgc ctgagaggtc caatgtggga acgtcagtaa tccaggtgac        700
agcttcagat gcagatgacc ccacttatgg aaatagcgcc aagttagtgt        750
acagtatcct cgaaggacaa ccctatttt cggtggaagc acagacaggt         800
atcatcagaa cagccctacc caacatggac agggaggcca aggaggagta        850
ccacgtggtg atccaggcca aggacatggg tggacatatg ggcggactct        900
cagggacaac caaagtgacg atcacactga ccgatgtcaa tgacaaccca        950
ccaaagtttc cgcagaggct ataccagatg tctgtgtcag aagcagccgt       1000
ccctggggag gaagtaggaa gagtgaaagc taaagatcca gacattggag       1050
aaaatggctt agtcacatac aatattgttg atggagatgg tatggaatcg       1100
```

| | |
|---|---|
| tttgaaatca caacggacta tgaaacacag gagggggtga taaagctgaa | 1150 |
| aaagcctgta gattttgaaa ccgaaagagc ctatagcttg aaggtagagg | 1200 |
| cagccaacgt gcacatcgac ccgaagttta tcagcaatgg cccttttcaag | 1250 |
| gacactgtga ccgtcaagat ctcagtagaa gatgctgatg agccccctat | 1300 |
| gttcttggcc ccaagttaca tccacgaagt ccaagaaaat gcagctgctg | 1350 |
| gcaccgtggt tgggagagtg catgccaaag accctgatgc tgccaacagc | 1400 |
| ccgataaggt attccatcga tcgtcacact gacctcgaca gattttttcac | 1450 |
| tattaatcca gaggatggtt ttattaaaac tacaaaacct ctggatagag | 1500 |
| aggaaacagc ctggctcaac atcactgtct ttgcagcaga aatccacaat | 1550 |
| cggcatcagg aagcccaagt cccagtggcc attagggtcc ttgatgtcaa | 1600 |
| cgataatgct cccaagtttg ctgcccctta tgaaggtttc atctgtgaga | 1650 |
| gtgatcagac caagccactt tccaaccagc caattgttac aattagtgca | 1700 |
| gatgacaagg atgacacggc caatggacca agatttatct tcagcctacc | 1750 |
| ccctgaaatc attcacaatc caaatttcac agtcagagac aaccgagata | 1800 |
| acacagcagg cgtgtacgcc cggcgtggag ggttcagtcg gcagaagcag | 1850 |
| gacttgtacc ttctgcccat agtgatcagc gatggcggca tcccgcccat | 1900 |
| gagtagcacc aacacccctca ccatcaaagt ctgcgggtgc gacgtgaacg | 1950 |
| gggcactgct ctcctgcaac gcagaggcct acattctgaa cgccggcctg | 2000 |
| agcacaggcg ccctgatcgc catcctcgcc tgcatcgtca ttctcctggt | 2050 |
| cattgtagta ttgtttgtga ccctgagaag gcaaaagaaa gaaccactca | 2100 |
| ttgtctttga ggaagaagat gtccgtgaga acatcattac ttatgatgat | 2150 |
| gaagggggtg gggaagaaga cacagaagcc tttgatattg ccaccctcca | 2200 |
| gaatcctgat ggtatcaatg gatttatccc ccgcaaagac atcaaacctg | 2250 |
| agtatcagta catgcctaga cctgggctcc ggccagcgcc caacagcgtg | 2300 |
| gatgtcgatg acttcatcaa cacgagaata caggaggcag acaatgaccc | 2350 |
| cacggctcct ccttatgact ccattcaaat ctacggttat gaaggcaggg | 2400 |
| gctcagtggc cgggtccctg agctccctag agtcggccac cacagattca | 2450 |
| gacttggact atgattatct acagaactgg ggacctcgtt ttaagaaact | 2500 |
| agcagatttg tatggttcca aagacactttt tgatgacgat tcttaacaat | 2550 |
| aacgatacaa atttggcctt aagaactgtg tctggcgttc tcaagaatct | 2600 |
| agaagatgtg taacaggtat ttttt | 2625 |

<210> SEQ ID NO 2
<211> LENGTH: 1371
<212> TYPE: DNA
<213> ORGANISM: Homo sapiens

<400> SEQUENCE: 2

| | |
|---|---|
| aactcaaaact cctctctctg ggaaaacgcg gtgcttgctc ctcccggagt | 50 |
| ggccttggca gggtgttgga gccctcggtc tgccccgtcc ggtctctggg | 100 |
| gccaaggctg ggtttccctc atgtatggca agagctctac tcgtgcggtg | 150 |
| cttcttctcc ttggcataca gctcacagct ctttggccta tagcagctgt | 200 |
| ggaaatttat acctcccggg tgctggaggc tgttaatggg acagatgctc | 250 |

-continued

| | |
|---|---|
| ggttaaaatg cactttctcc agctttgccc ctgtgggtga tgctctaaca | 300 |
| gtgacctgga attttcgtcc tctagacggg ggacctgagc agtttgtatt | 350 |
| ctactaccac atagatccct tccaacccat gagtgggcgg tttaaggacc | 400 |
| gggtgtcttg ggatgggaat cctgagcggt acgatgcctc catccttctc | 450 |
| tggaaactgc agttcgacga caatgggaca tacacctgcc aggtgaagaa | 500 |
| cccacctgat gttgatgggg tgataggggga gatccggctc agcgtcgtgc | 550 |
| acactgtacg cttctctgag atccacttcc tggctctggc cattggctct | 600 |
| gcctgtgcac tgatgatcat aatagtaatt gtagtggtcc tcttccagca | 650 |
| ttaccggaaa aagcgatggg ccgaaagagc tcataaagtg gtggagataa | 700 |
| aatcaaaaga agaggaaagg ctcaaccaag agaaaaaggt ctctgtttat | 750 |
| ttagaagaca cagactaaca attttagatg gaagctgaga tgatttccaa | 800 |
| gaacaagaac cctagtattt cttgaagtta atggaaactt ttctttggct | 850 |
| tttccagttg tgacccgttt tccaaccagt tctgcagcat attagattct | 900 |
| agacaagcaa caccctctg gagccagcac agtgctcctc catatcacca | 950 |
| gtcatacaca gcctcattat taaggtctta tttaatttca gagtgtaaat | 1000 |
| tttttcaagt gctcattagg ttttataaac aagaagctac attttgccc | 1050 |
| ttaagacact acttacagtg ttatgacttg tatacacata tattggtatc | 1100 |
| aaaggggata aaagccaatt tgtctgttac atttcctttc acgtatttct | 1150 |
| tttagcagca cttctgctac taaagttaat gtgtttactc tctttccttc | 1200 |
| ccacattctc aattaaaagg tgagctaagc ctccctcggtg tttctgatta | 1250 |
| acagtaaatc ctaaattcaa actgttaaat gacatttta ttttatgtc | 1300 |
| tctccttaac tatgagacac atcttgtttt actgaatttc tttcaatatt | 1350 |
| ccaggtgata gattttgtc g | 1371 |

<210> SEQ ID NO 3
<211> LENGTH: 1274
<212> TYPE: DNA
<213> ORGANISM: Homo sapiens

<400> SEQUENCE: 3

| | |
|---|---|
| ggcacgaggc gattcagggg agggagcaac tggagcctca ggccctccag | 50 |
| agtagtctgc ctgaccaccc tggagcccac agaagcccag gacgtctccc | 100 |
| gcgaggcctc cccgtgtgtg gctgaggatg gctgagcagc agggccggga | 150 |
| gcttgaggct gagtgccccg tctgctggaa ccccttcaac aacacgttcc | 200 |
| ataccccccaa aatgctggat tgctgccact ccttctgcgt ggaatgtctg | 250 |
| gcccacctca gccttgtgac tccagcccgg cgccgcctgc tgtgcccact | 300 |
| ctgtcgccag cccacagtgc tggcctcagg gcagcctgtc actgacttgc | 350 |
| ccacggacac tgccatgctc accctgctcc gcctggagcc ccaccatgtc | 400 |
| atcctggaag gccatcagct gtgcctcaag gaccagccca agagccgcta | 450 |
| cttcctgcgc cagcctcgag tctacacgct ggaccttggc cccagcctg | 500 |
| ggggccagac tgggccgccc ccagacacgg cctctgccac cgtgtctacg | 550 |
| cccatcctca tccccagcca ccactctttg agggagtgtt ccgcaaccc | 600 |
| tcagttccgc atctttgcct acctgatggc cgtcatcctc agtgtcactc | 650 |

| | |
|---|---|
| tgttgctcat attctccatc ttttggacca agcagttcct ttggggtgtg | 700 |
| gggtgagtgc tgttcccaga caagaaacca aaccttttc ggttgctgct | 750 |
| gggtatggtg actacggagc ctcatttggt attgtcttcc tttgtagtgt | 800 |
| tgtttatttt acaatccagg gattgttcag gccatgtgtt tgcttctggg | 850 |
| aacaatttaa aaaaaaaaca aaaaaacgaa aagcttgaag gactgggaga | 900 |
| tgtggagcga cctccgggtg tgagtgtggc gtcatggaag gcagagaag | 950 |
| cggttctgac cacagagctc cacagcaagt tgtgccaaag ggctgcacag | 1000 |
| tggtatccag gaacctgact agcccaaata gcaagttgca tttctcactg | 1050 |
| gagctgcttc aaaatcagtg catatttttt tgagttgctc ttttactatg | 1100 |
| ggttgctaaa aaaaaaaaaa aaaaaattgg gaagtgagct tcaattctgt | 1150 |
| gggtaaatgt gtgtttgttt ctctttgaat gtcttgccac tggttgcagt | 1200 |
| aaaagtgttc tgtattcatt aaaaaaaaaa aaaaaaaaaa aaaaaaaaaa | 1250 |
| aaaaaaaaaa aaaaaaaaaa aaaa | 1274 |

<210> SEQ ID NO 4
<211> LENGTH: 2032
<212> TYPE: DNA
<213> ORGANISM: Homo sapiens

<400> SEQUENCE: 4

| | |
|---|---|
| gaagcgcgct cccggggagg tgttgcagcc atggctacgg cagccggcgc | 50 |
| gacctacttt cagcgaggca gtctgttctg gttcacagtc atcaccctca | 100 |
| gctttggcta ctacacatgg gttgtcttct ggcctcagag tatcccttat | 150 |
| cagaaccttg ggcccctggg cccttcact cagtacttgg tggaccacca | 200 |
| tcacaccctc ctttgcaatg ggtattggct tgcctggctg attcatgtgg | 250 |
| gagagtcctt gtatgccata gcattgtgca agcataaagg catcacaagt | 300 |
| ggtcgggctc agctactctg gttcctacag actttcttct ttgggatagc | 350 |
| gtctctcacc atcttgattg cttacaaacg gaagcgccaa aaacaaactt | 400 |
| gaagttgtct gaaagcttgc tctacacttt tacattcatc ctcacccttt | 450 |
| tttttgtggg gtagaggagg tgcagtaatt tactcagtga tctttctact | 500 |
| ttctagaaac tgtccttcaa agctctttaa gaccccctcg ttagtcagtt | 550 |
| tcttctctta tatgctctgg ttgagcttga atagaccagt tgttacttaa | 600 |
| gaaagaaaca gagaaagatt ttagcttttc aatcctattt ggcagaggac | 650 |
| ttcagctacc ttcttacagt ctttggctgt gttggtaccc tcgtgtgctc | 700 |
| tgagctaagc cacatactaa actgactttt tggtttgtat acccttgctc | 750 |
| ccgccttctg atgaaaacac cttaccctca caaccaccat cttcctctc | 800 |
| ctttccaaag ctcttttccac cttgctgcac taagataaag tgacacttcc | 850 |
| actatatgtc aattccacac acatttatta ggtacctgtg aggtaggatc | 900 |
| ctatcctctc aaacttccat ttctcatgct acagagaaag ataaggaaga | 950 |
| tgagcaagtg cctggaatgg ggcaggctga gcagtcacac aggcatagag | 1000 |
| gcacgctgag aacctggagg ggagactgca gagtgccttc cctgatgctg | 1050 |
| cagccggaag tgatccttcc ctccacctgg ccccctgggac actgtgctct | 1100 |
| gcagtgtgca gggcctgatg gcactgctag attgctcctt cagctcaggg | 1150 |

| | |
|---|---|
| ccacagctta aacagcttta cctttcccct cagcacctgt cccactatct | 1200 |
| tgcacacagg tgctctaacc atgtttattg aacaaaggag ggaaactgat | 1250 |
| ttcactttca cttgttcatt atcattccaa ttttttatgtg aaaatggcac | 1300 |
| aacccatttg gggtaccctc accccaaaat aaaagcccaa gtctaccttt | 1350 |
| gactggtacc accttttttg tggtttcgtt ggtgagaaac ctttatcttt | 1400 |
| ttcataccttt tctattctca atcacttctc caaaagtgtg tctttccagc | 1450 |
| tctgatttat tcaaaacaca agcatttctg tttagagatt ctagcccatg | 1500 |
| ggttatctgg ctagttatta cctctcctgt tcacttagtt atactttatt | 1550 |
| attgctcaca ggctggggag gcagaatgac tctgtcacca ctaggagcca | 1600 |
| ttagggcttc ttccctggag gactgcctgc ttgcttctg gggacactag | 1650 |
| ccctcatttc ccttctgtgg tacagtgggg caaattattt gtattaagca | 1700 |
| aacatttatg ggaaacaacc cgctcccgaa aacggagccc ccaagtaaag | 1750 |
| cacaaccctg aaagattatg aactatgaat tgtctctagt agagataaat | 1800 |
| ttctgcaaac atatctcagt cttccctctg tttctctggt gattaagaag | 1850 |
| ttcctttttg gtaaggaaaa ggatttttaa ccatagagtt aggcatcatg | 1900 |
| gaaattcaaa ccagatttct taatacctgg tcttcctcaa agagaaataa | 1950 |
| taacagtaat agtggtgctg gaacaatat ggcagattat tgaatgaaat | 2000 |
| tgattaactt gaataaaatg ctgtgaattt tc | 2032 |

<210> SEQ ID NO 5
<211> LENGTH: 1572
<212> TYPE: DNA
<213> ORGANISM: Homo sapiens

<400> SEQUENCE: 5

| | |
|---|---|
| ggcacgaggc cgcagcggac tgcccttcc caagatggcg tcgaagatag | 50 |
| gttcgagacg gtggatgttg cagctgatca tgcagttggg ttcggtgctg | 100 |
| ctcacacgct gccccttttg gggctgcttc agccagctca tgctgtacgc | 150 |
| tgagagggct gaggcacgcc ggaagcccga catcccagtg ccttacctgt | 200 |
| atttcgacat gggggcagcc gtgctgtgcg ctagtttcat gtcctttggc | 250 |
| gtgaagcggc gctggttcgc gctgggggcc gcactccaat tggccattag | 300 |
| cacctacgcc gcctacatcg ggggctacgt ccactacggg gactggctga | 350 |
| aggtccgtat gtactcgcgc acagttgcca tcatcggcgg cttttcttgtg | 400 |
| ttggccagcg gtgctgggga gctgtaccgc cggaaacctc gcagccgctc | 450 |
| cctgcagtcc accggccagg tgttcctggg tatctacctc atctgtgtgg | 500 |
| cctactcact gcagcacagc aaggaggacc ggctggcgta tctgaaccat | 550 |
| ctcccaggag gggagctgat gatccagctg ttcttcgtgc tgtatggcat | 600 |
| cctggccctg gcctttctgt caggctacta cgtgaccctc gctgcccaga | 650 |
| tcctggctgt actgctgccc cctgtcatgc tgctcattga tggcaatgtt | 700 |
| gcttactggc acaacacgcg gcgtgttgag ttctggaacc agatgaagct | 750 |
| ccttggagag agtgtgggca tcttcggaac tgctgtcatc ctggccactg | 800 |
| atggctgagt tttatggcaa gaggctgaga tgggcacagg gagccactga | 850 |
| gggtcaccct gccttcctcc ttgctggccc agctgctgtt tatttatgct | 900 |

```
ttttggtctg tttgtttgat cttttgcttt tttaaaattg ttttttgcag        950
ttaagaggca gctcatttgt ccaaatttct gggctcagcg cttgggaggg       1000
caggagccct ggcactaatg ctgtacaggt tttttcctg ttaggagagc        1050
tgaggccagc tgcccactga gtctcctgtc cctgagaagg gagtatggca       1100
gggctgggat gcggctactg agagtgggag agtgggagac agaggaagga       1150
agatggagat tggaagtgag caaatgtgaa aaattcctct ttgaacctgg       1200
cagatgcagc taggctctgc agtgctgttt ggagactgtg agagggagtg       1250
tgtgtgttga cacatgtgga tcaggcccag gaagggcaca ggggctgagc       1300
actacagaag tcacatgggt tctcagggta tgccaggggc agaaacagta       1350
ccggctctct gtcactcacc ttgagagtag agcagaccct gttctgctct       1400
gggctgtgaa ggggtggagc aggcagtggc cagctttgcc cttcctgctg       1450
tctctgtttc tagctccatg gttggcctgg tgggggtgga gttccctccc       1500
aaacaccaga ccacacagtc ctccaaaaat aaacatttta tatagacaaa       1550
aaaaaaaaaa aaaaaaaaa  aa                                    1572

<210> SEQ ID NO 6
<211> LENGTH: 1451
<212> TYPE: DNA
<213> ORGANISM: Homo sapiens
<220> FEATURE:
<221> NAME/KEY: Unsure
<222> LOCATION: 1141
<223> OTHER INFORMATION: Unknown base

<400> SEQUENCE: 6
ggccgcggct cgcctttggc ccttcttatc aggatgaaaa cgcttctgtt         50
tggtgtctgg gccctgctgg ccttgatcct ttgcccaggg gtcccggaag        100
agttgtttga ggtttctatt tggccaagtc aggccctggt ggagtttgga        150
cagtccctag tgtgcaactg cagcactact tgcccagacc caggacccag        200
tggaattgag accttcttaa agaaaactca ggtggacaaa gggcctcagt        250
ggaaagagtt tcttctggag gatgtcacag agaattccat cctgcagtgc        300
ttcttctctt gtgcagggat tcaaaaggac acaagccttg gcatcactgt        350
gtatcagcca ccagagcaag tgatcctgga gctgcagcct gcctgggtgg        400
ccgtggacga agccttcaca gtgaagtgtc atgtacccga tgtagcaccc        450
ttggagagtc tcacccttgc ccttctccag ggtaaccaag aactgcatag        500
aaagaacttt acgagcttgg ctgtggcctc ccaaagagct gaagtcatca        550
tcagtgtcag agcccaaaag gagaatgaca gatgcaattc ttcctgccat        600
gcagaactgg acttgagttt gcaaggtggg aggctctttc aaggcagctc        650
acccatcaga atagtccgga tctttgaatt ctctcagagt ccccacatct        700
gggtctcttc ccttttggag gctgggatgg cggagactgt gagctgcgag       750
gtggctaggg tgtttccagc caaagaagtt atgttccaca tgttcctgga        800
agaccaagag ctgagctcct ccctttcctg ggaggggac acagcatggg        850
ccaatgctac cattcggacc atggaggctg gtgatcagga actgtcttgc        900
tttgcatctc tgggtgcaat ggaacagaag acaagaaagc tagtgcatag        950
ctacagcttc cctccaccaa tcctggagct aaaagaatca tacccattgg       1000
```

| | |
|---|---|
| cagggaccga cattaatgtg acctgctcag ggcatgtatt aacatcaccc | 1050 |
| agccctactc ttcggcttca gggagcccca gacctccctg ctggggagcc | 1100 |
| tgcctggctt ctacttactg ccagggagga agatgatggc ngaaatttct | 1150 |
| cctgcgaggc ctctttggtg gtgcagggtc agcggttgat gaaaaccact | 1200 |
| gtgatccagc tccatatcct aaagccacag ttagaggaat ccagttgccc | 1250 |
| tggcaaacag acctggctgg aagggatgga acacacgctc gcctgcgtcc | 1300 |
| caaagggaaa cccagctcca gccttggtgt gtacctggaa tggggtggtc | 1350 |
| tttgaccttg aagtgccaca gaaggcaacc tagaaccaca ctggaaccta | 1400 |
| ccgctacaca gccactaacc agctgggctc tgtcagcaaa gacattgctg | 1450 |
| t | 1451 |

<210> SEQ ID NO 7
<211> LENGTH: 2652
<212> TYPE: DNA
<213> ORGANISM: Homo sapiens

<400> SEQUENCE: 7

| | |
|---|---|
| ccacgcgtcc gttctgaggt gcattctttt tttgatgaga ggcatctcta | 50 |
| ggtaccatcc ctgacctggt cctcatgctg ccgaggctgt tgctgttgat | 100 |
| ctgtgctcca ctctgtgaac ctgccgagct gttttttgata gccagcccct | 150 |
| cccatcccac agaggggagc ccagtgaccc tgacgtgtaa gatgcccttt | 200 |
| ctacagagtt cagatgccca gttccagttc tgcttttca gagacacccg | 250 |
| ggccttgggc ccaggctgga gcagctcccc caagctccag atcgctgcca | 300 |
| tgtggaaaga agacacaggg tcatactggt gcgaggcaca gacaatggcg | 350 |
| tccaaagtct tgaggagcag gagatcccag ataaatgtgc acatcccggt | 400 |
| gtctcgccca atcctcatgc tcagggctcc cagggcccag gctgcagtgg | 450 |
| aggatgtgct ggagcttcac tgtgaggcc tgagaggctc tcctccaatc | 500 |
| ctgtactggt tttatcacga ggatatcacc ctggggagca ggtcggcccc | 550 |
| ctctggagga ggagcctcct tcaacctttc cctgactgaa gaacattctg | 600 |
| gaaactactc ctgtgaggcc aacaatggcc tgggggccca gcgcagtgag | 650 |
| gcggtgacac tcaacttcac agtgcctact ggggccagaa gcaatcatct | 700 |
| tacctcagga gtcattgagg ggctgctcag caccccttggt ccagccaccg | 750 |
| tggccttatt attttgctac ggcctcaaaa gaaaaatagg aagacgttca | 800 |
| gccagggatc cactcaggag ccttccagcc ttaccccaag agttcaccta | 850 |
| cctcaactca cctaccccag ggcagctaca gcctatatat gaaaatgtga | 900 |
| atgttgtaag tggggatgag gtttattcac tggcgtacta taaccagccg | 950 |
| gagcaggaat cagtagcagc agaaaccctg ggacacata tggaggacaa | 1000 |
| ggtttcctta gacatctatt ccaggctgag gaaagcaaac attacagatg | 1050 |
| tggactatga agatgctatg taaggttatg gaagattctg ctctttgaaa | 1100 |
| accatccatg accccaagcc tcaggcctga tatgttcttc agagatcctg | 1150 |
| gggcattagc tttccagtat acctcttctg gatgccattc tccatggcac | 1200 |
| tattccttca tctactgtga agtgaagttg gcgcagccct gaagaaacta | 1250 |
| cctaggagaa ctaatagaca caggagtgac agggactttg ttatcagaac | 1300 |

| | |
|---|---|
| cagattcctg ccggctcctt tgaaaacagg tcatattgtg ctcttctgtt | 1350 |
| tacaagagga aacaagatgg aataaaagaa attgggatct tgggttggag | 1400 |
| ggacagtgaa gcttagagca catgaactca aggttagtga ctctgcagga | 1450 |
| cttcacagag agagctgtgc ccatcattca gtccaagtgc tttctctgcc | 1500 |
| cagacagcac agaactccag ccccgctact tacatggatc atcgagtttc | 1550 |
| cacctaaaat atgattctat ttattttgag tcactgttac caaattagaa | 1600 |
| ctaaaacaaa gttacataaa aagttattgt gactccactt aattttagtg | 1650 |
| acgtatttt gtatatatag gccaacctat accacatcca aaattatgta | 1700 |
| tctattacag cccctagaag ctttataaat acagtgtgtc ttcttttatt | 1750 |
| cacaaaattt ttgaaatcgt ggtaatatgg tttgaaacct gtatcttaat | 1800 |
| tatttttttt ttaaattgag acagggtctc actctgtcac tcaatctgga | 1850 |
| atgcagtggc acaatcttgc ctcactgcaa cgcctgcctc tcaggctcaa | 1900 |
| gcaaacctct cacctcagcc tgctgagtag ctgggactac aggcacatgc | 1950 |
| caccaaaact ggccattttt tgtcttacgt agagacaaga tttcaccgtt | 2000 |
| ttgcccaggc tggtctcaaa ctcctgggct caagcaatgt attgaatttt | 2050 |
| aaaataacca ggcactcact cttatgaatt aataaacatt tggaggtata | 2100 |
| taaagtaaaa agttaaagtc tttcctgtaa gttaacacaa atgttaacta | 2150 |
| ttgttaaaaa ctttacaggt agctctctag atatttttct atttttgtat | 2200 |
| gtatacttat gcatacatgt aagtatataa acatttagaa gtgtacctat | 2250 |
| ctaacaaact attatgaaat actttcaaat ctgtaaatag atctattata | 2300 |
| ctattttaaa agtctctata gtagtgtgtt atatagataa atcataactt | 2350 |
| ttttcttttt ttattgtagt aaatatgcac aacataaaat tgatcatttt | 2400 |
| aaccattttt aagtgtacaa ttcagtggca ttaagtacta tcataatata | 2450 |
| ttttaatcct tctcatcact ggtggacatt aaggagactc tcaaaaaatt | 2500 |
| catattataa aaacaaagtt caaacaaatg tctttgtact agcatattat | 2550 |
| ggcactcctg ctggattatc tgaaggataa attgtaaat ctagtattgc | 2600 |
| tagattatgc atattaaata ttcttgttaa atagtcaaaa aaaaaaaaaa | 2650 |
| aa | 2652 |

<210> SEQ ID NO 8
<211> LENGTH: 3459
<212> TYPE: DNA
<213> ORGANISM: Homo sapiens

<400> SEQUENCE: 8

| | |
|---|---|
| ctcaatcagc tttatgcaga gaagaagctt actgagctca ctgctggtgc | 50 |
| tggtgtaggc aagtgctgct ttggcaatct gggctgacct ggcttgtctc | 100 |
| ctcagaactc cttctccaac cctggagcag gcttccatgc tgctgtgggc | 150 |
| gtccttgctg gcctttgctc cagtctgtgg acaatctgca gctgcacaca | 200 |
| aacctgtgat ttccgtccat cctccatgga ccacattctt caaaggagag | 250 |
| agagtgactc tgacttgcaa tggatttcag ttctatgcaa cagagaaaac | 300 |
| aacatggtat catcggcact actgggggaga aagttgacc ctgaccccag | 350 |
| gaaacaccct cgaggttcgg gaatctggac tgtacagatg ccaggcccgg | 400 |

```
ggctccccac gaagtaaccc tgtgcgcttg ctcttttctt cagactcctt      450
aatcctgcag gcaccatatt ctgtgtttga aggtgacaca ttggttctga      500
gatgccacag aagaaggaaa gagaaattga ctgctgtgaa atatacttgg      550 aatgaaaca ttctttccat ttctaataaa agctgggatc ttcttatccc       600
acaagcaagt tcaaataaca atggcaatta tcgatgcatt ggatatggag      650
atgagaatga tgtatttaga tcaaatttca aaataattaa aattcaagaa      700
ctatttccac atccagagct gaaagctaca gactctcagc ctacagaggg      750
gaattctgta aacctgagct gtgaaacaca gcttcctcca gagcggtcag      800
acaccccact tcacttcaac ttcttcagag atggcgaggt catcctgtca      850
gactggagca cgtacccgga actccagctc ccaaccgtct ggagagaaaa      900
ctcaggatcc tattggtgtg gtgctgaaac agtgaggggt aacatccaca      950
agcacagtcc ctcgctacag atccatgtgc agcggatccc tgtgtctggg     1000
gtgctcctgg agacccagcc ctcaggggc caggctgttg aaggggagat      1050
gctggtcctt gtctgctccg tggctgaagg cacaggggat accacattct     1100
cctggcaccg agaggacatg caggagagtc tggggaggaa aactcagcgt     1150
tccctgagag cagagctgga gctccctgcc atcagacaga gccatgcagg     1200
gggatactac tgtacagcag acaacagcta cggccctgtc cagagcatgg     1250
tgctgaatgt cactgtgaga gagacccag gcaacagaga tggccttgtc      1300
gccgcgggag ccactggagg gctgctcagt gctcttctcc tggctgtggc     1350
cctgctgttt cactgctggc gtcggaggaa gtcaggagtt ggtttcttgg     1400
gagacgaaac caggctccct cccgctccag gcccaggaga gtcctcccat     1450
tccatctgcc ctgcccaggt ggagcttcag tcgttgtatg ttgatgtaca     1500
ccccaaaaag ggagatttgg tatactctga gatccagact actcagctgg     1550
gagaagaaga ggaagctaat acctccagga cacttctaga ggataaggat     1600
gtctcagttg tctactctga ggtaaagaca caacacccag ataactcagc     1650
tggaaagatc agctctaagg atgaagaaag ttaagagaat gaaaagttac     1700
gggaacgtcc tactcatgtg atttctccct tgtccaaagt cccaggccca     1750
gtgcagtcct tgcggcacct ggaatgatca actcattcca gctttctaat     1800
tcttctcatg catatgcatt cactcccagg aatactcatt cgtctactct     1850
gatgttggga tggaatggcc tctgaaagac ttcactaaaa tgaccaggat     1900
ccacagttaa gagaagaccc tgtagtattt gctgtgggcc tgacctaatg     1950
cattccctag ggtctgcttt agagaagggg gataaagaga gagaaggact     2000
gttatgaaaa acagaagcac aaattttggt gaattgggat ttgcagagat     2050
gaaaaagact gggtgacctg gatctctgct taatacatct acaaccattg     2100
tctcactgga gactcacttg catcagtttg tttaactgtg agtggctgca     2150
caggcactgt gcaaacaatg aaaagcccct tcacttctgc ctgcacagct     2200
tacactgtca ggattcagtt gcagattaaa gaacccatct ggaatggttt     2250
acagagagag gaatttaaaa gaggacatca gaagagctgg agatgcaagc     2300
tctaggctgc gcttccaaaa gcaaatgata attatgttaa tgtcattagt     2350
gacaaagatt tgcaacatta gagaaaagag acacaaatat aaaattaaaa     2400
```

| | |
|---|---|
| acttaagtac caactctcca aaactaaatt tgaacttaaa atattagtat | 2450 |
| aaactcataa taaactctgc cttaaaaaa agataaatat ttcctacgtc | 2500 |
| tgttcactga ataattacc aaccccttag caataagcac tccttgcaga | 2550 |
| gaggttttat tctctaaata ccattcct ctcaaaggaa ataaggttgc | 2600 |
| ttttcttgta ggaactgtgt ctttgagtta ctaattagtt tatatgagaa | 2650 |
| taattcttgc aataaatgaa gaaggaataa aagaaatagg aagccacaaa | 2700 |
| tttgtatgga tatttcatga tacacctact ggttaaataa ttgacaaaaa | 2750 |
| ccagcagcca aatattagag gtctcctgat ggaagtgtac aataccacct | 2800 |
| acaaattatc catgccccaa gtgttaaaac tgaatccatt caagtctttc | 2850 |
| taactgaata cttgttttat agaaaatgca tggagaaaag gaatttgttt | 2900 |
| aaataacatt atgggattgc aaccagcaaa acataaactg agaaaaagtt | 2950 |
| ctatagggca aatcacctgg cttctataac aaataaatgg gaaaaaaatg | 3000 |
| aaataaaaag aagagaggga ggaagaaagg gagagagaag aaaagaaaaa | 3050 |
| tgaagaaaag taattagaat atttcaaca taaagaaaag acgaatattt | 3100 |
| aaggtgacag atatcccaac tacgctgatt tgatctttac aaattatatg | 3150 |
| agtgtatgaa tttgtcacat gtatcacccc caaaaaaaga gaaaaagaaa | 3200 |
| aatagaagac atataaatta atgagacga gacatgtcga ccaaaaggaa | 3250 |
| tgtgtgggtc ttgtttggat cctgactcaa attaagaaaa aataaaacta | 3300 |
| cctacgaaat actaagaaaa atttgtatac taatattaag aaattgttgt | 3350 |
| gtgttttgga tataagtgat agtttattgt agtgatgttt ttataaaagc | 3400 |
| aaaaggatat tcactttcag cgcttatact gaagtattag attaaagctt | 3450 |
| attaacgta | 3459 |

<210> SEQ ID NO 9
<211> LENGTH: 1869
<212> TYPE: DNA
<213> ORGANISM: Homo sapiens

<400> SEQUENCE: 9

| | |
|---|---|
| gccgagctga gcggatcctc acatgactgt gatccgattc tttccagcgg | 50 |
| cttctgcaac caagcgggtc ttaccccgg tcctccgcgt ctccagtcct | 100 |
| cgcacctgga accccaacgt ccccgagagt ccccgaatcc ccgctcccag | 150 |
| gctacctaag aggatgagcg gtgctccgac ggccggggca gccctgatgc | 200 |
| tctgcgccgc caccgccgtg ctactgagcg ctcaggcgg accgtgcag | 250 |
| tccaagtcgc cgcgctttgc gtcctgggac gagatgaatg tcctggcgca | 300 |
| cggactcctg cagctcggcc aggggctgcg cgaacacgcg gagcgcaccc | 350 |
| gcagtcagct gagcgcgctg gagcggcgcc tgagcgcgtg cgggtccgcc | 400 |
| tgtcagggaa ccgaggggtc caccgacctc ccgttagccc ctgagagccg | 450 |
| ggtggaccct gaggtccttc acagcctgca gacacaactc aaggctcaga | 500 |
| acagcaggat ccagcaactc ttccacaagg tggcccagca gcagcggcac | 550 |
| ctggagaagc agcacctgcg aattcagcat ctgcaaagcc agtttggcct | 600 |
| cctggaccac aagcacctag accatgaggt ggccaagcct gcccgaagaa | 650 |
| agaggctgcc cgagatggcc cagccagttg acccggctca caatgtcagc | 700 |

| | |
|---|---:|
| cgcctgcacc ggctgcccag ggattgccag gagctgttcc aggttgggga | 750 |
| gaggcagagt ggactatttg aaatccagcc tcagggtct ccgccatttt | 800 |
| tggtgaactg caagatgacc tcagatggag gctggacagt aattcagagg | 850 |
| cgccacgatg gctcagtgga cttcaaccgg ccctgggaag cctacaaggc | 900 |
| ggggtttggg gatccccacg gcgagttctg gctgggtctg gagaaggtgc | 950 |
| atagcatcac gggggaccgc aacagccgcc tggccgtgca gctgcgggac | 1000 |
| tgggatggca acgccgagtt gctgcagttc tccgtgcacc tgggtggcga | 1050 |
| ggacacggcc tatagcctgc agctcactgc acccgtggcc ggccagctgg | 1100 |
| gcgccaccac cgtcccaccc agcggcctct ccgtacccct ctccacttgg | 1150 |
| gaccaggatc acgacctccg cagggacaag aactgcgcca agagcctctc | 1200 |
| tggaggctgg tggtttggca cctgcagcca ttccaacctc aacggccagt | 1250 |
| acttccgctc catcccacag cagcggcaga agcttaagaa gggaatcttc | 1300 |
| tggaagacct ggcggggccg ctactacccg ctgcaggcca ccaccatgtt | 1350 |
| gatccagccc atggcagcag aggcagcctc ctagcgtcct ggctgggcct | 1400 |
| ggtcccaggc ccacgaaaga cggtgactct ggctctgcc cgaggatgtg | 1450 |
| gccgttccct gcctgggcag gggctccaag gaggggccat ctggaaactt | 1500 |
| gtggacagag aagaagacca cgactggaga agccccttt ctgagtgcag | 1550 |
| gggggctgca tgcgttgcct cctgagatcg aggctgcagg atatgctcag | 1600 |
| actctagagg cgtggaccaa ggggcatgga gcttcactcc ttgctggcca | 1650 |
| gggagttggg gactcagagg gaccacttgg ggccagccag actggcctca | 1700 |
| atggcggact cagtcacatt gactgacggg gaccagggct tgtgtgggtc | 1750 |
| gagagcgccc tcatggtgct ggtgctgttg tgtgtaggtc ccctggggac | 1800 |
| acaagcaggc gccaatggta tctgggcgga gctcacagag ttcttggaat | 1850 |
| aaaagcaacc tcagaacac | 1869 |

<210> SEQ ID NO 10
<211> LENGTH: 685
<212> TYPE: DNA
<213> ORGANISM: Homo sapiens

<400> SEQUENCE: 10

| | |
|---|---:|
| gatgtgctcc ttggagctgg tgtgcagtgt cctgactgta agatcaagtc | 50 |
| caaacctgtt ttggaattga ggaaacttct cttttgatct cagcccttgg | 100 |
| tggtccaggt cttcatgctg ctgtgggtga tattactggt cctggctcct | 150 |
| gtcagtggac agtttgcaag gacacccagg cccattattt tcctccagcc | 200 |
| tccatggacc acagtcttcc aaggagagag agtgaccctc acttgcaagg | 250 |
| gatttcgctt ctactcacca cagaaaacaa aatggtacca tcggtacctt | 300 |
| gggaaagaaa tactaagaga aaccccagac aatatccttg aggttcagga | 350 |
| atctggagag tacagatgcc aggcccaggg ctcccctctc agtagccctg | 400 |
| tgcacttgga ttttttcttca gagatgggat ttcctcatgc tgcccaggct | 450 |
| aatgttgaac tcctgggctc aagtgatctg ctcacctagg cctctcaaag | 500 |
| cgctgggatt acagcttcgc tgatcctgca agctccactt tctgtgtttg | 550 |
| aaggagactc tgtggttctg aggtgccggg caaaggcgga agtaacactg | 600 |

```
aataatacta tttacaagaa tgataatgtc ctggcattcc ttaataaaag          650
aactgacttc caaaaaaaaa aaaaaaaaaa aaaaa                          685

<210> SEQ ID NO 11
<211> LENGTH: 5645
<212> TYPE: DNA
<213> ORGANISM: Homo sapiens

<400> SEQUENCE: 11
cgcccgcgcg ctgcagcccc atctcctagc ggcagcccag gcgcggaggg           50
agcgagtccg ccccgaggta ggtccaggac gggcgcacag cagcagccga          100
ggctggccgg gagagggagg aagaggatgg cagggccacg ccccagccca          150
tgggccaggc tgctcctggc agccttgatc agcgtcagcc tctctgggac          200
cttggcaaac cgctgcaaga aggccccagt gaagagctgc acggagtgtg          250
tccgtgtgga taaggactgc gcctactgca cagacgagat gttcagggac          300
cggcgctgca acacccaggc ggagctgctg gccgcgggct gccagcggga          350
gagcatcgtg gtcatggaga gcagcttcca aatcacagag gagacccaga          400
ttgacaccac cctgcggcgc agccagatgt cccccccaagg cctgcgggtc          450 cgtctgcggc ccgtgaggga gcggcatttt gagctggagg tgtttgagcc          500
actggagagc cccgtggacc tgtacatcct catggacttc tccaactcca          550
tgtccgatga tctggacaac ctcaagaaga tggggcagaa cctggctcgg          600
gtcctgagcc agctcaccag cgactacact attggatttg gcaagtttgt          650
ggacaaagtc agcgtcccgc agacggacat gaggcctgag aagctgaagg          700
agccctggcc caacagtgac ccccccttct ccttcaagaa cgtcatcagc          750
ctgacagaag atgtggatga gttccggaat aaaactgcag gagagcggat          800
ctcaggcaac ctggatgctc ctgagggcgg cttcgatgcc atcctgcaga          850
cagctgtgtg cacgagggac attggctggc gccggacag cacccacctg          900 ctggtcttct ccaccgagtc agccttccac tatgaggctg atggcgccaa          950
cgtgctggct ggcatcatga gccgcaacga tgaacggtgc cacctggaca         1000
ccacgggcac ctacacccag tacaggacac aggactaccc gtcggtgccc         1050
accctggtgc gcctgctcgc caagcacaac atcatcccca tctttgctgt         1100
caccaactac tcctatagct actacgagaa gcttcacacc tatttccctg         1150
tctcctcact gggggtgctg caggaggact cgtccaacat cgtggagctg         1200
ctggaggagg ccttcaatcg gatccgctcc aacctggaca tccggccct          1250 agacagcccc cgaggccttc ggacagaggt cacctccaag atgttccaga         1300
agacgaggac tgggtccttt cacatccggc gggggaagt gggtatatac          1350 caggtgcagc tgcgggccct tgagcacgtg gatgggacgc acgtgtgcca         1400
gctgccggag gaccagaagg gcaacatcca tctgaaacct tccttctccg         1450
acggcctcaa gatggacgcg ggcatcatct gtgatgtgtg cacctgcgag         1500
ctgcaaaaag aggtgcggtc agctcgctgc agcttcaacg agacttcgt          1550 gtgcggacag tgtgtgtgca gcgagggctg gagtggccag acctgcaact         1600
gctccaccgg ctctctgagt gacattcagc cctgcctgcg ggagggcgag         1650
gacaagccgt gctccggccg tgggagtgc cagtgcgggc actgtgtgtg          1700
```

```
ctacggcgaa ggccgctacg agggtcagtt ctgcgagtat gacaacttcc       1750 agtgtcccg cacttccggg ttcctctgca atgaccgagg acgctgctcc        1800
atgggccagt gtgtgtgtga gcctggttgg acaggcccaa gctgtgactg        1850 tccctcagc aatgccacct gcatcgacag caatggggc atctgtaatg         1900 gacgtggcca ctgtgagtgt ggccgctgcc actgccacca gcagtcgctc        1950
tacacggaca ccatctgcga gatcaactac tcggcgatcc acccgggcct        2000
ctgcgaggac ctacgctcct gcgtgcagtg ccaggcgtgg ggcaccggcg        2050
agaagaaggg gcgcacgtgt gaggaatgca acttcaaggt caagatggtg       2100
gacgagctta agagagccga ggaggtggtg gtgcgctgct ccttccggga       2150
cgaggatgac gactgcacct acagctacac catggaaggt gacggcgccc       2200
ctgggcccaa cagcactgtc ctggtgcaca agaagaagga ctgccctccg       2250
ggctccttct ggtggctcat ccccctgctc ctcctcctcc tgccgctcct       2300
ggccctgcta ctgctgctat gctggaagta ctgtgcctgc tgcaaggcct       2350
gcctggcact tctcccgtgc tgcaaccgag gtcacatggt gggctttaag       2400
gaagaccact acatgctgcg ggagaacctg atggcctctg accacttgga       2450
cacgcccatg ctgcgcagcg ggaacctcaa gggccgtgac gtggtccgct       2500
ggaaggtcac caacaacatg cagcggcctg gctttgccac tcatgccgcc       2550
agcatcaacc ccacagagct ggtgcctac ggctgtcct gcgcctggc         2600 ccgcctttgc accgagaacc tgctgaagcc tgacactcgg gagtgcgccc       2650
agctgcgcca ggaggtggag gagaacctga acgaggtcta caggcagatc       2700
tccggtgtac acaagctcca gcagaccaag ttccggcagc agcccaatgc       2750
cgggaaaaag caagaccaca ccattgtgga cacagtgctg atggcgcccc       2800
gctcggccaa gccggccctg ctgaagctta cagagaagca ggtggaacag       2850
agggccttcc acgacctcaa ggtgccccc ggctactaca ccctcactgc        2900
agaccaggac gcccggggca tggtggagtt ccaggagggc gtggagctgg       2950
tggacgtacg ggtgcccctc ttatccggc ctgaggatga cgacgagaag        3000
cagctgctgg tggaggccat cgacgtgccc gcaggcactg ccaccctcgg       3050
ccgccgcctg gtaaacatca ccatcatcaa ggagcaagcc agagacgtgg       3100
tgtcctttga gcagctgagg ttctcggtca gccgcgggga ccaggtggcc       3150
cgcatccctg tcatccggcg tgtcctggac ggcgggaagt cccaggtctc       3200
ctaccgcaca caggatggca ccgcgcaggg caaccgggac tacatccccg       3250
tggagggtga gctgctgttc cagcctgggg aggcctggaa agagctgcag       3300
gtgaagctcc tggagctgca agaagttgac tccctcctgc ggggccgcca       3350
ggtccgccgt ttccacgtcc agctcagcaa ccctaagttt ggggcccacc       3400
tgggccagcc ccactccacc accatcatca tcagggaccc agatgaactg       3450
gaccggagct tcacgagtca gatgttgtca tcacagccac cccctcacgg       3500
cgacctgggc gccccgcaga accccaatgc taaggccgct gggtccagga       3550
agatccattt caactggctg ccccttctg gcaagccaat ggggtacagg        3600
gtaaagtact ggattcaggg tgactccgaa tccgaagccc acctgctcga       3650
cagcaaggtg ccctcagtgg agctcaccaa cctgtacccg tattgcgact       3700
```

```
atgagatgaa ggtgtgcgcc tacggggctc agggcgaggg accctacagc    3750
tccctggtgt cctgccgcac ccaccaggaa gtgcccagcg agccagggcg    3800
tctggccttc aatgtcgtct cctccacggt gacccagctg agctgggctg    3850
agccggctga gaccaacggt gagatcacag cctacgaggt ctgctatggc    3900
ctggtcaacg atgacaaccg acctattggg cccatgaaga aagtgctggt    3950
tgacaaccct aagaaccgga tgctgcttat tgagaacctt cgggagtccc    4000
agccctaccg ctacacggtg aaggcgcgca acggggccgg ctgggggcct    4050
gagcgggagg ccatcatcaa cctggccacc cagcccaaga ggcccatgtc    4100
catccccatc atccctgaca tccctatcgt ggacgcccag agcggggagg    4150
actacgacag cttccttatg tacagcgatg acgttctacg ctctccatcg    4200
ggcagccaga ggcccagcgt ctccgatgac actgagcacc tggtgaatgg    4250
ccggatggac tttgccttcc cgggcagcac caactccctg cacaggatga    4300
ccacgaccag tgctgctgcc tatggcaccc acctgagccc acacgtgccc    4350
caccgcgtgc taagcacatc ctccaccctc acacgggact acaactcact    4400
gacccgctca gaacactcac actcgaccac actgccgagg gactactcca    4450
ccctcacctc cgtctcctcc cacgactctc gcctgactgc tggtgtgccc    4500
gacacgccca cccgcctggt gttctctgcc ctggggccca catctctcag    4550
agtgagctgg caggagccgc ggtgcgagcg ccgctgcag ggctacagtg    4600
tggagtacca gctgctgaac ggcggtgagc tgcatcggct caacatcccc    4650
aaccctgccc agacctcggt ggtggtggaa gacctcctgc ccaaccactc    4700
ctacgtgttc cgcgtgcggg cccagagcca ggaaggctgg ggccgagagc    4750
gtgagggtgt catcaccatt gaatcccagg tgcaccgca gagcccactg    4800
tgtcccctgc caggctccgc cttcactttg agcactccca gtgccccagg    4850
cccgctggtg ttcactgccc tgagcccaga ctcgctgcag ctgagctggg    4900
agcggccacg gaggcccaat ggggatatcg tcggctacct ggtgacctgt    4950
gagatggccc aaggaggagg gccagccacc gcattccggg tggatggaga    5000
cagccccgag agccggctga ccgtgccggg cctcagcgag aacgtgccct    5050
acaagttcaa ggtgcaggcc aggaccactg agggcttcgg gccagagcgc    5100
gagggcatca tcaccataga gtcccaggat ggaggaccct tcccgcagct    5150
gggcagccgt gccgggctct ccagcacccc gctgcaaagc gagtacagca    5200
gcatcaccac cacccacacc agcgccaccg agcccttcct agtggatggg    5250
ccgaccctgg gggcccagca cctggaggca ggcggctccc tcacccggca    5300
tgtgacccag gagtttgtga gccggacact gaccaccagc ggaacccttA    5350
gcacccacat ggaccaacag ttcttccaaa cttgaccgca ccctgcccca    5400
ccccgccat gtcccactag gcgtcctccc gactcctctc ccggagcctc    5450
ctcagctact ccatccttgc acccctgggg gcccagccca cccgcatgca    5500
cagagcaggg gctaggtgtc tcctgggagg catgaagggg gcaaggtccg    5550
tcctctgtgg gcccaaacct atttgtaacc aaagagctgg gagcagcaca    5600
aggacccagc ctttgttctg cacttaataa atggttttgc tactg         5645
```

<210> SEQ ID NO 12

```
<211> LENGTH: 4381
<212> TYPE: DNA
<213> ORGANISM: Homo sapiens

<400> SEQUENCE: 12
gccttcaact accatcccac cacctgctga ggagaaaaat tcttcaagac          50
tcagagcaca cagccagcac cagaggcccc atgaccctgg acagaccagg         100 ggaggggcc accatgctga agacattcac tgttttgctc ttttgcattc          150
ggatgagtct gggtatgaca tcgatagtga tggaccctca accggagttg         200
tggatagagt ccaactaccc ccaggcccct tgggagaaca tcacgctttg         250
gtgccgaagc ccctctcgga tatcaagcaa gttcctgctg ctgaaggata         300
agacacaaat gacctggatc cgcccttccc acaagacctt ccaagtttca         350
ttccttatag gtgcccttac tgagtccaat gcaggtcttt accggtgctg         400
ctactggaag gagacaggct ggtcaaagcc cagtaaagtt ctagagttgg         450
aggcaccagg ccaactgccc aagcccatct tctggattca ggctgagacc         500
cccgctcttc ctgggtgtaa tgttaacatc ctctgccatg gctggctgca         550
ggatttggta ttcatgctgt ttaaagaggg atatgcagag cctgtggatt         600
accaagtccc aactgggaca atggccatat tctccattga caacctgaca         650
cctgaggatg aaggggttta catctgccgc actcatatcc agatgctccc         700
caccctgtgg tcagagccca gcaacccccct gaagctggtt gtagcaggac         750
tctaccccaa accaactttg acagcccatc ctgggcccat catggcacct         800
ggagaaagcc tgaatctcag gtgccaaggg ccaatctatg gaatgaccctt         850 tgctctaatg agggttgaag acttggagaa gtccttttac cacaagaaga         900
caataaaaaa tgaggcaaat tcttcttcc agtctttgaa gatccaagat         950
actggacatt acctctgttt ttactatgac gcatcatata gaggttcact        1000
ccttagtgat gtcctgaaaa tctgggtaac tgacactttc cccaagacct        1050
ggctacttgc tcggcccagt gctgtggtcc aaatgggtca gaatgtgagc        1100
ctacggtgtc gaggaccagt ggatggagtg ggtcttgcac tctataagaa        1150
aggagaagac aaaccacttc aattttggga tgccaccagc atcgatgaca        1200
acacatcatt cttcctcaac aatgtaacct acagtgatac tggcatctat        1250
agctgccact atcttctcac ctggaagacc tccattagga tgccatcaca        1300
caacactgtg gagcttatgg ttgtagataa gccccccaaa ccctccctgt        1350
cagcttggcc aagcactgtg ttcaagctag gaaaggccat caccccttcag        1400 tgccgagtat ctcatccagt actggaattt tctctggaat gggaagaaag        1450
agaaacattc caaagattct cagtaaacgg agacttcatc atcagtaatg        1500
ttgacgggaa aggcacaggg acctacagtt gcagctatcg cgtagagaca        1550
catcctaaca tgtggtcaca tcgcagtgag cccctgaagc tgatgggcc         1600 agcaggctat ctcacctgga attacgttct gaatgaagct atcaggttgt        1650
ctctaatcat gcagcttgtt gccttgctgt tggtagtgct gtggataagg        1700
tggaagtgtc ggagactcag aatcagagaa gcctggttgc tgggaacagc        1750 tcaagggtc accatgctct tcatagtcac ggcccttctc tgctgtggac         1800
tgtgcaatgg ggtattgata gaagagactg aaatagtcat gccaacccct        1850
```

-continued

| | |
|---|---|
| aagcctgagc tgtgggcaga gaccaacttt cctctggccc cgtggaagaa | 1900 |
| cttaaccctc tggtgcagaa gcccttctgg ctcaactaag gagtttgtgt | 1950 |
| tgctgaagga tgggaccggg tggatcgcca ctcgcccggc ctcagagcag | 2000 |
| gtccgggctg ccttcccct tggcgccctg acccagagcc acaccgggag | 2050 |
| ctaccactgc cattcatggg aggagatggc tgtatcggag cccagtgagg | 2100 |
| cacttgagct ggtggggaca gacatcctcc ccaaacctgt catttctgct | 2150 |
| tcccccacaa tccggggcca ggaactacaa ctccggtgca aggatggct | 2200 |
| ggcaggcatg gggtttgctc tgtataagga gggagagcaa gaacctgtcc | 2250 |
| agcaacttgg tgctgttgga agagaagcct tctttacaat ccagagaatg | 2300 |
| gaggataaag acgaaggcaa ttacagctgc cgcactcaca ctgaaaaact | 2350 |
| cccttcaag tggtctgagc ccagtgagcc gctggagctt gtcataaaag | 2400 |
| aaatgtaccc taagcccttc ttcaagacat gggccagccc tgtggtcacc | 2450 |
| cctggtgccc gagtgacttt caattgctcc accccccacc agcatatgag | 2500 |
| ctttattctt tacaaagatg gaagtgaaat agcatccagt gacaggtcct | 2550 |
| gggcaagtcc gggggccagt gcagctcact ttctaatcat ttcggtgggc | 2600 |
| attggtgatg gagggaatta cagctgccga tattatgact tttctatctg | 2650 |
| gtctgagccc agcgaccctg tggagctcgt ggtgacagaa ttctacccca | 2700 |
| aacccactct cctggcacag ccaggtcctg tggtgtttcc tgggaagagt | 2750 |
| gtgatcctgc gctgccaagg gactttccag ggcatgaggt tcgccctctt | 2800 |
| gcaggaggga gcccatgttc ccttacagtt tcggagtgtc tcagggaact | 2850 |
| cagctgactt ccttctccac actgttggag cagaggactc tgggaactat | 2900 |
| agctgtatct actatgagac aaccatgtca aacagggggt catatctcag | 2950 |
| tatgcccctt atgatctggg tgactgacac attccctaag ccatggttgt | 3000 |
| ttgctgagcc cagttctgtg gttcccatgg ggcagaatgt tactctctgg | 3050 |
| tgccgagggc cggtccatgg agtaggatac attctgcaca aagaaggaga | 3100 |
| agccacttca atgcagctct ggggatccac cagtaatgac ggggcattcc | 3150 |
| ccatcaccaa tatatctggt actagcatgg ggcgttacag ctgctgctac | 3200 |
| caccctgact ggaccagttc tatcaagata caacctagca acaccctgga | 3250 |
| actcctagtc acaggcttac tccccaaacc cagcctatta gcccagcctg | 3300 |
| gtcccatggt ggcccctggc gaaaatatga ctcttcagtg tcaaggggaa | 3350 |
| ctgccagact caacatttgt gctgttgaag gagggggctc aggagccttt | 3400 |
| agagcaacag aggccaagtg ggtacagggc tgacttctgg atgccagcag | 3450 |
| tgagaggtga agactctggg atctatagct gtgtttatta tttggactct | 3500 |
| actccctttg cagcttcaaa tcacagtgac tccctggaga tctgggtgac | 3550 |
| tgataagccc cctaaaccct ctctgtcagc ctggcccagc accatgttca | 3600 |
| agttagggaa ggacatcacc cttcagtgcc gaggaccct gccaggtgtt | 3650 |
| gaatttgttc tagaacatga tggagaagaa gcacctcagc agttttcaga | 3700 |
| ggatggagac tttgtcatca caacgtaga aggaaaaggc attggaaact | 3750 |
| acagctgcag ctaccgcctc caggcctacc tgatatctg gtcagagcct | 3800 |
| agtgatcccc tggagctggt gggggcagca gggcctgttg ctcaggagtg | 3850 |

| | |
|---|---|
| cactgtaggg aacattgtcc gaagtagcct aatcgtggtg gttgttgtag | 3900 |
| ccttgggggt agtgctagcc atagagtgga agaagtggcc tcgactgcga | 3950 |
| accagaggct cagagacaga cggaagagac cagaccattg cccttgaaga | 4000 |
| gtgtaaccaa gaaggagaac caggcacccc tgccaattct ccttcatcaa | 4050 |
| cctctcagag aatctctgtg gaactgcccg ttccaatata ataatctcct | 4100 |
| cctttacaag agctttcctc tcctctctct tgctctcaga gacctataaa | 4150 |
| tccaaccagt taccctgcaa gtcagcccca tctgctgttc cttggtctct | 4200 |
| aatcacctga gctgggtaaa ggggattctg ggagttgaga gctctgccag | 4250 |
| ggtgagatgt ttcctgaaga gaggttcccc acccctgtaa ctcctcactg | 4300 |
| tactgattta ctggcgcatg aaattctatt aaaaatgcat tcttctgaat | 4350 |
| aaaaagagta ttcactattt aacttcaatt t | 4381 |

<210> SEQ ID NO 13
<211> LENGTH: 1068
<212> TYPE: DNA
<213> ORGANISM: Homo sapiens

<400> SEQUENCE: 13

| | |
|---|---|
| cgccggagga gttctgcgtc tcggggtggt gactgggtcc agaatggctt | 50 |
| cggattcggg gaaccagggg accctctgca cgttggagtt cgcggtgcag | 100 |
| atgacctgtc agagctgtgt ggacgcggtg cgcaaatccc tgcaaggggt | 150 |
| ggcaggtgtc caggatgtgg aggtgcactt ggaggaccag atggtcttgg | 200 |
| tacacaccac tctacccagc caggaggtgc aggctctcct ggaaggcacg | 250 |
| gggcggcagg cggtactcaa gggcatgggc agcggccagt tgcagaatct | 300 |
| gggggcagca gtggccatcc tggggggggcc tggcaccgtg caggggtgg | 350 |
| tgcgcttcct acagctgacc cctgagcgct gcctcatcga gggaactatt | 400 |
| gacggcctgg agcctgggct gcatggactc cacgtccatc agtacgggga | 450 |
| ccttacaaac aactgcaaca gctgtgggaa tcactttaac cctgatggag | 500 |
| catctcatgg gggcccccag gactctgacc ggcaccgcgg agacctgggc | 550 |
| aatgtccgtg ctgatgctga cggccgcgcc atcttcagaa tggaggatga | 600 |
| gcagctgaag gtgtgggatg tgattggccg cagcctgatt attgatgagg | 650 |
| gagaagatga cctgggccgg ggaggccatc ccttatccaa gatcacaggg | 700 |
| aactccgggg agaggttggc ctgtggcatc attgcacgct ccgctggcct | 750 |
| tttccagaac cccaagcaga tctgctcttg cgatggcctc accatctggg | 800 |
| aggagcgagg ccggcccatc gctggcaagg gccgaaagga gtcagcgcag | 850 |
| cccccctgccc acctttgagc aggacctcac cttggctctg ttgctgtcct | 900 |
| ccagggcgag cactttccac ttccagaggg ggccagaggg actttgcctg | 950 |
| cccagtctttt ggagagctca gtacagggca ggagctgctg tggtgttccc | 1000 |
| ttggcaaatg aaagttttat tttcgtttgg gaaaaaaaaa aaaaaaaaa | 1050 |
| aaaaaaaaaa aaaaaaaa | 1068 |

<210> SEQ ID NO 14
<211> LENGTH: 2402
<212> TYPE: DNA
<213> ORGANISM: Homo sapiens
<220> FEATURE:

<221> NAME/KEY: Unsure
<222> LOCATION: 2138
<223> OTHER INFORMATION: Unknown base

<400> SEQUENCE: 14

| | | | | | |
|---|---|---|---|---|---|
| ggagaggtgc | gggccgaatc | cgagccgagc | gagaggaatc | cggcagtaga | 50 |
| gagcggactc | cagccggcgg | accctgcagc | cctcgcctgg | gacagcggcg | 100 |
| cgctgggcag | gcgcccaaga | gagcatcgag | cagcggaacc | cgcgaagccg | 150 |
| gcccgcagcc | gcgacccgcg | cagcctgccg | ctctcccgcc | gccggtccgg | 200 |
| gcagcatgag | gcgcgcggcg | ctctggctct | ggctgtgcgc | gctggcgctg | 250 |
| agcctgcagc | tggccctgcc | gcaaattgtg | gctactaatt | tgccccctga | 300 |
| agatcaagat | ggctctgggg | atgactctga | caacttctcc | ggctcaggtg | 350 |
| caggtgcttt | gcaagatatc | accttgtcac | agcagacccc | ctccacttgg | 400 |
| aaggacacgc | agctcctgac | ggctattccc | acgtctccag | aacccaccgg | 450 |
| cctggaggct | acagctgcct | ccacctccac | cctgccggct | ggagaggggc | 500 |
| ccaaggaggg | agaggctgta | gtcctgccag | aagtggagcc | tggcctcacc | 550 |
| gcccgggagc | aggaggccac | ccccgaccc | agggagacca | cacagctccc | 600 |
| gaccactcat | caggcctcaa | cgaccacagc | caccacggcc | caggagcccg | 650 |
| ccacctccca | cccccacagg | gacatgcagc | ctggccacca | tgagacctca | 700 |
| accctgcag | gacccagcca | agctgacctt | cacactcccc | acacagagga | 750 |
| tggaggtcct | tctgccaccg | agagggctgc | tgaggatgga | gcctccagtc | 800 |
| agctcccagc | agcagagggc | tctggggagc | aggacttcac | ctttgaaacc | 850 |
| tcgggggaga | atacggctgt | agtggccgtg | gagcctgacc | gccggaacca | 900 |
| gtccccagtg | gatcagggg | ccacggggc | ctcacagggc | ctcctggaca | 950 |
| ggaaagaggt | gctgggaggg | gtcattgccg | gaggcctcgt | ggggctcatc | 1000 |
| tttgctgtgt | gcctggtggg | tttcatgctg | taccgcatga | agaagaagga | 1050 |
| cgaaggcagc | tactccttgg | aggagccgaa | acaagccaac | ggcggggcct | 1100 |
| accagaagcc | caccaaacag | gaggaattct | atgcctgacg | cgggagccat | 1150 |
| gcgcccctc | cgccctgcca | ctcactaggc | ccccacttgc | ctcttccttg | 1200 |
| aagaactgca | ggccctggcc | tcccctgcca | ccaggccacc | tccccagcat | 1250 |
| tccagccct | ctggtcgctc | ctgcccacgg | agtcgtgggt | gtgctgggag | 1300 |
| ctccactctg | cttctctgac | ttctgcctgg | agacttaggg | caccaggggt | 1350 |
| ttctcgcata | ggacctttcc | accacagcca | gcacctggca | tcgcaccatt | 1400 |
| ctgactcggt | ttctccaaac | tgaagcagcc | tctccccagg | tccagctctg | 1450 |
| gaggggaggg | ggatccgact | gctttggacc | taaatggcct | catgtggctg | 1500 |
| gaagatctgc | gggtggggct | tggggctcac | acacctgtag | cacttactgg | 1550 |
| taggaccaag | catcttgggg | gggtggccgc | tgagtggcag | ggacaggagt | 1600 |
| cactttgttt | cgtggggagg | tctaatctag | atatcgactt | gttttttgcac | 1650 |
| atgtttcctc | tagttctttg | ttcatagccc | agtagacctt | gttacttctg | 1700 |
| aggtaagtta | agtaagttga | ttcggtatcc | ccccatcttg | cttccctaat | 1750 |
| ctatggtcgg | gagacagcat | cagggttaag | aagactttt | ttttttttt | 1800 |
| ttaaactagg | agaaccaaat | ctggaagcca | aaatgtaggc | ttagtttgtg | 1850 |

```
tgttgtctct tgagtttgtc gctcatgtgt gcaacagggt atggactatc        1900
tgtctggtgg ccccgtttct ggtggtctgt tggcaggctg gccagtccag        1950
gctgccgtgg ggccgccgcc tctttcaagc agtcgtgcct gtgtccatgc        2000
gctcagggcc atgctgaggc ctgggccgct gccacgttgg agaagcccgt        2050
gtgagaagtg aatgctggga ctcagccttc agacagagag gactgtaggg        2100
agggcggcag gggcctggag atcctcctgc agaccacncc cgtcctgcct        2150
gtgcgccgtc tccaggggct gcttcctcct ggaaattgac gaggggtgtc        2200
ttgggcagag ctggctctga cgcctccat ccaaggccag gttctccgtt         2250
agctcctgtg gccccaccct gggccctggg ctggaatcag gaatattttc        2300
caaagagtga tagtctttg cttttggcaa aactctactt aatccaatgg         2350 gttttttccct gtacagtaga ttttccaaat gtaataaact ttaatataaa       2400
gt                                                            2402

<210> SEQ ID NO 15
<211> LENGTH: 1145
<212> TYPE: DNA
<213> ORGANISM: Homo sapiens

<400> SEQUENCE: 15
gctccggcca gccgcggtcc agagcgcgcg aggttcgggg agctccgcca          50
ggctgctggt acctgcgtcc gcccggcgag caggacaggc tgctttggtt         100
tgtgacctcc aggcaggacg gccatcctct ccagaatgaa gatcttcttg         150
ccagtgctgc tggctgccct tctgggtgtg gagcgagcca gctcgctgat         200
gtgcttctcc tgcttgaacc agaagagcaa tctgtactgc ctgaagccga         250
ccatctgctc cgaccaggac aactactgcg tgactgtgtc tgctagtgcc         300
ggcattggga atctcgtgac atttggccac agcctgagca gacctgttc          350 cccggcctgc cccatcccag aaggcgtcaa tgttggtgtg gcttccatgg         400
gcatcagctg ctgccagagc tttctgtgca atttcagtgc ggccgatggc         450
gggctgcggg caagcgtcac cctgctgggt gccgggctgc tgctgagcct         500
gctgccggcc ctgctgcggt ttggcccctg accgccagag ccctgtcccc         550
cgatccccca gctcaggaag gaaagcccag cccttctgg atcccacagt          600 gtatgggagc cctgactcc tcacgtgcct gatctgtgcc cttggtccca         650
ggtcaggccc accccctgca cctccacctg ccccagcccc tgcctctgcc         700
caagtgggcc agctgccctc acttctgggg tggatgatgt gaccttcctt         750
gggggactgc ggaagggacg agggttccct ggagtcttac ggtccaacat         800
cagaccaagt cccatggaca tgctgacagg gtccccaggg agaccgtgtc         850
agtagggatg tgtgcctggc tgtgtacgtg ggtgtgcagt gcacgtgaga         900
gcacgtggcg gcttctgggg gccatgtttg gggagggagg tgtgccagca         950
gcctggagag cctcagtccc tgtagccccc tgccctggca cagctgcatg        1000
cacttcaagg gcagcctttg ggggttgggg tttctgccac ttccgggtct        1050
aggccctgcc caaatccagc cagtcctgcc ccagcccacc cccacattgg        1100
agccctcctg ctgctttggt gcctcaaata aatacagatg  tcccc            1145

<210> SEQ ID NO 16
```

<211> LENGTH: 1743
<212> TYPE: DNA
<213> ORGANISM: Homo sapiens

<400> SEQUENCE: 16

| | | | | | |
|---|---|---|---|---|---|
| cagcaggtca | cagcccctcg | aggcgacagc | ggccccgccg | caccagagca | 50 |
| gtggtacagg | catggatggg | aagaaatgca | gcgtatggat | gttcctacct | 100 |
| cttgtattta | ctttgtttac | ttcagctgga | ttgtggatag | tatacttcat | 150 |
| agctgtggaa | gatgacaaaa | ttttaccatt | aaattcagct | gaaggaaac | 200 |
| ctggtgtgaa | gcatgcacca | tatataagca | ttgcaggtga | tgatcctcct | 250 |
| gcaagctgtg | tgtttagtca | agttatgaac | atggcagcct | tcctagccct | 300 |
| tgtggtagct | gttctgcgct | tcatacaact | gaaaccgaag | gttttaaacc | 350 |
| cgtggctgaa | tattagtgga | ttggtggctc | tgtgtctggc | ttccttcgga | 400 |
| atgaccttac | ttggtaattt | tcagctcaca | aatgatgaag | aaatccataa | 450 |
| cgtcggaact | tccttgacct | ttggatttgg | cacattgacc | tgctggatcc | 500 |
| aggctgcgct | gacactcaag | gtcaacatca | agaatgaagg | acggagagtt | 550 |
| ggaattccac | gggttattct | gtcggcatct | atcactctct | gtgtggtcct | 600 |
| ctacttcatc | ctcatggccc | aaagcatcca | catgtatgca | gccagggtcc | 650 |
| agtggggcct | ggtcatgtgc | ttcctgtctt | attttggcac | ctttgccgtg | 700 |
| gagttccggc | attaccgcta | tgagattgtt | tgctctgagt | accaggagaa | 750 |
| tttcctaagc | ttctcagaaa | gcctgtcaga | agcttctgaa | tatcagactg | 800 |
| accaggtgta | aaccatcagt | ttttccttgc | tggtgaggtg | ggtgtgacag | 850 |
| tgggggaggg | gccagtagga | cacactcaca | ggacttgaca | tagaacctca | 900 |
| tttcacacac | acacacacac | acacattcat | ggccacattt | gccaaatgag | 950 |
| cttttcaggg | cgagttattt | ctttaatgaa | aaagcacaag | cccttatgtg | 1000 |
| tcgaaataca | cgctgttaca | ctgaaaatat | atgcacgaca | gagcaagaag | 1050 |
| cttgtgcatg | atcacttctt | atccgtcccc | ttcccagcac | tccctcctct | 1100 |
| tcccattctc | tccacatgtc | tcaagcaccc | taccgagtag | ggcaggccaa | 1150 |
| atgttccttg | ggagtaatgc | caactcccga | cgttgccttc | aggtccaaag | 1200 |
| ggcttggaac | cagctcgtga | ggaagttctg | aatctggcac | taatattctt | 1250 |
| gagtggataa | tagtgtatca | tagaatagga | cggaaattgt | attgagatgt | 1300 |
| gaccctgtgt | cgcctgtgga | aaggcatagt | gagaagaact | ttcccacgaa | 1350 |
| agcccccttc | atcgttgttc | agtggtcggc | tgtgtggatc | ccaggagaga | 1400 |
| catatgccac | agactgtgag | agcaaagccc | gccgctgtga | tctggacttg | 1450 |
| atgcactgtg | actgagaatg | atttccaaat | gtgaatatgt | gtagggacgt | 1500 |
| ggtctatcag | gcctggaaca | agatgggggc | agtgaaggta | tggtttagtg | 1550 |
| tttgctttca | tagtatgcca | tgtacaatgt | tttatatttc | atagtttctt | 1600 |
| ttaagtaact | accatgagtc | tctctaagcc | tcatggacaa | agatgtagac | 1650 |
| caaatgcaag | agctgagctt | gctttgggtt | caaccatgat | caaagaaaaa | 1700 |
| ctgaggtcac | ctgcaggctt | acgtgggaag | ctaagacaat | atc | 1743 |

<210> SEQ ID NO 17
<211> LENGTH: 1939
<212> TYPE: DNA

<213> ORGANISM: Homo sapiens

<400> SEQUENCE: 17

```
ctgcctccac tgctctgtgc tgggatcatg gaacttgcac tgctgtgtgg        50
gctggtggtg atggctggtg tgattccaat ccagggcggg atcctgaacc       100
tgaacaagat ggtcaagcaa gtgactggga aaatgcccat cctctcctac       150
tggccctacg gctgtcactg cggactaggt ggcagaggcc aacccaaaga       200
tgccacggac tggtgctgcc agacccatga ctgctgctat gaccacctga       250
agacccaggg gtgcggcatc tacaaggact attacagata caacttttcc       300
caggggaaca tccactgctc tgacaaggga agctggtgtg agcagcagct       350
gtgtgcctgt gacaaggagg tggccttctg cctgaagcgc aacctggaca       400
cctaccagaa gcgactgcgt ttctactggc ggccccactg ccgggggcag       450
accctgggt gctagaagcc cacccctct accctgttcc tcagcatgga         500
gctctggcat ccccacctca gtatctaacc tgaaccagcc tggcttttca       550
aacactccgg ggggaggtag tcccagcctc ccccggaacc ctctaccaat       600
gccttctgac cttctgaagc tttccgaatc ctcccagttg aggcagtagc       650
tgtgtcctct gagggtggat gggaatcttg ggagaagccc aagcaaggga       700
gccctcagag gtggtgtttg gaccaaagca tcggggtggg ggaggggtct       750
gccgctgtcc cccacctgct ggcccccttg tccttcctca ccccctccaa       800
tatagtctcg gagctacaac tgcagcagcc actataaagg gcaatattga       850
tctttctgtc catgtggctc tatcttttaa aacctcaagg ccctccactg       900
tcctaagata aagcctctca taggcactgg ggaccctgca cagtctggcc       950
atgtgaccct ctccccaggc aagtctgaa gtccctgcag gtggaggcca      1000
tgcctgtctt aaactcagtt gcatccctgg tgcccaaagc aacaccagaa      1050
ccaagaagga gctccataaa tccttcttgg gtgaagccta gacaaagccg      1100
ccaggtcttg tggctccagg caccagagcc ttgagtactt tctcctgcct      1150
ccaggcattg gctcagggtg aattacaagg ggctactgaa tggctattac      1200
tttcatcacg actgatcccc acctcctcag ggtcaaaggg ctactttctg      1250
gaagtctccc caggctgact ccttctccct gactgcaagg gctcactccc      1300
tcctccaagc tccacaatg cttcatggct ctgccgctta cctagcttgg       1350
cctagagtgg caaatggaac ttctctgatc tcccccaact agactggagc      1400
ccccgaagga tggagaccat gtctgtgcca tctctgtttc ccctgttttc      1450
ccacatacta ggtgctcaat tcatgcctgt gaatggcgtg agcccataat      1500
ggatacacag aggttgcagc agatggtgtg ggtacctcac ccagatatct      1550
tccaggccca aggcccctct ccctgagtga ggccaggtgt tggcagccaa      1600
ctgctccaat ctgcctcctt cccctaaata ctgcccctggt ctagtgggag     1650
ctgccttccc cctgccccac ctctcccacc aagaggccac ctgtcactca      1700
tggccaggag agtgacacca tggagggtac aattgccagc tccccccgtgt    1750
ctgtgcagca ttgtctgggt tgaatgacac tctcaaattg ttcctgggat      1800
cgggctgagg ccaggcctct cctggaacca cctctctgct tggtctgacc      1850
ccttggccta tccagttttc ctggttccct cacaggtttc tccagaaagt      1900
```

```
actccctcag taaagcattt gcacaagaaa aaaaaaaaa                   1939
```

<210> SEQ ID NO 18
<211> LENGTH: 5420
<212> TYPE: DNA
<213> ORGANISM: Homo sapiens
<220> FEATURE:
<221> NAME/KEY: Unsure
<222> LOCATION: 5094
<223> OTHER INFORMATION: Unknown base

<400> SEQUENCE: 18

```
ggctgaaaga gcctgagctg tgcctctcca ttccactgct gtggcagggt         50
cagaaatctt ggatagagaa aaccttttgc aaacgggaat gtatctttgt        100
aattcctagc acgaaagact ctaacaggtg ttgctgtggc cagttcacca        150
accagcatat ccccccctctg ccaagtgcaa cacccagcaa aaatgaagag        200
gaaagcaaac aggtggagac tcagcctgag aaatggtctg ttgccaagca        250
cacccagagc tacccaacag attcctatgg agttcttgaa ttccagggtg        300
gcggatattc caataaagcc atgtatatcc gtgtatccta tgacaccaag        350
ccagactcac tgctccatct catggtgaaa gattggcagc tggaactccc        400
caagctctta atatctgtgc atggaggcct ccagaacttt gagatgcagc        450
ccaagctgaa acaagtcttt gggaaaggcc tgatcaaggc tgctatgacc        500
accggggcct ggatcttcac cggggggtgtc agcacaggtg ttatcagcca        550
cgtagggggat gccttgaaag accactcctc caagtccaga ggccgggttt        600
gtgctatagg aattgctcca tggggcatcg tggagaataa ggaagacctg        650
gttggaaagg atgtaacaag agtgtaccag accatgtcca accctctaag        700
taagctctct gtgctcaaca actcccacac ccacttcatc ctggctgaca        750
atggcaccct gggcaagtat ggcgccgagg tgaagctgcg aaggctgctg        800
gaaaagcaca tctcccctcca gaagatcaac acaagactgg ggcagggcgt        850
gccccctcgtg ggtctcgtgg tggaggggggg ccctaacgtg gtgtccatcg        900
tcttggaata cctgcaagaa gagcctccca tccctgtggt gatttgtgat        950
ggcagcggac gtgcctcgga catcctgtcc tttgcgcaca agtactgtga       1000
agaaggcgga ataataaatg agtccctcag ggagcagctt ctagttacca       1050
ttcagaaaac atttaattat aataaggcac aatcacatca gctgtttgca       1100
attataatgg agtgcatgaa gaagaaagaa ctcgtcactg tgttcagaat       1150
gggttctgag ggccagcagg acatcgagat ggcaattta actgccctgc       1200
tgaaaggaac aaacgtatct gctccagatc agctgagctt ggcactggct       1250
tggaaccgcg tggacatagc acgaagccag atctttgtct ttgggcccca       1300
ctggacgccc ctgggaagcc tggcacccc gacggacagc aaagccacgg       1350
agaaggagaa gaagccaccc atggccacca ccaagggagg aagaggaaaa       1400
gggaaaggca agaagaaagg gaaagtgaaa gaggaagtgg aggaagaaac       1450
tgaccccgg aagatagagc tgctgaactg ggtgaatgct tggagcaag        1500
cgatgctaga tgctttagtc ttagatcgtg tcgactttgt gaagctcctg       1550
attgaaaacg gagtgaacat gcaacacttt ctgaccattc cgaggctgga       1600
ggagctctat aacacaagac tgggtccacc aaacacactt catctgctgg       1650
```

```
tgagggatgt gaaaaagagc aaccttccgc ctgattacca catcagcctc       1700
atagacatcg ggctcgtgct ggagtacctc atggggaggag cctaccgctg      1750 caactacact cggaaaaact ttcggaccct ttacaacaac ttgtttggac       1800
caaagaggcc taaagctctt aaacttctgg gaatggaaga tgatgagcct      1850
ccagctaaag ggaagaaaaa aaaaaaaag aaaaggagg aagagatcga        1900 cattgatgtg gacgaccctg ccgtgagtcg gttccagtat cccttccacg      1950
agctgatggt gtgggcagtg ctgatgaaac gccagaaaat ggcagtgttc      2000
ctctggcagc gaggggaaga gagcatggcc aaggccctgg tggcctgcaa      2050
gctctacaag gccatggccc acgagtcctc cgagagtgat ctggtggatg      2100
acatctccca ggacttggat aacaattcca aagacttcgg ccagcttgct      2150
ttggagttat tagaccagtc ctataagcat gacgagcaga tcgctatgaa      2200
actcctgacc tacgagctga aaaactggag caactcgacc tgcctcaaac      2250
tggccgtggc agccaaacac cgggacttca ttgctcacac ctgcagccag      2300
atgctgctga ccgatatgtg gatgggaaga ctgcggatgc ggaagaaccc      2350
cggcctgaag gttatcatgg ggattcttct acccccacc atcttgtttt       2400 tggaatttcg cacatatgat gatttctcgt atcaaacatc caaggaaaac      2450
gaggatggca agaaaaaga agaggaaaat acggatgcaa atgcagatgc       2500
tggctcaaga aagggggatg aggagaacga gcataaaaaa cagagaagta      2550
ttcccatcgg aacaaagatc tgtgaattct ataacgcgcc cattgtcaag      2600
ttctggtttt acacaatatc atacttgggc tacctgctgc tgtttaacta      2650
cgtcatcctg gtgcggatgg atggctggcc gtccctccag gagtggatcg      2700
tcatctccta catcgtgagc ctggcgttag agaagatacg agagatcctc      2750
atgtcagaac caggcaaact cagccagaaa atcaaagttt ggcttcagga      2800
gtactggaac atcacagatc tcgtggccat ttccacattc atgattggag      2850
caattcttcg cctacagaac cagccctaca tgggctatgg ccgggtgatc      2900
tactgtgtgg atatcatctt ctggtacatc cgtgtcctgg acatctttgg      2950
tgtcaacaag tatctggggc catacgtgat gatgattgga aagatgatga      3000
tcgacatgct gtactttgtg gtcatcatgc tggtcgtgct catgagtttc      3050
ggagtagccc gtcaagccat tctgcatcca gaggagaagc cctcttggaa      3100
actggcccga acatcttct acatgcccta ctggatgatc tatggagagg       3150
tgtttgcaga ccagatagac ctctacgcca tggaaattaa tcctccttgt      3200
ggtgagaacc tatatgatga ggagggcaag cggcttcctc cctgtatccc      3250
cggcgcctgg ctcactccag cactcatggc gtgctatcta ctggtcgcca      3300
acatcctgct ggtgaacctg ctgattgctg tgttcaacaa tactttcttt      3350
gaagtaaaat caatatccaa ccaggtgtgg aagttccagc gatatcagct      3400
gattatgaca tttcatgaca ggccagtcct gcccccaccg atgatcattt      3450
taagccacat ctcacatcatc attatgcgtc tcagcggccg ctgcaggaaa     3500
aagagagaag gggaccaaga ggaacgggat cgtggattga agctcttcct     3550
tagcgacgag gagctaaaga ggctgcatga gttcgaggag cagtgcgtgc      3600
aggagcactt ccgggagaag gaggatgagc agcagtcgtc cagcgacgag      3650
```

| | |
|---|---|
| cgcatccggg tcacttctga aagagttgaa aatatgtcaa tgaggttgga | 3700 |
| agaaatcaat gaaagagaaa cttttatgaa aacttccctg cagactgttg | 3750 |
| accttcgact tgctcagcta gaagaattat ctaacagaat ggtgaatgct | 3800 |
| cttgaaaatc ttgcgggaat cgacaggtct gacctgatcc aggcacggtc | 3850 |
| ccgggcttct tctgaatgtg aggcaacgta tcttctccgg caaagcagca | 3900 |
| tcaatagcgc tgatggctac agcttgtatc gatatcattt taacggagaa | 3950 |
| gagttattat ttgaggatac atctctctcc acgtcaccag ggacaggagt | 4000 |
| caggaaaaaa acctgttcct tccgtataaa ggaagagaag gacgtgaaaa | 4050 |
| cgcacctagt cccagaatgt cagaacagtc ttcacctttc actgggcaca | 4100 |
| agcacatcag caaccccaga tggcagtcac cttgcagtag atgacttaaa | 4150 |
| gaacgctgaa gagtcaaaat taggtccaga tattgggatt caaaggaag | 4200 |
| atgatgaaag acagacagac tctaaaaaag aagaaactat ttccccaagt | 4250 |
| ttaaataaaa cagatgtgat acatggacag gacaaatcag atgttcaaaa | 4300 |
| cactcagcta acagtggaaa cgacaaatat agaaggcact atttcctatc | 4350 |
| ccctggaaga aaccaaaatt acacgctatt tccccgatga aacgatcaat | 4400 |
| gcttgtaaaa caatgaagtc cagaagcttc gtctattccc ggggaagaaa | 4450 |
| gctggtcggt ggggttaacc aggatgtaga gtacagttca atcacggacc | 4500 |
| agcaattgac gacggaatgg caatgccaag ttcaaaagat cacgcgctct | 4550 |
| catagcacag atattcctta cattgtgtcg gaagctgcag tgcaagctga | 4600 |
| gcaaaaagag cagtttgcag atatgcaaga tgaacaccat gtcgctgaag | 4650 |
| caattcctcg aatccctcgc ttgtccctaa ccattactga cagaaatggg | 4700 |
| atggaaaact tactgtctgt gaagccagat caaactttgg gattcccatc | 4750 |
| tctcaggtca aaaagtttac atggacatcc taggaatgtg aaatccattc | 4800 |
| agggaaagtt agacagatct ggacatgcca gtagtgtaag cagcttagta | 4850 |
| attgtgtctg gaatgacagc agaagaaaaa aaggttaaga aagagaaagc | 4900 |
| ttccacagaa actgaatgct agtctgtttt gtttctttaa tttttttttt | 4950 |
| taacagtcag aaacccacta atgggtgtca tcttggccca tcctaaacac | 5000 |
| atmtccaatt tcctaaaaac attttcccctt aaaaaatttt ggaaattcag | 5050 |
| acttgattta caatttaatg cactaaaagt agtattttgt tagnatatgt | 5100 |
| tagtaggctt agttttttca gttgcagtag tatcaaatga aagtgatgat | 5150 |
| actgtaacga agataaattg gctaatcagt atacaagatt atacaatctc | 5200 |
| tttattactg agggccacca aatagcctag gaagtgccct cgagcactga | 5250 |
| agtcaccatt aggtcactca agaagtaagc aactagctgg gcacagtggc | 5300 |
| tcatgcctgt aatcctagca ctttgggagg ccaaggcaga agatagctt | 5350 |
| gagtccagga gtttgagacc agcctgggca acatagtgat accccatctc | 5400 |
| ttaaaaaaaa aaaaaaaaa | 5420 |

<210> SEQ ID NO 19
<211> LENGTH: 1664
<212> TYPE: DNA
<213> ORGANISM: Homo sapiens

<400> SEQUENCE: 19

```
ctgaatcttc gtttctctcc cagggaccct ccattttcca tatccaggaa      50
aatgtgatgc gccacaggta tcagcgtctg gatcgccact tcacgtttta     100
gccacaagtg actcagtgga agatccagag tcaacagagg ctcgtcagga     150
agatgtctac agaaaaggta gaccaaaagg aggaagctgg ggaaaaagag     200
gtgtgcggag accagatcaa aggaccggac aaagaggagg aaccaccagc     250
tgctgcatcc catggccagg ggtggcgtcc aggtggcaga gcagctagga     300
acgcaaggcc tgaacctggg gccagacacc ctgctctccc ggccatggtc     350
aacgaccctc cagtacctgc cttactgtgg gcccaggagg tgggccaagt     400
cttggcaggc cgtgcccgca ggctgctgct gcagtttggg gtgctcttct     450
gcaccatcct cctttttgctc tgggtgtctg tcttcctcta tggctccttc     500
tactattcct atatgccgac agtcagccac ctcagccctg tgcatttcta     550
ctacaggacc gactgtgatt cctccaccac ctcactctgc tccttccctg     600
ttgccaatgt ctcgctgact aagggtggac gtgatcgggt gctgatgtat     650
ggacagccgt atcgtgttac cttagagctt gagctgccag agtcccctgt     700
gaatcaagat ttgggcatgt tcttggtcac catttcctgc tacaccagag     750
gtggccgaat catctccact tcttcgcgtt cggtgatgct gcattaccgc     800
tcagacctgc tccagatgct ggacacactg gtcttctcta gcctcctgct     850
atttggcttt gcagagcaga agcagctgct ggaggtggaa ctctacgcag     900
actatagaga gaactcgtac gtgccgacca ctggagcgat cattgagatc     950
cacagcaagc gcatccagct gtatggagcc tacctccgca tccacgcgca    1000
cttcactggg ctcagatacc tgctatacaa cttcccgatg acctgcgcct    1050
tcataggtgt tgccagcaac ttcaccttcc tcagcgtcat cgtgctcttc    1100
agctacatgc agtgggtgtg gggggcatc tggccccgac accgcttctc    1150
tttgcaggtt aacatccgaa aaagagacaa ttcccggaag gaagtccaac    1200
gaaggatctc tgctcatcag ccagggcctg aaggccagga ggagtcaact    1250
ccgcaatcag atgttacaga ggatggtgag agccctgaag atccctcagg    1300
gacagagggt cagctgtccg aggaggagaa accagatcag cagcccctga    1350
gcggagaaga ggagctagag cctgaggcca gtgatggttc aggctcctgg    1400
gaaagatgcag ctttgctgac ggaggccaac ctgcctgctc ctgctcctgc    1450
ttctgcttct gccccctgtcc tagagactct gggcagctct gaacctgctg    1500
ggggtgctct ccgacagcgc cccacctgct ctagttcctg aagaaagggg    1550
gcagactcct cacattccag cactttccca cctgactcct ctccctcgt    1600
ttttccttca ataaactatt ttgtgtcagc ttcaaaaaaa aaaaaaaaaa    1650
aaaaaaaaa  aaaa                                           1664
```

<210> SEQ ID NO 20
<211> LENGTH: 4719
<212> TYPE: DNA
<213> ORGANISM: Homo sapiens

<400> SEQUENCE: 20

```
aaccggctgc ggggatgggg ccaccgctcc cgctgctgct gctgctactg      50
ctgctgctgc cgccacgcgt cctgcctgcc gcccccttcgt ccgtccccg     100
```

```
cggccggcag ctcccggggc gtctgggctg cctgctcgag gagggcctct        150
gcggagcgtc cgaggcctgt gtgaacgatg gagtgtttgg aaggtgccag        200
aaggttccgg caatggactt ttaccgctac gaggtgtcgc ccgtggccct        250
gcagcgcctc cgcgtggcgt tgcagaagct ttccggcaca ggtttcacgt        300
ggcaggatga ctatactcag tatgtgatgg accaggaact tgcagacctc        350
ccgaaaacct acctgaggcg tcctgaagca tccagcccag ccaggccctc        400
aaaacacagc gttggcagcg agaggaggta cagtcgggag ggcggtgctg        450
ccctggccaa cgccctccga cgccaccgc ccttcctgga ggccctgtcc         500
caggccccag cctcagacgt gctcgccagg acccatacgg cgcaggacag        550
accccccgct gagggtgatg accgcttctc cgagagcatc ctgacctatg        600
tggcccacac gtctgcgctg acgtaccctc ccgggccccg acccagctc         650 cgggaggacc tcctgccgcg gaccctcggc cagctccagc cagatgagct        700
cagccctaag gtggacagtg gtgtggacag acaccatctg atggcggccc        750
tcagtgccta tgctgcccag aggccccag ctccccccgg ggagggcagc         800
ctggagccac agtaccttct gcgtgcaccc tcaagaatgc ccaggccttt        850
gctggcacca gccgcccccc agaagtggcc ttcacctctg ggagattccg        900
aagacccctc cagcacaggc gatggagcac ggattcatac cctcctgaag        950
gacctgcaga ggcagccggc tgaggtgagg ggcctgagtg gcctggagct        1000
ggacggcatg gctgagctga tggctggcct gatgcaaggc gtggaccatg       1050
gagtagctcg aggcagccct gggagagcgg ccctgggaga gtctggagaa       1100
caggcggatg gccccaaggc caccctccgt ggagacagct ttccagatga       1150
cggagtgcag gacgacgatg atagacttta ccaagaggtc caccgtctga       1200
gtgccacact cggggggcctc ctgcaggacc acgggtctcg actcttacct      1250
ggagccctcc cctttgcaag gcccctcgac atggagagga agaagtccga       1300
gcaccctgag tcttccctgt cttcagaaga ggagactgcc ggagtggaga       1350
acgtcaagag ccagacgtat tccaaagatc tgctggggca gcagccgcat       1400
tcggagcccg gggccgctgc gtttggggag ctccaaaacc agatgcctgg       1450
gccctcgaag gaggagcaga gccttccagc gggtgctcag gaggccctca       1500
gcgacggcct gcaattggag gtccagcctt ccgaggaaga ggcgcggggc       1550
tacatcgtga cagacagaga ccccctgcgc cccgaggaag aaggcggct        1600 ggtggaggac gtcgcccgcc tcctgcaggt gcccagcagt gcgttcgctg       1650
acgtggaggt tctcggacca gcagtgacct tcaaagtgag cgccaatgtc       1700
caaaacgtga ccactgagga tgtggagaag gccacagttg acaacaaaga       1750
caaactggag gaaacctctg gactgaaaat tcttcaaacc ggagtcgggt       1800
cgaaaagcaa actcaagttc ctgcctcctc aggcggagca agaagactcc       1850
accaagttca tcgcgctcac cctggtctcc ctcgcctgca tcctgggcgt       1900
cctcctggcc tctggcctca tctactgcct ccgccatagc tctcagcaca       1950
ggctgaagga gaagctctcg ggactagggg gcgacccagg tgcagatgcc       2000
actgccgcct accaggagct gtgccgcag cgtatggcca cgcggccacc       2050
agaccgacct gagggcccgc acacgtcacg catcagcagc gtctcatccc       2100
```

```
agttcagcga cgggccgatc cccagcccct ccgcacgcag cagcgcctca    2150
tcctggtccg aggagcctgt gcagtccaac atggacatct ccaccggcca    2200
catgatcctg tcctacatgg aggaccacct gaagaacaag aaccggctgg    2250
agaaggagtg ggaagcgctg tgcgcctacc aggcggagcc caacagctcg    2300
ttcgtggccc agagggagga gaacgtgccc aagaaccgct ccctggctgt    2350
gctgacctat gaccactccc gggtcctgct gaaggcggaa acagccaca     2400
gccactcaga ctacatcaac gctagcccca tcatggatca cgacccgagg    2450
aaccccgcgt acatcgccac ccagggaccg ctgcccgcca ccgtggctga    2500
cttttggcag atggtgtggg agagcggctg cgtggtgatc gtcatgctga    2550
cacccctcgc ggagaacggc gtccggcagt gctaccacta ctggccggat    2600
gaaggctcca atctctacca catctatgag gtgaacctgg tctccgagca    2650
catctggtgt gaggacttcc tggtgaggag cttctatctg aagaacctgc    2700
agaccaacga gacgcgcacc gtgacgcagt ccacttcct gagttggtat     2750
gaccgaggag tcccttcctc ctcaaggtcc ctcctggact ccgcagaaa     2800
agtaaacaaa tgctacaggg gccgttcttg tccgataatt gttcattgca    2850
gtgacggtgc aggccggagc ggcacctacg tcctgatcga catggttctc    2900
aacaagatgg ccaaaggtgc taagagatt gatatcgcag cgaccctgga     2950
gcacttgagg gaccagagac ccggcatggt ccagacgaag gagcagtttg    3000
agttcgcgct gacagccgtg gctgaggagg tgaacgccat cctcaaggcc    3050
cttccccagt gagcggcagc gtcaggggcc tcaggggagc ccccacccca    3100
cggatgttgt caggaatcat gatctgactt taattgtgtg tcttctatta    3150
taactgcata gtaatagggc ccttagctct cccgtagtca gcgcagttta    3200
gcagttaaaa gtgtattttt gtttaatcaa acaataataa agagagattt    3250
gtggaaaaat ccagttacgg gtggagggga atcggttcat caattttcac    3300
ttgcttaaaa aaaatacttt ttcttaaagc acccgttcac cttcttggtt    3350
gaagttgtgt taacaatgca gtagccagca cgttcgaggc ggtttccagg    3400
aagagtgtgc ttgtcatctg ccactttcgg gagggtggat ccactgtgca    3450
ggagtggccg gggaagctgg cagcactcag tgaggccgcc cggcacacaa    3500
ggcacgtttg gcatttctct ttgagagagt ttatcattgg gagaagccgc    3550
ggggacagaa ctgaacgtcc tgcagcttcg gggcaagtga gacaatcaca    3600
gctcctcgct gcgtctccat caacactgcg ccgggtacca tggacggccc    3650
cgtcagccac accggtcagc ccaagcagag tgattcaggg gctccccggg    3700
ggcagacacc tgtgcacccc atgagtagtg cccacttgag gctggcactc    3750
ccctgacctc acctttgcaa agttacagat gcaccccaac attgagatgt    3800
gtttttaatg ttaaaatatt gatttctacg ttatgaaaac agatgccccc    3850
gtgaatgctt acctgtgaga taaccacaac caggaagaac aaatctgggc    3900
attgagcaag ctatgagggt ccccgggagc acacgaaccc tgccaggccc    3950
ccgctggctc ctccaggcac gtcccggacc tgtggggccc cagagagggg    4000
acatttccct cctgggagag aaggagatca gggcaactcg gagagggctg    4050
cgagcatttc cctcccggga gaggaaatca gggcgacctg cacgcactgc    4100
```

| | |
|---|---|
| gtagagcctg gaagggaagt gagaaaccag ccgaccggcc ctgcccctct | 4150 |
| tcccgggatc acttaatgaa ccacgtgttt tgacatcatg ttaacctaag | 4200 |
| cacgtacaga tgattccgga tttgacaaaa taacatttga gtatccgatt | 4250 |
| cgccatcacc cctaccccg aaataggaca actcacttca ttgaccagga | 4300 |
| tgatcacatg gaaggcggcg cagaggcagc tgtgtgggct gcagatttcc | 4350 |
| tgtgtggggt tcagcgtata aaacgcacct ccatcccgcc cttcccacag | 4400 |
| cattcctcca tcttagatag atggtactct ccaaaggccc taccagaggg | 4450 |
| aacacggcct actgagcgga cagaatgatg ccaaaatatt gcttatgtct | 4500 |
| ctacatggta ttgtaatgaa tatctgcttt aatatagcta tcatttcttt | 4550 |
| tccaaaatta cttctcttta tctggaattt aattaatcga aatgaattta | 4600 |
| tctgaatata ggaagcatat gcctacttgt aatttctaac tacttatgtt | 4650 |
| tgaagagaaa cctccggtgt gagatataca aatatattta attgtgtcat | 4700 |
| attaaacttc ccggaattc | 4719 |

<210> SEQ ID NO 21
<211> LENGTH: 1453
<212> TYPE: DNA
<213> ORGANISM: Homo sapiens

<400> SEQUENCE: 21

| | |
|---|---|
| gcatctggtt tgtcagatcc gagaggctct gaaactgcgg agcggccacc | 50 |
| ggacgccttc tggagcaggt agcagcatgc agccgcctcc aagtctgtgc | 100 |
| ggacgcgccc tggttgcgct ggttcttgcc tgcggcctgt cgcggatctg | 150 |
| gggagaggag agaggcttcc cgcctgacag ggccactccg cttttgcaaa | 200 |
| ccgcagagat aatgacgcca cccactaaga ccttatggcc caagggttcc | 250 |
| aacgccagtc tggcgcggtc gttggcacct gcggaggtgc ctaaaggaga | 300 |
| caggacggca ggatctccgc cacgcaccat ctcccctccc ccgtgccaag | 350 |
| gacccatcga gatcaaggag actttcaaat acatcaacac ggttgtgtcc | 400 |
| tgccttgtgt tcgtgctggg gatcatcggg aactccacac ttctgagaat | 450 |
| tatctacaag aacaagtgca tgcgaaacgg tcccaatatc ttgatcgcca | 500 |
| gcttggctct gggagacctg ctgcacatcg tcattgacat ccctatcaat | 550 |
| gtctacaagc tgctggcaga ggactggcca tttggagctg agatgtgtaa | 600 |
| gctggtgcct ttcatacaga aagcctccgt gggaatcact gtgctgagtc | 650 |
| tatgtgctct gagtattgac agatatcgag ctgttgcttc ttggagtaga | 700 |
| attaaaggaa ttggggttcc aaaatggaca gcagtagaaa ttgtttttga | 750 |
| ttgggtggtc tctgtggttc tggctgtccc tgaagccata ggttttgata | 800 |
| taattacgat ggactacaaa ggaagttatc tgcgaatctg cttgcttcat | 850 |
| cccgttcaga agacagcttt catgcagttt tacaagacag caaagattg | 900 |
| gtggctgttc agtttctatt tctgcttgcc attggccatc actgcatttt | 950 |
| tttatacact aatgacctgt gaaatgttga gaaagaaaag tggcatgcag | 1000 |
| attgctttaa atgatcacct aaagcagaga cgggaagtgg ccaaaaccgt | 1050 |
| cttttgcctg gtccttgtct ttgccctctg ctggcttccc cttcacctca | 1100 |
| gcaggattct gaagctcact ctttataatc agaatgatcc caatagatgt | 1150 |

-continued

```
gaactttga gctttctgtt ggtattggac tatattggta tcaacatggc            1200
ttcactgaat tcctgcatta acccaattgc tctgtatttg gtgagcaaaa            1250
gattcaaaaa ctgctttaag tcatgcttat gctgctggtg ccagtcattt            1300
gaagaaaaac agtccttgga ggaaaagcag tcgtgcttaa agttcaaagc            1350
taatgatcac ggatatgaca acttccgttc cagtaataaa tacagctcat            1400
cttgaaagaa aaaaaaaaaa aaaaaaaaaa aaaaaaaaa  aaaaaaaaaa            1450 aaa 1453
```

<210> SEQ ID NO 22
<211> LENGTH: 796
<212> TYPE: PRT
<213> ORGANISM: Homo sapiens

<400> SEQUENCE: 22

Met Lys Glu Asn Tyr Cys Leu Gln Ala Ala Leu Val Cys Leu Gly
1               5                   10                  15

Met Leu Cys His Ser His Ala Phe Ala Pro Glu Arg Arg Gly His
                20                  25                  30

Leu Arg Pro Ser Phe His Gly His His Glu Lys Gly Lys Glu Gly
                35                  40                  45

Gln Val Leu Gln Arg Ser Lys Arg Gly Trp Val Trp Asn Gln Phe
                50                  55                  60

Phe Val Ile Glu Glu Tyr Thr Gly Pro Asp Pro Val Leu Val Gly
65              70                  75

Arg Leu His Ser Asp Ile Asp Ser Gly Asp Gly Asn Ile Lys Tyr
                80                  85                  90

Ile Leu Ser Gly Glu Gly Ala Gly Thr Ile Phe Val Ile Asp Asp
                95                  100                 105

Lys Ser Gly Asn Ile His Ala Thr Lys Thr Leu Asp Arg Glu Glu
                110                 115                 120

Arg Ala Gln Tyr Thr Leu Met Ala Gln Ala Val Asp Arg Asp Thr
                125                 130                 135

Asn Arg Pro Leu Glu Pro Pro Ser Glu Phe Ile Val Lys Val Gln
                140                 145                 150

Asp Ile Asn Asp Asn Pro Pro Glu Phe Leu His Glu Thr Tyr His
                155                 160                 165

Ala Asn Val Pro Glu Arg Ser Asn Val Gly Thr Ser Val Ile Gln
                170                 175                 180

Val Thr Ala Ser Asp Ala Asp Asp Pro Thr Tyr Gly Asn Ser Ala
                185                 190                 195

Lys Leu Val Tyr Ser Ile Leu Glu Gly Gln Pro Tyr Phe Ser Val
                200                 205                 210

Glu Ala Gln Thr Gly Ile Ile Arg Thr Ala Leu Pro Asn Met Asp
                215                 220                 225

Arg Glu Ala Lys Glu Glu Tyr His Val Val Ile Gln Ala Lys Asp
                230                 235                 240

Met Gly Gly His Met Gly Gly Leu Ser Gly Thr Thr Lys Val Thr
                245                 250                 255

Ile Thr Leu Thr Asp Val Asn Asp Asn Pro Pro Lys Phe Pro Gln
                260                 265                 270

Arg Leu Tyr Gln Met Ser Val Ser Glu Ala Ala Val Pro Gly Glu
                275                 280                 285

Glu Val Gly Arg Val Lys Ala Lys Asp Pro Asp Ile Gly Glu Asn

```
                    290                 295                 300
Gly Leu Val Thr Tyr Asn Ile Val Asp Gly Asp Gly Met Glu Ser
                    305                 310                 315
Phe Glu Ile Thr Thr Asp Tyr Glu Thr Gln Glu Gly Val Ile Lys
                    320                 325                 330
Leu Lys Lys Pro Val Asp Phe Glu Thr Glu Arg Ala Tyr Ser Leu
                    335                 340                 345
Lys Val Glu Ala Ala Asn Val His Ile Asp Pro Lys Phe Ile Ser
                    350                 355                 360
Asn Gly Pro Phe Lys Asp Thr Val Thr Lys Ile Ser Val Glu
                    365                 370                 375
Asp Ala Asp Glu Pro Pro Met Phe Leu Ala Pro Ser Tyr Ile His
                    380                 385                 390
Glu Val Gln Glu Asn Ala Ala Gly Thr Val Val Gly Arg Val
                    395                 400                 405
His Ala Lys Asp Pro Asp Ala Ala Asn Ser Pro Ile Arg Tyr Ser
                    410                 415                 420
Ile Asp Arg His Thr Asp Leu Asp Arg Phe Phe Thr Ile Asn Pro
                    425                 430                 435
Glu Asp Gly Phe Ile Lys Thr Thr Lys Pro Leu Asp Arg Glu Glu
                    440                 445                 450
Thr Ala Trp Leu Asn Ile Thr Val Phe Ala Ala Glu Ile His Asn
                    455                 460                 465
Arg His Gln Glu Ala Gln Val Pro Val Ala Ile Arg Val Leu Asp
                    470                 475                 480
Val Asn Asp Asn Ala Pro Lys Phe Ala Ala Pro Tyr Glu Gly Phe
                    485                 490                 495
Ile Cys Glu Ser Asp Gln Thr Lys Pro Leu Ser Asn Gln Pro Ile
                    500                 505                 510
Val Thr Ile Ser Ala Asp Asp Lys Asp Thr Ala Asn Gly Pro
                    515                 520                 525
Arg Phe Ile Phe Ser Leu Pro Pro Glu Ile Ile His Asn Pro Asn
                    530                 535                 540
Phe Thr Val Arg Asp Asn Arg Asp Asn Thr Ala Gly Val Tyr Ala
                    545                 550                 555
Arg Arg Gly Gly Phe Ser Arg Gln Lys Gln Asp Leu Tyr Leu Leu
                    560                 565                 570
Pro Ile Val Ile Ser Asp Gly Gly Ile Pro Pro Met Ser Ser Thr
                    575                 580                 585
Asn Thr Leu Thr Ile Lys Val Cys Gly Cys Asp Val Asn Gly Ala
                    590                 595                 600
Leu Leu Ser Cys Asn Ala Glu Ala Tyr Ile Leu Asn Ala Gly Leu
                    605                 610                 615
Ser Thr Gly Ala Leu Ile Ala Ile Leu Ala Cys Ile Val Ile Leu
                    620                 625                 630
Leu Val Ile Val Val Leu Phe Val Thr Leu Arg Arg Gln Lys Lys
                    635                 640                 645
Glu Pro Leu Ile Val Phe Glu Glu Asp Val Arg Glu Asn Ile
                    650                 655                 660
Ile Thr Tyr Asp Asp Glu Gly Gly Gly Glu Glu Asp Thr Glu Ala
                    665                 670                 675
Phe Asp Ile Ala Thr Leu Gln Asn Pro Asp Gly Ile Asn Gly Phe
                    680                 685                 690
```

```
Ile Pro Arg Lys Asp Ile Lys Pro Glu Tyr Gln Tyr Met Pro Arg
            695                 700                 705

Pro Gly Leu Arg Pro Ala Pro Asn Ser Val Asp Val Asp Asp Phe
            710                 715                 720

Ile Asn Thr Arg Ile Gln Glu Ala Asp Asn Asp Pro Thr Ala Pro
            725                 730                 735

Pro Tyr Asp Ser Ile Gln Ile Tyr Gly Tyr Glu Gly Arg Gly Ser
            740                 745                 750

Val Ala Gly Ser Leu Ser Ser Leu Glu Ser Ala Thr Thr Asp Ser
            755                 760                 765

Asp Leu Asp Tyr Asp Tyr Leu Gln Asn Trp Gly Pro Arg Phe Lys
            770                 775                 780

Lys Leu Ala Asp Leu Tyr Gly Ser Lys Asp Thr Phe Asp Asp Asp
            785                 790                 795

Ser

<210> SEQ ID NO 23
<211> LENGTH: 215
<212> TYPE: PRT
<213> ORGANISM: Homo sapiens

<400> SEQUENCE: 23

Met Tyr Gly Lys Ser Ser Thr Arg Ala Val Leu Leu Leu Leu Gly
  1               5                  10                  15

Ile Gln Leu Thr Ala Leu Trp Pro Ile Ala Ala Val Glu Ile Tyr
             20                  25                  30

Thr Ser Arg Val Leu Glu Ala Val Asn Gly Thr Asp Ala Arg Leu
             35                  40                  45

Lys Cys Thr Phe Ser Ser Phe Ala Pro Val Gly Asp Ala Leu Thr
             50                  55                  60

Val Thr Trp Asn Phe Arg Pro Leu Asp Gly Gly Pro Glu Gln Phe
             65                  70                  75

Val Phe Tyr Tyr His Ile Asp Pro Phe Gln Pro Met Ser Gly Arg
             80                  85                  90

Phe Lys Asp Arg Val Ser Trp Asp Gly Asn Pro Glu Arg Tyr Asp
             95                 100                 105

Ala Ser Ile Leu Leu Trp Lys Leu Gln Phe Asp Asp Asn Gly Thr
            110                 115                 120

Tyr Thr Cys Gln Val Lys Asn Pro Pro Asp Val Asp Gly Val Ile
            125                 130                 135

Gly Glu Ile Arg Leu Ser Val Val His Thr Val Arg Phe Ser Glu
            140                 145                 150

Ile His Phe Leu Ala Leu Ala Ile Gly Ser Ala Cys Ala Leu Met
            155                 160                 165

Ile Ile Ile Val Ile Val Val Leu Phe Gln His Tyr Arg Lys
            170                 175                 180

Lys Arg Trp Ala Glu Arg Ala His Lys Val Val Glu Ile Lys Ser
            185                 190                 195

Lys Glu Glu Glu Arg Leu Asn Gln Glu Lys Lys Val Ser Val Tyr
            200                 205                 210

Leu Glu Asp Thr Asp
            215

<210> SEQ ID NO 24
<211> LENGTH: 796
<212> TYPE: PRT
```

<213> ORGANISM: Homo sapiens

<400> SEQUENCE: 24

```
Met Lys Glu Asn Tyr Cys Leu Gln Ala Ala Leu Val Cys Leu Gly
  1               5                  10                  15

Met Leu Cys His Ser His Ala Phe Ala Pro Glu Arg Arg Gly His
                 20                  25                  30

Leu Arg Pro Ser Phe His Gly His His Glu Lys Gly Lys Glu Gly
                 35                  40                  45

Gln Val Leu Gln Arg Ser Lys Arg Gly Trp Val Trp Asn Gln Phe
                 50                  55                  60

Phe Val Ile Glu Glu Tyr Thr Gly Pro Asp Pro Val Leu Val Gly
                 65                  70                  75

Arg Leu His Ser Asp Ile Asp Ser Gly Asp Gly Asn Ile Lys Tyr
                 80                  85                  90

Ile Leu Ser Gly Glu Gly Ala Gly Thr Ile Phe Val Ile Asp Asp
                 95                 100                 105

Lys Ser Gly Asn Ile His Ala Thr Lys Thr Leu Asp Arg Glu Glu
                110                 115                 120

Arg Ala Gln Tyr Thr Leu Met Ala Gln Ala Val Asp Arg Asp Thr
                125                 130                 135

Asn Arg Pro Leu Glu Pro Pro Ser Glu Phe Ile Val Lys Val Gln
                140                 145                 150

Asp Ile Asn Asp Asn Pro Pro Glu Phe Leu His Glu Thr Tyr His
                155                 160                 165

Ala Asn Val Pro Glu Arg Ser Asn Val Gly Thr Ser Val Ile Gln
                170                 175                 180

Val Thr Ala Ser Asp Ala Asp Asp Pro Thr Tyr Gly Asn Ser Ala
                185                 190                 195

Lys Leu Val Tyr Ser Ile Leu Glu Gly Gln Pro Tyr Phe Ser Val
                200                 205                 210

Glu Ala Gln Thr Gly Ile Ile Arg Thr Ala Leu Pro Asn Met Asp
                215                 220                 225

Arg Glu Ala Lys Glu Glu Tyr His Val Val Ile Gln Ala Lys Asp
                230                 235                 240

Met Gly Gly His Met Gly Gly Leu Ser Gly Thr Thr Lys Val Thr
                245                 250                 255

Ile Thr Leu Thr Asp Val Asn Asp Asn Pro Pro Lys Phe Pro Gln
                260                 265                 270

Arg Leu Tyr Gln Met Ser Val Ser Glu Ala Ala Val Pro Gly Glu
                275                 280                 285

Glu Val Gly Arg Val Lys Ala Lys Asp Pro Asp Ile Gly Glu Asn
                290                 295                 300

Gly Leu Val Thr Tyr Asn Ile Val Asp Gly Asp Gly Met Glu Ser
                305                 310                 315

Phe Glu Ile Thr Thr Asp Tyr Glu Thr Gln Glu Gly Val Ile Lys
                320                 325                 330

Leu Lys Lys Pro Val Asp Phe Glu Thr Glu Arg Ala Tyr Ser Leu
                335                 340                 345

Lys Val Glu Ala Ala Asn Val His Ile Asp Pro Lys Phe Ile Ser
                350                 355                 360

Asn Gly Pro Phe Lys Asp Thr Val Thr Val Lys Ile Ser Val Glu
                365                 370                 375

Asp Ala Asp Glu Pro Pro Met Phe Leu Ala Pro Ser Tyr Ile His
```

-continued

```
                380                 385                 390
Glu Val Gln Glu Asn Ala Ala Gly Thr Val Val Gly Arg Val
                395                 400                 405
His Ala Lys Asp Pro Asp Ala Ala Asn Ser Pro Ile Arg Tyr Ser
                410                 415                 420
Ile Asp Arg His Thr Asp Leu Asp Arg Phe Phe Thr Ile Asn Pro
                425                 430                 435
Glu Asp Gly Phe Ile Lys Thr Thr Lys Pro Leu Asp Arg Glu Glu
                440                 445                 450
Thr Ala Trp Leu Asn Ile Thr Val Phe Ala Ala Glu Ile His Asn
                455                 460                 465
Arg His Gln Glu Ala Gln Val Pro Val Ala Ile Arg Val Leu Asp
                470                 475                 480
Val Asn Asp Asn Ala Pro Lys Phe Ala Ala Pro Tyr Glu Gly Phe
                485                 490                 495
Ile Cys Glu Ser Asp Gln Thr Lys Pro Leu Ser Asn Gln Pro Ile
                500                 505                 510
Val Thr Ile Ser Ala Asp Lys Asp Thr Ala Asn Gly Pro
                515                 520                 525
Arg Phe Ile Phe Ser Leu Pro Pro Glu Ile His Asn Pro Asn
                530                 535                 540
Phe Thr Val Arg Asp Asn Arg Asp Asn Thr Ala Gly Val Tyr Ala
                545                 550                 555
Arg Arg Gly Gly Phe Ser Arg Gln Lys Gln Asp Leu Tyr Leu Leu
                560                 565                 570
Pro Ile Val Ile Ser Asp Gly Gly Ile Pro Pro Met Ser Ser Thr
                575                 580                 585
Asn Thr Leu Thr Ile Lys Val Cys Gly Cys Asp Val Asn Gly Ala
                590                 595                 600
Leu Leu Ser Cys Asn Ala Glu Ala Tyr Ile Leu Asn Ala Gly Leu
                605                 610                 615
Ser Thr Gly Ala Leu Ile Ala Ile Leu Ala Cys Ile Val Ile Leu
                620                 625                 630
Leu Val Ile Val Val Leu Phe Val Thr Leu Arg Arg Gln Lys Lys
                635                 640                 645
Glu Pro Leu Ile Val Phe Glu Glu Glu Asp Val Arg Glu Asn Ile
                650                 655                 660
Ile Thr Tyr Asp Asp Glu Gly Gly Gly Glu Glu Asp Thr Glu Ala
                665                 670                 675
Phe Asp Ile Ala Thr Leu Gln Asn Pro Asp Gly Ile Asn Gly Phe
                680                 685                 690
Ile Pro Arg Lys Asp Ile Lys Pro Glu Tyr Gln Tyr Met Pro Arg
                695                 700                 705
Pro Gly Leu Arg Pro Ala Pro Asn Ser Val Asp Val Asp Asp Phe
                710                 715                 720
Ile Asn Thr Arg Ile Gln Glu Ala Asp Asn Asp Pro Thr Ala Pro
                725                 730                 735
Pro Tyr Asp Ser Ile Gln Ile Tyr Gly Tyr Glu Gly Arg Gly Ser
                740                 745                 750
Val Ala Gly Ser Leu Ser Ser Leu Glu Ser Ala Thr Thr Asp Ser
                755                 760                 765
Asp Leu Asp Tyr Asp Tyr Leu Gln Asn Trp Gly Pro Arg Phe Lys
                770                 775                 780
```

```
Lys Leu Ala Asp Leu Tyr Gly Ser Lys Asp Thr Phe Asp Asp
                785                 790                 795

Ser

<210> SEQ ID NO 25
<211> LENGTH: 123
<212> TYPE: PRT
<213> ORGANISM: Homo sapiens

<400> SEQUENCE: 25

Met Ala Thr Ala Ala Gly Ala Thr Tyr Phe Gln Arg Gly Ser Leu
  1               5                  10                  15

Phe Trp Phe Thr Val Ile Thr Leu Ser Phe Gly Tyr Tyr Thr Trp
                 20                  25                  30

Val Val Phe Trp Pro Gln Ser Ile Pro Tyr Gln Asn Leu Gly Pro
                 35                  40                  45

Leu Gly Pro Phe Thr Gln Tyr Leu Val Asp His His Thr Leu
                 50                  55                  60

Leu Cys Asn Gly Tyr Trp Leu Ala Trp Leu Ile His Val Gly Glu
                 65                  70                  75

Ser Leu Tyr Ala Ile Ala Leu Cys Lys His Lys Gly Ile Thr Ser
                 80                  85                  90

Gly Arg Ala Gln Leu Leu Trp Phe Leu Gln Thr Phe Phe Phe Gly
                 95                 100                 105

Ile Ala Ser Leu Thr Ile Leu Ile Ala Tyr Lys Arg Lys Arg Gln
                110                 115                 120

Lys Gln Thr

<210> SEQ ID NO 26
<211> LENGTH: 257
<212> TYPE: PRT
<213> ORGANISM: Homo sapiens

<400> SEQUENCE: 26

Met Ala Ser Lys Ile Gly Ser Arg Arg Trp Met Leu Gln Leu Ile
  1               5                  10                  15

Met Gln Leu Gly Ser Val Leu Leu Thr Arg Cys Pro Phe Trp Gly
                 20                  25                  30

Cys Phe Ser Gln Leu Met Leu Tyr Ala Glu Arg Ala Glu Ala Arg
                 35                  40                  45

Arg Lys Pro Asp Ile Pro Val Pro Tyr Leu Tyr Phe Asp Met Gly
                 50                  55                  60

Ala Ala Val Leu Cys Ala Ser Phe Met Ser Phe Gly Val Lys Arg
                 65                  70                  75

Arg Trp Phe Ala Leu Gly Ala Ala Leu Gln Leu Ala Ile Ser Thr
                 80                  85                  90

Tyr Ala Ala Tyr Ile Gly Gly Tyr Val His Tyr Gly Asp Trp Leu
                 95                 100                 105

Lys Val Arg Met Tyr Ser Arg Thr Val Ala Ile Ile Gly Gly Phe
                110                 115                 120

Leu Val Leu Ala Ser Gly Ala Gly Glu Leu Tyr Arg Arg Lys Pro
                125                 130                 135

Arg Ser Arg Ser Leu Gln Ser Thr Gly Gln Val Phe Leu Gly Ile
                140                 145                 150

Tyr Leu Ile Cys Val Ala Tyr Ser Leu Gln His Ser Lys Glu Asp
                155                 160                 165
```

-continued

```
Arg Leu Ala Tyr Leu Asn His Leu Pro Gly Gly Glu Leu Met Ile
                170                 175                 180

Gln Leu Phe Phe Val Leu Tyr Gly Ile Leu Ala Leu Ala Phe Leu
            185                 190                 195

Ser Gly Tyr Tyr Val Thr Leu Ala Ala Gln Ile Leu Ala Val Leu
            200                 205                 210

Leu Pro Pro Val Met Leu Leu Ile Asp Gly Asn Val Ala Tyr Trp
            215                 220                 225

His Asn Thr Arg Arg Val Glu Phe Trp Asn Gln Met Lys Leu Leu
            230                 235                 240

Gly Glu Ser Val Gly Ile Phe Gly Thr Ala Val Ile Leu Ala Thr
            245                 250                 255

Asp Gly

<210> SEQ ID NO 27
<211> LENGTH: 460
<212> TYPE: PRT
<213> ORGANISM: Homo sapiens
<220> FEATURE:
<221> NAME/KEY: Unsure
<222> LOCATION: 381
<223> OTHER INFORMATION: Unknown amino acid

<400> SEQUENCE: 27

Gly Arg Gly Ser Pro Leu Ala Leu Leu Ile Arg Met Lys Thr Leu
 1               5                  10                  15

Leu Phe Gly Val Trp Ala Leu Leu Ala Leu Ile Leu Cys Pro Gly
            20                  25                  30

Val Pro Glu Glu Leu Phe Glu Val Ser Ile Trp Pro Ser Gln Ala
            35                  40                  45

Leu Val Glu Phe Gly Gln Ser Leu Val Cys Asn Cys Ser Thr Thr
            50                  55                  60

Cys Pro Asp Pro Gly Pro Ser Gly Ile Glu Thr Phe Leu Lys Lys
            65                  70                  75

Thr Gln Val Asp Lys Gly Pro Gln Trp Lys Glu Phe Leu Leu Glu
            80                  85                  90

Asp Val Thr Glu Asn Ser Ile Leu Gln Cys Phe Phe Ser Cys Ala
            95                  100                 105

Gly Ile Gln Lys Asp Thr Ser Leu Gly Ile Thr Val Tyr Gln Pro
            110                 115                 120

Pro Glu Gln Val Ile Leu Glu Leu Gln Pro Ala Trp Val Ala Val
            125                 130                 135

Asp Glu Ala Phe Thr Val Lys Cys His Val Pro Ser Val Ala Pro
            140                 145                 150

Leu Glu Ser Leu Thr Leu Ala Leu Leu Gln Gly Asn Gln Glu Leu
            155                 160                 165

His Arg Lys Asn Phe Thr Ser Leu Ala Val Ala Ser Gln Arg Ala
            170                 175                 180

Glu Val Ile Ile Ser Val Arg Ala Gln Lys Glu Asn Asp Arg Cys
            185                 190                 195

Asn Ser Ser Cys His Ala Glu Leu Asp Leu Ser Leu Gln Gly Gly
            200                 205                 210

Arg Leu Phe Gln Gly Ser Ser Pro Ile Arg Ile Val Arg Ile Phe
            215                 220                 225

Glu Phe Ser Gln Ser Pro His Ile Trp Val Ser Ser Leu Leu Glu
            230                 235                 240
```

```
Ala Gly Met Ala Glu Thr Val Ser Cys Glu Val Ala Arg Val Phe
            245                 250                 255

Pro Ala Lys Glu Val Met Phe His Met Phe Leu Glu Asp Gln Glu
            260                 265                 270

Leu Ser Ser Ser Leu Ser Trp Glu Gly Asp Thr Ala Trp Ala Asn
            275                 280                 285

Ala Thr Ile Arg Thr Met Glu Ala Gly Asp Gln Glu Leu Ser Cys
            290                 295                 300

Phe Ala Ser Leu Gly Ala Met Glu Gln Lys Thr Arg Lys Leu Val
            305                 310                 315

His Ser Tyr Ser Phe Pro Pro Ile Leu Glu Leu Lys Glu Ser
            320                 325                 330

Tyr Pro Leu Ala Gly Thr Asp Ile Asn Val Thr Cys Ser Gly His
            335                 340                 345

Val Leu Thr Ser Pro Ser Pro Thr Leu Arg Leu Gln Gly Ala Pro
            350                 355                 360

Asp Leu Pro Ala Gly Glu Pro Ala Trp Leu Leu Leu Thr Ala Arg
            365                 370                 375

Glu Glu Asp Asp Gly Xaa Asn Phe Ser Cys Glu Ala Ser Leu Val
            380                 385                 390

Val Gln Gly Gln Arg Leu Met Lys Thr Thr Val Ile Gln Leu His
            395                 400                 405

Ile Leu Lys Pro Gln Leu Glu Ser Ser Cys Pro Gly Lys Gln
            410                 415                 420

Thr Trp Leu Glu Gly Met Glu His Thr Leu Ala Cys Val Pro Lys
            425                 430                 435

Gly Asn Pro Ala Pro Ala Leu Val Cys Thr Trp Asn Gly Val Val
            440                 445                 450

Phe Asp Leu Glu Val Pro Gln Lys Ala Thr
            455                 460

<210> SEQ ID NO 28
<211> LENGTH: 332
<212> TYPE: PRT
<213> ORGANISM: Homo sapiens

<400> SEQUENCE: 28

Met Leu Pro Arg Leu Leu Leu Ile Cys Ala Pro Leu Cys Glu
  1               5                  10                  15

Pro Ala Glu Leu Phe Leu Ile Ala Ser Pro Ser His Pro Thr Glu
             20                  25                  30

Gly Ser Pro Val Thr Leu Thr Cys Lys Met Pro Phe Leu Gln Ser
             35                  40                  45

Ser Asp Ala Gln Phe Gln Phe Cys Phe Phe Arg Asp Thr Arg Ala
             50                  55                  60

Leu Gly Pro Gly Trp Ser Ser Ser Pro Lys Leu Gln Ile Ala Ala
             65                  70                  75

Met Trp Lys Glu Asp Thr Gly Ser Tyr Trp Cys Glu Ala Gln Thr
             80                  85                  90

Met Ala Ser Lys Val Leu Arg Ser Arg Ser Gln Ile Asn Val
             95                 100                 105

His Ile Pro Val Ser Arg Pro Ile Leu Met Leu Arg Ala Pro Arg
            110                 115                 120

Ala Gln Ala Ala Val Glu Asp Val Leu Glu Leu His Cys Glu Ala
            125                 130                 135
```

```
Leu Arg Gly Ser Pro Pro Ile Leu Tyr Trp Phe Tyr His Glu Asp
                140                 145                 150

Ile Thr Leu Gly Ser Arg Ser Ala Pro Ser Gly Gly Gly Ala Ser
                155                 160                 165

Phe Asn Leu Ser Leu Thr Glu Glu His Ser Gly Asn Tyr Ser Cys
                170                 175                 180

Glu Ala Asn Asn Gly Leu Gly Ala Gln Arg Ser Glu Ala Val Thr
                185                 190                 195

Leu Asn Phe Thr Val Pro Thr Gly Ala Arg Ser Asn His Leu Thr
                200                 205                 210

Ser Gly Val Ile Glu Gly Leu Leu Ser Thr Leu Gly Pro Ala Thr
                215                 220                 225

Val Ala Leu Leu Phe Cys Tyr Gly Leu Lys Arg Lys Ile Gly Arg
                230                 235                 240

Arg Ser Ala Arg Asp Pro Leu Arg Ser Leu Pro Ala Leu Pro Gln
                245                 250                 255

Glu Phe Thr Tyr Leu Asn Ser Pro Thr Pro Gly Gln Leu Gln Pro
                260                 265                 270

Ile Tyr Glu Asn Val Asn Val Val Ser Gly Asp Glu Val Tyr Ser
                275                 280                 285

Leu Ala Tyr Tyr Asn Gln Pro Glu Gln Glu Ser Val Ala Ala Glu
                290                 295                 300

Thr Leu Gly Thr His Met Glu Asp Lys Val Ser Leu Asp Ile Tyr
                305                 310                 315

Ser Arg Leu Arg Lys Ala Asn Ile Thr Asp Val Asp Tyr Glu Asp
                320                 325                 330

Ala Met

<210> SEQ ID NO 29
<211> LENGTH: 515
<212> TYPE: PRT
<213> ORGANISM: Homo sapiens

<400> SEQUENCE: 29

Met Leu Leu Trp Ala Ser Leu Leu Ala Phe Ala Pro Val Cys Gly
  1               5                  10                  15

Gln Ser Ala Ala Ala His Lys Pro Val Ile Ser Val His Pro Pro
                 20                  25                  30

Trp Thr Thr Phe Phe Lys Gly Glu Arg Val Thr Leu Thr Cys Asn
                 35                  40                  45

Gly Phe Gln Phe Tyr Ala Thr Glu Lys Thr Thr Trp Tyr His Arg
                 50                  55                  60

His Tyr Trp Gly Glu Lys Leu Thr Leu Thr Pro Gly Asn Thr Leu
                 65                  70                  75

Glu Val Arg Glu Ser Gly Leu Tyr Arg Cys Gln Ala Arg Gly Ser
                 80                  85                  90

Pro Arg Ser Asn Pro Val Arg Leu Leu Phe Ser Ser Asp Ser Leu
                 95                 100                 105

Ile Leu Gln Ala Pro Tyr Ser Val Phe Glu Gly Asp Thr Leu Val
                110                 115                 120

Leu Arg Cys His Arg Arg Arg Lys Glu Lys Leu Thr Ala Val Lys
                125                 130                 135

Tyr Thr Trp Asn Gly Asn Ile Leu Ser Ile Ser Asn Lys Ser Trp
                140                 145                 150

Asp Leu Leu Ile Pro Gln Ala Ser Ser Asn Asn Asn Gly Asn Tyr
```

```
                         155                 160                 165

Arg Cys Ile Gly Tyr Gly Asp Glu Asn Asp Val Phe Arg Ser Asn
                170                 175                 180

Phe Lys Ile Ile Lys Ile Gln Glu Leu Phe Pro His Pro Glu Leu
            185                 190                 195

Lys Ala Thr Asp Ser Gln Pro Thr Glu Gly Asn Ser Val Asn Leu
        200                 205                 210

Ser Cys Glu Thr Gln Leu Pro Pro Glu Arg Ser Asp Thr Pro Leu
    215                 220                 225

His Phe Asn Phe Arg Asp Gly Glu Val Ile Leu Ser Asp Trp
230                 235                 240

Ser Thr Tyr Pro Glu Leu Gln Leu Pro Thr Val Trp Arg Glu Asn
                245                 250                 255

Ser Gly Ser Tyr Trp Cys Gly Ala Glu Thr Val Arg Gly Asn Ile
            260                 265                 270

His Lys His Ser Pro Ser Leu Gln Ile His Val Gln Arg Ile Pro
        275                 280                 285

Val Ser Gly Val Leu Leu Glu Thr Gln Pro Ser Gly Gly Gln Ala
    290                 295                 300

Val Glu Gly Glu Met Leu Val Leu Val Cys Ser Val Ala Glu Gly
305                 310                 315

Thr Gly Asp Thr Thr Phe Ser Trp His Arg Glu Asp Met Gln Glu
                320                 325                 330

Ser Leu Gly Arg Lys Thr Gln Arg Ser Leu Arg Ala Glu Leu Glu
            335                 340                 345

Leu Pro Ala Ile Arg Gln Ser His Ala Gly Gly Tyr Tyr Cys Thr
        350                 355                 360

Ala Asp Asn Ser Tyr Gly Pro Val Gln Ser Met Val Leu Asn Val
    365                 370                 375

Thr Val Arg Glu Thr Pro Gly Asn Arg Asp Gly Leu Val Ala Ala
380                 385                 390

Gly Ala Thr Gly Gly Leu Leu Ser Ala Leu Leu Leu Ala Val Ala
                395                 400                 405

Leu Leu Phe His Cys Trp Arg Arg Arg Lys Ser Gly Val Gly Phe
            410                 415                 420

Leu Gly Asp Glu Thr Arg Leu Pro Pro Ala Pro Gly Pro Gly Glu
        425                 430                 435

Ser Ser His Ser Ile Cys Pro Ala Gln Val Glu Leu Gln Ser Leu
    440                 445                 450

Tyr Val Asp Val His Pro Lys Lys Gly Asp Leu Val Tyr Ser Glu
455                 460                 465

Ile Gln Thr Thr Gln Leu Gly Glu Glu Glu Ala Asn Thr Ser
                470                 475                 480

Arg Thr Leu Leu Glu Asp Lys Asp Val Ser Val Val Tyr Ser Glu
            485                 490                 495

Val Lys Thr Gln His Pro Asp Asn Ser Ala Gly Lys Ile Ser Ser
        500                 505                 510

Lys Asp Glu Glu Ser
            515

<210> SEQ ID NO 30
<211> LENGTH: 453
<212> TYPE: PRT
<213> ORGANISM: Homo sapiens
```

<400> SEQUENCE: 30

```
Met Thr Val Ile Arg Phe Phe Pro Ala Ala Ser Ala Thr Lys Arg
  1               5                  10                  15

Val Leu Pro Pro Val Leu Arg Val Ser Ser Pro Arg Thr Trp Asn
                 20                  25                  30

Pro Asn Val Pro Glu Ser Pro Arg Ile Pro Ala Pro Arg Leu Pro
                 35                  40                  45

Lys Arg Met Ser Gly Ala Pro Thr Ala Gly Ala Ala Leu Met Leu
                 50                  55                  60

Cys Ala Ala Thr Ala Val Leu Leu Ser Ala Gln Gly Gly Pro Val
                 65                  70                  75

Gln Ser Lys Ser Pro Arg Phe Ala Ser Trp Asp Glu Met Asn Val
                 80                  85                  90

Leu Ala His Gly Leu Leu Gln Leu Gly Gln Gly Leu Arg Glu His
                 95                 100                 105

Ala Glu Arg Thr Arg Ser Gln Leu Ser Ala Leu Glu Arg Arg Leu
                110                 115                 120

Ser Ala Cys Gly Ser Ala Cys Gln Gly Thr Glu Gly Ser Thr Asp
                125                 130                 135

Leu Pro Leu Ala Pro Glu Ser Arg Val Asp Pro Glu Val Leu His
                140                 145                 150

Ser Leu Gln Thr Gln Leu Lys Ala Gln Asn Ser Arg Ile Gln Gln
                155                 160                 165

Leu Phe His Lys Val Ala Gln Gln Arg His Leu Glu Lys Gln
                170                 175                 180

His Leu Arg Ile Gln His Leu Gln Ser Gln Phe Gly Leu Leu Asp
                185                 190                 195

His Lys His Leu Asp His Glu Val Ala Lys Pro Ala Arg Arg Lys
                200                 205                 210

Arg Leu Pro Glu Met Ala Gln Pro Val Asp Pro Ala His Asn Val
                215                 220                 225

Ser Arg Leu His Arg Leu Pro Arg Asp Cys Gln Glu Leu Phe Gln
                230                 235                 240

Val Gly Glu Arg Gln Ser Gly Leu Phe Glu Ile Gln Pro Gln Gly
                245                 250                 255

Ser Pro Pro Phe Leu Val Asn Cys Lys Met Thr Ser Asp Gly Gly
                260                 265                 270

Trp Thr Val Ile Gln Arg Arg His Asp Gly Ser Val Asp Phe Asn
                275                 280                 285

Arg Pro Trp Glu Ala Tyr Lys Ala Gly Phe Gly Asp Pro His Gly
                290                 295                 300

Glu Phe Trp Leu Gly Leu Glu Lys Val His Ser Ile Thr Gly Asp
                305                 310                 315

Arg Asn Ser Arg Leu Ala Val Gln Leu Arg Asp Trp Asp Gly Asn
                320                 325                 330

Ala Glu Leu Leu Gln Phe Ser Val His Leu Gly Gly Glu Asp Thr
                335                 340                 345

Ala Tyr Ser Leu Gln Leu Thr Ala Pro Val Ala Gly Gln Leu Gly
                350                 355                 360

Ala Thr Thr Val Pro Pro Ser Gly Leu Ser Val Pro Phe Ser Thr
                365                 370                 375

Trp Asp Gln Asp His Asp Leu Arg Arg Asp Lys Asn Cys Ala Lys
                380                 385                 390
```

```
Ser Leu Ser Gly Gly Trp Trp Phe Gly Thr Cys Ser His Ser Asn
            395                 400                 405

Leu Asn Gly Gln Tyr Phe Arg Ser Ile Pro Gln Gln Arg Gln Lys
            410                 415                 420

Leu Lys Lys Gly Ile Phe Trp Lys Thr Trp Arg Gly Arg Tyr Tyr
            425                 430                 435

Pro Leu Gln Ala Thr Thr Met Leu Ile Gln Pro Met Ala Ala Glu
            440                 445                 450

Ala Ala Ser

<210> SEQ ID NO 31
<211> LENGTH: 124
<212> TYPE: PRT
<213> ORGANISM: Homo sapiens

<400> SEQUENCE: 31

Met Leu Leu Trp Val Ile Leu Val Leu Ala Pro Val Ser Gly
  1               5                  10                 15

Gln Phe Ala Arg Thr Pro Arg Pro Ile Ile Phe Leu Gln Pro Pro
            20                  25                  30

Trp Thr Thr Val Phe Gln Gly Glu Arg Val Thr Leu Thr Cys Lys
            35                  40                  45

Gly Phe Arg Phe Tyr Ser Pro Gln Lys Thr Lys Trp Tyr His Arg
            50                  55                  60

Tyr Leu Gly Lys Glu Ile Leu Arg Glu Thr Pro Asp Asn Ile Leu
            65                  70                  75

Glu Val Gln Glu Ser Gly Glu Tyr Arg Cys Gln Ala Gln Gly Ser
            80                  85                  90

Pro Leu Ser Ser Pro Val His Leu Asp Phe Ser Glu Met Gly
            95                  100                 105

Phe Pro His Ala Ala Gln Ala Asn Val Glu Leu Leu Gly Ser Ser
            110                 115                 120

Asp Leu Leu Thr

<210> SEQ ID NO 32
<211> LENGTH: 1752
<212> TYPE: PRT
<213> ORGANISM: Homo sapiens

<400> SEQUENCE: 32

Met Ala Gly Pro Arg Pro Ser Pro Trp Ala Arg Leu Leu Ala
  1               5                  10                 15

Ala Leu Ile Ser Val Ser Leu Ser Gly Thr Leu Ala Asn Arg Cys
            20                  25                  30

Lys Lys Ala Pro Val Lys Ser Cys Thr Glu Cys Val Arg Val Asp
            35                  40                  45

Lys Asp Cys Ala Tyr Cys Thr Asp Glu Met Phe Arg Asp Arg Arg
            50                  55                  60

Cys Asn Thr Gln Ala Glu Leu Leu Ala Ala Gly Cys Gln Arg Glu
            65                  70                  75

Ser Ile Val Val Met Glu Ser Ser Phe Gln Ile Thr Glu Glu Thr
            80                  85                  90

Gln Ile Asp Thr Thr Leu Arg Arg Ser Gln Met Ser Pro Gln Gly
            95                  100                 105

Leu Arg Val Arg Leu Arg Pro Gly Glu Glu Arg His Phe Glu Leu
            110                 115                 120
```

```
Glu Val Phe Glu Pro Leu Glu Ser Pro Val Asp Leu Tyr Ile Leu
            125                 130                 135

Met Asp Phe Ser Asn Ser Met Ser Asp Leu Asp Asn Leu Lys
            140                 145                 150

Lys Met Gly Gln Asn Leu Ala Arg Val Leu Ser Gln Leu Thr Ser
            155                 160                 165

Asp Tyr Thr Ile Gly Phe Gly Lys Phe Val Asp Lys Val Ser Val
            170                 175                 180

Pro Gln Thr Asp Met Arg Pro Glu Lys Leu Lys Glu Pro Trp Pro
            185                 190                 195

Asn Ser Asp Pro Pro Phe Ser Phe Lys Asn Val Ile Ser Leu Thr
            200                 205                 210

Glu Asp Val Asp Glu Phe Arg Asn Lys Leu Gln Gly Glu Arg Ile
            215                 220                 225

Ser Gly Asn Leu Asp Ala Pro Glu Gly Gly Phe Asp Ala Ile Leu
            230                 235                 240

Gln Thr Ala Val Cys Thr Arg Asp Ile Gly Trp Arg Pro Asp Ser
            245                 250                 255

Thr His Leu Leu Val Phe Ser Thr Glu Ser Ala Phe His Tyr Glu
            260                 265                 270

Ala Asp Gly Ala Asn Val Leu Ala Gly Ile Met Ser Arg Asn Asp
            275                 280                 285

Glu Arg Cys His Leu Asp Thr Thr Gly Thr Tyr Thr Gln Tyr Arg
            290                 295                 300

Thr Gln Asp Tyr Pro Ser Val Pro Thr Leu Val Arg Leu Leu Ala
            305                 310                 315

Lys His Asn Ile Ile Pro Ile Phe Ala Val Thr Asn Tyr Ser Tyr
            320                 325                 330

Ser Tyr Tyr Glu Lys Leu His Thr Tyr Phe Pro Val Ser Ser Leu
            335                 340                 345

Gly Val Leu Gln Glu Asp Ser Ser Asn Ile Val Glu Leu Leu Glu
            350                 355                 360

Glu Ala Phe Asn Arg Ile Arg Ser Asn Leu Asp Ile Arg Ala Leu
            365                 370                 375

Asp Ser Pro Arg Gly Leu Arg Thr Glu Val Thr Ser Lys Met Phe
            380                 385                 390

Gln Lys Thr Arg Thr Gly Ser Phe His Ile Arg Arg Gly Glu Val
            395                 400                 405

Gly Ile Tyr Gln Val Gln Leu Arg Ala Leu Glu His Val Asp Gly
            410                 415                 420

Thr His Val Cys Gln Leu Pro Glu Asp Gln Lys Gly Asn Ile His
            425                 430                 435

Leu Lys Pro Ser Phe Ser Asp Gly Leu Lys Met Asp Ala Gly Ile
            440                 445                 450

Ile Cys Asp Val Cys Thr Cys Glu Leu Gln Lys Glu Val Arg Ser
            455                 460                 465

Ala Arg Cys Ser Phe Asn Gly Asp Phe Val Cys Gly Gln Cys Val
            470                 475                 480

Cys Ser Glu Gly Trp Ser Gly Gln Thr Cys Asn Cys Ser Thr Gly
            485                 490                 495

Ser Leu Ser Asp Ile Gln Pro Cys Leu Arg Glu Gly Glu Asp Lys
            500                 505                 510

Pro Cys Ser Gly Arg Gly Glu Cys Gln Cys Gly His Cys Val Cys
            515                 520                 525
```

```
Tyr Gly Glu Gly Arg Tyr Glu Gly Gln Phe Cys Glu Tyr Asp Asn
                530                 535                 540

Phe Gln Cys Pro Arg Thr Ser Gly Phe Leu Cys Asn Asp Arg Gly
                545                 550                 555

Arg Cys Ser Met Gly Gln Cys Val Cys Glu Pro Gly Trp Thr Gly
                560                 565                 570

Pro Ser Cys Asp Cys Pro Leu Ser Asn Ala Thr Cys Ile Asp Ser
                575                 580                 585

Asn Gly Gly Ile Cys Asn Gly Arg Gly His Cys Glu Cys Gly Arg
                590                 595                 600

Cys His Cys His Gln Gln Ser Leu Tyr Thr Asp Thr Ile Cys Glu
                605                 610                 615

Ile Asn Tyr Ser Ala Ile His Pro Gly Leu Cys Glu Asp Leu Arg
                620                 625                 630

Ser Cys Val Gln Cys Gln Ala Trp Gly Thr Gly Glu Lys Lys Gly
                635                 640                 645

Arg Thr Cys Glu Glu Cys Asn Phe Lys Val Lys Met Val Asp Glu
                650                 655                 660

Leu Lys Arg Ala Glu Glu Val Val Val Arg Cys Ser Phe Arg Asp
                665                 670                 675

Glu Asp Asp Asp Cys Thr Tyr Ser Tyr Thr Met Glu Gly Asp Gly
                680                 685                 690

Ala Pro Gly Pro Asn Ser Thr Val Leu Val His Lys Lys Lys Asp
                695                 700                 705

Cys Pro Pro Gly Ser Phe Trp Trp Leu Ile Pro Leu Leu Leu Leu
                710                 715                 720

Leu Leu Pro Leu Leu Ala Leu Leu Leu Leu Leu Cys Trp Lys Tyr
                725                 730                 735

Cys Ala Cys Cys Lys Ala Cys Leu Ala Leu Leu Pro Cys Cys Asn
                740                 745                 750

Arg Gly His Met Val Gly Phe Lys Glu Asp His Tyr Met Leu Arg
                755                 760                 765

Glu Asn Leu Met Ala Ser Asp His Leu Asp Thr Pro Met Leu Arg
                770                 775                 780

Ser Gly Asn Leu Lys Gly Arg Asp Val Val Arg Trp Lys Val Thr
                785                 790                 795

Asn Asn Met Gln Arg Pro Gly Phe Ala Thr His Ala Ala Ser Ile
                800                 805                 810

Asn Pro Thr Glu Leu Val Pro Tyr Gly Leu Ser Leu Arg Leu Ala
                815                 820                 825

Arg Leu Cys Thr Glu Asn Leu Leu Lys Pro Asp Thr Arg Glu Cys
                830                 835                 840

Ala Gln Leu Arg Gln Glu Val Glu Glu Asn Leu Asn Glu Val Tyr
                845                 850                 855

Arg Gln Ile Ser Gly Val His Lys Leu Gln Gln Thr Lys Phe Arg
                860                 865                 870

Gln Gln Pro Asn Ala Gly Lys Lys Gln Asp His Thr Ile Val Asp
                875                 880                 885

Thr Val Leu Met Ala Pro Arg Ser Ala Lys Pro Ala Leu Leu Lys
                890                 895                 900

Leu Thr Glu Lys Gln Val Glu Gln Arg Ala Phe His Asp Leu Lys
                905                 910                 915

Val Ala Pro Gly Tyr Tyr Thr Leu Thr Ala Asp Gln Asp Ala Arg
```

-continued

```
                    920                 925                 930
Gly Met Val Glu Phe Gln Glu Gly Val Glu Leu Val Asp Val Arg
                935                 940                 945

Val Pro Leu Phe Ile Arg Pro Glu Asp Asp Glu Lys Gln Leu
            950                 955                 960

Leu Val Glu Ala Ile Asp Val Pro Ala Gly Thr Ala Thr Leu Gly
                965                 970                 975

Arg Arg Leu Val Asn Ile Thr Ile Ile Lys Glu Gln Ala Arg Asp
                980                 985                 990

Val Val Ser Phe Glu Gln Pro Glu Phe Ser Val Ser Arg Gly Asp
                995                1000                1005

Gln Val Ala Arg Ile Pro Val Ile Arg Arg Val Leu Asp Gly Gly
               1010                1015                1020

Lys Ser Gln Val Ser Tyr Arg Thr Gln Asp Gly Thr Ala Gln Gly
               1025                1030                1035

Asn Arg Asp Tyr Ile Pro Val Glu Gly Glu Leu Leu Phe Gln Pro
               1040                1045                1050

Gly Glu Ala Trp Lys Glu Leu Gln Val Lys Leu Leu Glu Leu Gln
               1055                1060                1065

Glu Val Asp Ser Leu Leu Arg Gly Arg Gln Val Arg Arg Phe His
               1070                1075                1080

Val Gln Leu Ser Asn Pro Lys Phe Gly Ala His Leu Gly Gln Pro
               1085                1090                1095

His Ser Thr Thr Ile Ile Ile Arg Asp Pro Asp Glu Leu Asp Arg
               1100                1105                1110

Ser Phe Thr Ser Gln Met Leu Ser Ser Gln Pro Pro His Gly
               1115                1120                1125

Asp Leu Gly Ala Pro Gln Asn Pro Asn Ala Lys Ala Ala Gly Ser
               1130                1135                1140

Arg Lys Ile His Phe Asn Trp Leu Pro Pro Ser Gly Lys Pro Met
               1145                1150                1155

Gly Tyr Arg Val Lys Tyr Trp Ile Gln Gly Asp Ser Glu Ser Glu
               1160                1165                1170

Ala His Leu Leu Asp Ser Lys Val Pro Ser Val Glu Leu Thr Asn
               1175                1180                1185

Leu Tyr Pro Tyr Cys Asp Tyr Glu Met Lys Val Cys Ala Tyr Gly
               1190                1195                1200

Ala Gln Gly Glu Gly Pro Tyr Ser Ser Leu Val Ser Cys Arg Thr
               1205                1210                1215

His Gln Glu Val Pro Ser Glu Pro Gly Arg Leu Ala Phe Asn Val
               1220                1225                1230

Val Ser Ser Thr Val Thr Gln Leu Ser Trp Ala Glu Pro Ala Glu
               1235                1240                1245

Thr Asn Gly Glu Ile Thr Ala Tyr Glu Val Cys Tyr Gly Leu Val
               1250                1255                1260

Asn Asp Asp Asn Arg Pro Ile Gly Pro Met Lys Lys Val Leu Val
               1265                1270                1275

Asp Asn Pro Lys Asn Arg Met Leu Leu Ile Glu Asn Leu Arg Glu
               1280                1285                1290

Ser Gln Pro Tyr Arg Tyr Thr Val Lys Ala Arg Asn Gly Ala Gly
               1295                1300                1305

Trp Gly Pro Glu Arg Glu Ala Ile Ile Asn Leu Ala Thr Gln Pro
               1310                1315                1320
```

```
Lys Arg Pro Met Ser Ile Pro Ile Pro Asp Ile Pro Ile Val
                1325                1330                1335

Asp Ala Gln Ser Gly Glu Asp Tyr Asp Ser Phe Leu Met Tyr Ser
            1340                1345                1350

Asp Asp Val Leu Arg Ser Pro Ser Gly Ser Gln Arg Pro Ser Val
            1355                1360                1365

Ser Asp Asp Thr Glu His Leu Val Asn Gly Arg Met Asp Phe Ala
            1370                1375                1380

Phe Pro Gly Ser Thr Asn Ser Leu His Arg Met Thr Thr Thr Ser
            1385                1390                1395

Ala Ala Ala Tyr Gly Thr His Leu Ser Pro His Val Pro His Arg
            1400                1405                1410

Val Leu Ser Thr Ser Ser Thr Leu Thr Arg Asp Tyr Asn Ser Leu
            1415                1420                1425

Thr Arg Ser Glu His Ser His Ser Thr Thr Leu Pro Arg Asp Tyr
            1430                1435                1440

Ser Thr Leu Thr Ser Val Ser Ser His Asp Ser Arg Leu Thr Ala
            1445                1450                1455

Gly Val Pro Asp Thr Pro Thr Arg Leu Val Phe Ser Ala Leu Gly
            1460                1465                1470

Pro Thr Ser Leu Arg Val Ser Trp Gln Glu Pro Arg Cys Glu Arg
            1475                1480                1485

Pro Leu Gln Gly Tyr Ser Val Glu Tyr Gln Leu Leu Asn Gly Gly
            1490                1495                1500

Glu Leu His Arg Leu Asn Ile Pro Asn Pro Ala Gln Thr Ser Val
            1505                1510                1515

Val Val Glu Asp Leu Leu Pro Asn His Ser Tyr Val Phe Arg Val
            1520                1525                1530

Arg Ala Gln Ser Gln Glu Gly Trp Gly Arg Glu Arg Glu Gly Val
            1535                1540                1545

Ile Thr Ile Glu Ser Gln Val His Pro Gln Ser Pro Leu Cys Pro
            1550                1555                1560

Leu Pro Gly Ser Ala Phe Thr Leu Ser Thr Pro Ser Ala Pro Gly
            1565                1570                1575

Pro Leu Val Phe Thr Ala Leu Ser Pro Asp Ser Leu Gln Leu Ser
            1580                1585                1590

Trp Glu Arg Pro Arg Arg Pro Asn Gly Asp Ile Val Gly Tyr Leu
            1595                1600                1605

Val Thr Cys Glu Met Ala Gln Gly Gly Gly Pro Ala Thr Ala Phe
            1610                1615                1620

Arg Val Asp Gly Asp Ser Pro Glu Ser Arg Leu Thr Val Pro Gly
            1625                1630                1635

Leu Ser Glu Asn Val Pro Tyr Lys Phe Lys Val Gln Ala Arg Thr
            1640                1645                1650

Thr Glu Gly Phe Gly Pro Glu Arg Glu Gly Ile Ile Thr Ile Glu
            1655                1660                1665

Ser Gln Asp Gly Gly Pro Phe Pro Gln Leu Gly Ser Arg Ala Gly
            1670                1675                1680

Leu Phe Gln His Pro Leu Gln Ser Glu Tyr Ser Ser Ile Thr Thr
            1685                1690                1695

Thr His Thr Ser Ala Thr Glu Pro Phe Leu Val Asp Gly Pro Thr
            1700                1705                1710

Leu Gly Ala Gln His Leu Glu Ala Gly Gly Ser Leu Thr Arg His
            1715                1720                1725
```

Val Thr Gln Glu Phe Val Ser Arg Thr Leu Thr Thr Ser Gly Thr
        1730                1735                1740

Leu Ser Thr His Met Asp Gln Gln Phe Phe Gln Thr
        1745                1750

<210> SEQ ID NO 33
<211> LENGTH: 1336
<212> TYPE: PRT
<213> ORGANISM: Homo sapiens

<400> SEQUENCE: 33

Met Thr Leu Asp Arg Pro Gly Glu Gly Ala Thr Met Leu Lys Thr
 1                5                  10                  15

Phe Thr Val Leu Leu Phe Cys Ile Arg Met Ser Leu Gly Met Thr
                20                  25                  30

Ser Ile Val Met Asp Pro Gln Pro Glu Leu Trp Ile Glu Ser Asn
                35                  40                  45

Tyr Pro Gln Ala Pro Trp Glu Asn Ile Thr Leu Trp Cys Arg Ser
                50                  55                  60

Pro Ser Arg Ile Ser Ser Lys Phe Leu Leu Lys Asp Lys Thr
                65                  70                  75

Gln Met Thr Trp Ile Arg Pro Ser His Lys Thr Phe Gln Val Ser
                80                  85                  90

Phe Leu Ile Gly Ala Leu Thr Glu Ser Asn Ala Gly Leu Tyr Arg
                95                 100                 105

Cys Cys Tyr Trp Lys Glu Thr Gly Trp Ser Lys Pro Ser Lys Val
                110                115                 120

Leu Glu Leu Glu Ala Pro Gly Gln Leu Pro Lys Pro Ile Phe Trp
                125                130                 135

Ile Gln Ala Glu Thr Pro Ala Leu Pro Gly Cys Asn Val Asn Ile
                140                145                 150

Leu Cys His Gly Trp Leu Gln Asp Leu Val Phe Met Leu Phe Lys
                155                160                 165

Glu Gly Tyr Ala Glu Pro Val Asp Tyr Gln Val Pro Thr Gly Thr
                170                175                 180

Met Ala Ile Phe Ser Ile Asp Asn Leu Thr Pro Glu Asp Glu Gly
                185                190                 195

Val Tyr Ile Cys Arg Thr His Ile Gln Met Leu Pro Thr Leu Trp
                200                205                 210

Ser Glu Pro Ser Asn Pro Leu Lys Leu Val Ala Gly Leu Tyr
                215                220                 225

Pro Lys Pro Thr Leu Thr Ala His Pro Gly Pro Ile Met Ala Pro
                230                235                 240

Gly Glu Ser Leu Asn Leu Arg Cys Gln Gly Pro Ile Tyr Gly Met
                245                250                 255

Thr Phe Ala Leu Met Arg Val Glu Asp Leu Glu Lys Ser Phe Tyr
                260                265                 270

His Lys Lys Thr Ile Lys Asn Glu Ala Asn Phe Phe Phe Gln Ser
                275                280                 285

Leu Lys Ile Gln Asp Thr Gly His Tyr Leu Cys Phe Tyr Tyr Asp
                290                295                 300

Ala Ser Tyr Arg Gly Ser Leu Leu Ser Asp Val Leu Lys Ile Trp
                305                310                 315

Val Thr Asp Thr Phe Pro Lys Thr Trp Leu Leu Ala Arg Pro Ser
                320                325                 330

```
Ala Val Val Gln Met Gly Gln Asn Val Ser Leu Arg Cys Arg Gly
            335                 340                 345
Pro Val Asp Gly Val Gly Leu Ala Leu Tyr Lys Lys Gly Glu Asp
            350                 355                 360
Lys Pro Leu Gln Phe Leu Asp Ala Thr Ser Ile Asp Asp Asn Thr
            365                 370                 375
Ser Phe Phe Leu Asn Asn Val Thr Tyr Ser Asp Thr Gly Ile Tyr
            380                 385                 390
Ser Cys His Tyr Leu Leu Thr Trp Lys Thr Ser Ile Arg Met Pro
            395                 400                 405
Ser His Asn Thr Val Glu Leu Met Val Asp Lys Pro Pro Lys
            410                 415                 420
Pro Ser Leu Ser Ala Trp Pro Ser Thr Val Phe Lys Leu Gly Lys
            425                 430                 435
Ala Ile Thr Leu Gln Cys Arg Val Ser His Pro Val Leu Glu Phe
            440                 445                 450
Ser Leu Glu Trp Glu Glu Arg Glu Thr Phe Gln Arg Phe Ser Val
            455                 460                 465
Asn Gly Asp Phe Ile Ile Ser Asn Val Asp Gly Lys Gly Thr Gly
            470                 475                 480
Thr Tyr Ser Cys Ser Tyr Arg Val Glu Thr His Pro Asn Met Trp
            485                 490                 495
Ser His Arg Ser Glu Pro Leu Lys Leu Met Gly Pro Ala Gly Tyr
            500                 505                 510
Leu Thr Trp Asn Tyr Val Leu Asn Glu Ala Ile Arg Leu Ser Leu
            515                 520                 525
Ile Met Gln Leu Val Ala Leu Leu Leu Val Val Leu Trp Ile Arg
            530                 535                 540
Trp Lys Cys Arg Arg Leu Arg Ile Arg Glu Ala Trp Leu Leu Gly
            545                 550                 555
Thr Ala Gln Gly Val Thr Met Leu Phe Ile Val Thr Ala Leu Leu
            560                 565                 570
Cys Cys Gly Leu Cys Asn Gly Val Leu Ile Glu Glu Thr Glu Ile
            575                 580                 585
Val Met Pro Thr Pro Lys Pro Glu Leu Trp Ala Glu Thr Asn Phe
            590                 595                 600
Pro Leu Ala Pro Trp Lys Asn Leu Thr Leu Trp Cys Arg Ser Pro
            605                 610                 615
Ser Gly Ser Thr Lys Glu Phe Val Leu Leu Lys Asp Gly Thr Gly
            620                 625                 630
Trp Ile Ala Thr Arg Pro Ala Ser Glu Gln Val Arg Ala Ala Phe
            635                 640                 645
Pro Leu Gly Ala Leu Thr Gln Ser His Thr Gly Ser Tyr His Cys
            650                 655                 660
His Ser Trp Glu Glu Met Ala Val Ser Glu Pro Ser Glu Ala Leu
            665                 670                 675
Glu Leu Val Gly Thr Asp Ile Leu Pro Lys Pro Val Ile Ser Ala
            680                 685                 690
Ser Pro Thr Ile Arg Gly Gln Glu Leu Gln Leu Arg Cys Lys Gly
            695                 700                 705
Trp Leu Ala Gly Met Gly Phe Ala Leu Tyr Lys Glu Gly Glu Gln
            710                 715                 720
Glu Pro Val Gln Gln Leu Gly Ala Val Gly Arg Glu Ala Phe Phe
```

```
                725                 730                 735
Thr Ile Gln Arg Met Glu Asp Lys Asp Glu Gly Asn Tyr Ser Cys
            740                 745                 750
Arg Thr His Thr Glu Lys Leu Pro Phe Lys Trp Ser Glu Pro Ser
            755                 760                 765
Glu Pro Leu Glu Leu Val Ile Lys Glu Met Tyr Pro Lys Pro Phe
            770                 775                 780
Phe Lys Thr Trp Ala Ser Pro Val Val Thr Pro Gly Ala Arg Val
            785                 790                 795
Thr Phe Asn Cys Ser Thr Pro His Gln His Met Ser Phe Ile Leu
            800                 805                 810
Tyr Lys Asp Gly Ser Glu Ile Ala Ser Ser Asp Arg Ser Trp Ala
            815                 820                 825
Ser Pro Gly Ala Ser Ala His Phe Leu Ile Ser Val Gly
            830                 835                 840
Ile Gly Asp Gly Asn Tyr Ser Cys Arg Tyr Tyr Asp Phe Ser
            845                 850                 855
Ile Trp Ser Glu Pro Ser Asp Pro Val Glu Leu Val Val Thr Glu
            860                 865                 870
Phe Tyr Pro Lys Pro Thr Leu Leu Ala Gln Pro Gly Pro Val Val
            875                 880                 885
Phe Pro Gly Lys Ser Val Ile Leu Arg Cys Gln Gly Thr Phe Gln
            890                 895                 900
Gly Met Arg Phe Ala Leu Leu Gln Glu Gly Ala His Val Pro Leu
            905                 910                 915
Gln Phe Arg Ser Val Ser Gly Asn Ser Ala Asp Phe Leu Leu His
            920                 925                 930
Thr Val Gly Ala Glu Asp Ser Gly Asn Tyr Ser Cys Ile Tyr Tyr
            935                 940                 945
Glu Thr Thr Met Ser Asn Arg Gly Ser Tyr Leu Ser Met Pro Leu
            950                 955                 960
Met Ile Trp Val Thr Asp Thr Phe Pro Lys Pro Trp Leu Phe Ala
            965                 970                 975
Glu Pro Ser Ser Val Val Pro Met Gly Gln Asn Val Thr Leu Trp
            980                 985                 990
Cys Arg Gly Pro Val His Gly Val Gly Tyr Ile Leu His Lys Glu
            995                 1000                1005
Gly Glu Ala Thr Ser Met Gln Leu Trp Gly Ser Thr Ser Asn Asp
            1010                1015                1020
Gly Ala Phe Pro Ile Thr Asn Ile Ser Gly Thr Ser Met Gly Arg
            1025                1030                1035
Tyr Ser Cys Cys Tyr His Pro Asp Trp Thr Ser Ser Ile Lys Ile
            1040                1045                1050
Gln Pro Ser Asn Thr Leu Glu Leu Leu Val Thr Gly Leu Leu Pro
            1055                1060                1065
Lys Pro Ser Leu Leu Ala Gln Pro Gly Pro Met Val Ala Pro Gly
            1070                1075                1080
Glu Asn Met Thr Leu Gln Cys Gln Gly Glu Leu Pro Asp Ser Thr
            1085                1090                1095
Phe Val Leu Leu Lys Glu Gly Ala Gln Glu Pro Leu Glu Gln Gln
            1100                1105                1110
Arg Pro Ser Gly Tyr Arg Ala Asp Phe Trp Met Pro Ala Val Arg
            1115                1120                1125
```

-continued

Gly Glu Asp Ser Gly Ile Tyr Ser Cys Val Tyr Tyr Leu Asp Ser
                1130                1135                1140

Thr Pro Phe Ala Ala Ser Asn His Ser Asp Ser Leu Glu Ile Trp
                1145                1150                1155

Val Thr Asp Lys Pro Pro Lys Pro Ser Leu Ser Ala Trp Pro Ser
                1160                1165                1170

Thr Met Phe Lys Leu Gly Lys Asp Ile Thr Leu Gln Cys Arg Gly
                1175                1180                1185

Pro Leu Pro Gly Val Glu Phe Val Leu Glu His Asp Gly Glu Glu
                1190                1195                1200

Ala Pro Gln Gln Phe Ser Glu Asp Gly Asp Phe Val Ile Asn Asn
                1205                1210                1215

Val Glu Gly Lys Gly Ile Gly Asn Tyr Ser Cys Ser Tyr Arg Leu
                1220                1225                1230

Gln Ala Tyr Pro Asp Ile Trp Ser Glu Pro Ser Asp Pro Leu Glu
                1235                1240                1245

Leu Val Gly Ala Ala Gly Pro Val Ala Gln Glu Cys Thr Val Gly
                1250                1255                1260

Asn Ile Val Arg Ser Ser Leu Ile Val Val Val Val Ala Leu
                1265                1270                1275

Gly Val Val Leu Ala Ile Glu Trp Lys Lys Trp Pro Arg Leu Arg
                1280                1285                1290

Thr Arg Gly Ser Glu Thr Asp Gly Arg Asp Gln Thr Ile Ala Leu
                1295                1300                1305

Glu Glu Cys Asn Gln Glu Gly Glu Pro Gly Thr Pro Ala Asn Ser
                1310                1315                1320

Pro Ser Ser Thr Ser Gln Arg Ile Ser Val Glu Leu Pro Val Pro
                1325                1330                1335

Ile

<210> SEQ ID NO 34
<211> LENGTH: 1907
<212> TYPE: PRT
<213> ORGANISM: Homo sapiens

<400> SEQUENCE: 34

Met Ala Pro Glu Pro Ala Pro Gly Arg Thr Met Val Pro Leu Val
  1               5                  10                  15

Pro Ala Leu Val Met Leu Gly Leu Val Ala Gly Ala His Gly Asp
                 20                  25                  30

Ser Lys Pro Val Phe Ile Lys Val Pro Glu Asp Gln Thr Gly Leu
                 35                  40                  45

Ser Gly Gly Val Ala Ser Phe Val Cys Gln Ala Thr Gly Glu Pro
                 50                  55                  60

Lys Pro Arg Ile Thr Trp Met Lys Lys Gly Lys Lys Val Ser Ser
                 65                  70                  75

Gln Arg Phe Glu Val Ile Glu Phe Asp Asp Gly Ala Gly Ser Val
                 80                  85                  90

Leu Arg Ile Gln Pro Leu Arg Val Gln Arg Asp Glu Ala Ile Tyr
                 95                 100                 105

Glu Cys Thr Ala Thr Asn Ser Leu Gly Glu Ile Asn Thr Ser Ala
                110                 115                 120

Lys Leu Ser Val Leu Glu Glu Glu Gln Leu Pro Pro Gly Phe Pro
                125                 130                 135

Ser Ile Asp Met Gly Pro Gln Leu Lys Val Val Glu Lys Ala Arg

-continued

```
                140                 145                 150
Thr Ala Thr Met Leu Cys Ala Ala Gly Gly Asn Pro Asp Pro Glu
                155                 160                 165
Ile Ser Trp Phe Lys Asp Phe Leu Pro Val Asp Pro Ala Thr Ser
                170                 175                 180
Asn Gly Arg Ile Lys Gln Leu Arg Ser Gly Ala Leu Gln Ile Glu
                185                 190                 195
Ser Ser Glu Glu Ser Asp Gln Gly Lys Tyr Glu Cys Val Ala Thr
                200                 205                 210
Asn Ser Ala Gly Thr Arg Tyr Ser Ala Pro Ala Asn Leu Tyr Val
                215                 220                 225
Arg Val Arg Arg Val Ala Pro Arg Phe Ser Ile Pro Pro Ser Ser
                230                 235                 240
Gln Glu Val Met Pro Gly Gly Ser Val Asn Leu Thr Cys Val Ala
                245                 250                 255
Val Gly Ala Pro Met Pro Tyr Val Lys Trp Met Met Gly Ala Glu
                260                 265                 270
Glu Leu Thr Lys Glu Asp Glu Met Pro Val Gly Arg Asn Val Leu
                275                 280                 285
Glu Leu Ser Asn Val Val Arg Ser Ala Asn Tyr Thr Cys Val Ala
                290                 295                 300
Ile Ser Ser Leu Gly Met Ile Glu Ala Thr Ala Gln Val Thr Val
                305                 310                 315
Lys Ala Leu Pro Lys Pro Pro Ile Asp Leu Val Val Thr Glu Thr
                320                 325                 330
Thr Ala Thr Ser Val Thr Leu Thr Trp Asp Ser Gly Asn Ser Glu
                335                 340                 345
Pro Val Thr Tyr Tyr Gly Ile Gln Tyr Arg Ala Ala Gly Thr Glu
                350                 355                 360
Gly Pro Phe Gln Glu Val Asp Gly Val Ala Thr Thr Arg Tyr Ser
                365                 370                 375
Ile Gly Gly Leu Ser Pro Phe Ser Glu Tyr Ala Phe Arg Val Leu
                380                 385                 390
Ala Val Asn Ser Ile Gly Arg Gly Pro Pro Ser Glu Ala Val Arg
                395                 400                 405
Ala Arg Thr Gly Glu Gln Ala Pro Ser Ser Pro Pro Arg Arg Val
                410                 415                 420
Gln Ala Arg Met Leu Ser Ala Ser Thr Met Leu Val Gln Trp Glu
                425                 430                 435
Pro Pro Glu Glu Pro Asn Gly Leu Val Arg Gly Tyr Arg Val Tyr
                440                 445                 450
Tyr Thr Pro Asp Ser Arg Arg Pro Pro Asn Ala Trp His Lys His
                455                 460                 465
Asn Thr Asp Ala Gly Leu Leu Thr Thr Val Gly Ser Leu Leu Pro
                470                 475                 480
Gly Ile Thr Tyr Ser Leu Arg Val Leu Ala Phe Thr Ala Val Gly
                485                 490                 495
Asp Gly Pro Pro Ser Pro Thr Ile Gln Val Lys Thr Gln Gln Gly
                500                 505                 510
Val Pro Ala Gln Pro Ala Asp Phe Gln Ala Glu Val Glu Ser Asp
                515                 520                 525
Thr Arg Ile Gln Leu Ser Trp Leu Leu Pro Pro Gln Glu Arg Ile
                530                 535                 540
```

-continued

```
Ile Met Tyr Glu Leu Val Tyr Trp Ala Ala Glu Asp Glu Asp Gln
            545                 550                 555

Gln His Lys Val Thr Phe Asp Pro Thr Ser Ser Tyr Thr Leu Glu
            560                 565                 570

Asp Leu Lys Pro Asp Thr Leu Tyr Arg Phe Gln Leu Ala Ala Arg
            575                 580                 585

Ser Asp Met Gly Val Gly Val Phe Thr Pro Thr Ile Glu Ala Arg
            590                 595                 600

Thr Ala Gln Ser Thr Pro Ser Ala Pro Pro Gln Lys Val Met Cys
            605                 610                 615

Val Ser Met Gly Ser Thr Thr Val Arg Val Ser Trp Val Pro Pro
            620                 625                 630

Pro Ala Asp Ser Arg Asn Gly Val Ile Thr Gln Tyr Ser Val Ala
            635                 640                 645

His Glu Ala Val Asp Gly Glu Asp Arg Gly Arg His Val Val Asp
            650                 655                 660

Gly Ile Ser Arg Glu His Ser Ser Trp Asp Leu Val Gly Leu Glu
            665                 670                 675

Lys Trp Thr Glu Tyr Arg Val Trp Val Arg Ala His Thr Asp Val
            680                 685                 690

Gly Pro Gly Pro Glu Ser Ser Pro Val Leu Val Arg Thr Asp Glu
            695                 700                 705

Asp Val Pro Ser Gly Pro Pro Arg Lys Val Glu Val Glu Pro Leu
            710                 715                 720

Asn Ser Thr Ala Val His Val Tyr Trp Lys Leu Pro Val Pro Ser
            725                 730                 735

Lys Gln His Gly Gln Ile Arg Gly Tyr Gln Val Thr Tyr Val Arg
            740                 745                 750

Leu Glu Asn Gly Glu Pro Arg Gly Leu Pro Ile Ile Gln Asp Val
            755                 760                 765

Met Leu Ala Glu Ala Gln Trp Arg Pro Glu Glu Ser Glu Asp Tyr
            770                 775                 780

Glu Thr Thr Ile Ser Gly Leu Thr Pro Glu Thr Thr Tyr Ser Val
            785                 790                 795

Thr Val Ala Ala Tyr Thr Thr Lys Gly Asp Gly Ala Arg Ser Lys
            800                 805                 810

Pro Lys Ile Val Thr Thr Thr Gly Ala Val Pro Gly Arg Pro Thr
            815                 820                 825

Met Met Ile Ser Thr Thr Ala Met Asn Thr Ala Leu Leu Gln Trp
            830                 835                 840

His Pro Pro Lys Glu Leu Pro Gly Glu Leu Leu Gly Tyr Arg Leu
            845                 850                 855

Gln Tyr Cys Arg Ala Asp Glu Ala Arg Pro Asn Thr Ile Asp Phe
            860                 865                 870

Gly Lys Asp Asp Gln His Phe Thr Val Thr Gly Leu His Lys Gly
            875                 880                 885

Thr Thr Tyr Ile Phe Arg Leu Ala Ala Lys Asn Arg Ala Gly Leu
            890                 895                 900

Gly Glu Glu Phe Glu Lys Glu Ile Arg Thr Pro Glu Asp Leu Pro
            905                 910                 915

Ser Gly Phe Pro Gln Asn Leu His Val Thr Gly Leu Thr Thr Ser
            920                 925                 930

Thr Thr Glu Leu Ala Trp Asp Pro Pro Val Leu Ala Glu Arg Asn
            935                 940                 945
```

-continued

Gly Arg Ile Ile Ser Tyr Thr Val Val Phe Arg Asp Ile Asn Ser
                950                 955                 960

Gln Gln Glu Leu Gln Asn Ile Thr Thr Asp Thr Arg Phe Thr Leu
                965                 970                 975

Thr Gly Leu Lys Pro Asp Thr Thr Tyr Asp Ile Lys Val Arg Ala
                980                 985                 990

Trp Thr Ser Lys Gly Ser Gly Pro Leu Ser Pro Ser Ile Gln Ser
                995                1000                1005

Arg Thr Met Pro Val Glu Gln Val Phe Ala Lys Asn Phe Arg Val
               1010                1015                1020

Ala Ala Ala Met Lys Thr Ser Val Leu Leu Ser Trp Glu Val Pro
               1025                1030                1035

Asp Ser Tyr Lys Ser Ala Val Pro Phe Lys Ile Leu Tyr Asn Gly
               1040                1045                1050

Gln Ser Val Glu Val Asp Gly His Ser Met Arg Lys Leu Ile Ala
               1055                1060                1065

Asp Leu Gln Pro Asn Thr Glu Tyr Ser Phe Val Leu Met Asn Arg
               1070                1075                1080

Gly Ser Ser Ala Gly Gly Leu Gln His Leu Val Ser Ile Arg Thr
               1085                1090                1095

Ala Pro Asp Leu Leu Pro His Lys Pro Leu Pro Ala Ser Ala Tyr
               1100                1105                1110

Ile Glu Asp Gly Arg Phe Asp Leu Ser Met Pro His Val Gln Asp
               1115                1120                1125

Pro Ser Leu Val Arg Trp Phe Tyr Ile Val Val Pro Ile Asp
               1130                1135                1140

Arg Val Gly Gly Ser Met Leu Thr Pro Arg Trp Ser Thr Pro Glu
               1145                1150                1155

Glu Leu Glu Leu Asp Glu Leu Leu Glu Ala Ile Glu Gln Gly Gly
               1160                1165                1170

Glu Glu Gln Arg Arg Arg Arg Gln Ala Glu Arg Leu Lys Pro
               1175                1180                1185

Tyr Val Ala Ala Gln Leu Asp Val Leu Pro Glu Thr Phe Thr Leu
               1190                1195                1200

Gly Asp Lys Lys Asn Tyr Arg Gly Phe Tyr Asn Arg Pro Leu Ser
               1205                1210                1215

Pro Asp Leu Ser Tyr Gln Cys Phe Val Leu Ala Ser Leu Lys Glu
               1220                1225                1230

Pro Met Asp Gln Lys Arg Tyr Ala Ser Ser Pro Tyr Ser Asp Glu
               1235                1240                1245

Ile Val Val Gln Val Thr Pro Ala Gln Gln Gln Glu Glu Pro Glu
               1250                1255                1260

Met Leu Trp Val Thr Gly Pro Val Leu Ala Val Ile Leu Ile Ile
               1265                1270                1275

Leu Ile Val Ile Ala Ile Leu Leu Phe Lys Arg Lys Arg Thr His
               1280                1285                1290

Ser Pro Ser Ser Lys Asp Glu Gln Ser Ile Gly Leu Lys Asp Ser
               1295                1300                1305

Leu Leu Ala His Ser Ser Asp Pro Val Glu Met Arg Arg Leu Asn
               1310                1315                1320

Tyr Gln Thr Pro Gly Met Arg Asp His Pro Pro Ile Pro Ile Thr
               1325                1330                1335

Asp Leu Ala Asp Asn Ile Glu Arg Leu Lys Ala Asn Asp Gly Leu

```
                        1340                 1345                 1350
Lys Phe Ser Gln Glu Tyr Glu Ser Ile Asp Pro Gly Gln Gln Phe
                1355                 1360                 1365
Thr Trp Glu Asn Ser Asn Leu Glu Val Asn Lys Pro Lys Asn Arg
                1370                 1375                 1380
Tyr Ala Asn Val Ile Ala Tyr Asp His Ser Arg Val Ile Leu Thr
                1385                 1390                 1395
Ser Ile Asp Gly Val Pro Gly Ser Asp Tyr Ile Asn Ala Asn Tyr
                1400                 1405                 1410
Ile Asp Gly Tyr Arg Lys Gln Asn Ala Tyr Ile Ala Thr Gln Gly
                1415                 1420                 1425
Pro Leu Pro Glu Thr Met Gly Asp Phe Trp Arg Met Val Trp Glu
                1430                 1435                 1440
Gln Arg Thr Ala Thr Val Val Met Met Thr Arg Leu Glu Glu Lys
                1445                 1450                 1455
Ser Arg Val Lys Cys Asp Gln Tyr Trp Pro Ala Arg Gly Thr Glu
                1460                 1465                 1470
Thr Cys Gly Leu Ile Gln Val Thr Leu Leu Asp Thr Val Glu Leu
                1475                 1480                 1485
Ala Thr Tyr Thr Val Arg Thr Phe Ala Leu His Lys Ser Gly Ser
                1490                 1495                 1500
Ser Glu Lys Arg Glu Leu Arg Gln Phe Gln Phe Met Ala Trp Pro
                1505                 1510                 1515
Asp His Gly Val Pro Glu Tyr Pro Thr Pro Ile Leu Ala Phe Leu
                1520                 1525                 1530
Arg Arg Val Lys Ala Cys Asn Pro Leu Asp Ala Gly Pro Met Val
                1535                 1540                 1545
Val His Cys Ser Ala Gly Val Gly Arg Thr Gly Cys Phe Ile Val
                1550                 1555                 1560
Ile Asp Ala Met Leu Glu Arg Met Lys His Glu Lys Thr Val Asp
                1565                 1570                 1575
Ile Tyr Gly His Val Thr Cys Met Arg Ser Gln Arg Asn Tyr Met
                1580                 1585                 1590
Val Gln Thr Glu Asp Gln Tyr Val Phe Ile His Glu Ala Leu Leu
                1595                 1600                 1605
Glu Ala Ala Thr Cys Gly His Thr Glu Val Pro Ala Arg Asn Leu
                1610                 1615                 1620
Tyr Ala His Ile Gln Lys Leu Gly Gln Val Pro Pro Gly Glu Ser
                1625                 1630                 1635
Val Thr Ala Met Glu Leu Glu Phe Lys Leu Leu Ala Ser Ser Lys
                1640                 1645                 1650
Ala His Thr Ser Arg Phe Ile Ser Ala Asn Leu Pro Cys Asn Lys
                1655                 1660                 1665
Phe Lys Asn Arg Leu Val Asn Ile Met Pro Tyr Glu Leu Thr Arg
                1670                 1675                 1680
Val Cys Leu Gln Pro Ile Arg Gly Val Glu Gly Ser Asp Tyr Ile
                1685                 1690                 1695
Asn Ala Ser Phe Leu Asp Gly Tyr Arg Gln Gln Lys Ala Tyr Ile
                1700                 1705                 1710
Ala Thr Gln Gly Pro Leu Ala Glu Ser Thr Glu Asp Phe Trp Arg
                1715                 1720                 1725
Met Leu Trp Glu His Asn Ser Thr Ile Ile Val Met Leu Thr Lys
                1730                 1735                 1740
```

```
Leu Arg Glu Met Gly Arg Glu Lys Cys His Gln Tyr Trp Pro Ala
            1745                1750                1755

Glu Arg Ser Ala Arg Tyr Gln Tyr Phe Val Val Asp Pro Met Ala
            1760                1765                1770

Glu Tyr Asn Met Pro Gln Tyr Ile Leu Arg Glu Phe Lys Val Thr
            1775                1780                1785

Asp Ala Arg Asp Gly Gln Ser Arg Thr Ile Arg Gln Phe Gln Phe
            1790                1795                1800

Thr Asp Trp Pro Glu Gln Gly Val Pro Lys Thr Gly Glu Gly Phe
            1805                1810                1815

Ile Asp Phe Ile Gly Gln Val His Lys Thr Lys Glu Gln Phe Gly
            1820                1825                1830

Gln Asp Gly Pro Ile Thr Val His Cys Ser Ala Gly Val Gly Arg
            1835                1840                1845

Thr Gly Val Phe Ile Thr Leu Ser Ile Val Leu Glu Arg Met Arg
            1850                1855                1860

Tyr Glu Gly Val Val Asp Met Phe Gln Thr Val Lys Thr Leu Arg
            1865                1870                1875

Thr Gln Arg Pro Ala Met Val Gln Thr Glu Asp Gln Tyr Gln Leu
            1880                1885                1890

Cys Tyr Arg Ala Ala Leu Glu Tyr Leu Gly Ser Phe Asp His Tyr
            1895                1900                1905

Ala Thr

<210> SEQ ID NO 35
<211> LENGTH: 310
<212> TYPE: PRT
<213> ORGANISM: Homo sapiens

<400> SEQUENCE: 35

Met Arg Arg Ala Ala Leu Trp Leu Trp Leu Cys Ala Leu Ala Leu
  1               5                  10                  15

Ser Leu Gln Leu Ala Leu Pro Gln Ile Val Ala Thr Asn Leu Pro
                 20                  25                  30

Pro Glu Asp Gln Asp Gly Ser Gly Asp Asp Ser Asp Asn Phe Ser
                 35                  40                  45

Gly Ser Gly Ala Gly Ala Leu Gln Asp Ile Thr Leu Ser Gln Gln
                 50                  55                  60

Thr Pro Ser Thr Trp Lys Asp Thr Gln Leu Leu Thr Ala Ile Pro
                 65                  70                  75

Thr Ser Pro Glu Pro Thr Gly Leu Glu Ala Thr Ala Ala Ser Thr
                 80                  85                  90

Ser Thr Leu Pro Ala Gly Glu Gly Pro Lys Glu Gly Glu Ala Val
                 95                 100                 105

Val Leu Pro Glu Val Glu Pro Gly Leu Thr Ala Arg Glu Gln Glu
                110                 115                 120

Ala Thr Pro Arg Pro Arg Glu Thr Thr Gln Leu Pro Thr Thr His
                125                 130                 135

Gln Ala Ser Thr Thr Thr Ala Thr Thr Ala Gln Glu Pro Ala Thr
                140                 145                 150

Ser His Pro His Arg Asp Met Gln Pro Gly His His Glu Thr Ser
                155                 160                 165

Thr Pro Ala Gly Pro Ser Gln Ala Asp Leu His Thr Pro His Thr
                170                 175                 180

Glu Asp Gly Gly Pro Ser Ala Thr Glu Arg Ala Ala Glu Asp Gly
```

```
                            185                 190                 195

Ala Ser Ser Gln Leu Pro Ala Ala Glu Gly Ser Gly Glu Gln Asp
                200                 205                 210

Phe Thr Phe Glu Thr Ser Gly Glu Asn Thr Ala Val Val Ala Val
            215                 220                 225

Glu Pro Asp Arg Arg Asn Gln Ser Pro Val Asp Gln Gly Ala Thr
        230                 235                 240

Gly Ala Ser Gln Gly Leu Leu Asp Arg Lys Glu Val Leu Gly Gly
    245                 250                 255

Val Ile Ala Gly Gly Leu Val Gly Leu Ile Phe Ala Val Cys Leu
260                 265                 270

Val Gly Phe Met Leu Tyr Arg Met Lys Lys Lys Asp Glu Gly Ser
                275                 280                 285

Tyr Ser Leu Glu Glu Pro Lys Gln Ala Asn Gly Gly Ala Tyr Gln
            290                 295                 300

Lys Pro Thr Lys Gln Glu Glu Phe Tyr Ala
        305                 310

<210> SEQ ID NO 36
<211> LENGTH: 131
<212> TYPE: PRT
<213> ORGANISM: Homo sapiens

<400> SEQUENCE: 36

Met Lys Ile Phe Leu Pro Val Leu Leu Ala Ala Leu Leu Gly Val
 1               5                  10                  15

Glu Arg Ala Ser Ser Leu Met Cys Phe Ser Cys Leu Asn Gln Lys
            20                  25                  30

Ser Asn Leu Tyr Cys Leu Lys Pro Thr Ile Cys Ser Asp Gln Asp
        35                  40                  45

Asn Tyr Cys Val Thr Val Ser Ala Ser Ala Gly Ile Gly Asn Leu
    50                  55                  60

Val Thr Phe Gly His Ser Leu Ser Lys Thr Cys Ser Pro Ala Cys
65                  70                  75

Pro Ile Pro Glu Gly Val Asn Val Gly Val Ala Ser Met Gly Ile
                80                  85                  90

Ser Cys Cys Gln Ser Phe Leu Cys Asn Phe Ser Ala Ala Asp Gly
            95                 100                 105

Gly Leu Arg Ala Ser Val Thr Leu Leu Gly Ala Gly Leu Leu Leu
        110                 115                 120

Ser Leu Leu Pro Ala Leu Leu Arg Phe Gly Pro
    125                 130

<210> SEQ ID NO 37
<211> LENGTH: 249
<212> TYPE: PRT
<213> ORGANISM: Homo sapiens

<400> SEQUENCE: 37

Met Asp Gly Lys Lys Cys Ser Val Trp Met Phe Leu Pro Leu Val
 1               5                  10                  15

Phe Thr Leu Phe Thr Ser Ala Gly Leu Trp Ile Val Tyr Phe Ile
            20                  25                  30

Ala Val Glu Asp Asp Lys Ile Leu Pro Leu Asn Ser Ala Glu Arg
        35                  40                  45

Lys Pro Gly Val Lys His Ala Pro Tyr Ile Ser Ile Ala Gly Asp
    50                  55                  60
```

-continued

Asp Pro Pro Ala Ser Cys Val Phe Ser Gln Val Met Asn Met Ala
                65                  70                  75

Ala Phe Leu Ala Leu Val Val Ala Val Leu Arg Phe Ile Gln Leu
            80                  85                  90

Lys Pro Lys Val Leu Asn Pro Trp Leu Asn Ile Ser Gly Leu Val
            95                 100                 105

Ala Leu Cys Leu Ala Ser Phe Gly Met Thr Leu Leu Gly Asn Phe
           110                 115                 120

Gln Leu Thr Asn Asp Glu Glu Ile His Asn Val Gly Thr Ser Leu
           125                 130                 135

Thr Phe Gly Phe Gly Thr Leu Thr Cys Trp Ile Gln Ala Ala Leu
           140                 145                 150

Thr Leu Lys Val Asn Ile Lys Asn Glu Gly Arg Arg Val Gly Ile
           155                 160                 165

Pro Arg Val Ile Leu Ser Ala Ser Ile Thr Leu Cys Val Val Leu
           170                 175                 180

Tyr Phe Ile Leu Met Ala Gln Ser Ile His Met Tyr Ala Ala Arg
           185                 190                 195

Val Gln Trp Gly Leu Val Met Cys Phe Leu Ser Tyr Phe Gly Thr
           200                 205                 210

Phe Ala Val Glu Phe Arg His Tyr Arg Tyr Glu Ile Val Cys Ser
           215                 220                 225

Glu Tyr Gln Glu Asn Phe Leu Ser Phe Ser Glu Ser Leu Ser Glu
           230                 235                 240

Ala Ser Glu Tyr Gln Thr Asp Gln Val
           245

<210> SEQ ID NO 38
<211> LENGTH: 145
<212> TYPE: PRT
<213> ORGANISM: Homo sapiens

<400> SEQUENCE: 38

Met Glu Leu Ala Leu Leu Cys Gly Leu Val Val Met Ala Gly Val
  1               5                  10                  15

Ile Pro Ile Gln Gly Gly Ile Leu Asn Leu Asn Lys Met Val Lys
            20                  25                  30

Gln Val Thr Gly Lys Met Pro Ile Leu Ser Tyr Trp Pro Tyr Gly
            35                  40                  45

Cys His Cys Gly Leu Gly Gly Arg Gly Gln Pro Lys Asp Ala Thr
            50                  55                  60

Asp Trp Cys Cys Gln Thr His Asp Cys Cys Tyr Asp His Leu Lys
            65                  70                  75

Thr Gln Gly Cys Gly Ile Tyr Lys Asp Tyr Tyr Arg Tyr Asn Phe
            80                  85                  90

Ser Gln Gly Asn Ile His Cys Ser Asp Lys Gly Ser Trp Cys Glu
            95                 100                 105

Gln Gln Leu Cys Ala Cys Asp Lys Glu Val Ala Phe Cys Leu Lys
           110                 115                 120

Arg Asn Leu Asp Thr Tyr Gln Lys Arg Leu Arg Phe Tyr Trp Arg
           125                 130                 135

Pro His Cys Arg Gly Gln Thr Pro Gly Cys
           140                 145

<210> SEQ ID NO 39

```
<211> LENGTH: 1533
<212> TYPE: PRT
<213> ORGANISM: Homo sapiens

<400> SEQUENCE: 39

Met Tyr Ile Arg Val Ser Tyr Asp Thr Lys Pro Asp Ser Leu Leu
 1               5                  10                  15

His Leu Met Val Lys Asp Trp Gln Leu Glu Leu Pro Lys Leu Leu
                20                  25                  30

Ile Ser Val His Gly Gly Leu Gln Asn Phe Glu Met Gln Pro Lys
                35                  40                  45

Leu Lys Gln Val Phe Gly Lys Gly Leu Ile Lys Ala Ala Met Thr
                50                  55                  60

Thr Gly Ala Trp Ile Phe Thr Gly Gly Val Ser Thr Gly Val Ile
                65                  70                  75

Ser His Val Gly Asp Ala Leu Lys Asp His Ser Ser Lys Ser Arg
                80                  85                  90

Gly Arg Val Cys Ala Ile Gly Ile Ala Pro Trp Gly Ile Val Glu
                95                 100                 105

Asn Lys Glu Asp Leu Val Gly Lys Asp Val Thr Arg Val Tyr Gln
               110                 115                 120

Thr Met Ser Asn Pro Leu Ser Lys Leu Ser Val Leu Asn Asn Ser
               125                 130                 135

His Thr His Phe Ile Leu Ala Asp Asn Gly Thr Leu Gly Lys Tyr
               140                 145                 150

Gly Ala Glu Val Lys Leu Arg Arg Leu Leu Glu Lys His Ile Ser
               155                 160                 165

Leu Gln Lys Ile Asn Thr Arg Leu Gly Gln Gly Val Pro Leu Val
               170                 175                 180

Gly Leu Val Val Glu Gly Gly Pro Asn Val Val Ser Ile Val Leu
               185                 190                 195

Glu Tyr Leu Gln Glu Glu Pro Pro Ile Pro Val Val Ile Cys Asp
               200                 205                 210

Gly Ser Gly Arg Ala Ser Asp Ile Leu Ser Phe Ala His Lys Tyr
               215                 220                 225

Cys Glu Glu Gly Gly Ile Ile Asn Glu Ser Leu Arg Glu Gln Leu
               230                 235                 240

Leu Val Thr Ile Gln Lys Thr Phe Asn Tyr Asn Lys Ala Gln Ser
               245                 250                 255

His Gln Leu Phe Ala Ile Ile Met Glu Cys Met Lys Lys Lys Glu
               260                 265                 270

Leu Val Thr Val Phe Arg Met Gly Ser Glu Gly Gln Gln Asp Ile
               275                 280                 285

Glu Met Ala Ile Leu Thr Ala Leu Leu Lys Gly Thr Asn Val Ser
               290                 295                 300

Ala Pro Asp Gln Leu Ser Leu Ala Leu Ala Trp Asn Arg Val Asp
               305                 310                 315

Ile Ala Arg Ser Gln Ile Phe Val Phe Gly Pro His Trp Thr Pro
               320                 325                 330

Leu Gly Ser Leu Ala Pro Pro Thr Asp Ser Lys Ala Thr Glu Lys
               335                 340                 345

Glu Lys Lys Pro Pro Met Ala Thr Thr Lys Gly Gly Arg Gly Lys
               350                 355                 360

Gly Lys Gly Lys Lys Gly Lys Val Lys Glu Glu Val Glu Glu
               365                 370                 375
```

```
Glu Thr Asp Pro Arg Lys Ile Glu Leu Leu Asn Trp Val Asn Ala
            380                 385                 390
Leu Glu Gln Ala Met Leu Asp Ala Leu Val Leu Asp Arg Val Asp
            395                 400                 405
Phe Val Lys Leu Leu Ile Glu Asn Gly Val Asn Met Gln His Phe
            410                 415                 420
Leu Thr Ile Pro Arg Leu Glu Glu Leu Tyr Asn Thr Arg Leu Gly
            425                 430                 435
Pro Pro Asn Thr Leu His Leu Leu Val Arg Asp Val Lys Lys Ser
            440                 445                 450
Asn Leu Pro Pro Asp Tyr His Ile Ser Leu Ile Asp Ile Gly Leu
            455                 460                 465
Val Leu Glu Tyr Leu Met Gly Gly Ala Tyr Arg Cys Asn Tyr Thr
            470                 475                 480
Arg Lys Asn Phe Arg Thr Leu Tyr Asn Asn Leu Phe Gly Pro Lys
            485                 490                 495
Arg Pro Lys Ala Leu Lys Leu Leu Gly Met Glu Asp Asp Glu Pro
            500                 505                 510
Pro Ala Lys Gly Lys Lys Lys Lys Lys Lys Glu Glu Glu
            515                 520                 525
Ile Asp Ile Asp Val Asp Asp Pro Ala Val Ser Arg Phe Gln Tyr
            530                 535                 540
Pro Phe His Glu Leu Met Val Trp Ala Val Leu Met Lys Arg Gln
            545                 550                 555
Lys Met Ala Val Phe Leu Trp Gln Arg Gly Glu Glu Ser Met Ala
            560                 565                 570
Lys Ala Leu Val Ala Cys Lys Leu Tyr Lys Ala Met Ala His Glu
            575                 580                 585
Ser Ser Glu Ser Asp Leu Val Asp Asp Ile Ser Gln Asp Leu Asp
            590                 595                 600
Asn Asn Ser Lys Asp Phe Gly Gln Leu Ala Leu Glu Leu Leu Asp
            605                 610                 615
Gln Ser Tyr Lys His Asp Glu Gln Ile Ala Met Lys Leu Leu Thr
            620                 625                 630
Tyr Glu Leu Lys Asn Trp Ser Asn Ser Thr Cys Leu Lys Leu Ala
            635                 640                 645
Val Ala Ala Lys His Arg Asp Phe Ile Ala His Thr Cys Ser Gln
            650                 655                 660
Met Leu Leu Thr Asp Met Trp Met Gly Arg Leu Arg Met Arg Lys
            665                 670                 675
Asn Pro Gly Leu Lys Val Ile Met Gly Ile Leu Leu Pro Pro Thr
            680                 685                 690
Ile Leu Phe Leu Glu Phe Arg Thr Tyr Asp Asp Phe Ser Tyr Gln
            695                 700                 705
Thr Ser Lys Glu Asn Glu Asp Gly Lys Glu Lys Glu Glu Asn
            710                 715                 720
Thr Asp Ala Asn Ala Asp Ala Gly Ser Arg Lys Gly Asp Glu Glu
            725                 730                 735
Asn Glu His Lys Lys Gln Arg Ser Ile Pro Ile Gly Thr Lys Ile
            740                 745                 750
Cys Glu Phe Tyr Asn Ala Pro Ile Val Lys Phe Trp Phe Tyr Thr
            755                 760                 765
Ile Ser Tyr Leu Gly Tyr Leu Leu Leu Phe Asn Tyr Val Ile Leu
```

```
                        770             775             780
Val Arg Met Asp Gly Trp Pro Ser Leu Gln Glu Trp Ile Val Ile
                        785             790             795
Ser Tyr Ile Val Ser Leu Ala Leu Glu Lys Ile Arg Glu Ile Leu
                        800             805             810
Met Ser Glu Pro Gly Lys Leu Ser Gln Lys Ile Lys Val Trp Leu
                        815             820             825
Gln Glu Tyr Trp Asn Ile Thr Asp Leu Val Ala Ile Ser Thr Phe
                        830             835             840
Met Ile Gly Ala Ile Leu Arg Leu Gln Asn Gln Pro Tyr Met Gly
                        845             850             855
Tyr Gly Arg Val Ile Tyr Cys Val Asp Ile Ile Phe Trp Tyr Ile
                        860             865             870
Arg Val Leu Asp Ile Phe Gly Val Asn Lys Tyr Leu Gly Pro Tyr
                        875             880             885
Val Met Met Ile Gly Lys Met Met Ile Asp Met Leu Tyr Phe Val
                        890             895             900
Val Ile Met Leu Val Val Leu Met Ser Phe Gly Val Ala Arg Gln
                        905             910             915
Ala Ile Leu His Pro Glu Glu Lys Pro Ser Trp Lys Leu Ala Arg
                        920             925             930
Asn Ile Phe Tyr Met Pro Tyr Trp Met Ile Tyr Gly Glu Val Phe
                        935             940             945
Ala Asp Gln Ile Asp Leu Tyr Ala Met Glu Ile Asn Pro Pro Cys
                        950             955             960
Gly Glu Asn Leu Tyr Asp Glu Glu Gly Lys Arg Leu Pro Pro Cys
                        965             970             975
Ile Pro Gly Ala Trp Leu Thr Pro Ala Leu Met Ala Cys Tyr Leu
                        980             985             990
Leu Val Ala Asn Ile Leu Leu Val Asn Leu Leu Ile Ala Val Phe
                        995             1000            1005
Asn Asn Thr Phe Phe Glu Val Lys Ser Ile Ser Asn Gln Val Trp
                        1010            1015            1020
Lys Phe Gln Arg Tyr Gln Leu Ile Met Thr Phe His Asp Arg Pro
                        1025            1030            1035
Val Leu Pro Pro Pro Met Ile Ile Leu Ser His Ile Tyr Ile Ile
                        1040            1045            1050
Ile Met Arg Leu Ser Gly Arg Cys Arg Lys Lys Arg Glu Gly Asp
                        1055            1060            1065
Gln Glu Glu Arg Asp Arg Gly Leu Lys Leu Phe Leu Ser Asp Glu
                        1070            1075            1080
Glu Leu Lys Arg Leu His Glu Phe Glu Glu Gln Cys Val Gln Glu
                        1085            1090            1095
His Phe Arg Glu Lys Glu Asp Glu Gln Gln Ser Ser Ser Asp Glu
                        1100            1105            1110
Arg Ile Arg Val Thr Ser Glu Arg Val Glu Asn Met Ser Met Arg
                        1115            1120            1125
Leu Glu Glu Ile Asn Glu Arg Glu Thr Phe Met Lys Thr Ser Leu
                        1130            1135            1140
Gln Thr Val Asp Leu Arg Leu Ala Gln Leu Glu Glu Leu Ser Asn
                        1145            1150            1155
Arg Met Val Asn Ala Leu Glu Asn Leu Ala Gly Ile Asp Arg Ser
                        1160            1165            1170
```

```
Asp Leu Ile Gln Ala Arg Ser Arg Ala Ser Ser Glu Cys Glu Ala
            1175                1180                1185

Thr Tyr Leu Leu Arg Gln Ser Ser Ile Asn Ser Ala Asp Gly Tyr
            1190                1195                1200

Ser Leu Tyr Arg Tyr His Phe Asn Gly Glu Glu Leu Leu Phe Glu
            1205                1210                1215

Asp Thr Ser Leu Ser Thr Ser Pro Gly Thr Gly Val Arg Lys Lys
            1220                1225                1230

Thr Cys Ser Phe Arg Ile Lys Glu Glu Lys Asp Val Lys Thr His
            1235                1240                1245

Leu Val Pro Glu Cys Gln Asn Ser Leu His Leu Ser Leu Gly Thr
            1250                1255                1260

Ser Thr Ser Ala Thr Pro Asp Gly Ser His Leu Ala Val Asp Asp
            1265                1270                1275

Leu Lys Asn Ala Glu Glu Ser Lys Leu Gly Pro Asp Ile Gly Ile
            1280                1285                1290

Ser Lys Glu Asp Asp Glu Arg Gln Thr Asp Ser Lys Lys Glu Glu
            1295                1300                1305

Thr Ile Ser Pro Ser Leu Asn Lys Thr Asp Val Ile His Gly Gln
            1310                1315                1320

Asp Lys Ser Asp Val Gln Asn Thr Gln Leu Thr Val Glu Thr Thr
            1325                1330                1335

Asn Ile Glu Gly Thr Ile Ser Tyr Pro Leu Glu Thr Lys Ile
            1340                1345                1350

Thr Arg Tyr Phe Pro Asp Glu Thr Ile Asn Ala Cys Lys Thr Met
            1355                1360                1365

Lys Ser Arg Ser Phe Val Tyr Ser Arg Gly Arg Lys Leu Val Gly
            1370                1375                1380

Gly Val Asn Gln Asp Val Glu Tyr Ser Ser Ile Thr Asp Gln Gln
            1385                1390                1395

Leu Thr Thr Glu Trp Gln Cys Gln Val Gln Lys Ile Thr Arg Ser
            1400                1405                1410

His Ser Thr Asp Ile Pro Tyr Ile Val Ser Glu Ala Ala Val Gln
            1415                1420                1425

Ala Glu Gln Lys Glu Gln Phe Ala Asp Met Gln Asp Glu His His
            1430                1435                1440

Val Ala Glu Ala Ile Pro Arg Ile Pro Arg Leu Ser Leu Thr Ile
            1445                1450                1455

Thr Asp Arg Asn Gly Met Glu Asn Leu Leu Ser Val Lys Pro Asp
            1460                1465                1470

Gln Thr Leu Gly Phe Pro Ser Leu Arg Ser Lys Ser Leu His Gly
            1475                1480                1485

His Pro Arg Asn Val Lys Ser Ile Gln Gly Lys Leu Asp Arg Ser
            1490                1495                1500

Gly His Ala Ser Ser Val Ser Ser Leu Val Ile Val Ser Gly Met
            1505                1510                1515

Thr Ala Glu Glu Lys Lys Val Lys Lys Glu Lys Ala Ser Thr Glu
            1520                1525                1530

Thr Glu Cys

<210> SEQ ID NO 40
<211> LENGTH: 462
<212> TYPE: PRT
<213> ORGANISM: Homo sapiens
```

```
<400> SEQUENCE: 40

Met Ser Thr Glu Lys Val Asp Gln Lys Glu Ala Gly Glu Lys
 1               5                  10                  15

Glu Val Cys Gly Asp Gln Ile Lys Gly Pro Asp Lys Glu Glu
                20                  25                  30

Pro Pro Ala Ala Ala Ser His Gly Gln Gly Trp Arg Pro Gly
                35                  40                  45

Arg Ala Ala Arg Asn Ala Arg Pro Glu Pro Gly Ala Arg His Pro
                50                  55                      60

Ala Leu Pro Ala Met Val Asn Asp Pro Val Pro Ala Leu Leu
                65                  70                  75

Trp Ala Gln Glu Val Gly Gln Val Leu Ala Gly Arg Ala Arg Arg
                80                  85                      90

Leu Leu Leu Gln Phe Gly Val Leu Phe Cys Thr Ile Leu Leu Leu
                95                  100                     105

Leu Trp Val Ser Val Phe Leu Tyr Gly Ser Phe Tyr Tyr Ser Tyr
                110                 115                     120

Met Pro Thr Val Ser His Leu Ser Pro Val His Phe Tyr Tyr Arg
                125                 130                     135

Thr Asp Cys Asp Ser Ser Thr Thr Ser Leu Cys Ser Phe Pro Val
                140                 145                     150

Ala Asn Val Ser Leu Thr Lys Gly Gly Arg Asp Arg Val Leu Met
                155                 160                     165

Tyr Gly Gln Pro Tyr Arg Val Thr Leu Glu Leu Glu Leu Pro Glu
                170                 175                     180

Ser Pro Val Asn Gln Asp Leu Gly Met Phe Leu Val Thr Ile Ser
                185                 190                     195

Cys Tyr Thr Arg Gly Gly Arg Ile Ile Ser Thr Ser Arg Ser
                200                 205                 210

Val Met Leu His Tyr Arg Ser Asp Leu Leu Gln Met Leu Asp Thr
                215                 220                     225

Leu Val Phe Ser Ser Leu Leu Leu Phe Gly Phe Ala Glu Gln Lys
                230                 235                     240

Gln Leu Leu Glu Val Glu Leu Tyr Ala Asp Tyr Arg Glu Asn Ser
                245                 250                     255

Tyr Val Pro Thr Thr Gly Ala Ile Ile Glu Ile His Ser Lys Arg
                260                 265                     270

Ile Gln Leu Tyr Gly Ala Tyr Leu Arg Ile His Ala His Phe Thr
                275                 280                     285

Gly Leu Arg Tyr Leu Leu Tyr Asn Phe Pro Met Thr Cys Ala Phe
                290                 295                     300

Ile Gly Val Ala Ser Asn Phe Thr Phe Leu Ser Val Ile Val Leu
                305                 310                     315

Phe Ser Tyr Met Gln Trp Val Trp Gly Ile Trp Pro Arg His
                320                 325                 330

Arg Phe Ser Leu Gln Val Asn Ile Arg Lys Arg Asp Asn Ser Arg
                335                 340                     345

Lys Glu Val Gln Arg Arg Ile Ser Ala His Gln Pro Gly Pro Glu
                350                 355                     360

Gly Gln Glu Glu Ser Thr Pro Gln Ser Asp Val Thr Glu Asp Gly
                365                 370                     375

Glu Ser Pro Glu Asp Pro Ser Gly Thr Glu Gly Gln Leu Ser Glu
                380                 385                     390
```

```
Glu Glu Lys Pro Asp Gln Gln Pro Leu Ser Gly Glu Glu Leu
            395                 400                 405

Glu Pro Glu Ala Ser Asp Gly Ser Gly Ser Trp Glu Asp Ala Ala
            410                 415                 420

Leu Leu Thr Glu Ala Asn Leu Pro Ala Pro Ala Pro Ala Ser Ala
            425                 430                 435

Ser Ala Pro Val Leu Glu Thr Leu Gly Ser Ser Glu Pro Ala Gly
            440                 445                 450

Gly Ala Leu Arg Gln Arg Pro Thr Cys Ser Ser Ser
            455                 460

<210> SEQ ID NO 41
<211> LENGTH: 1015
<212> TYPE: PRT
<213> ORGANISM: Homo sapiens

<400> SEQUENCE: 41

Met Gly Pro Pro Leu Pro Leu Leu Leu Leu Leu Leu Leu
 1               5                  10                  15

Pro Pro Arg Val Leu Pro Ala Ala Pro Ser Ser Val Pro Arg Gly
            20                  25                  30

Arg Gln Leu Pro Gly Arg Leu Gly Cys Leu Leu Glu Glu Gly Leu
            35                  40                  45

Cys Gly Ala Ser Glu Ala Cys Val Asn Asp Gly Val Phe Gly Arg
            50                  55                  60

Cys Gln Lys Val Pro Ala Met Asp Phe Tyr Arg Tyr Glu Val Ser
            65                  70                  75

Pro Val Ala Leu Gln Arg Leu Arg Val Ala Leu Gln Lys Leu Ser
            80                  85                  90

Gly Thr Gly Phe Thr Trp Gln Asp Asp Tyr Thr Gln Tyr Val Met
            95                  100                 105

Asp Gln Glu Leu Ala Asp Leu Pro Lys Thr Tyr Leu Arg Arg Pro
            110                 115                 120

Glu Ala Ser Ser Pro Ala Arg Pro Ser Lys His Ser Val Gly Ser
            125                 130                 135

Glu Arg Arg Tyr Ser Arg Glu Gly Gly Ala Ala Leu Ala Asn Ala
            140                 145                 150

Leu Arg Arg His Leu Pro Phe Leu Glu Ala Leu Ser Gln Ala Pro
            155                 160                 165

Ala Ser Asp Val Leu Ala Arg Thr His Thr Ala Gln Asp Arg Pro
            170                 175                 180

Pro Ala Glu Gly Asp Asp Arg Phe Ser Glu Ser Ile Leu Thr Tyr
            185                 190                 195

Val Ala His Thr Ser Ala Leu Thr Tyr Pro Pro Gly Pro Arg Thr
            200                 205                 210

Gln Leu Arg Glu Asp Leu Leu Pro Arg Thr Leu Gly Gln Leu Gln
            215                 220                 225

Pro Asp Glu Leu Ser Pro Lys Val Asp Ser Gly Val Asp Arg His
            230                 235                 240

His Leu Met Ala Ala Leu Ser Ala Tyr Ala Ala Gln Arg Pro Pro
            245                 250                 255

Ala Pro Pro Gly Glu Gly Ser Leu Glu Pro Gln Tyr Leu Leu Arg
            260                 265                 270

Ala Pro Ser Arg Met Pro Arg Pro Leu Leu Ala Pro Ala Ala Pro
            275                 280                 285
```

```
Gln Lys Trp Pro Ser Pro Leu Gly Asp Ser Glu Asp Pro Ser Ser
            290                 295                 300

Thr Gly Asp Gly Ala Arg Ile His Thr Leu Lys Asp Leu Gln
            305                 310                 315

Arg Gln Pro Ala Glu Val Arg Gly Leu Ser Gly Leu Glu Leu Asp
            320                 325                 330

Gly Met Ala Glu Leu Met Ala Gly Leu Met Gln Gly Val Asp His
            335                 340                 345

Gly Val Ala Arg Gly Ser Pro Gly Arg Ala Ala Leu Gly Glu Ser
            350                 355                 360

Gly Glu Gln Ala Asp Gly Pro Lys Ala Thr Leu Arg Gly Asp Ser
            365                 370                 375

Phe Pro Asp Asp Gly Val Gln Asp Asp Asp Arg Leu Tyr Gln
            380                 385                 390

Glu Val His Arg Leu Ser Ala Thr Leu Gly Gly Leu Leu Gln Asp
            395                 400                 405

His Gly Ser Arg Leu Leu Pro Gly Ala Leu Pro Phe Ala Arg Pro
            410                 415                 420

Leu Asp Met Glu Arg Lys Lys Ser Glu His Pro Glu Ser Ser Leu
            425                 430                 435

Ser Ser Glu Glu Glu Thr Ala Gly Val Glu Asn Val Lys Ser Gln
            440                 445                 450

Thr Tyr Ser Lys Asp Leu Leu Gly Gln Gln Pro His Ser Glu Pro
            455                 460                 465

Gly Ala Ala Ala Phe Gly Glu Leu Gln Asn Gln Met Pro Gly Pro
            470                 475                 480

Ser Lys Glu Glu Gln Ser Leu Pro Ala Gly Ala Gln Glu Ala Leu
            485                 490                 495

Ser Asp Gly Leu Gln Leu Glu Val Gln Pro Ser Glu Glu Glu Ala
            500                 505                 510

Arg Gly Tyr Ile Val Thr Asp Arg Asp Pro Leu Arg Pro Glu Glu
            515                 520                 525

Gly Arg Arg Leu Val Glu Asp Val Ala Arg Leu Leu Gln Val Pro
            530                 535                 540

Ser Ser Ala Phe Ala Asp Val Glu Val Leu Gly Pro Ala Val Thr
            545                 550                 555

Phe Lys Val Ser Ala Asn Val Gln Asn Val Thr Thr Glu Asp Val
            560                 565                 570

Glu Lys Ala Thr Val Asp Asn Lys Asp Lys Leu Glu Glu Thr Ser
            575                 580                 585

Gly Leu Lys Ile Leu Gln Thr Gly Val Gly Ser Lys Ser Lys Leu
            590                 595                 600

Lys Phe Leu Pro Pro Gln Ala Glu Gln Glu Asp Ser Thr Lys Phe
            605                 610                 615

Ile Ala Leu Thr Leu Val Ser Leu Ala Cys Ile Leu Gly Val Leu
            620                 625                 630

Leu Ala Ser Gly Leu Ile Tyr Cys Leu Arg His Ser Ser Gln His
            635                 640                 645

Arg Leu Lys Glu Lys Leu Ser Gly Leu Gly Gly Asp Pro Gly Ala
            650                 655                 660

Asp Ala Thr Ala Ala Tyr Gln Glu Leu Cys Arg Gln Arg Met Ala
            665                 670                 675

Thr Arg Pro Pro Asp Arg Pro Glu Gly Pro His Thr Ser Arg Ile
            680                 685                 690
```

```
Ser Ser Val Ser Ser Gln Phe Ser Asp Gly Pro Ile Pro Ser Pro
            695                 700                 705

Ser Ala Arg Ser Ser Ala Ser Ser Trp Ser Glu Pro Val Gln
        710                 715                 720

Ser Asn Met Asp Ile Ser Thr Gly His Met Ile Leu Ser Tyr Met
            725                 730                 735

Glu Asp His Leu Lys Asn Lys Asn Arg Leu Glu Lys Glu Trp Glu
            740                 745                 750

Ala Leu Cys Ala Tyr Gln Ala Glu Pro Asn Ser Ser Phe Val Ala
            755                 760                 765

Gln Arg Glu Glu Asn Val Pro Lys Asn Arg Ser Leu Ala Val Leu
            770                 775                 780

Thr Tyr Asp His Ser Arg Val Leu Leu Lys Ala Glu Asn Ser His
            785                 790                 795

Ser His Ser Asp Tyr Ile Asn Ala Ser Pro Ile Met Asp His Asp
            800                 805                 810

Pro Arg Asn Pro Ala Tyr Ile Ala Thr Gln Gly Pro Leu Pro Ala
            815                 820                 825

Thr Val Ala Asp Phe Trp Gln Met Val Trp Glu Ser Gly Cys Val
            830                 835                 840

Val Ile Val Met Leu Thr Pro Leu Ala Glu Asn Gly Val Arg Gln
            845                 850                 855

Cys Tyr His Tyr Trp Pro Asp Glu Gly Ser Asn Leu Tyr His Ile
            860                 865                 870

Tyr Glu Val Asn Leu Val Ser Glu His Ile Trp Cys Glu Asp Phe
            875                 880                 885

Leu Val Arg Ser Phe Tyr Leu Lys Asn Leu Gln Thr Asn Glu Thr
            890                 895                 900

Arg Thr Val Thr Gln Phe His Phe Leu Ser Trp Tyr Asp Arg Gly
            905                 910                 915

Val Pro Ser Ser Arg Ser Leu Leu Asp Phe Arg Arg Lys Val
            920                 925                 930

Asn Lys Cys Tyr Arg Gly Arg Ser Cys Pro Ile Ile Val His Cys
            935                 940                 945

Ser Asp Gly Ala Gly Arg Ser Gly Thr Tyr Val Leu Ile Asp Met
            950                 955                 960

Val Leu Asn Lys Met Ala Lys Gly Ala Lys Glu Ile Asp Ile Ala
            965                 970                 975

Ala Thr Leu Glu His Leu Arg Asp Gln Arg Pro Gly Met Val Gln
            980                 985                 990

Thr Lys Glu Gln Phe Glu Phe Ala Leu Thr Ala Val Ala Glu Glu
            995                1000                1005

Val Asn Ala Ile Leu Lys Ala Leu Pro Gln
           1010                1015

<210> SEQ ID NO 42
<211> LENGTH: 442
<212> TYPE: PRT
<213> ORGANISM: Homo sapiens

<400> SEQUENCE: 42

Met Gln Pro Pro Pro Ser Leu Cys Gly Arg Ala Leu Val Ala Leu
  1               5                  10                  15

Val Leu Ala Cys Gly Leu Ser Arg Ile Trp Gly Glu Glu Arg Gly
             20                  25                  30
```

-continued

Phe Pro Pro Asp Arg Ala Thr Pro Leu Leu Gln Thr Ala Glu Ile
                35                  40                  45

Met Thr Pro Pro Thr Lys Thr Leu Trp Pro Lys Gly Ser Asn Ala
            50                  55                  60

Ser Leu Ala Arg Ser Leu Ala Pro Ala Glu Val Pro Lys Gly Asp
            65                  70                  75

Arg Thr Ala Gly Ser Pro Pro Arg Thr Ile Ser Pro Pro Cys
            80                  85                  90

Gln Gly Pro Ile Glu Ile Lys Glu Thr Phe Lys Tyr Ile Asn Thr
            95                 100                 105

Val Val Ser Cys Leu Val Phe Val Leu Gly Ile Ile Gly Asn Ser
                110                 115                 120

Thr Leu Leu Arg Ile Ile Tyr Lys Asn Lys Cys Met Arg Asn Gly
                125                 130                 135

Pro Asn Ile Leu Ile Ala Ser Leu Ala Leu Gly Asp Leu Leu His
                140                 145                 150

Ile Val Ile Asp Ile Pro Ile Asn Val Tyr Lys Leu Leu Ala Glu
                155                 160                 165

Asp Trp Pro Phe Gly Ala Glu Met Cys Lys Leu Val Pro Phe Ile
                170                 175                 180

Gln Lys Ala Ser Val Gly Ile Thr Val Leu Ser Leu Cys Ala Leu
                185                 190                 195

Ser Ile Asp Arg Tyr Arg Ala Val Ala Ser Trp Ser Arg Ile Lys
                200                 205                 210

Gly Ile Gly Val Pro Lys Trp Thr Ala Val Glu Ile Val Leu Ile
                215                 220                 225

Trp Val Val Ser Val Val Leu Ala Val Pro Glu Ala Ile Gly Phe
                230                 235                 240

Asp Ile Ile Thr Met Asp Tyr Lys Gly Ser Tyr Leu Arg Ile Cys
                245                 250                 255

Leu Leu His Pro Val Gln Lys Thr Ala Phe Met Gln Phe Tyr Lys
                260                 265                 270

Thr Ala Lys Asp Trp Trp Leu Phe Ser Phe Tyr Phe Cys Leu Pro
                275                 280                 285

Leu Ala Ile Thr Ala Phe Phe Tyr Thr Leu Met Thr Cys Glu Met
                290                 295                 300

Leu Arg Lys Lys Ser Gly Met Gln Ile Ala Leu Asn Asp His Leu
                305                 310                 315

Lys Gln Arg Arg Glu Val Ala Lys Thr Val Phe Cys Leu Val Leu
                320                 325                 330

Val Phe Ala Leu Cys Trp Leu Pro Leu His Leu Ser Arg Ile Leu
                335                 340                 345

Lys Leu Thr Leu Tyr Asn Gln Asn Asp Pro Asn Arg Cys Glu Leu
                350                 355                 360

Leu Ser Phe Leu Leu Val Leu Asp Tyr Ile Gly Ile Asn Met Ala
                365                 370                 375

Ser Leu Asn Ser Cys Ile Asn Pro Ile Ala Leu Tyr Leu Val Ser
                380                 385                 390

Lys Arg Phe Lys Asn Cys Phe Lys Ser Cys Leu Cys Cys Trp Cys
                395                 400                 405

Gln Ser Phe Glu Glu Lys Gln Ser Leu Glu Glu Lys Gln Ser Cys
                410                 415                 420

```
Leu Lys Phe Lys Ala Asn Asp His Gly Tyr Asp Asn Phe Arg Ser
            425                 430                 435

Ser Asn Lys Tyr Ser Ser Ser
                440
```